(12) United States Patent
Bridgeman et al.

(10) Patent No.: US 11,697,677 B2
(45) Date of Patent: Jul. 11, 2023

(54) CHIMERIC MOLECULES PROVIDING TARGETED COSTIMULATION FOR ADOPTIVE CELL THERAPY

(71) Applicant: Instil Bio (UK) Limited, Manchester (GB)

(72) Inventors: John Bridgeman, Manchester (GB); Robert Hawkins, Manchester (GB); Ruben Rodriguez, Dallas, TX (US); Sujita Sukumaran, Dallas, TX (US); Xingliang Zhou, Dallas, TX (US); Eric Gschweng, Dallas, TX (US)

(73) Assignee: INSTIL BIO (UK) LIMITED, Manchester (GB)

( * ) Notice: Subject to any disclaimer, the term of this patent is extended or adjusted under 35 U.S.C. 154(b) by 0 days.

(21) Appl. No.: 17/822,251

(22) Filed: Aug. 25, 2022

(65) Prior Publication Data

US 2023/0059511 A1 Feb. 23, 2023

Related U.S. Application Data

(63) Continuation-in-part of application No. PCT/US2022/073741, filed on Jul. 14, 2022.

(60) Provisional application No. 63/222,916, filed on Jul. 16, 2021.

(51) Int. Cl.
C07K 14/705 (2006.01)
C07K 14/725 (2006.01)
C07K 16/28 (2006.01)

(52) U.S. Cl.
CPC .... *C07K 14/7051* (2013.01); *C07K 14/70517* (2013.01); *C07K 14/70521* (2013.01); *C07K 14/70578* (2013.01); *C07K 16/2803* (2013.01); *C07K 16/2818* (2013.01); *C07K 16/2827* (2013.01); *C07K 16/2878* (2013.01); *C07K 2317/565* (2013.01); *C07K 2317/622* (2013.01); *C07K 2317/76* (2013.01); *C07K 2319/02* (2013.01); *C07K 2319/03* (2013.01); *C07K 2319/33* (2013.01)

(58) Field of Classification Search
None
See application file for complete search history.

(56) References Cited

U.S. PATENT DOCUMENTS

| | | |
|---|---|---|
| 5,399,346 A | 3/1995 | Anderson et al. |
| 5,580,859 A | 12/1996 | Feigner et al. |
| 5,589,466 A | 12/1996 | Feigner et al. |
| 5,858,358 A | 1/1999 | June et al. |
| 5,883,223 A | 3/1999 | Gray |
| 6,326,193 B1 | 12/2001 | Liu et al. |
| 6,352,694 B1 | 3/2002 | June et al. |
| 6,534,055 B1 | 3/2003 | June et al. |
| 6,692,964 B1 | 2/2004 | June et al. |
| 6,797,514 B2 | 9/2004 | Berenson et al. |
| 6,867,041 B2 | 3/2005 | Berenson et al. |
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |
| 7,067,318 B2 | 6/2006 | June et al. |
| 7,144,575 B2 | 12/2006 | June et al. |
| 7,172,869 B2 | 2/2007 | June et al. |
| 7,175,843 B2 | 2/2007 | June et al. |
| 7,232,566 B2 | 6/2007 | June et al. |
| 7,232,888 B2 | 6/2007 | Begent et al. |
| 7,446,190 B2 | 11/2008 | Sadelain et al. |
| 7,626,011 B2 | 12/2009 | Begent et al. |
| 7,741,465 B1 | 6/2010 | Eshhar et al. |
| 9,598,489 B2 | 3/2017 | Powell, Jr. |
| 9,995,753 B2 * | 6/2018 | Loo ................. G01N 33/6854 |
| 10,117,896 B2 | 11/2018 | Powell, Jr. et al. |
| 10,640,569 B2 | 5/2020 | Beatty et al. |
| 10,654,928 B2 | 5/2020 | Kloss et al. |
| 10,829,735 B2 * | 11/2020 | Bedoya ................. A61P 35/02 |
| 10,844,117 B2 | 11/2020 | Powell, Jr. |
| 10,881,688 B2 | 1/2021 | Leek et al. |
| 10,981,969 B2 | 4/2021 | June et al. |
| 2004/0043401 A1 | 3/2004 | Sadelain et al. |
| 2004/0101519 A1 | 5/2004 | June et al. |
| 2006/0034810 A1 | 2/2006 | Riley et al. |
| 2006/0121005 A1 | 6/2006 | Berenson et al. |
| 2014/0050708 A1 | 2/2014 | Powell, Jr. et al. |

(Continued)

FOREIGN PATENT DOCUMENTS

| WO | WO 2001/029058 | 4/2001 |
|---|---|---|
| WO | WO 2001/096584 | 12/2001 |

(Continued)

OTHER PUBLICATIONS

International Search Report and Written Opinion issued in PCT/US2022/073741 dated Nov. 22, 2022; 12 pages.

(Continued)

*Primary Examiner* — Ilia I Ouspenski

(74) *Attorney, Agent, or Firm* — Knobbe, Martens, Olson & Bear, LLP

(57) ABSTRACT

The present invention relates to a chimeric molecule useful in adoptive cell therapy (ACT), and cells comprising the same. The chimeric molecule can act as a modulator of cellular activity enhancing responses when an endogenous T-cell receptor (TCR) is engaged with its cognate antigen. The present invention also provides proteins, nucleic acids encoding the chimeric molecule and therapeutic uses thereof.

25 Claims, 41 Drawing Sheets

Specification includes a Sequence Listing.

(56) References Cited

U.S. PATENT DOCUMENTS

| | | |
|---|---|---|
| 2014/0099309 A1 | 4/2014 | Powell, Jr. et al. |
| 2014/0286987 A1 | 9/2014 | Spencer et al. |
| 2017/0209492 A1 | 7/2017 | June et al. |
| 2017/0246278 A1 | 8/2017 | Valdes et al. |
| 2018/0044404 A1 | 2/2018 | Oda et al. |
| 2018/0125890 A1 | 5/2018 | Anderson et al. |
| 2018/0273640 A1 | 9/2018 | Liang et al. |
| 2018/0280437 A1 | 10/2018 | Wiltzius et al. |
| 2018/0319862 A1* | 11/2018 | Thompson ............ A61P 35/00 |
| 2019/0023764 A1 | 1/2019 | Wu et al. |
| 2020/0009190 A1 | 1/2020 | Oda et al. |
| 2020/0078402 A1 | 3/2020 | Ostertag et al. |
| 2020/0115448 A1 | 4/2020 | Liu et al. |
| 2021/0277149 A1* | 9/2021 | Patel ............... G01N 33/56972 |
| 2022/0160760 A1 | 5/2022 | Bridgeman et al. |
| 2022/0348631 A1 | 11/2022 | Bridgeman et al. |
| 2023/0002470 A1 | 1/2023 | Bridgeman et al. |
| 2023/0002504 A1 | 1/2023 | Bridgeman et al. |
| 2023/0055694 A1 | 2/2023 | Bridgeman et al. |

FOREIGN PATENT DOCUMENTS

| | | |
|---|---|---|
| WO | WO 2015/112626 A9 | 7/2015 |
| WO | WO 2016/141357 A1 | 9/2016 |
| WO | WO 2017/079705 A1 | 5/2017 |
| WO | WO 2018/156711 A1 | 8/2018 |
| WO | WO 2018/208849 A1 | 11/2018 |
| WO | WO 2020/016661 A2 | 1/2020 |
| WO | WO 2020/152451 A1 | 7/2020 |
| WO | WO 2021/048850 A1 | 3/2021 |

OTHER PUBLICATIONS

Alvarez-Vallina et al., Antigen-Specific Targeting of CD28-Mediated T Cell Co-Stimulation Using Chimeric Single-Chain Antibody Variable Fragment-CD28 Receptors. Euro J Immunol. Oct. 1, 1996; 26(10):2304-2309.

Lanitis et al., Chimeric Antigen Receptor T Cells with Dissociated Signaling Domains Exhibit Focused Antitumor Activity with Reduced Potential for Toxicity In Vivo. Cancer Immun Res. Jul. 1, 2013; 1(1): 43-53.

Li et al., Chimeric Antigen Receptor-Engineered T Cells for Liver Cancers, Progress and Obstacles. Tumor Biol. Mar. 2017; 39(3): 1-8.

Levin-Piaeda O., CD40 Costimulation Enhances CAR-T Cell Activation—Joint Meeting of the Israeli Immunol. Society (IIS) and Israeli Society for Cancer Research (ISCR) 2019; pp. 1-2 (Sep. 25, 2019) Retrieved from the Internet: URL: https://program.eventact.com/lecture?id=204321&code=430912; 1 page.

Mata et al., Inducible Activation of MyD88 and CD40 in Car T Cells Results in Controllable and Potent Antitumor Activity in Preclinical Solid Tumor. Cancer Disc. Nov. 1, 2017; 7(11): 1306-1319.

Weinkove et al., Selecting Costimulatory Domains for Chimeric Antigen Receptors: Functional and Clinical Considerations. Clin Transl Immunol. Jan. 1, 2019; 8(5): e1049.

International Search Report and Written Opinion issued in PCT/GB2020/050120 dated Apr. 7, 2020; 11 pages.

International Search Report and Written Opinion issued in PCT/US2021/042075 dated Oct. 27, 2021; 12 pages.

International Search Report and Written Opinion issued in PCT/US2021/042079 dated Oct. 28, 2021; 12 pages.

U.S. Appl. No. 17/562,618, filed Dec. 27, 2021, Bridgeman et al.
U.S. Appl. No. 17/823,223, filed Aug. 30, 2022, Bridgeman et al.
U.S. Appl. No. 17/807,109, filed Jun. 15, 2022, Bridgeman et al.
U.S. Appl. No. 17/936,102, filed Sep. 28, 2022, Bridgeman et al.

ClinicalTrials.gov: NCT01653717; "CD19-specific T-cell for Chronic Lymphocytic Leukemia (CLL)". Jul. 31, 2012. NIH U.S. National Library of Medicine; downloaded in 7 pages.

GenBank accession No. NP_003028.1; last updated Mar. 6, 2000, 3 pages.

International Search Report and Written Opinion issued in PCT/US2022/033580 dated Nov. 7, 2022; 14 pages.

Ahonen et al., The CD40-TRAF6 Axis Controls Affinity Maturation and the Generation of Long-lived Plasma Cells. Nat Immunol. May 2002;3(5): 451-456.

Altschul et al., Basic local alignment search tool. J Mol Biol. Oct. 5, 1990; 215(3): 405-410.

Clayton et al., CD3 eta and CD3 zeta are alternatively spliced products of a common genetic locus and are transcriptionally and/or post-transcriptionally regulated during T-cell development. PNAS. Jun. 15, 1991;88(12): 5202-5206.

ClinicalTrials.gov: NCT00968760; "CD19-specific T Cell Infusion in Patients with B-Lineage Lymphoid Malignancies". Aug. 31, 2009. NIH U.S. National Library of Medicine; downloaded in 10 pages.

ClinicalTrials.gov: NCT01653717; "CD19-specific T-cell for Chronic Lymphocytic Leukemia (CLL)". Jul. 31, 2021. NIH U.S. National Library of Medicine; downloaded in 7 pages.

Davis et al., T-cell Antigen Receptor Genes and T-cell Recognition. Nature Aug. 1, 1988; 334(6181):395-402.

Davis et al., Ligand Recognition by (alpha)(beta) T Cell Receptors. Annu Rev Immunol. (1998) 16: 523-544.

Garland et al., The Use of Teflon Cell Culture Bags to Expand Functionally Active CD8+ cytotoxic T Lymphocytes. J Immunol Meth. Jul. 30, 1999;227(1-2): 53-63.

GenBank accession No. NM_000733; provided by RefSeq Jul. 2008, 5 pages.

GenBank accession No. NM_000734.4; provided by RefSeq Jul. 2008, 5 pages.

GenBank accession No. NM_000073; provided by RefSeq Jul. 2008, 5 pages.

GenBank accession No. NM_007648.5; last updated Jun. 16, 2018, 4 pages.

GenBank accession No. NM_009850.2; last updated Nov. 15, 2007, 4 pages.

GenBank accession No. NM_031162.4, last updated Jan. 5, 2011, 5 pages.

GenBank accession No. NM_198053.3; provided by RefSeq Jul. 2008, 5 pages.

GenBank accession No. NM_001113391, NM_001113392, NM_001113393; dated Aug. 13, 2022, and NM_001113394.2 [Obsolete]; dated May 12, 2013, total 19 pages.

GenBank accession No. NM_001378515.1 & 001378516.1; provided by RefSeq Jul. 2008, 8 pages.

GenBank accession No. NP_000064.1; provided by RefSeq Jul. 2008, 4 pages.

GenBank accession No. NP_000724.1 & NP_000725.1; provided by RefSeq Jul. 2008, 8 pages.

GenBank accession No. NP_001241.1; provided by RefSeq Nov. 2014, 3 pages.

GenBank accession No. NP_001552.2; provided by RefSeq Jul. 2008, 3 pages.

GenBank accession No. NP_001758.2; provided by RefSeq Jun. 2016, 4 pages.

GenBank accession No. NP_003028.1; provided by RefSeq Jul. 2008, 3 pages.

GenBank accession No. NP_003318.1; provided by RefSeq Jul. 2008, 3 pages.

GenBank accession No. NP_004186.1; provided by RefSeq Feb. 2011, 3 pages.

GenBank accession No. NP_006130.1: provided by RefSeq Jul. 2011, 5 pages.

GenBank accession No. NP_031674.1; last updated on Feb. 15, 2003, 3 pages.

GenBank accession No. NP_033980.1; last updated Jan. 7, 2022, 3 pages.

GenBank accession No. NP_112439.1; last updated Nov. 19, 2004, 3 pages.

GenBank accession No. NP_596867; provided by RefSeq Jul. 2008, 5 pages.

GenBank accession No. NP_932170.1; provided by RefSeq Jul. 2008, 4 pages.

(56) References Cited

OTHER PUBLICATIONS

GenBank accession No. NP_001106862.1, NP_001106863.1, and NP_001106864.2; last updated Feb. 14, 2002, total 10 pages.
GenBank accession No. NP_001315538.1; provided by RefSeq Jun. 2016, 3 pages.
GenBank accession No. NP_001317683.1; last updated Sep. 3, 2016, 3 pages.
GenBank accession No. NP_001365444.1 & NP_001365445.1; last updated Feb. 20, 2020, 6 pages.
GenBank accession No. NP_001139345.1; provided by RefSeq May 2020, 3 pages.
Govers et al., "TCRs Genetically Linked to CD28 and CD3s do not mispair with endogenous TCR chains and mediate enhanced T cell persistence and anti-melanoma activity". J Immunol. Nov. 15, 2014;193(10): 5315-26.
Grupp et al., Chimeric Antigen Receptor—Modified T Cells for Acute Lymphoid Leukemia. New Engl J Med. Apr. 18, 2013;368(16): 1509-1518.
Guedan et al., Enhancing Car T Cell Persistence through ICOS and 3-1BB Costimulation. JCI Insight. Jan. 11, 2018; 3(1): e96976 in 17 pages.
Guest et al., The role of extracellular spacer regions in the optimal design of chimeric immune receptors: evaluation of four different scFvs and antigens. J Immunother. May 1, 2005; 28(3): 203-211.
Haanen et al., Selective Expansion of Cross-reactive CD8+ Memory T Cells by Viral Variants. J Exp Med., Nov. 1, 1999;190(9): 1319-1328.
Hudecek et al., Receptor affinity and extracellular domain modifications affect tumor recognition by ROR1-specific chimeric antigen receptor T cells. Clin Cancer Res. Jun. 15, 2013; 19(12): 3153-3164.
Hudecek et al., The nonsignalling extracellular spacer domain of chimeric antigen receptors is decisive for in vivo antitumor activity. Cancer Immunol Res. Feb. 2015; 3(2): 125-135.
Hurton et al., Tethered IL-15 Augments Antitumor Activity and Promotes a Stem-cell Memory Aubset in Tumor-specific T Cells. PNAS USA. Nov. 29, 2016;113(48): E7788-E7797.
Izumoto et al., Phase II Clinical Trial of Wilms Tumor 1 Peptide Vaccination for Patients with Recurrent Glioblastoma Multiforme. J Neurosurg. 2008. 108(5): 963-971.
Kochenderfer et al., Chemotherapy-refractory diffuse large B-cell lymphoma and indolent B-cell malignancies can be effectively treated with autologous T cells expressing an anti-CD19 chimeric antigen receptor. J Clin Oncol. Feb. 20, 2015; 33(6): 540-550.
Mackey et al., Distinct Contributions of Different CD40 TRAF Binding Sites to CD154-induced Dendritic Cell Maturation and IL-12 Secretion. Eur J Immunol. Mar. 2003; 33(3): 779-789.
Manuri et al., piggyBac Transposon/Transposase System to Generate CD19-specific T Cells for the Treatment of B-lineage Malignancies. Hum Gene Ther. Apr. 1, 2010;21(4): 427-437.
Mátés et al., Molecular Evolution of a Novel Hyperactive Sleeping Beauty Transposase Enables Robust Stable Gene Transfer in Vertebrates. Nat Genet. Jun. 2009;41(6): 753-761.
Monjezi et al., Enhanced CAR T-cell engineering using non-viral Sleeping Beauty transposition from minicircle vectors. Leukemia. Jan. 2017;31(1): 186-194.
Morgan et al., "Cancer Regression in Patients After Transfer of Genetically Engineered Lymphocytes". Science Oct. 6, 2006;314(5796): 126-129.
Morita et al., Enhanced Expression of Anti-CD19 Chimeric Antigen Receptor in piggyBac Transposon-engineered T Cells. Mol Ther Meth Clin Dev. Mar. 16, 2018;8: 131-140; online 2017.

Mukundan et al., TNF Receptor-associated Factor 6 is an Essential Mediator of CD40-activated Proinflammatory Pathways in Monocytes and Macrophages. J Immunol. Jan. 15, 2005; 174(2): 1081-1090.
Nakazawa et al., PiggyBac-mediated Cancer Immunotherapy Using EBV-specific Cytotoxic T-cells Expressing HER2-specific Chimeric Antigen Receptor. Mol Ther. Dec. 1, 2011;19(12): 2133-2143.
Orloff et al., Biochemical characterization of the η chain of the T-cell receptor: A unique subunit related to ζ. J Biol Chem. Sep. 5, 1989;264(25): 14812-14817.
Park H.H., Structure of TRAF Family: Current Understanding of Receptor Recognition. Front Immunol. Aug. 30, 2018; 9: 1999 in 7 pages.
Pearson et al., Improved tools for biological sequence comparison. PNAS USA Apr. 1988; 85(8): 2444-2448.
Rapoport et al., NY-ESO-1 Specific TCR Engineered T-cells Mediate Sustained Antigen-specific Antitumor Effects in Myeloma. Nat Med. Aug. 2015;21(8): 914-921.
Rosenberg et al., Use of Tumor-Infiltrating Lymphocytes and Interleukin-2 in the Immunotherapy of Patients with Metastatic Melanoma. New England J Med. Dec. 22, 1988;319(25): 1676-1680.
Rosenberg et al., Gene Transfer Into Humans—Immunotherapy of Patients with Advanced Melanoma, Using Tumor-infiltrating Lymphocytes Modified by Retroviral Gene Transduction. New England J Med. Aug. 30, 1990;323(9): 570-578.
Rosenberg et al., Durable Complete Responses in Heavily Pretreated Patients with Metastatic Melanoma Using T-cell Transfer Immunotherapy. Clin Cancer Res. 2011, 17(13): 4550-4557.
Sambrook et al., Molecular Cloning: A Laboratory Manual. Cold Spring Harbor Laboratory, New York; 2001, TOC; 18 pages.
Scholler et al., Decade-long Safety and Function of Retroviral-modified Chimeric Antigen Receptor T Cells. Sci Transl Med. May 2, 2012;4(132): 132ra53; in 16 pages.
Singh et al., Redirecting Specificity of T-cell Populations for CD19 Using the Sleeping Beauty System. Cancer Res. Apr. 15, 2008;68(8): 2961-2971.
Ten Berge et al., Selective Expansion of a Peripheral Blood CD8+ Memory T cell Subset Expressing Both Granzyme B and L-selectin During Primary Viral Infection in Renal Allograft Recipients. Transplant Proc. Dec. 1, 1998;30(8): 3975-3977.
Thokala et al., Redirecting Specificity of T Cells Using the Sleeping Beauty System to Express Chimeric Antigen Receptors by Mix-and-Matching of VL and VH Domains Targeting CD123+ Tumors. PLoS ONE. Aug. 22, 2016;11(8): eQ159477 in 23 pages.
UniProtKB/Swiss-Prot: Accession No. P01861; "Nucleotide Sequence of a human immunoglobulin C gamma 4 gene". Dated: Jul. 21, 1986; Downloaded in 7 pages.
Wilkie et al., Retargeting of human T cells to tumor-associated MUC1: the evaluation of a chimeric antigen receptor. J Immunol. Apr. 1, 2008; 180(7): 4901-4909.
Ye et al., The Structural Basis for the Recognition of Diverse Receptor Sequences by TRAF2. Mol Cell. Sep. 1999; 4: 321-330.
Finney et al., Chimeric Receptors Providing Both Primary and Costimulatory Signaling in T Cells from a Single Gene Product. J Immunol. Sep. 15, 1998;161(6):2791-2797.
Maher et al., Human T-lymphocyte Cytotoxicity and Proliferation directed by a Single Chimeric TCRζ/CD28 Receptor. Nature Biotech. Jan. 1, 2002;20(1): 70-75.
Yu et al., Reducing affinity as a strategy to boost immunomodulatory antibody agonism. Nature. Feb. 2023;1:1-9.

* cited by examiner

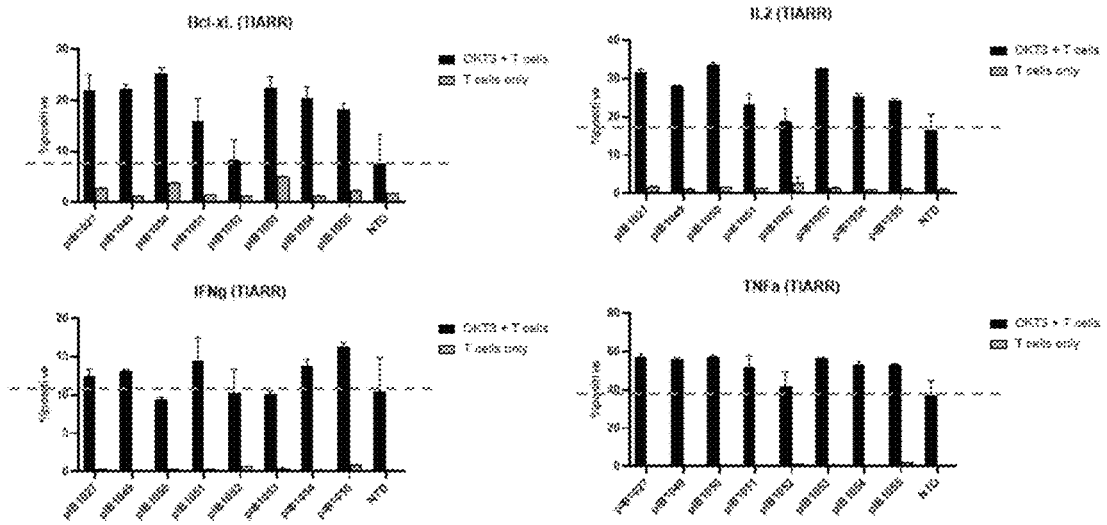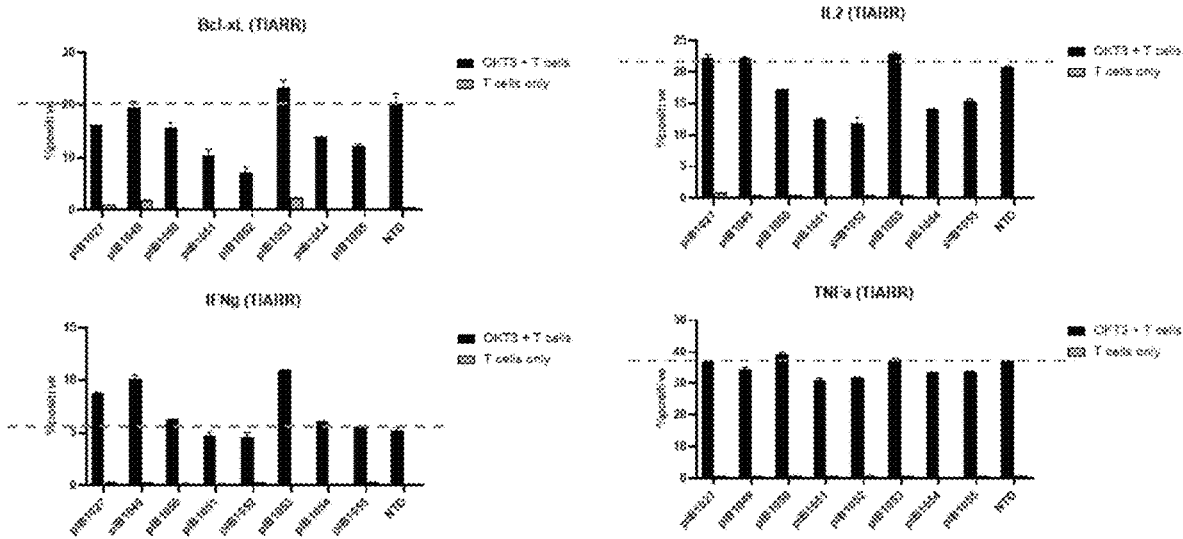
Fig. 2

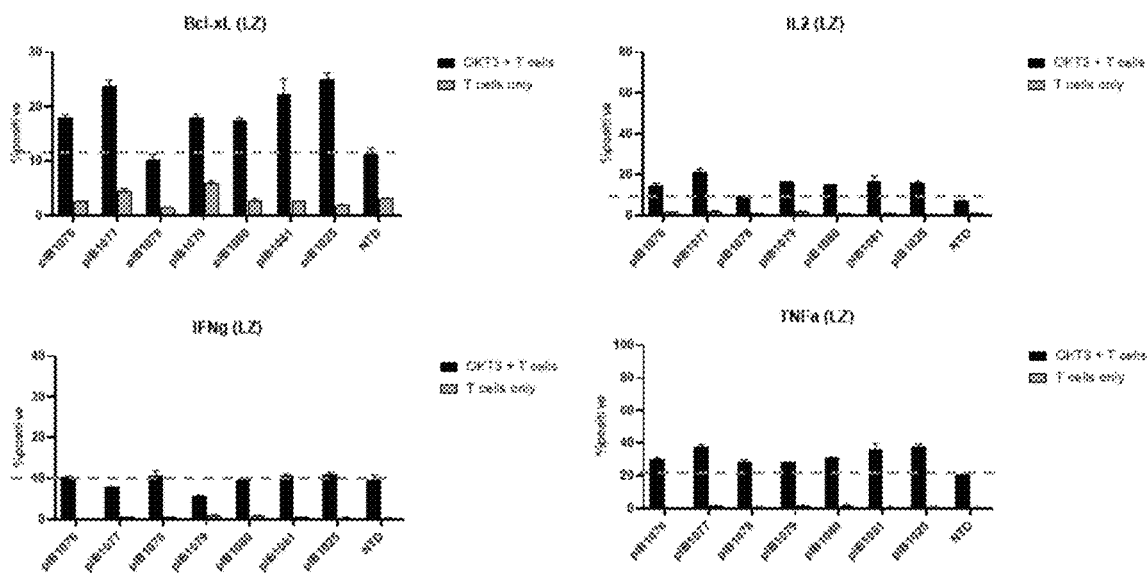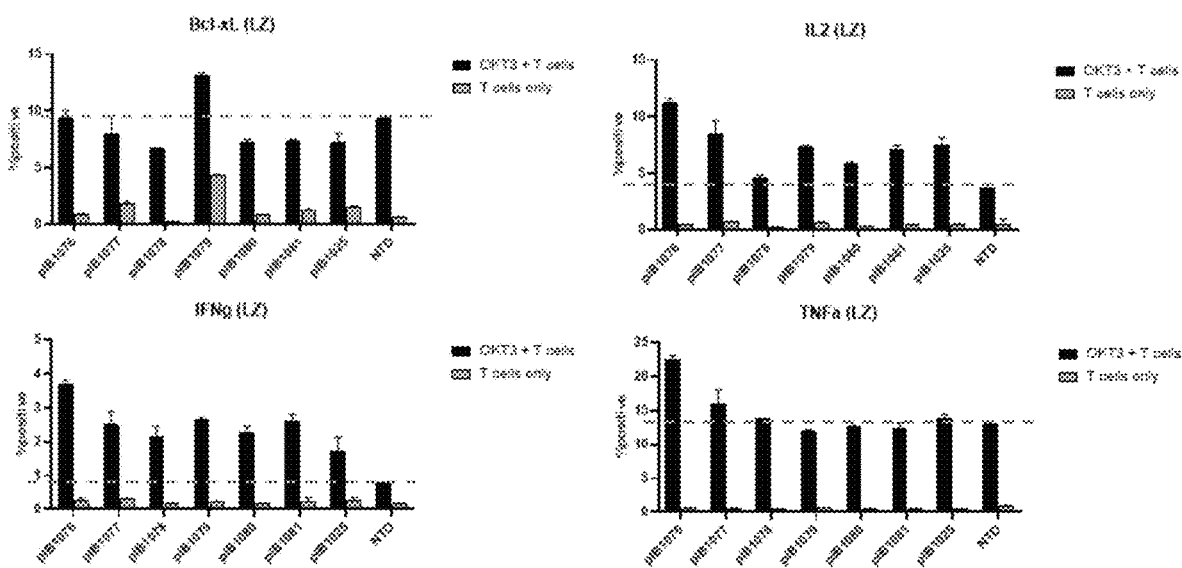
Fig. 4

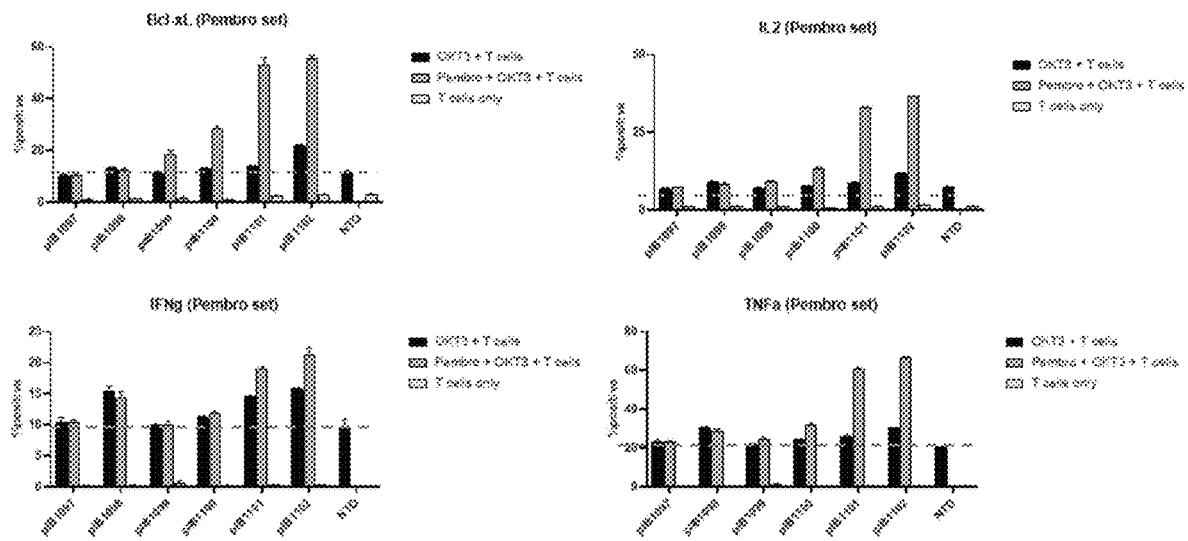
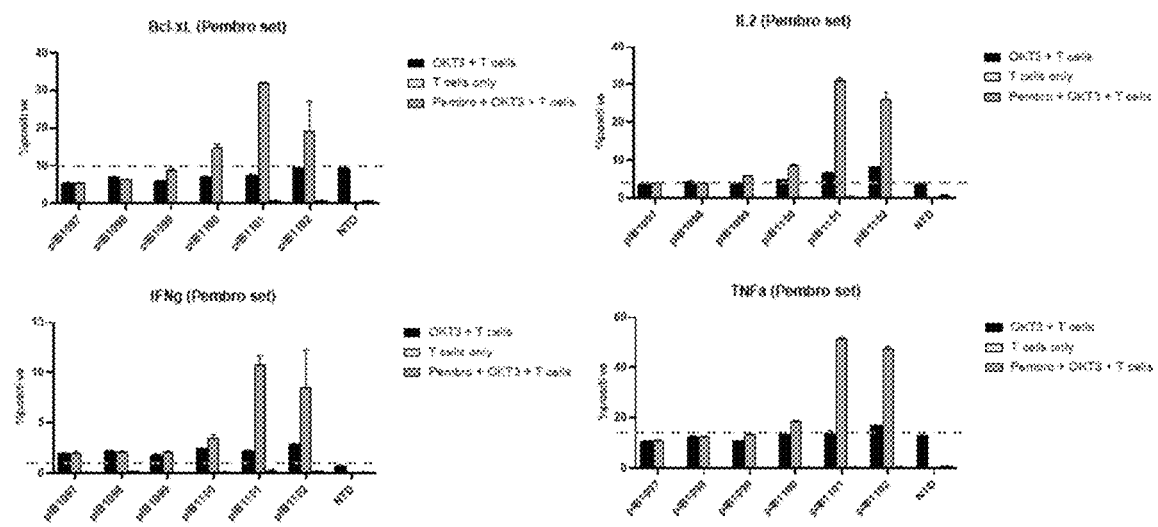
Fig. 6

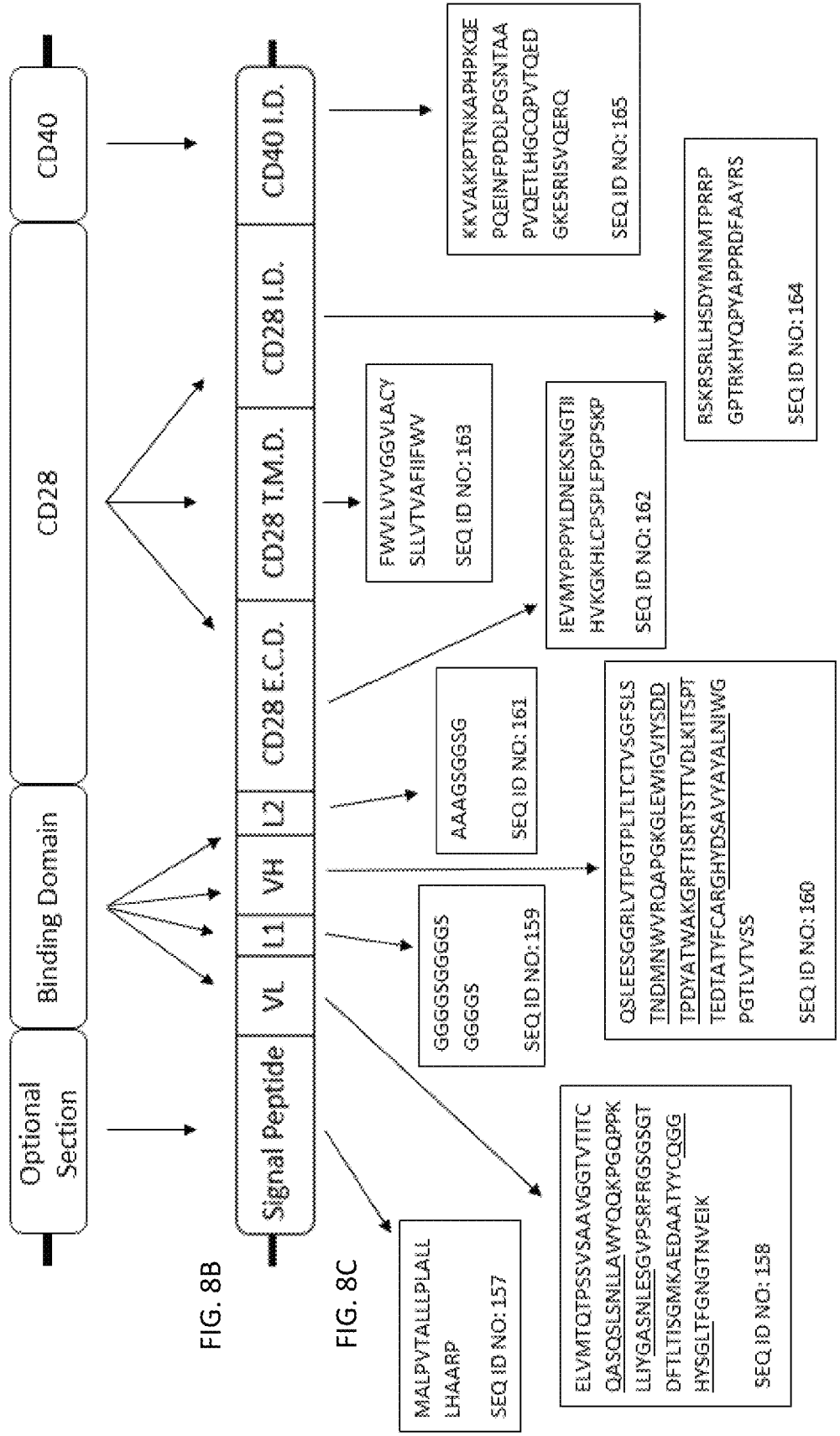

Anti-pembro CoStAR Sequence ("Universal CoStAR")
*MALPVTALLLPLALLLHAARP*ELVMTQTPSSVSAAVGGTVTITC<u>QASQSLSNLLA</u>WYQQKPGQPPKLLIY<u>GASNLES</u>GV
PSRFRGSGSGTDFTLTISGMKAEDAATYYC<u>QGGHYSGLT</u>FGNGTNVEIKGGGGSGGGGSGGGGSQSLEESGGRLVTP
GTPLTLTCTVSGFSLS<u>TNDMN</u>WVRQAPGKGLEWIG<u>VIYSDDTPDYATWAKG</u>RFTISRTSTTVDLKITSPTTEDTATYFCA
R<u>GHYDSAVYAYALNI</u>WGPGTLVTVSSAAAGSGGSGIEVMYPPPYLDNEKSNGTIIHVKGKHLCPSPLFPGPSKPFWVLV
VVGGVLACYSLLVTVAFIIFWVRSKRSRLLHSDYMNMTPRRPGPTRKHYQPYAPPRDFAAYRSKKVAKKPTNKAPHPK
QEPQEINFPDDLPGSNTAAPVQETLHGCQPVTQEDGKESRISVQERQ          SEQ ID NO: 166

FIG. 9

Anti-pembro CoStAR Sequence ("Universal CoStAR"), lacking the optional signal domain
ELVMTQTPSSVSAAVGGTVTITC<u>QASQSLSNLLA</u>WYQQKPGQPPKLLIY<u>GASNLES</u>GVPSRFRGSGSGTDFTLTISGMK
AEDAATYYC<u>QGGHYSGLT</u>FGNGTNVEIKGGGGSGGGGSGGGGSQSLEESGGRLVTPGTPLTLTCTVSGFSLS<u>TNDMN</u>
WVRQAPGKGLEWIG<u>VIYSDDTPDYATWAKG</u>RFTISRTSTTVDLKITSPTTEDTATYFCAR<u>GHYDSAVYAYALNI</u>WGPGT
LVTVSSAAAGSGGSGIEVMYPPPYLDNEKSNGTIIHVKGKHLCPSPLFPGPSKPFWVLVVVGGVLACYSLLVTVAFIIFWV
RSKRSRLLHSDYMNMTPRRPGPTRKHYQPYAPPRDFAAYRSKKVAKKPTNKAPHPKQEPQEINFPDDLPGSNTAAPV
QETLHGCQPVTQEDGKESRISVQERQ          SEQ ID NO: 167

FIG. 10

| | | |
|---|---|---|
| SEQ ID NO: 166 | MALPVTALLLPLALLLHAARPE----------LVMTQTPSSVSAAVGGTVTITCQASQSL | 50 |
| SEQ ID NO: 123 | MALPVTALLLPLALLLHAARPEQKLISEEDLELVMTQTPSSVSAAVGGTVTITCQASQSL | 60 |
| | ********************* ***************************** | |
| SEQ ID NO: 166 | SNLLAWYQQKPGQPPKLLIYGASNLESGVPSRFRGSGSGTDFTLTISGMKAEDAATYYCQ | 110 |
| SEQ ID NO: 123 | SNLLAWYQQKPGQPPKLLIYGASNLESGVPSRFRGSGSGTDFTLTISGMKAEDAATYYCQ | 120 |
| | ************************************************************ | |
| SEQ ID NO: 166 | GGHYSGLTFGNGTNVEIKGGGGSGGGGSGGGGSQSLEESGGRLVTPGTPLTLTCTVSGFS | 170 |
| SEQ ID NO: 123 | GGHYSGLTFGNGTNVEIKGGGGSGGGGSGGGGSQSLEESGGRLVTPGTPLTLTCTVSGFS | 180 |
| | ************************************************************ | |
| SEQ ID NO: 166 | LSTNDMNWVRQAPGKGLEWIGVIYSDDTPDYATWAKGRFTISRTSTTVDLKITSPTTEDT | 230 |
| SEQ ID NO: 123 | LSTNDMNWVRQAPGKGLEWIGVIYSDDTPDYATWAKGRFTISRTSTTVDLKITSPTTEDT | 240 |
| | ************************************************************ | |
| SEQ ID NO: 166 | ATYFCARGHYDSAVYAYALNIWGPGTLVTVSSAAAGSGGSGI------------------ | 272 |
| SEQ ID NO: 123 | ATYFCARGHYDSAVYAYALNIWGPGTLVTVSSAAAGSGGSGILVKQSPMLVAYDNAVNLS | 300 |
| | ***************************************** | |
| SEQ ID NO: 166 | ------------------------------------------------------------ | 272 |
| SEQ ID NO: 123 | CKYSYNLFSREFRASLHKGLDSAVEVCVVYGNYSQQLQVYSKTGFNCDGKLGNESVTFYL | 360 |
| SEQ ID NO: 166 | ---------------EVMYPPPYLDNEKSNGTIIHVKGKHLCPSPLFPGPSKPFWVLVVV | 317 |
| SEQ ID NO: 123 | QNLYVNQTDIYFCKIEVMYPPPYLDNEKSNGTIIHVKGKHLCPSPLFPGPSKPFWVLVVV | 420 |
| | ********************************************* | |
| SEQ ID NO: 166 | GGVLACYSLLVTVAFIIFWVRSKRSRLLHSDYMNMTPRRPGPTRKHYQPYAPPRDFAAYR | 377 |
| SEQ ID NO: 123 | GGVLACYSLLVTVAFIIFWVRSKRSRLLHSDYMNMTPRRPGPTRKHYQPYAPPRDFAAYR | 480 |
| | ************************************************************ | |
| SEQ ID NO: 166 | SKKVAKKPTNKAPHPKQEPQEINFPDDLPGSNTAAPVQETLHGCQPVTQEDGKESRISVQ | 437 |
| SEQ ID NO: 123 | SKKVAKKPTNKAPHPKQEPQEINFPDDLPGSNTAAPVQETLHGCQPVTQEDGKESRISVQ | 540 |
| | ************************************************************ | |
| SEQ ID NO: 166 | ERQ | 440 |
| SEQ ID NO: 123 | ERQ | 543 |
| | *** | |

FIG. 11

CHIMERIC MOLECULES PROVIDING TARGETED COSTIMULATION FOR ADOPTIVE CELL THERAPY

CROSS-REFERENCE TO RELATED APPLICATIONS

This application is a continuation in part of PCT Patent Application Serial No. PCT/US2022/073741, filed Jul. 14, 2022, which claims priority to U.S. Provisional Application Serial No. 63/222,916, filed Jul. 16, 2021, both of which are hereby expressly incorporated by reference in its entirety.

RELATED APPLICATIONS AND INCORPORATION BY REFERENCE

Reference is made to U.S. Provisional Patent Application No. 63/222,916, filed Jul. 16, 2021, U.S. Provisional Patent Application Ser. No. 63/053,498 filed Jul. 17, 2020, U.S. Provisional Patent Application Ser. No. 63/222,916, filed Jul. 16, 2021, PCT Patent Application Serial No. PCT/US2021/042079 filed Jul. 16, 2021, and to U.S. Provisional Patent Application Ser. No. 63/345,821, filed May 25, 2022, the contents of which are incorporated herein by reference in their entireties.

Reference is made to GB patent application Serial No. 1900858.0, filed 22 Jan. 2019, U.S. patent application Ser. No. 62/951,770, filed 20 Dec. 2019, International application PCT/GB2020/050120, filed 20 Jan. 2020, and U.S. provisional patent application 63/053,494, filed Jul. 17, 2020.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

REFERENCE TO SEQUENCE LISTING

The present application is being filed along with a Sequence Listing in electronic format. The Sequence Listing is provided as a file entitled ReplacementSeqListing_INSTB006C2.xml, created on Aug. 25, 2022, which is 267,014 bytes in size. The information in the electronic format of the Sequence Listing is incorporated herein by reference in its entirety.

FIELD OF THE INVENTION

The present invention relates to a chimeric molecule useful in adoptive cell therapy (ACT), and cells comprising the same. The chimeric molecule can act as a modulator of cellular activity enhancing responses when an endogenous T-cell receptor (TCR) is engaged with its cognate antigen. The present invention also provides proteins, nucleic acids encoding the chimeric molecule and therapeutic uses thereof.

BACKGROUND OF THE INVENTION

Adoptive cell therapy (ACT) using autologous T-cells to mediate cancer regression has shown much promise in early clinical trials. Several general approaches have been taken such as the use of naturally occurring tumor reactive or tumor infiltrating lymphocytes (TILs) expanded ex vivo. Additionally, T-cells may be genetically modified to retarget them towards defined tumor antigens. This can be done via the gene transfer of peptide (p)-major histocompatibility complex (MHC) specific T-cell Receptors (TCRs) or synthetic fusions between tumor specific single chain antibody fragment (scFv) and T-cell signaling domains (e.g. CD3), the latter being termed chimeric antigen receptors (CARs).

TIL and TCR transfer has proven particularly good when targeting melanoma (Rosenberg et al. 2011; Morgan 2006), whereas CAR therapy has shown much promise in the treatment of certain B-cell malignancies (Grupp et al. 2013).

Costimulatory signals are useful to achieve robust CAR T cell expansion, function, persistence and antitumor activity. The success of CAR therapy in leukemia has been partly attributed to the incorporation of costimulatory domains (e.g. CD28 or CD137) into the CAR construct, signals from which synergize with the signal provided by CD3ζ to enhance anti-tumor activity. The basis of this observation relates to the classical signal 1/signal 2 paradigm of T-cell activation. Here signal 1, provided by the TCR complex, synergizes with signal 2 provided by costimulatory receptors such as CD28, CD137 or CD134 to permit the cells to undergo clonal expansion, IL2 production and long term survival without the activation induced cell death (AICD) associated with signal 1 alone. Furthermore the involvement of signal 2 enhances the signal generated through signal 1 allowing the cells to respond better to low avidity interactions such as those encountered during anti-tumor responses.

Targeted costimulation will have beneficial effects for non-CAR-based T-cell therapies. For example, incorporating costimulatory domains into a chimeric TCR has been shown to enhance responses of T-cells towards pMHC (Govers 2014). While tumor infiltrating lymphocytes (TILs) utilize their endogenous TCRs to mediate tumor recognition, it has not been possible to engineer the endogenous TCR. Thus TIL are subject to substantial limitations as tumor cells express very few costimulatory ligands. The ability to induce targeted costimulation of TIL, or indeed any other adoptive T-cell therapy product, would be beneficial.

Citation or identification of any document in this application is not an admission that such document is available as prior art to the present invention.

SUMMARY OF THE INVENTION

Provided herein are chimeric molecules, in particular chimeric proteins, designed to provide costimulation when the endogenous TCR is engaged with its cognate antigen. Mechanistically, the proposed constructs may be incorporated in the endogenous TCR complex. When the endogenous TCR complex machinery is engaged with their cognate antigen, the TCR receptor complex aggregates, forcing the clustering of these chimeric constructs. This clustering results in the activation of their signaling domains, causing an increase in costimulation. This costimulation manifests itself in a measurable improvement in the effector function of the recipient T cell: increased in activation markers, increase cytokine secretion (IL-2 in particular) and increased proliferation.

Some embodiments herein relate to a chimeric molecule, advantageously a chimeric protein, that provides costimulation to the T cell when the endogenous T cell receptor is engaged. This molecule may comprise a TCR clustering domain and a signaling domain that may contain a CD40 intracellular domain or signaling fragment thereof.

The TCR clustering domain may be one or more of the proteins typically found in the TCR complex, such as but not limited to, CD3D, CD3E, CD3G, CD3Z, CD3-eta and the constant chains of pre-TCR alpha (PTCRA) TCR alpha, TCR beta, TCR gamma or TCR delta.

The signaling domain may also comprise, an additional full length costimulatory domain, including but not limited to CD2, CD9, CD26, CD27, CD28, CD29, CD38, CD40, CD43, CD46, CD49d, CD55, CD73, CD81, CD82, CD99, CD100, CD134 (OX40), CD137 (41BB), CD150 (SLAM), CD270 (HVEM), CD278 (ICOS), CD357 (GITR), or EphB6.

While CD3D, CD3E, CD3G, CD3Z work alone; the constructs containing TCR constant chains (either alpha/beta or gamma/delta) are preferably co-expressed with their respective partner in bicistronic configuration: TCR alpha with TCR beta and TCR gamma with TCR delta. Therefore, TCR alpha containing constructs are advantageously co-expressed with TCR beta and vice versa; and TCR gamma containing constructs should be co-expressed with TCR delta and vice versa. In the context of TILs and any other alpha-beta T cells; the preferred configuration includes TCR gamma-delta; and in gamma-delta T cells, the preferred configuration includes TCR alpha-beta to minimize interference/disruption with the endogenous TCR machinery and the TCR pairing.

For CD3D, CD3E, CD3G and CD3Z, the transmembrane and extracellular portions are advantageously utilized. However, the present invention also contemplates portions or the totality of their intracellular components, which could potentially minimize the disruption of the endogenous TCR complex signaling or help to further amplify the endogenous TCR signaling.

In another aspect, the invention provides a chimeric protein comprising a clustering domain and a signaling domain that may contain a CD40 intracellular domain or signaling fragment thereof. In some embodiments, the clustering domain is capable of oligomerization and/or self assembly. In some embodiments, clustering comprises formation of a homodimer or homotrimer. In some embodiments, clustering comprises oligomerization with a different protein to form a heterodimer or heterotrimer. In some embodiments, the chimeric protein is constitutive as signaling, for example independent of receptor engagement by an extracellular ligand or independent of receptor engagement by an extracellular ligand attached to a different cell. In some embodiments, the clustering domain comprises a transmembrane domain. In some embodiments, the clustering domain comprises a transmembrane domain and further comprises activating mutations that promote dimerization or oligomerization. In some embodiments, the clustering domain comprises an extracellular domain, such as but not limited to an extracellular domain of a receptor. In some embodiments, the clustering domain comprises an extracellular domain of a receptor and further comprises activating mutations in the extracellular domain that promote dimerization or oligomerization. In some embodiments, the clustering domain comprises a leucine zipper. In some embodiments, the leucine zipper comprises or constitutes a transmembrane domain. In some embodiments, the leucine zipper comprises or constitutes a soluble domain. Non-limiting examples of clustering domains include clustering domains of the thrombopoietin receptor (TpoR), erythropoietin receptor (EpoR), growth hormone receptor (GHR), glycophorin A (GPA) transmembrane domain, and activating mutants thereof. In some embodiments, clustering may be modulated by a small molecule. In some embodiments, clustering may be modulated by post-translational modifications.

In another aspect, the invention provides a chimeric protein which comprises an extracellular ligand binding domain linked to an intracellular signaling domain by a transmembrane domain. In some embodiments, the extracellular ligand binding domain is selected or engineered to bind to an extracellular ligand that maintains two or more copies of the chimeric protein in proximity to one another such that the signaling domain is activated. The extracellular ligand binding domain is considered one part of a specific binding pair (sbp) and the extracellular ligand is the second part of the specific binding pair. In some embodiments, one member of the sbp comprises a protein or receptor or extracellular portion thereof and the second sbp comprises a binding protein specific for the first member of the sbp. In some embodiments, the extracellular sbp is bivalent. In some embodiments, the extracellular sbp is trivalent. Non-limiting examples of extracellular ligands include antibodies and bivalent antigen binding fragments thereof. Non-limiting examples of extracellular ligand binding domains of chimeric proteins of the invention (i.e., sbp members) include, without limitation, NKG2A, CD27, CD137, GITR, PD-1, PD-L1, FasL, OX40, CTLA4, ICOS, CD40, EGFR, HER2 and extracellular portions thereof. Complementary sbp members include, without limitation, pembrolizumab for PD1, trastuzumab for HER2, cetuximab for EGFR, tremelimumab for CTLA4, varlilumab for CD27, and urelumab for CD137. In some embodiments, the intracellular signaling domain comprises a CD40 intracellular domain or signaling fragment thereof.

In some embodiments, the CD40 signaling domain comprises SEQ ID NO:154, SEQ ID NO:155, or SEQ ID NO:156. In some embodiments, the CD40 signaling fragment comprises, consists, or consists essentially of an SH3 motif (KPTNKAPH, PTNKAPHP or PTNKAPH), TRAF2 motif (PKQE, PKQET, PVQE, PVQET, SVQE, SVQET), TRAF6 motif (QEPQEINFP or QEPQEINFP), PKA motif (KKPTNKA, SRISVQE, or a combination thereof, or is a full length CD40 intracellular domain. In some embodiments, one or more of the SH3, TRAF2, TRAF6, or PKA motifs of the CD40 signaling domain is mutated. In some embodiments, one or more of the SH3, TRAF2, TRAF6, or PKA motifs of the CD40 signaling domain is present in multiple copies.

Disclosed in this application is an engineered protein. In some embodiments, the engineered protein has at least 80%, 85%, 90%, 95%, 96%, 97%, 98%, 99%, 100%, or any integer that is between 80 and 100%, identity to SEQ ID NO: 166, wherein the sequence is not SEQ ID NO: 123.

In some embodiments, the engineered protein has at least 80%, 85%, 90%, 95%, 96%, 97%, 98%, 99%, 100%, or any integer that is between 80 and 100%, identity to SEQ ID NO: 167, wherein the sequence is not SEQ ID NO: 123.

In some embodiments, the engineered protein further comprises a binding domain, CD28 domain, and CD40 domain. In some embodiments, the engineered protein further comprises a signal peptide sequence. In some embodiments, the signal peptide sequence has at least 80%, 85%, 90%, 95%, 96%, 97%, 98%, 99%, 100%, or any integer that is between 80 and 100%, identity to the amino acid sequence of SEQ ID NO: 157. In some embodiments, the binding domain comprises a VL sequence, a VH sequence, and an at least one linker. In some embodiments, the at least one linker has at least 80%, 85%, 90%, 95%, 96%, 97%, 98%, 99%, 100%, or any integer that is between 80 and 100%, identity to the amino acid sequence of SEQ ID NO: 159 or 161. In some embodiments, the binding domain comprises two linker sequences. In some embodiments, the two linker sequences have at least 80%, 85%, 90%, 95%, 96%, 97%, 98%, 99%, 100%, or any integer that is between 80 and 100%, identity to amino acid sequences SEQ ID NO: 159 and SEQ ID NO: 161, respectively. In some embodiments, the VL sequence has at least 80%, 85%, 90%, 95%, 96%, 97%, 98%, 99%, 100%, or any integer that is between 80 and 100%, identity to the amino acid sequence of SEQ ID NO: 158. In some embodiments, the VH sequence has at least 80%, 85%, 90%, 95%, 96%, 97%, 98%, 99%, 100%, or any integer that is between 80 and 100%, identity to the amino acid sequence of SEQ ID NO: 160. In some embodiments, the CD40 domain has at least 80%, 85%, 90%, 95%, 96%, 97%, 98%, 99%, 100%, or any integer that is between 80 and 100%, identity to the amino acid sequence of SEQ ID NO: 165. In some embodiments, the CD28 domain comprises a CD28 transmembrane domain. In some embodiments, the CD28 transmembrane domain has at least 80%, 85%, 90%, 95%, 96%, 97%, 98%, 99%, 100%, or any integer that is between 80 and 100%, identity to SEQ ID NO: 163. In some embodiments, the CD28 domain comprises a CD28 extracellular domain. In some embodiments, the CD28 extracellular domain has at least 80%, 85%, 90%, 95%, 96%, 97%, 98%, 99%, 100%, or any integer that is between 80 and 100%, identity to SEQ ID NO: 162. In some embodiments, the CD28 domain comprises a CD28 intracellular domain. In some embodiments, the CD28 intracellular domain has at least 80%, 85%, 90%, 95%, 96%, 97%, 98%, 99%, 100%, or any integer that is between 80 and 100%, identity to SEQ ID NO: 164. In some embodiments, the protein further comprises 1, 2, 3, 4, 5, or all 6 CDR sequence(s) selected from the group consisting of:

QASQSLSNLLA, (SEQ ID NO: 168)

GASNLES, (SEQ ID NO: 169)

QGGHYSGL, (SEQ ID NO: 170)

TNDMN, (SEQ ID NO: 171)

VIYSDDTPDYATWAKG, (SEQ ID NO: 172)

and/or

GHYDSAVYAYALNI. (SEQ ID NO: 173)

In some embodiments, the binding domain and CD28 domain are connected by an at least one linker.

In some embodiments, an engineered protein is provided. It can comprise an amino acid sequence that is at least 80% identical to the amino acid sequence of SEQ ID NO: 166 or 167, wherein the amino acid sequence does not include at least one of:

QKLISEEDLE (SEQ ID NO: 174)

or

LVKQSPMLVAYDNAVNLSCKYSYNLFSREFRASLHKGLDSAVEVCVVYGN YSQQLQVYSKTGFNCDGKLGNESVTFYLQNLYVNQTDIYFCKI. (SEQ ID NO: 175)

In some embodiments, a CoStAR is provided. It can comprise: a) an optional signal peptide; b) a binding domain, wherein the binding domain binds to an anti-pembrolizumab antibody or binding fragment thereof; c) a CD28 domain; and d) a CD40 domain. Wherein a) is optionally linked to b), wherein b) is linked to c), wherein c) is linked to d), and wherein the CoStAR comprises an amino acid sequence that: i) lacks at least one of:

QKLISEEDLE (SEQ ID NO: 174)

or

LVKQSPMLVAYDNAVNLSCKYSYNLFSREFRASLHKGLDSAVEVCVVYGN YSQQLQVYSKTGFNCDGKLGNESVTFYLQNLYVNQTDIYFCKI; (SEQ ID NO: 175)

ii) has an amino acid sequence that is greater than 95% identical to SEQ ID NO: 166 or 167; iii) has an amino acid sequence that is greater than 80% identical to SEQ ID NO: 166 or 167 and is not SEQ ID NO: 123; or iv) any combination of i-iv.

In some embodiments, a fusion protein is provided. The fusion protein comprises a) a means for binding to an antibody that binds to pembrolizumab; b) a CD28 domain; and c) CD40 domain. Wherein a) is linked to b), wherein b) is linked to c), and wherein the fusion protein comprises an amino acid sequence that: i) lacks at least one of:

QKLISEEDLE (SEQ ID NO: 174)

or

LVKQSPMLVAYDNAVNLSCKYSYNLFSREFRASLHKGLDSAVEVCVVYGN YSQQLQVYSKTGFNCDGKLGNESVTFYLQNLYVNQTDIYFCKI; (SEQ ID NO: 175)

ii) has an amino acid sequence that is greater than 95% identical to SEQ ID NO: 166 or 167; iii) has an amino acid sequence that is greater than 80% identical to SEQ ID NO: 166 or 167 and is not SEQ ID NO: 123; or iv) any combination of i-iv.

In some embodiments, a fusion protein is provided that comprises the amino acid sequence of SEQ ID NO: 166.

In some embodiments, a fusion protein is provided that comprises the amino acid sequence of SEQ ID NO: 167.

In some embodiments, a nucleic acid which encodes the protein of any one of the preceding claims.

Also disclosed herein is a nucleic acid which encodes a protein of any one of the embodiments of the present application.

Also disclosed herein is a vector which comprises a nucleic acid of any one of the embodiments of the present application.

Also disclosed herein is a cell which expresses a protein of any one of the embodiments of the present application.

Also disclosed herein is a cell which expresses at least two proteins of any one of the embodiments of the present application.

Also disclosed herein is a method of making the cell of any one of the embodiments of the present application which comprises the step of transducing or transfecting a cell with a vector of any one of the embodiments of the present application.

Also disclosed herein is a method for preparing a population of cells that express a protein of any one of the embodiments of the present application, comprising detecting expression of the protein on the surface of cells transfected or transduced with a vector according to any one of the embodiments of the present application and selecting cells which are identified as expressing the protein.

Also disclosed herein is a cell population produced by the method of any one of the methods disclosed in the present application.

Also disclosed herein is a cell population which is enriched for cell expression a protein of any one of the embodiments of the present application.

Also disclosed herein is a method for treating a disease in a subject in need thereof, which comprises the step of administering the cell of any one of the embodiments of the present application, or the cell population of any one of the embodiments of the present application, to the subject.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53 (c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

(FIG. 1A) TCR incorporated antigen agnostic receptor (TIAAR) comprises modifying components of the TCR complex and associated signaling adaptors. (FIG. 1B) A constitutive costimulatory receptor comprising transmembrane domains (TMDs) and features that enable inducible or constitutive activation. (FIG. 1C) An inducible costimulatory receptor capable of induction and activation by extracellular ligand binding.

FIG. 2—Cytokine production by TCR incorporated antigen agnostic receptor (TIAAR) transduced cells. Cytokine production (Bcl-xL, IL2, IFNg and TNFa) from genetically modified and non-transduced T cells (NTD) of two donors was determined after overnight stimulation with either Ba/F3 OKT3 targets or left unstimulated (i.e., T cells only).

FIG. 4—Cytokine production in leucine zipper based universal CoStAR (LZ) transduced cells. Cytokine production (Bcl-xL, IL2, IFNg and TNFa) from genetically modified and non-transduced T cells (NTD) of two donors was determined after overnight stimulation with either Ba/F3 OKT3 targets or left unstimulated (i.e., T cells only).

FIG. 6—Cytokine production in inducible universal CoStAR transduced cells. Cytokine production (Bcl-xL, IL2, IFNg and TNFa) from genetically modified and non-transduced T cells (NTD) of two donors was determined after overnight stimulation with either Ba/F3 OKT3 targets or left unstimulated (i.e., T cells only). The universal CoStAR is inducible by pembrolizumab.

FIG. 8A—is a schematic of a protein of some embodiments provided herein. It is a protein comprising, Universal CoStAR sequence, comprising an optional section, a binding domain, a CD28 domain, and a CD40 domain.

FIG. 8B—is a schematic of some embodiments provided herein.

FIG. 8C—outlines a set of sequences of some embodiments provided herein.

FIG. 9—depicts a sequence of an anti-pembrolizumab CoStAR Sequence ("Universal CoStAR") (SEQ ID NO: 166), containing an optional signal domain.

FIG. 10—depicts a sequence of an anti-pembrolizumab CoStAR Sequence ("Universal CoStAR") (SEQ ID NO: 166), without the optional signal domain.

FIG. 11—depicts a sequence alignment between the anti-pembrolizumab CoStAR Sequence ("Universal CoStAR") (SEQ ID NO: 166) and the vector clone pIB1102 (SEQ ID NO: 123).

(right panel) of transduction was performed with constructs CTP386.1 and CTP387.1 across a variety of TIL organ types (x-axis).

Figure 13:
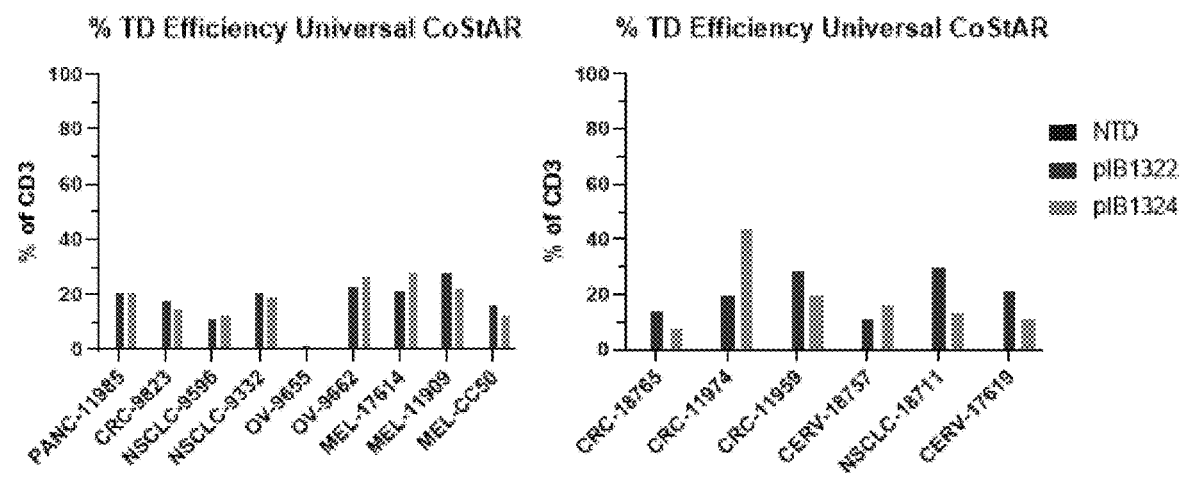

FIG. 13—depicts the transduction efficiency of constructs into TILs after 21 days. Round 1 (left panel) and Round 2 (right panel) of transduction was performed with constructs 322 and 1324 across a variety of TIL organ types (x-axis).

Figure 14:
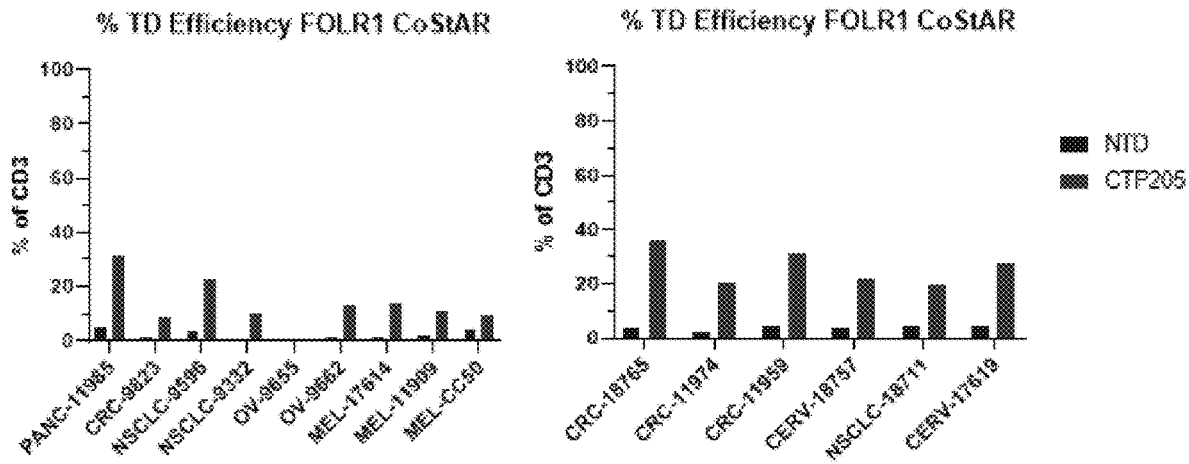

FIG. 14—depicts the transduction efficiency of constructs into TILs after 21 days. Round 1 (left panel) and Round 2 (right panel) of transduction was performed with construct CTP205 across a variety of TIL organ types (x-axis).

Figure 15A:
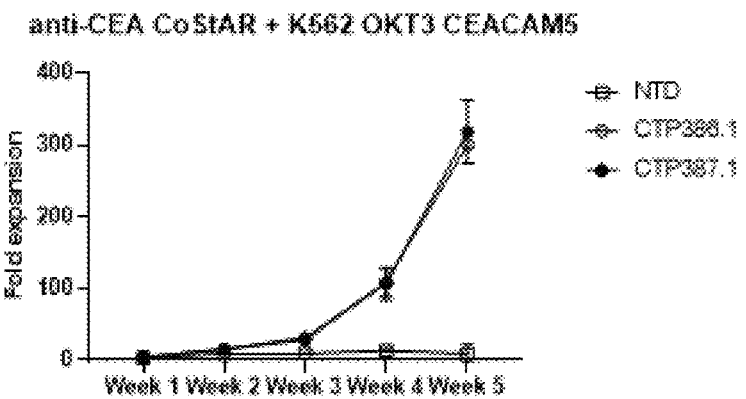
Figure 15B:
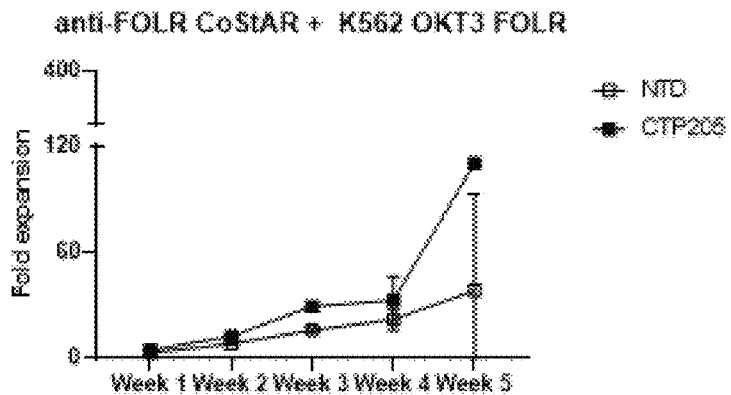
Figure 15C:
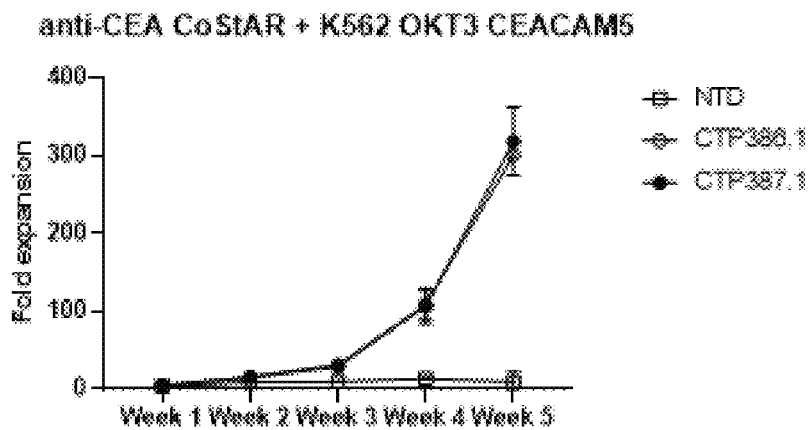
Figure 15D:
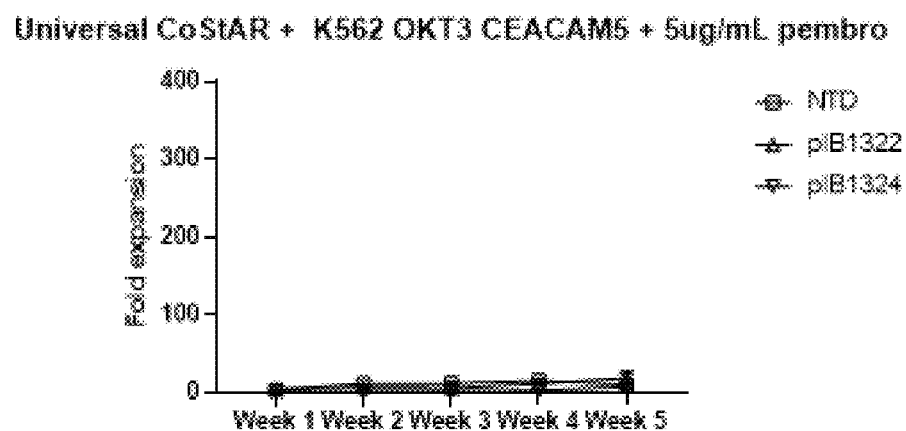
Figure 15E:

FIGS. 15A-15E— depict the fold-expansion of TILs following a serial stimulation assay. Anti-CEA or anti-FOLR modified TILs from CRC 9823 were treated every 7 days with the target K562 OKT3 CEACAM5 or OKT3 FOLR, respectively. The readout was measured using the cell count over time. Shown in panels are the fold-expansion for anti-CEA TILs with K562 OKT3 CEACAM5 exposure (FIG. 15A), anti-FOLR TILs with OKT3 FOLR exposure (FIG. 15B), a universal CoStAR with K562 OKT3 CEACAM5 exposure (FIG. 15C), a universal CoStAR with K562 OKT3 CEACAM5 exposure and 5 ug/mL pembro (FIG. 15D), and a universal CoStAR with K562 OKT3 CEACAM5 exposure and 250 ug/mL pembro (FIG. 15E).

Figure 16A:
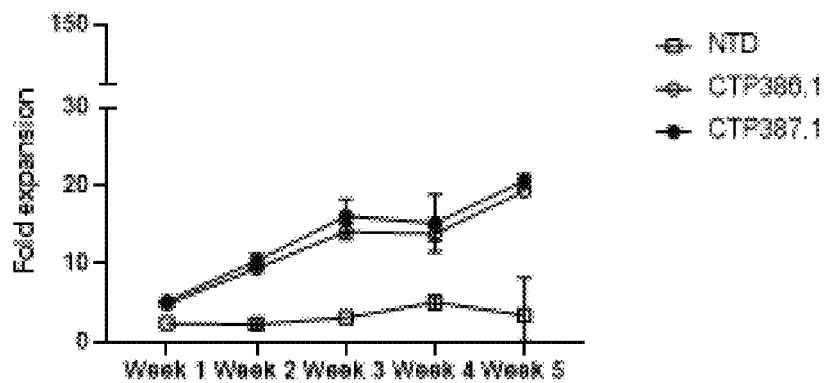
Figure 16B:
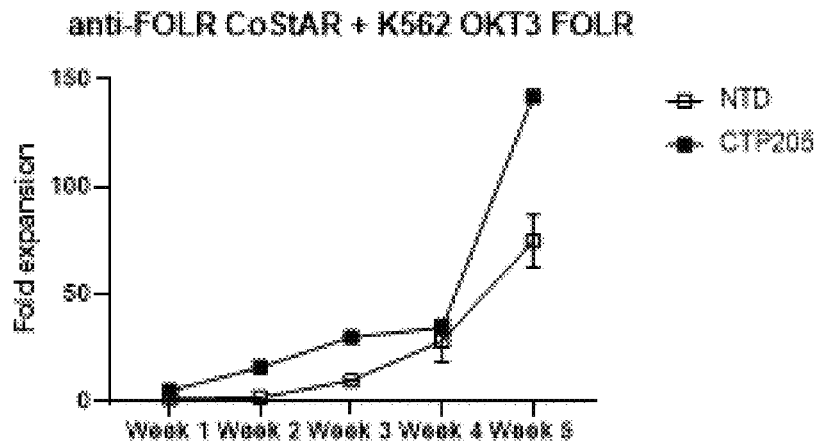
Figure 16C:
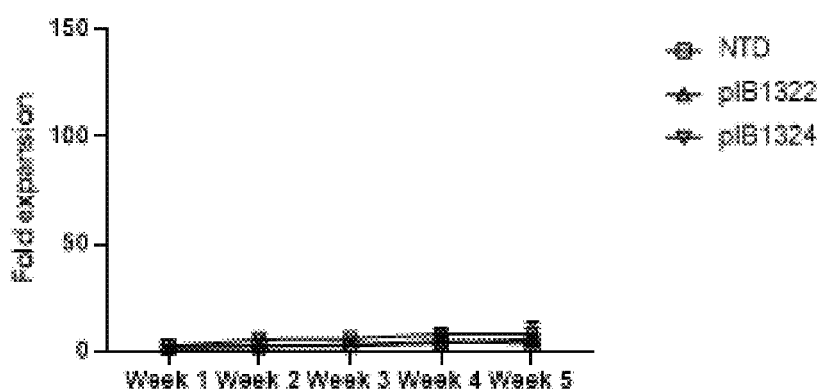
Figure 16D:
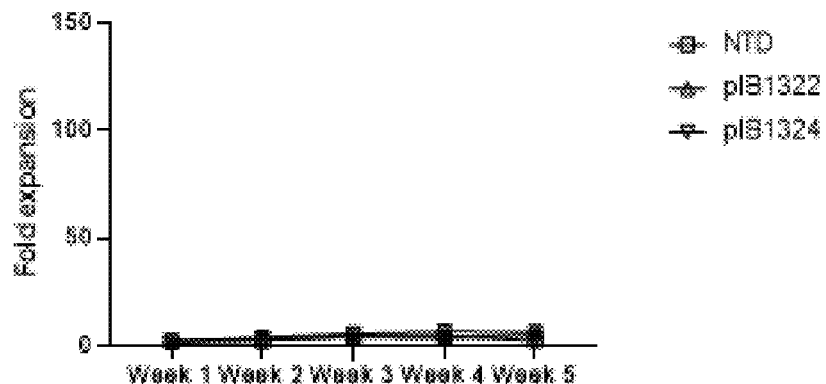
Figure 16E:
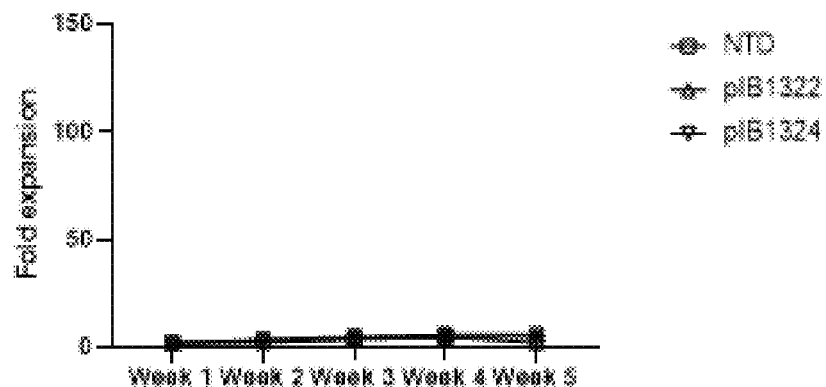

FIGS. 16A-16E— depict the fold-expansion of TILs following a serial stimulation assay. Anti-CEA or anti-FOLR modified TILs from Mel 11909 were treated every 7 days with the target K562 OKT3 CEACAM5 or OKT3 FOLR, respectively. The readout was measured using the cell count over time. Shown in panels are the fold-expansion for anti-CEA TILs with K562 OKT3 CEACAM5 exposure (FIG. 16A), anti-FOLR TILs with OKT3 FOLR exposure (FIG. 16B), a universal CoStAR with K562 OKT3 CEACAM5 exposure (FIG. 16C), a universal CoStAR with K562 OKT3 CEACAM5 exposure and 5 ug/mL pembro (FIG. 16D), and a universal CoStAR with K562 OKT3 CEACAM5 exposure and 250 ug/mL pembro (FIG. 16E).

Figure 17A:
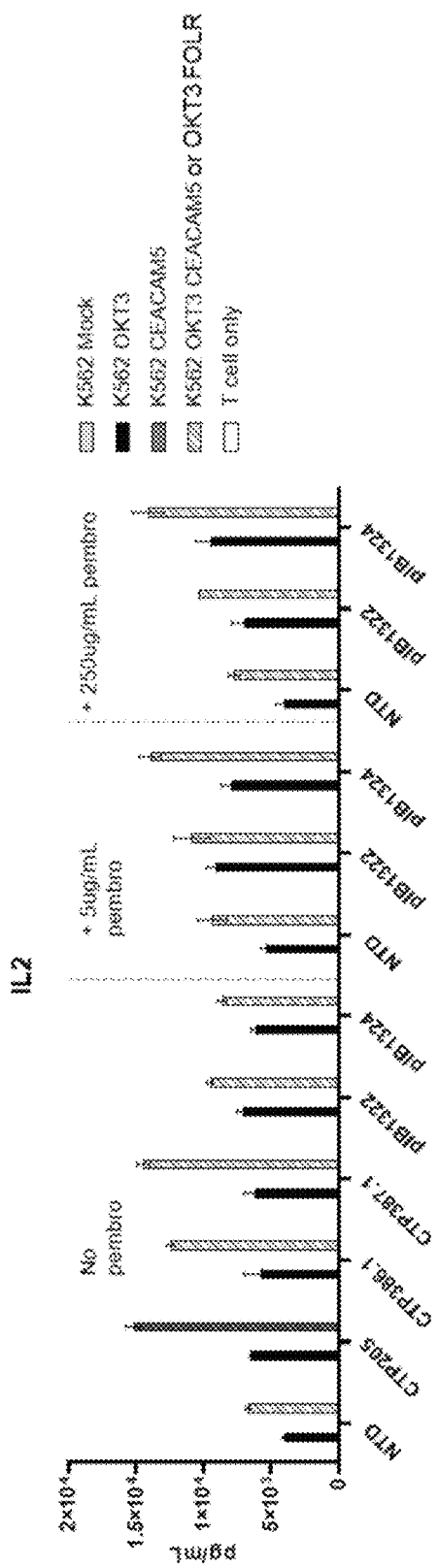
Figure 17B:
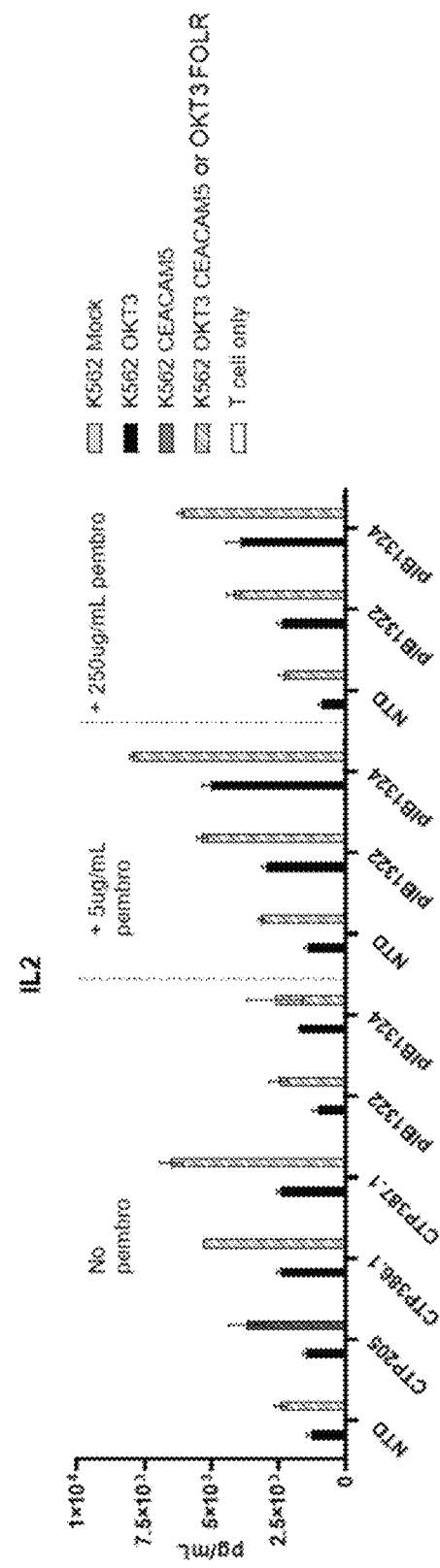

FIGS. 17A-17B— depict the increase in IL2 production (pg/mL) in anti-CEA, anti-FOLR, and Universal CoStAR modified TLS from CRC983 (FIG. 17A) or Mel 11909 (FIG. 17B).

Figure 18:
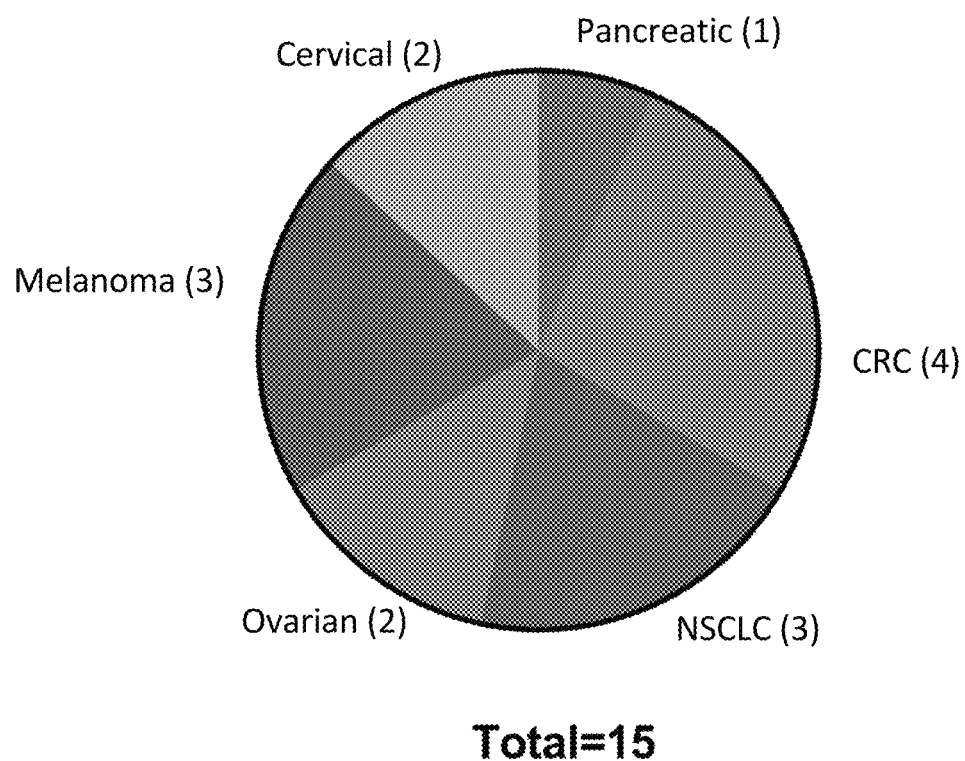

FIG. 18—depicts a pie chart of the tumor types (n=15) used as digests to generate TIL cells in Example 3.

Figure 19:
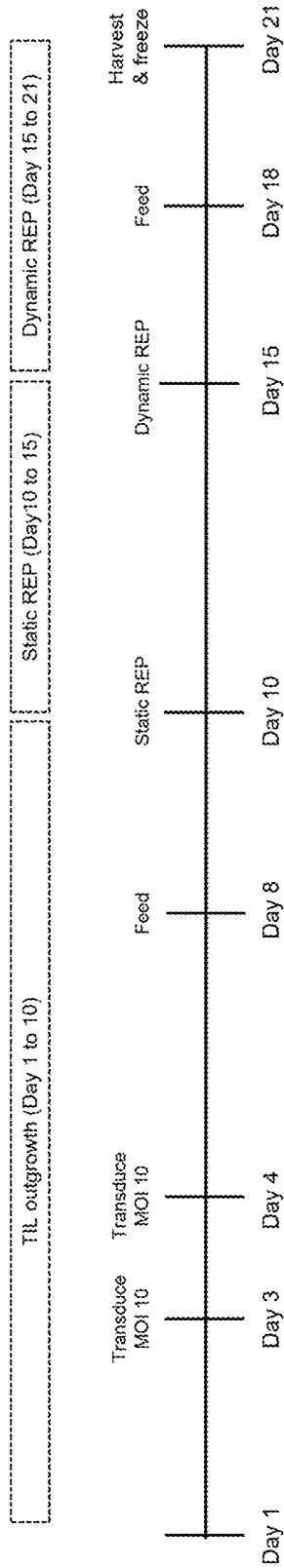

FIG. 19—depicts an example timeline for transducing CoStAR constructs into cells using the protocol outlined in Example 3.

Figure 20:
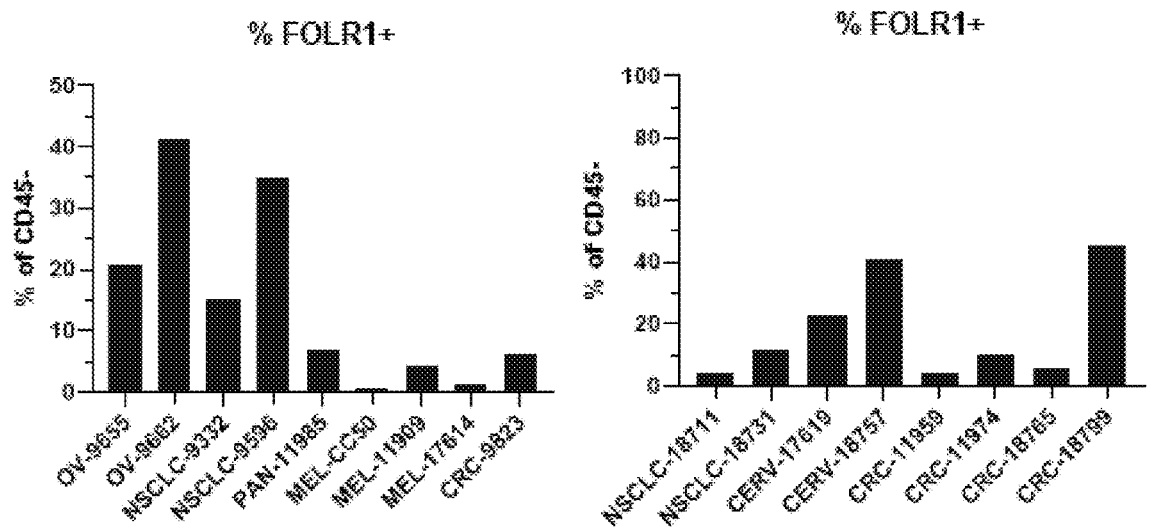

FIG. 20—depicts the transduction efficiency of constructs into TILs after 1 day. Round 1 (left panel) and Round 2 (right panel) of transduction was performed with across a variety of TIL organ types (x-axis). Plotted on the y-axis, is the percent of cells with positive expression of FOLR1 following transduction.

Figure 21:
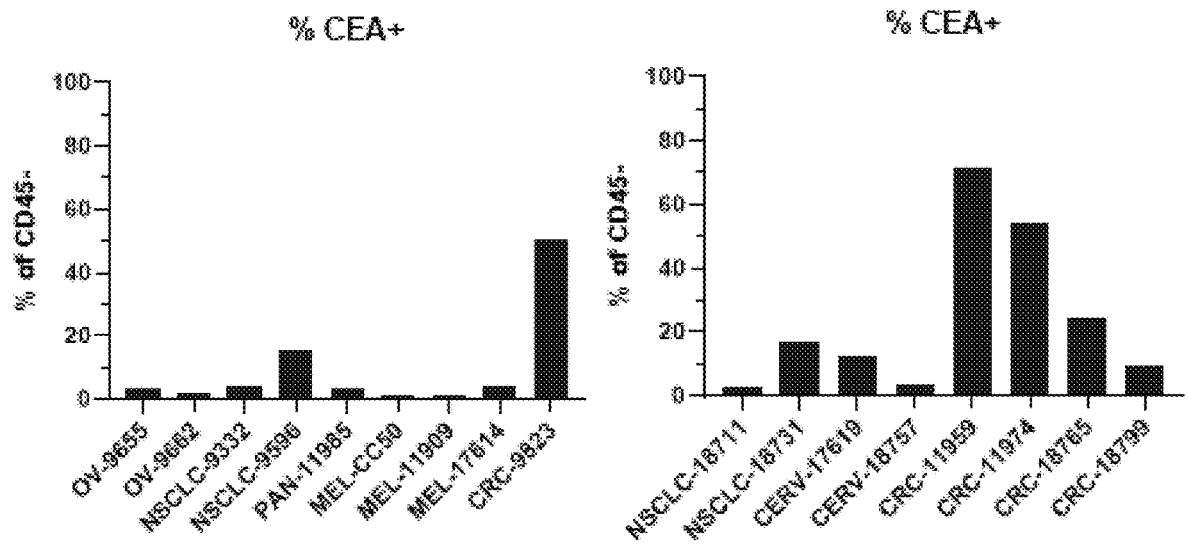

FIG. 21—depicts the transduction efficiency of constructs into TILs after 1 day. Round 1 (left panel) and Round 2 (right panel) of transduction was performed across a variety of TIL organ types (x-axis). Plotted on the y-axis, is the percent of cells with positive expression of CEA following transduction.

Figure 22:
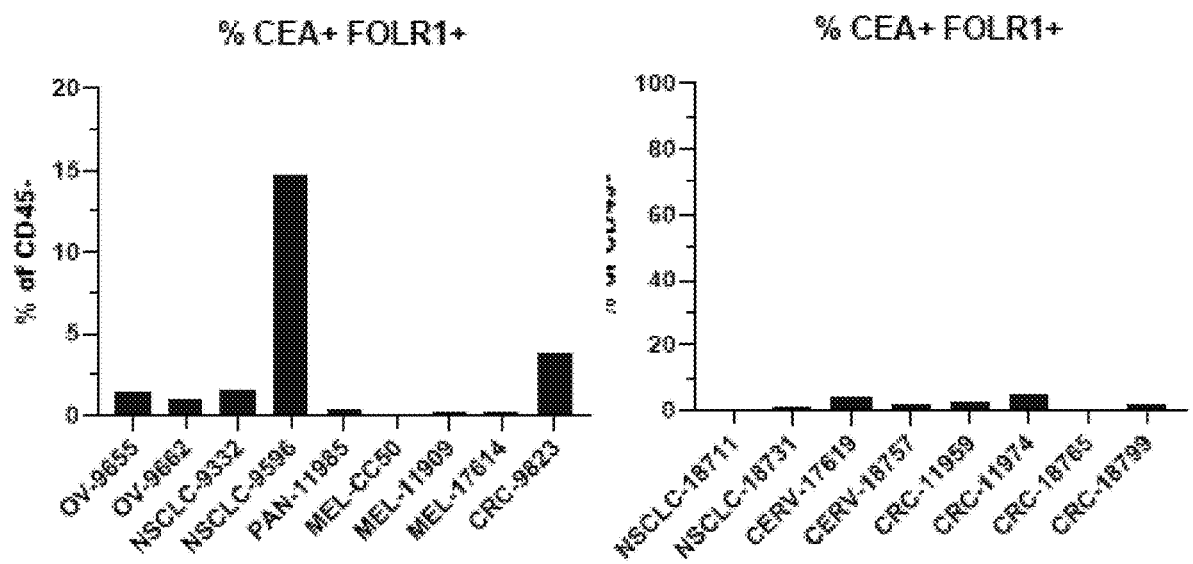

FIG. 22—depicts the transduction efficiency of constructs into TILs after 1 day. Round 1 (left panel) and Round 2 (right panel) of transduction was performed across a variety of TIL organ types (x-axis). Plotted on the y-axis, is the percent of cells with positive expression of both FOLR1 and CEA following transduction.

Figure 23:
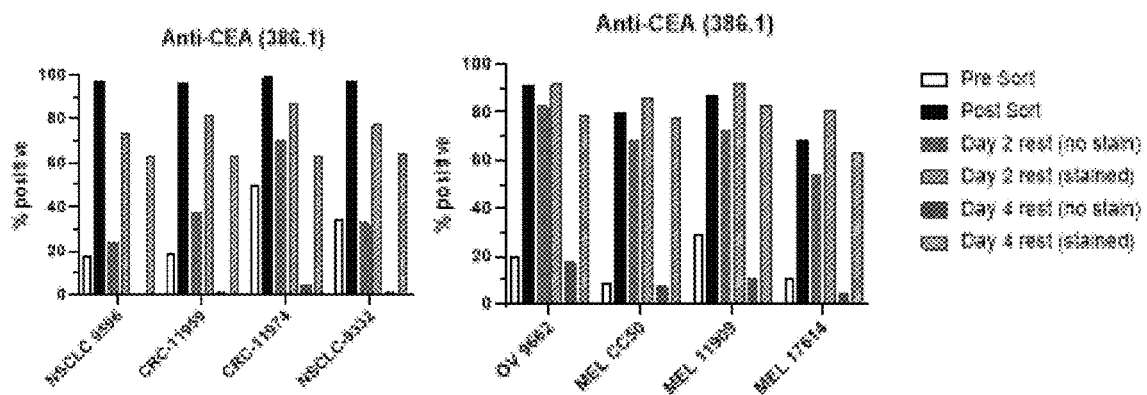

FIG. 23—depicts the round 1 (left panel) and round 2 (right panel) of Anti-CEA (386.1) cells that were percent positive for CEA expression after pre-sort, post-sort, day 2, and day 4 as outlined in Example 4.

Figure 24:
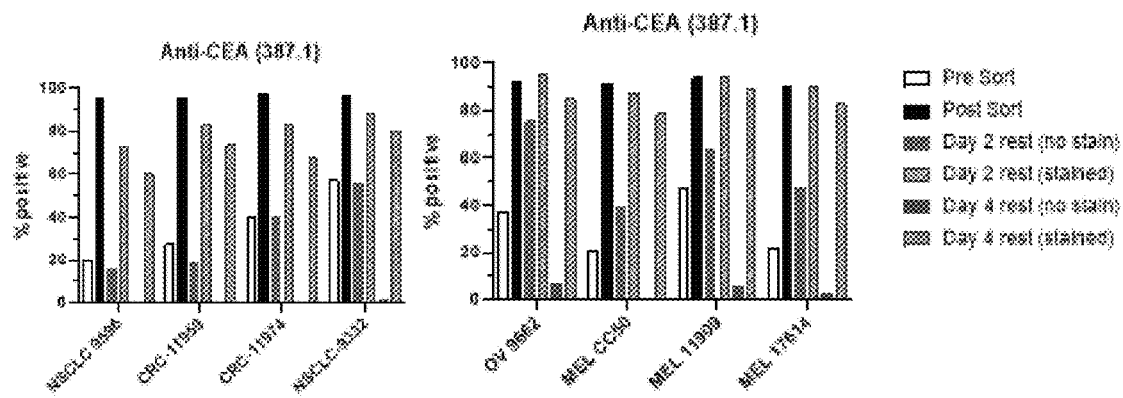

FIG. 24—depicts the round 1 (left panel) and round 2 (right panel) of Anti-CEA (387.1) cells that were percent positive for CEA expression after pre-sort, post-sort, day 2, and day 4 as outlined in Example 4.

Figure 25:
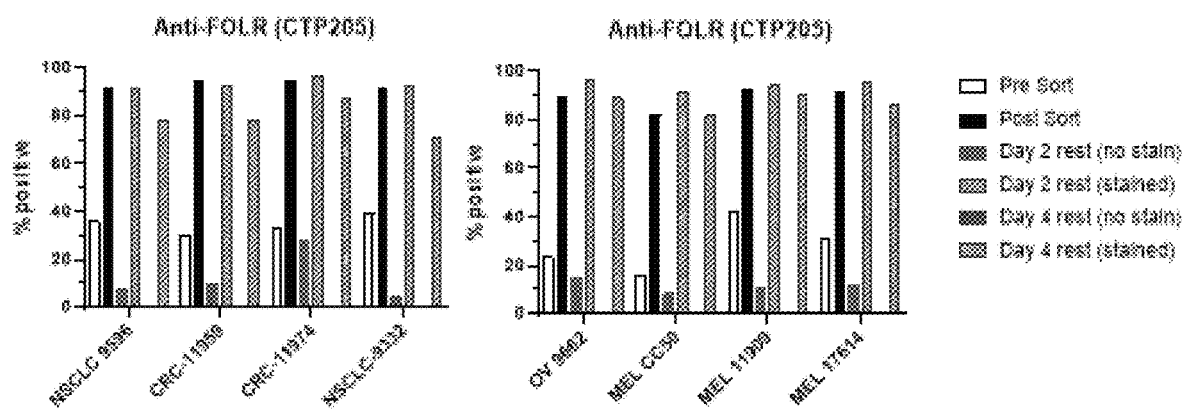

FIG. 25—depicts the round 1 (left panel) and round 2 (right panel) of Anti-FOLR cells that were percent positive for FOLR expression after pre-sort, post-sort, day 2, and day 4 as outlined in Example 4.

Figure 26:
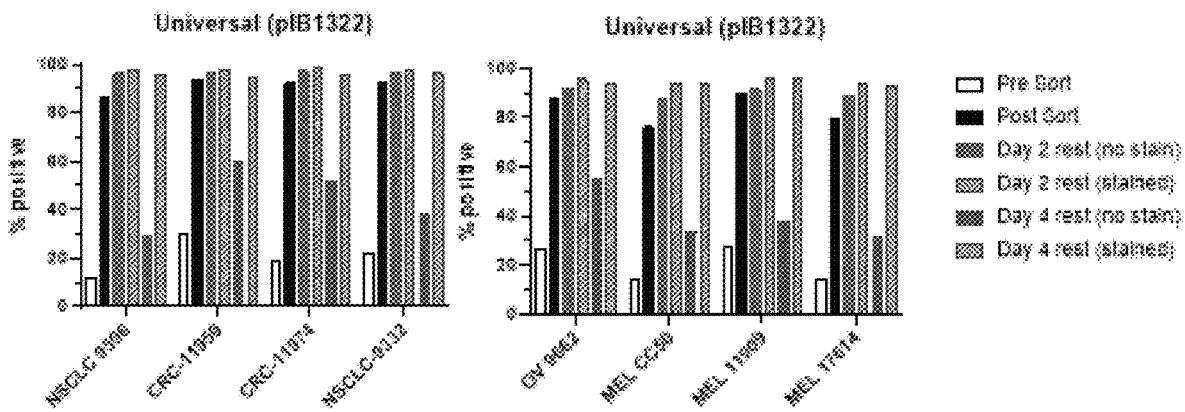

FIG. 26—depicts the round 1 (left panel) and round 2 (right panel) of Universal CoStAR (pIB1322) cells that were percent positive for both FOLR and CEA after pre-sort, post-sort, day 2, and day 4 as outlined in Example 4.

Figure 27:
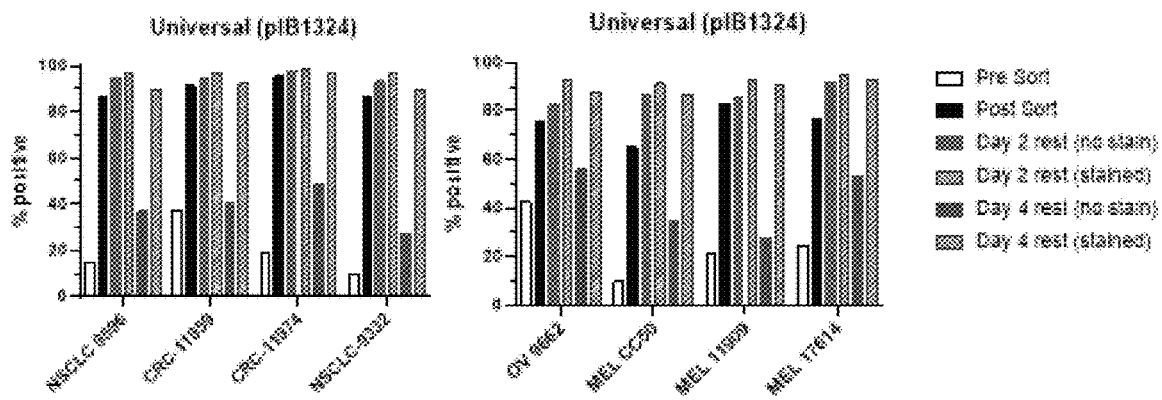

FIG. 27—depicts the round 1 (left panel) and round 2 (right panel) of Universal CoStAR (pIB1324) cells that were percent positive for both FOLR and CEA after pre-sort, post-sort, day 2, and day 4 as outlined in Example 4.

Figure 28A:
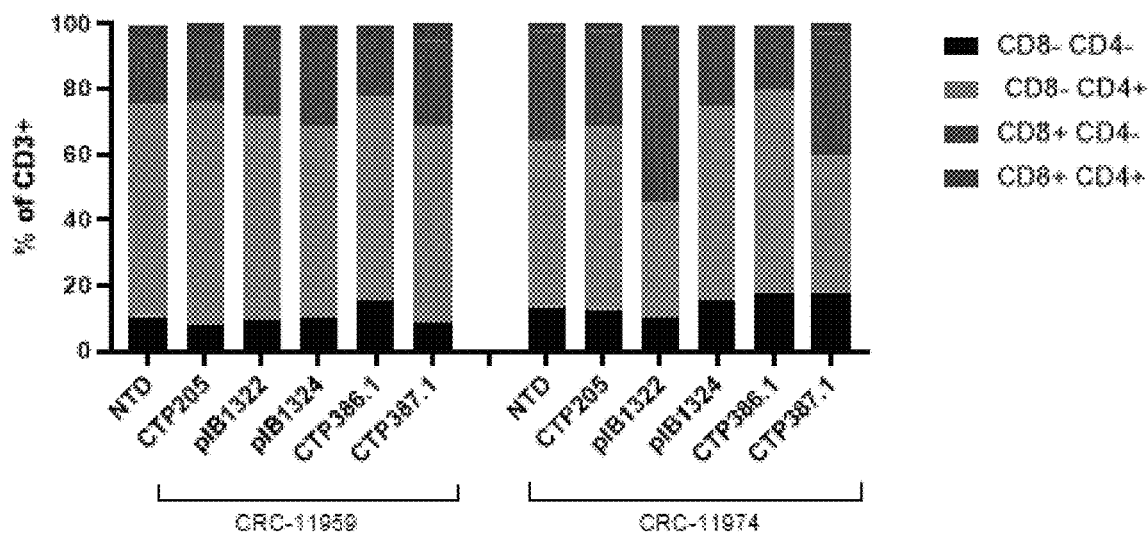
Figure 28B:
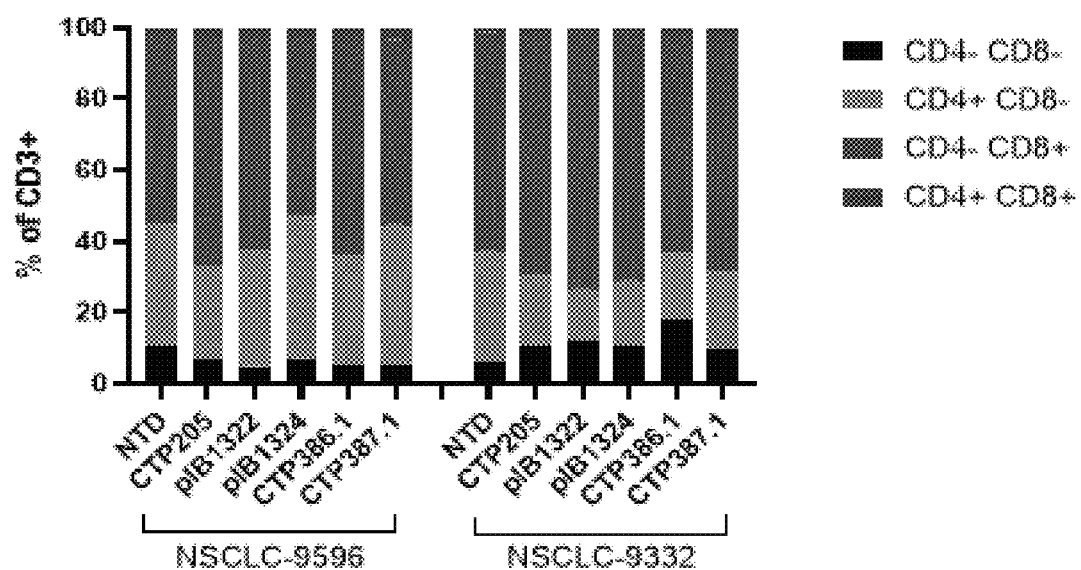
Figure 28C:
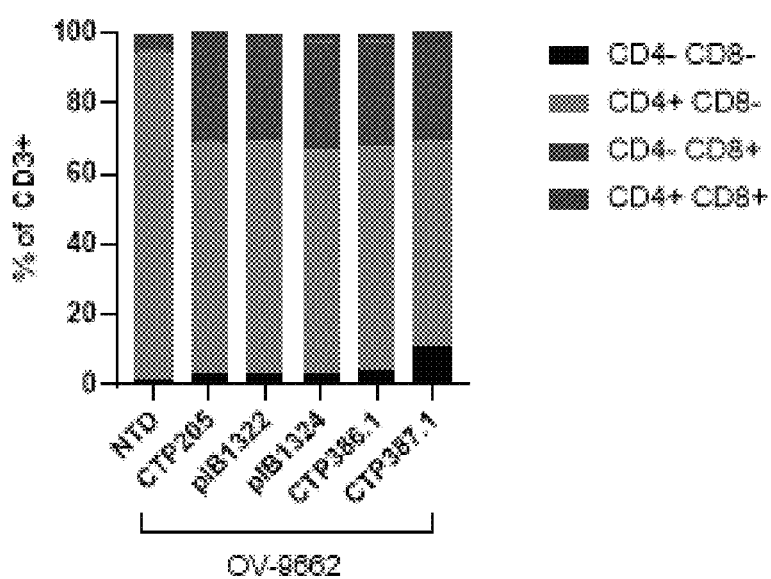
Figure 28D:
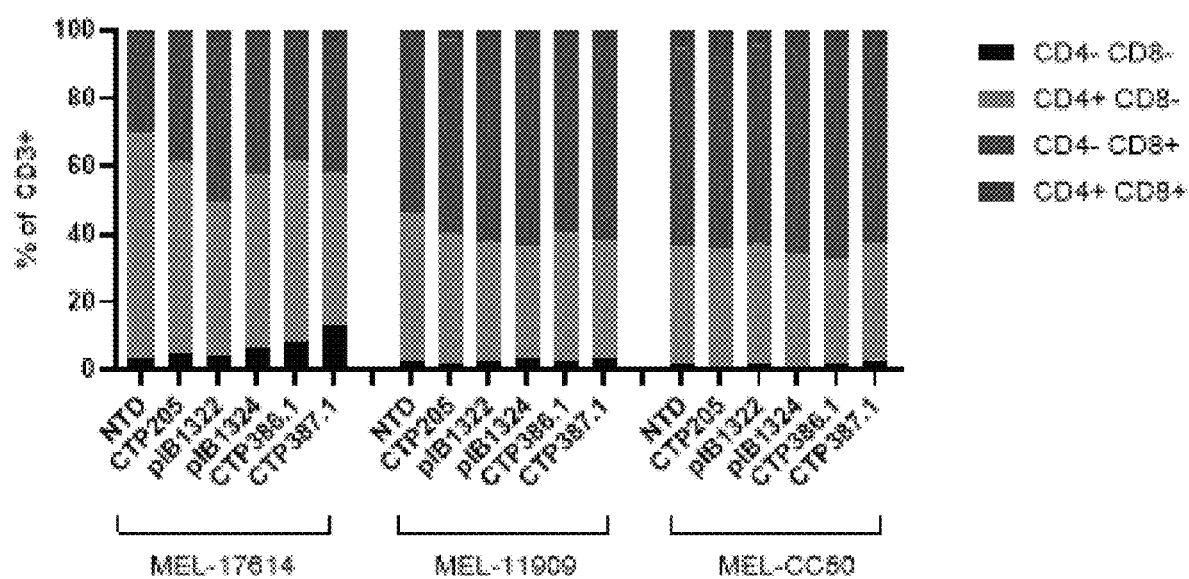

FIGS. 28A-28D— depict the ratio of CD4 to CD8 positive TIL cells of those enriched for FOLR and/or CEA expression after 21 days. FIG. 28A depicts the ratio in CRC cells, FIG. 28B depicts the ratio in NSCLC cells, FIG. 28C depicts the ratio in ovarian cells, and FIG. 28D depicts the ratio in melanoma cells.

Figure 29:
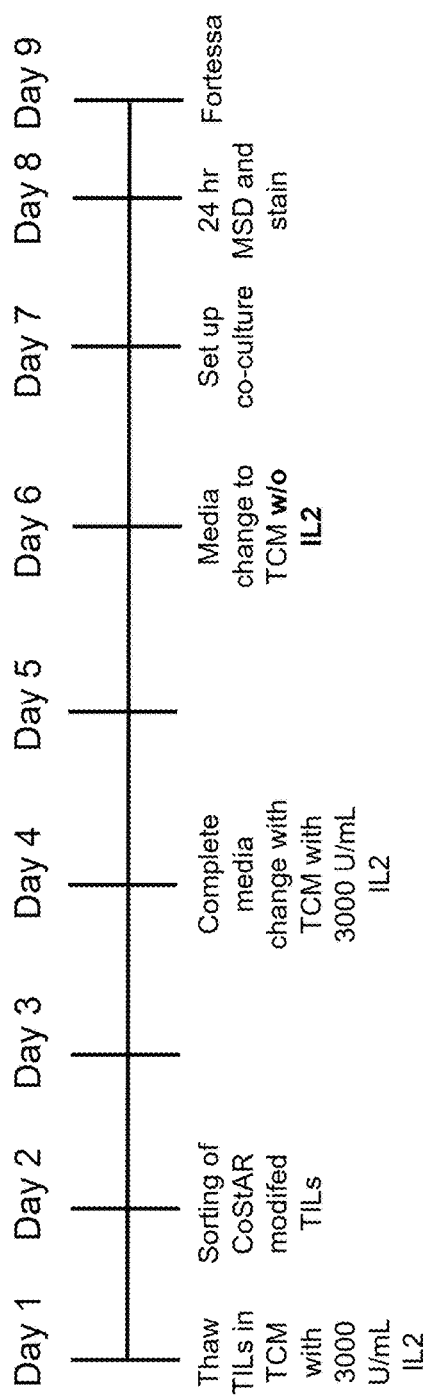

FIG. 29—depicts an example timeline for sorting TIL cells and testing for function, using the protocol outlined in Example 4.

Figure 30A:
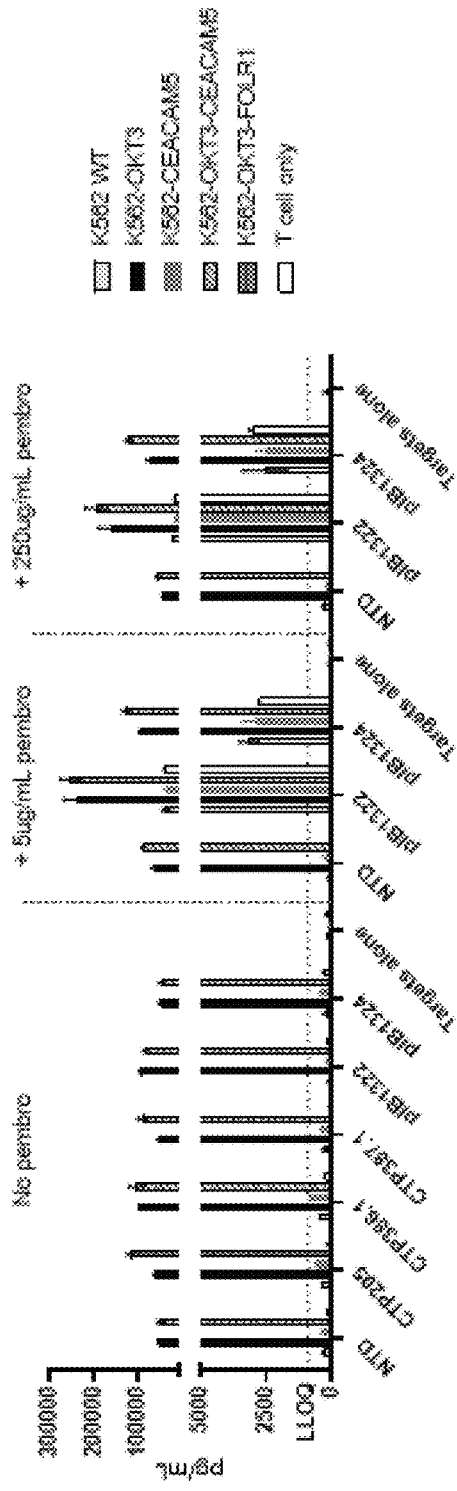
Figure 30B:
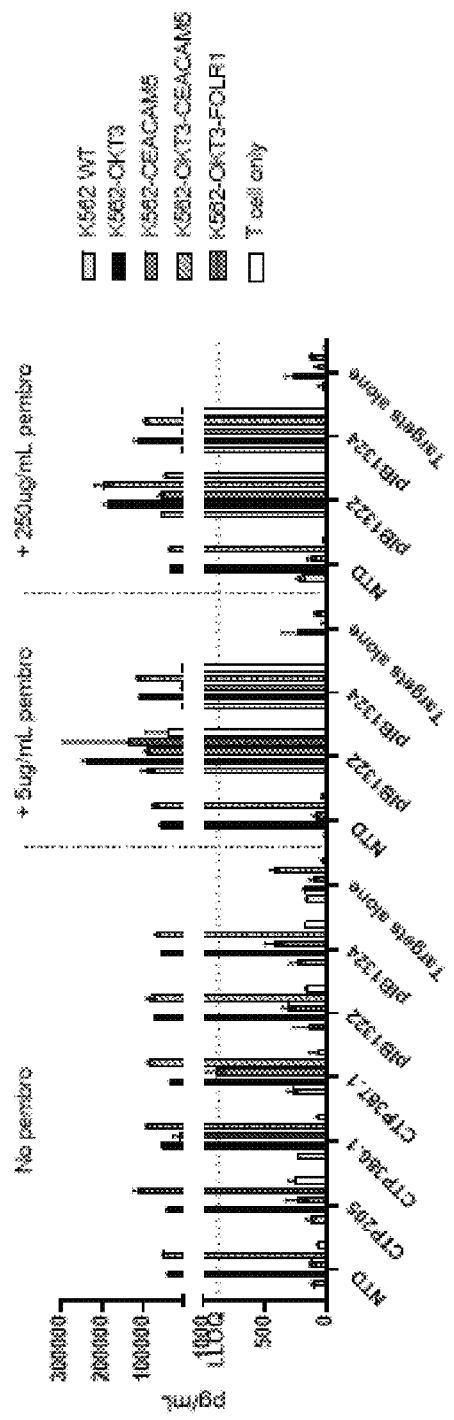
Figure 30C:
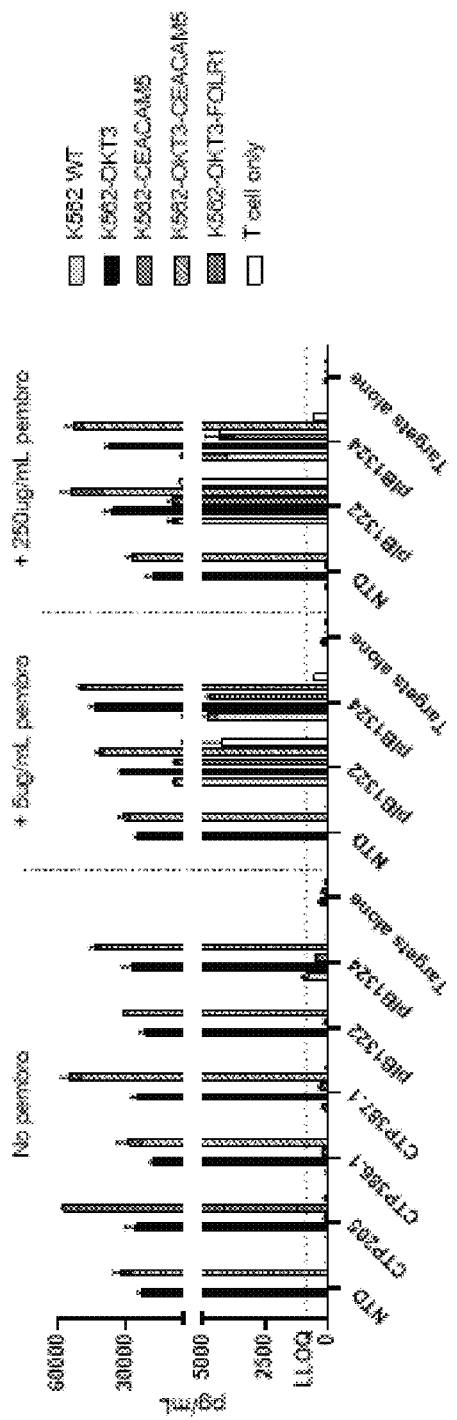
Figure 30D:
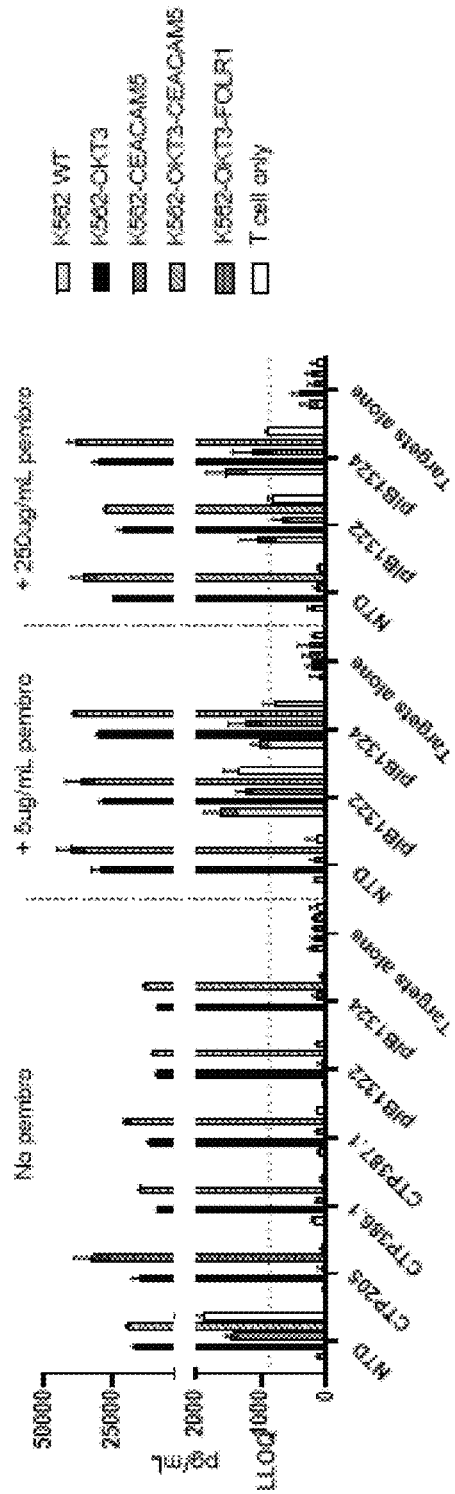
Figure 30E:
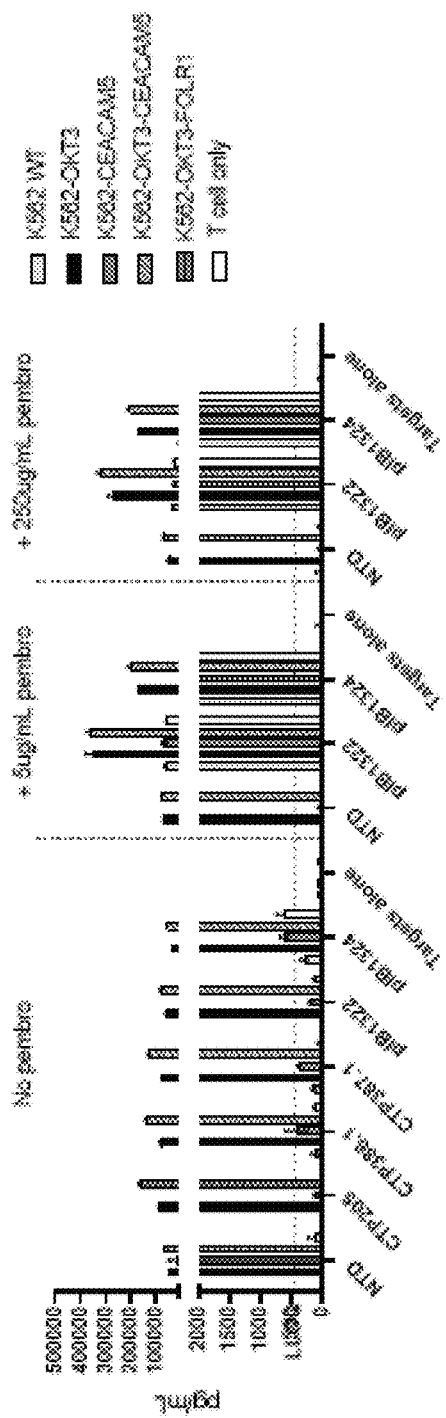
Figure 30F:
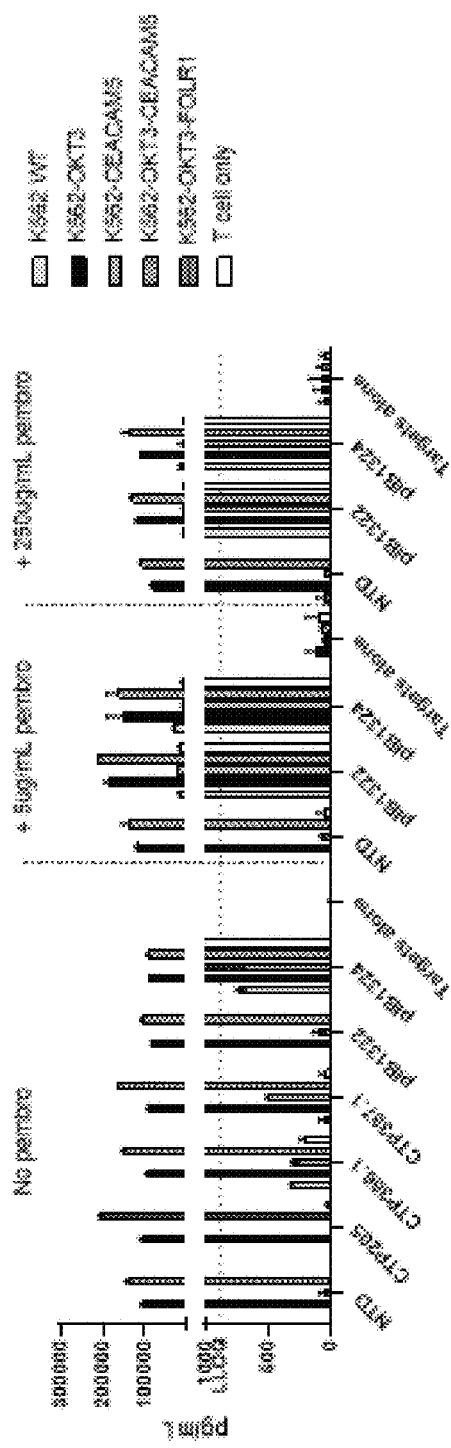
Figure 30G:
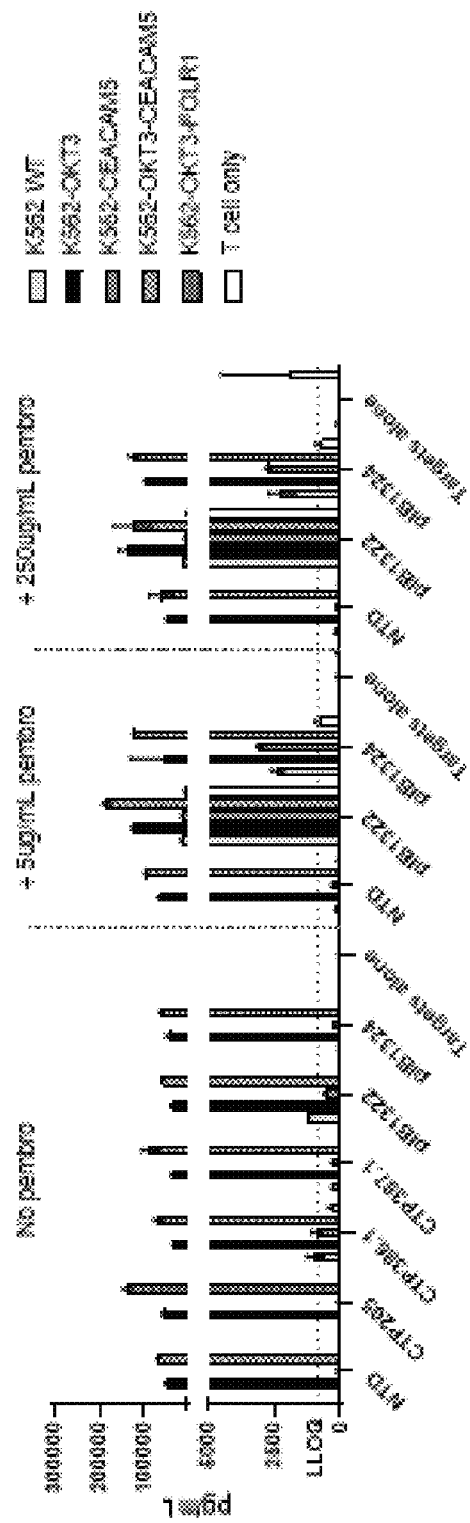
Figure 30H:
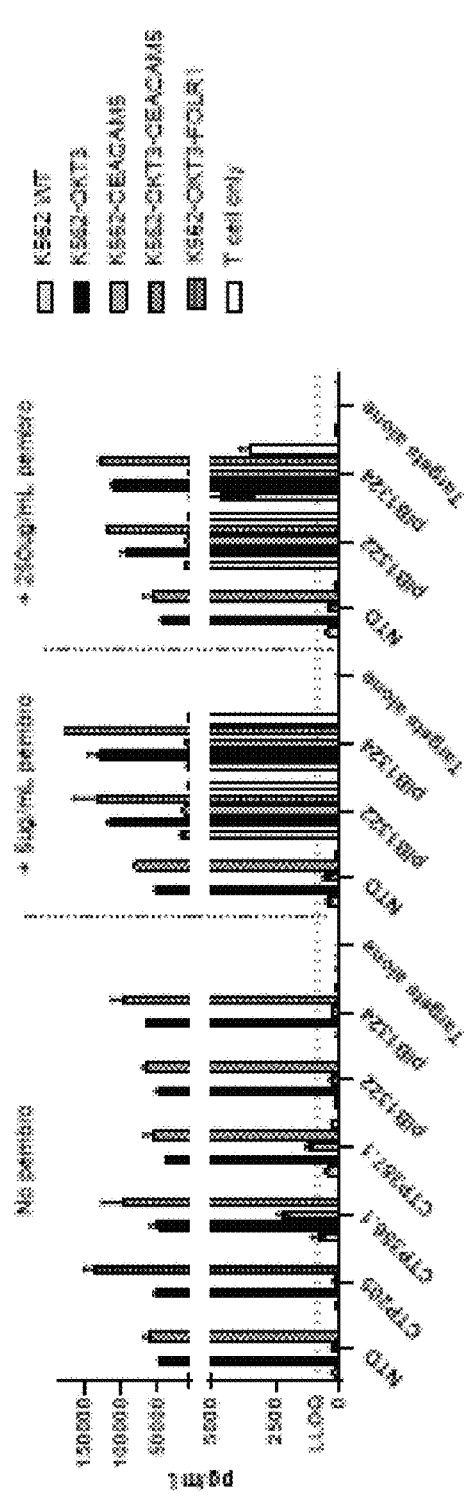

FIG. 30A-30H—depicts the increase in IFNg production (pg/mL) in TIL and K562 cells lines following co-culturing, across the cell types CRC-11974 (FIG. 30A), CRC-11959 (FIG. 30B), NSCLC-9332 (FIG. 30C), NSCLC-9596 (FIG. 30D), Ovarian cells (FIG. 30E), Melanoma-CC60 (FIG. 30F), Melanoma-11909 (FIG. 30G), and Melanoma-17614 (FIG. 30H).

Figure 31A:
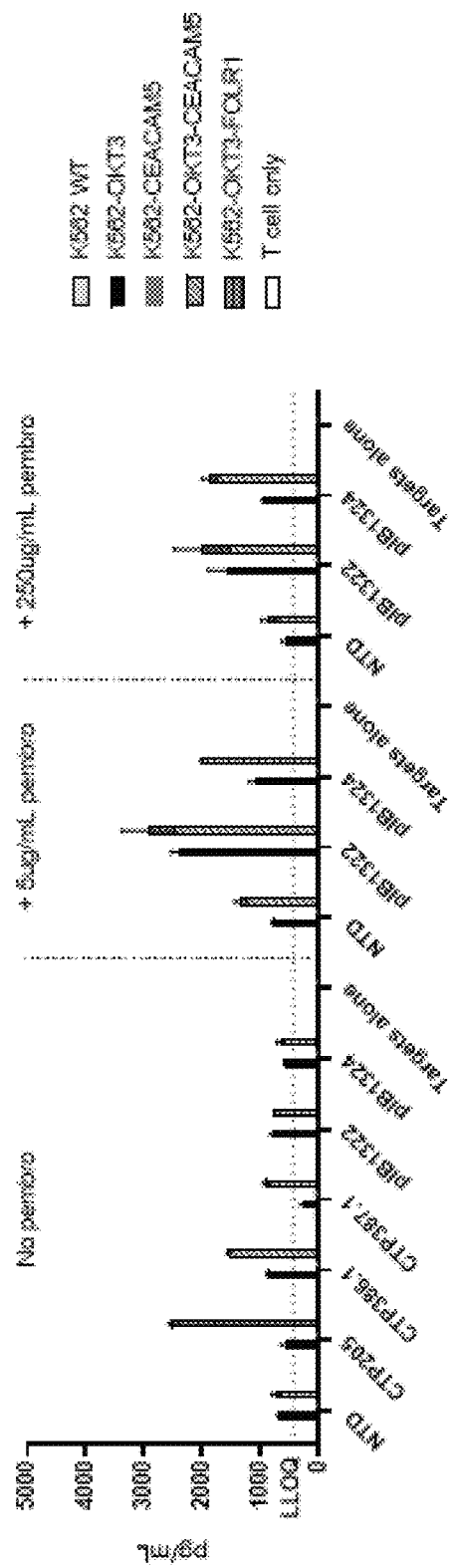
Figure 31B:
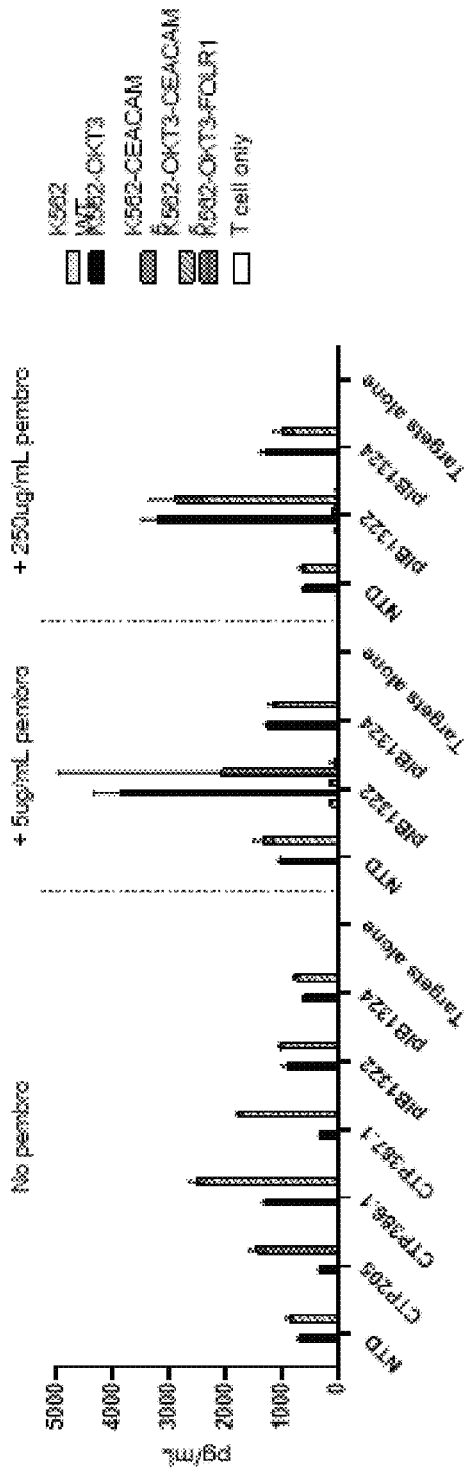
Figure 31C:
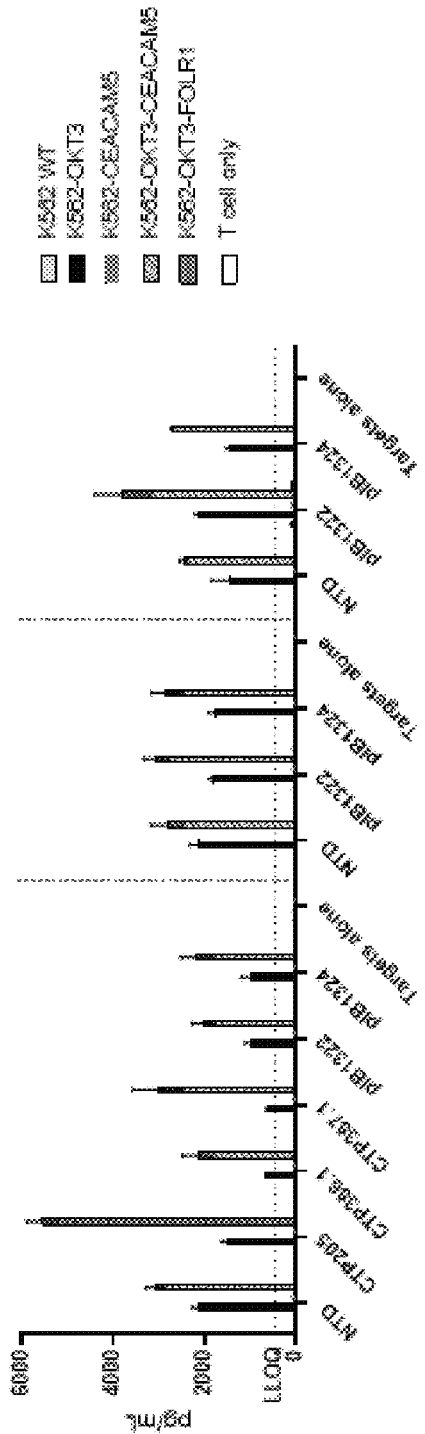
Figure 31D:
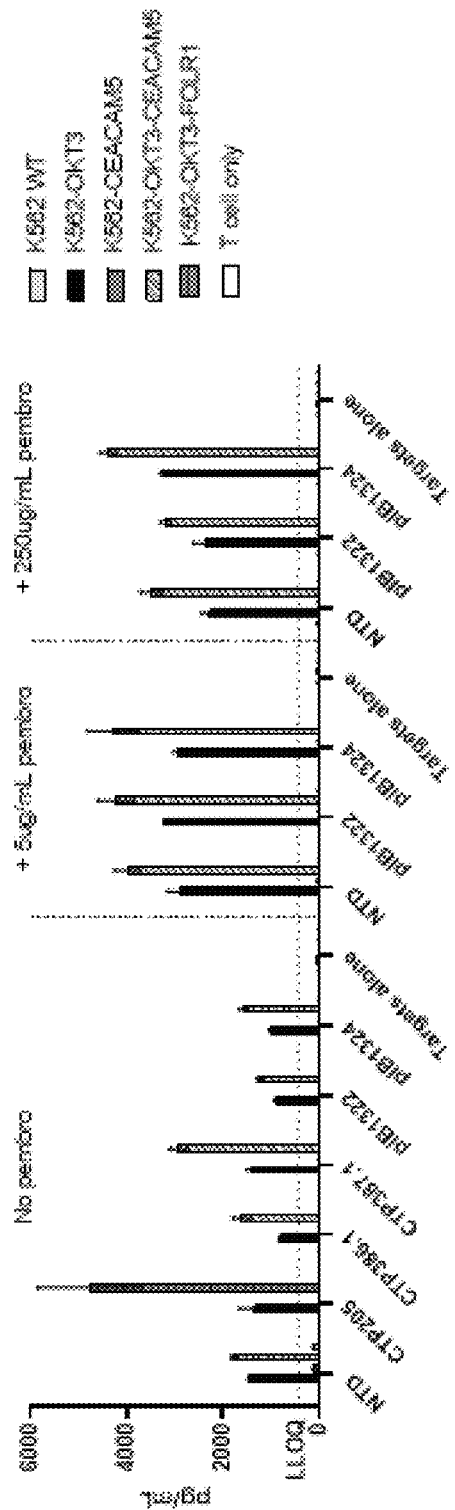
Figure 31E:
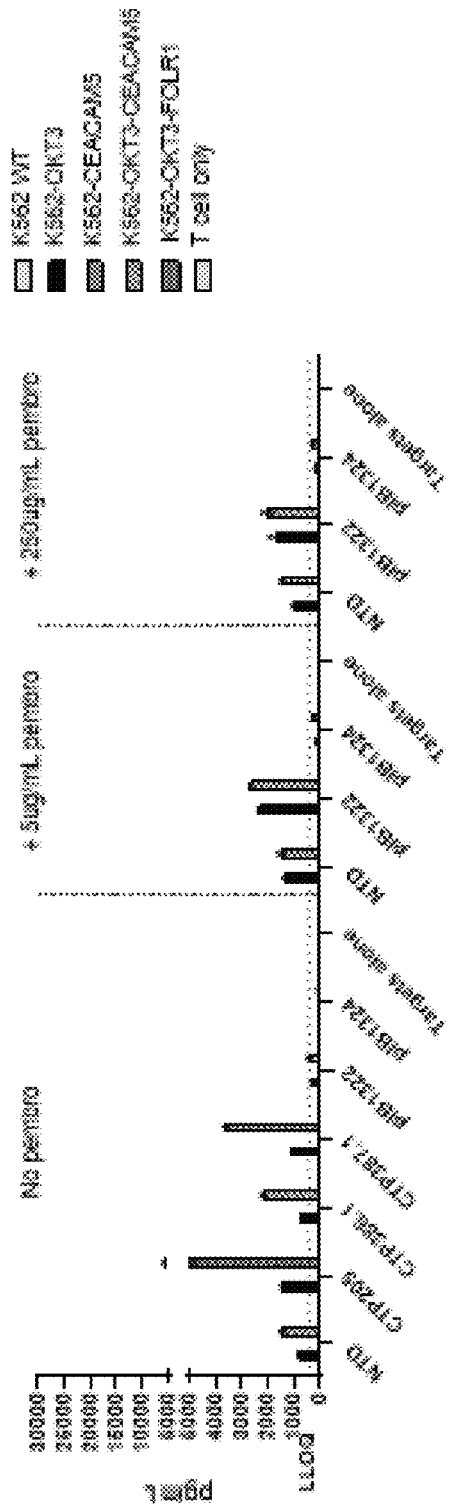
Figure 31F:
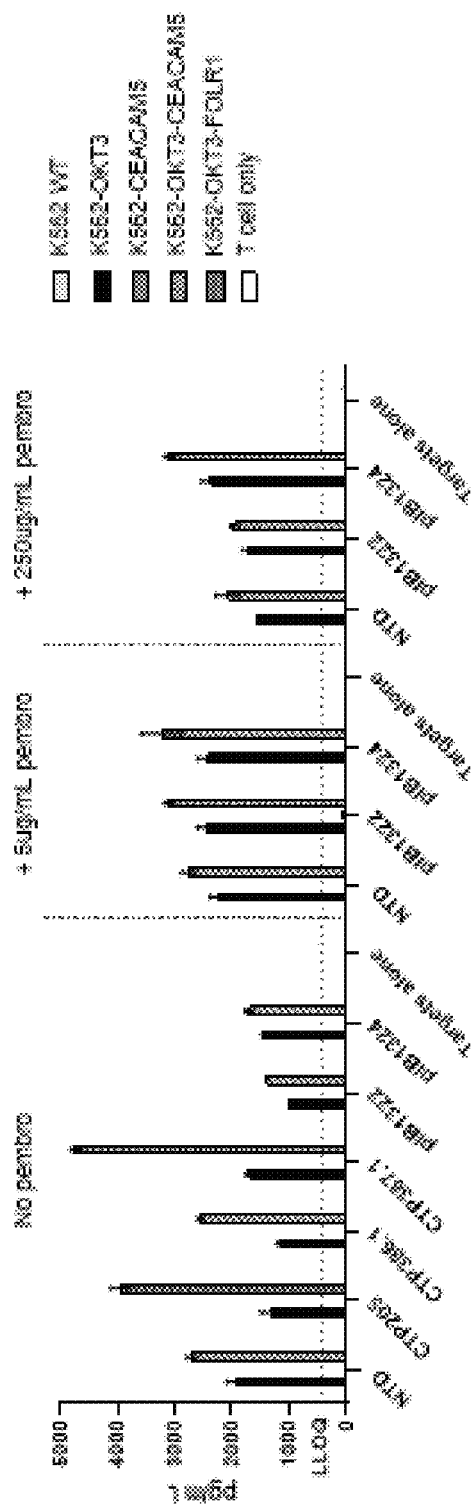
Figure 31G:
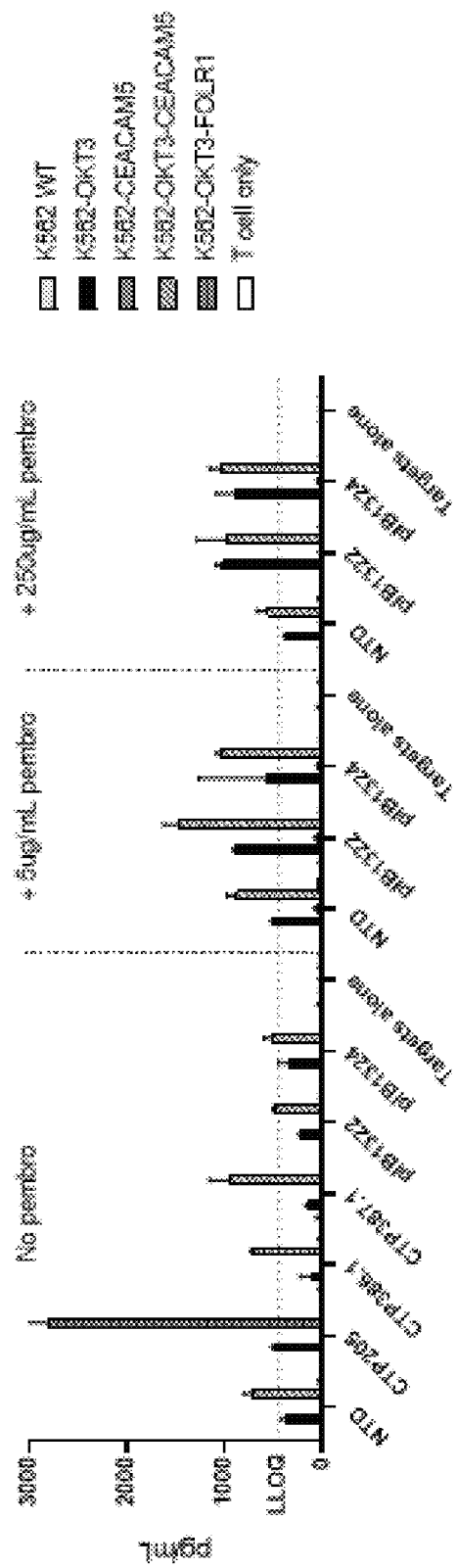
Figure 31H:
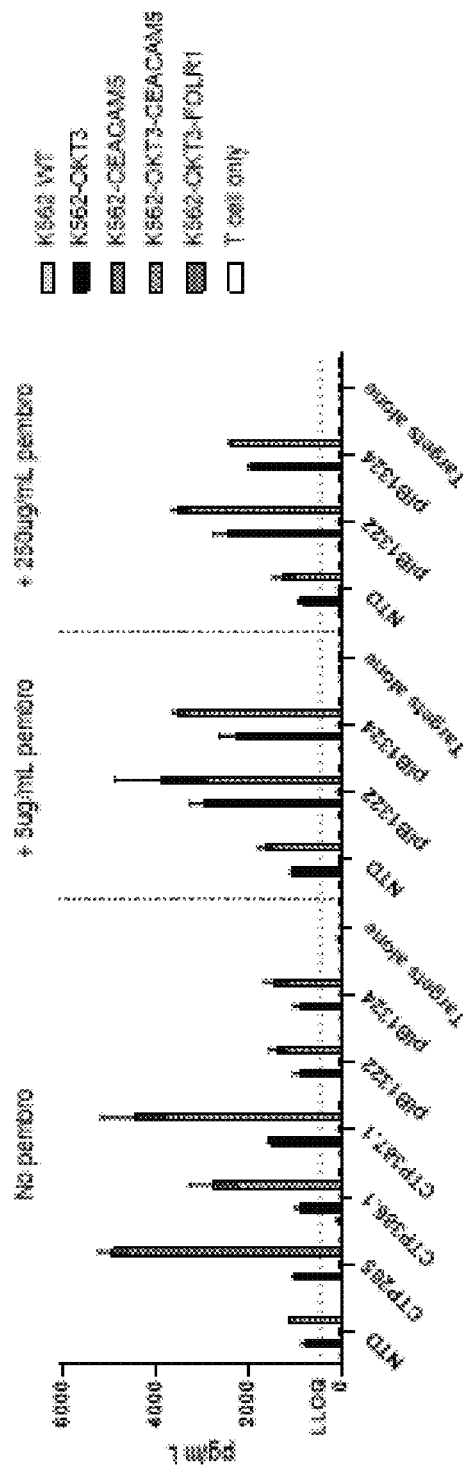

FIG. 31A-31H—depicts the increase in IL2 production (pg/mL) in TIL and K562 cells lines following co-culturing, across the cell types CRC-11974 (FIG. 31A), CRC-11959 (FIG. 31B), NSCLC-9332 (FIG. 31C), NSCLC-9596 (FIG. 31D), Ovarian cells (FIG. 31E), Melanoma-CC60 (FIG. 31F), Melanoma-11909 (FIG. 31G), and Melanoma-17614 (FIG. 31H).

Figure 32A:
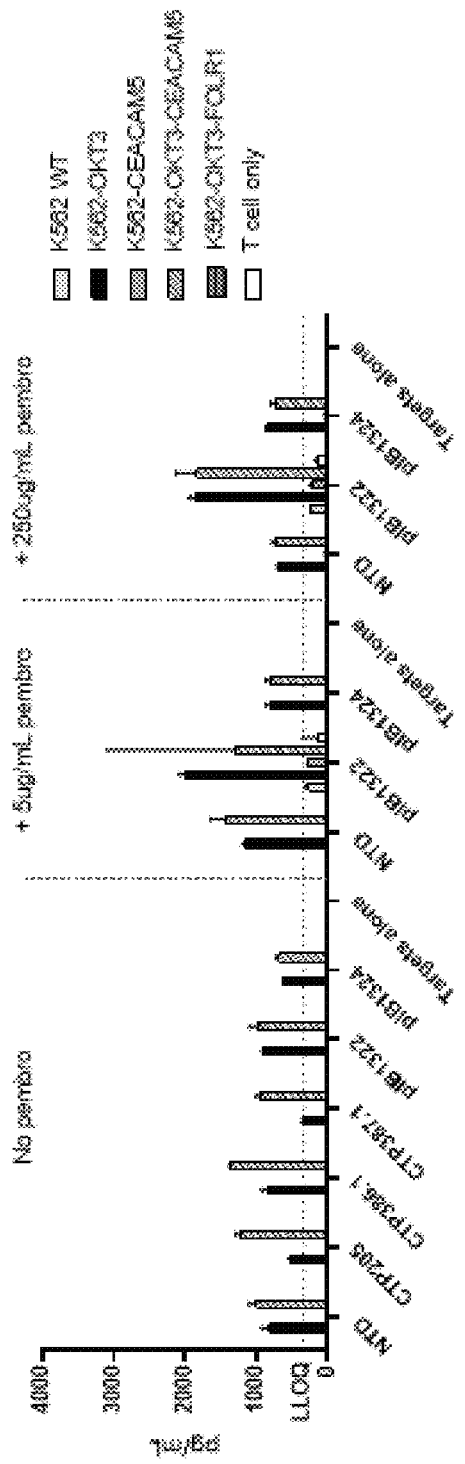
Figure 32B:
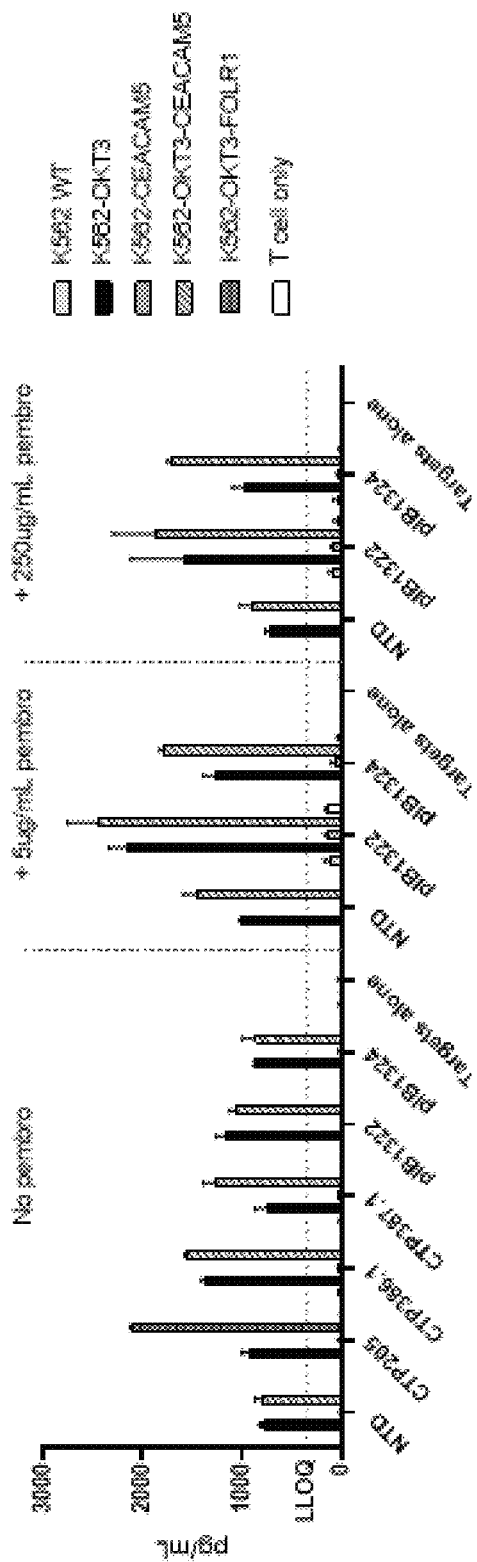
Figure 32C:
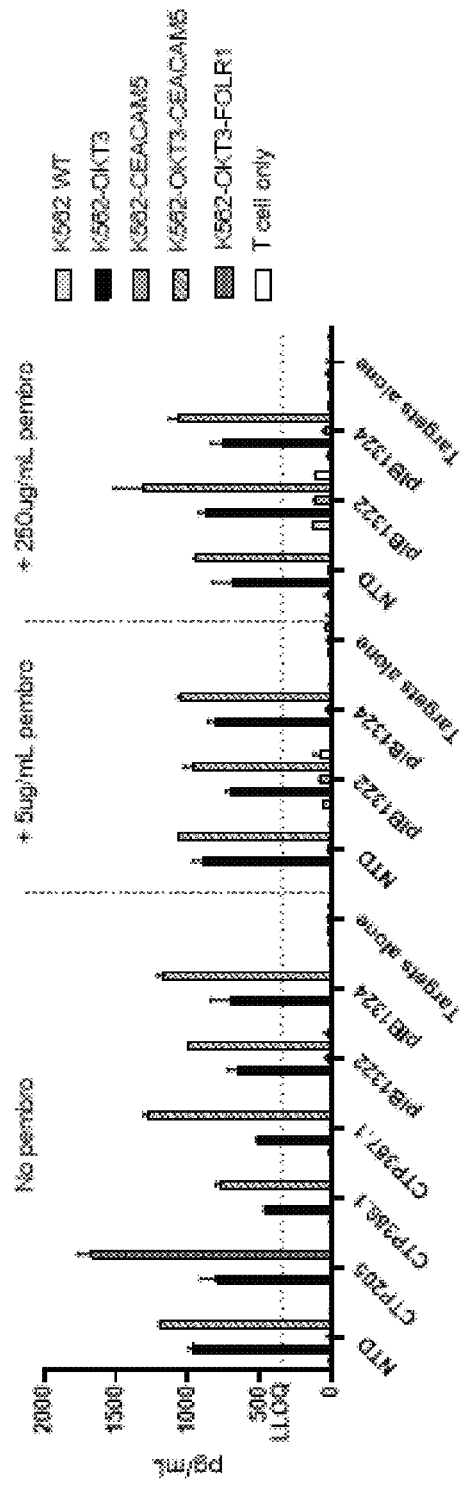
Figure 32D:
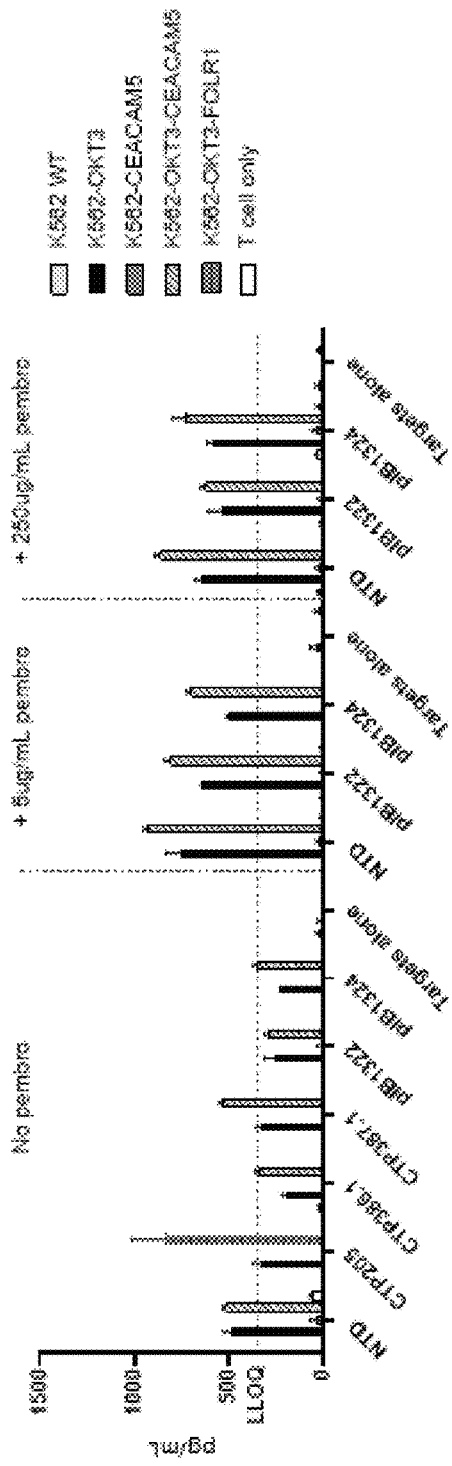
Figure 32E:
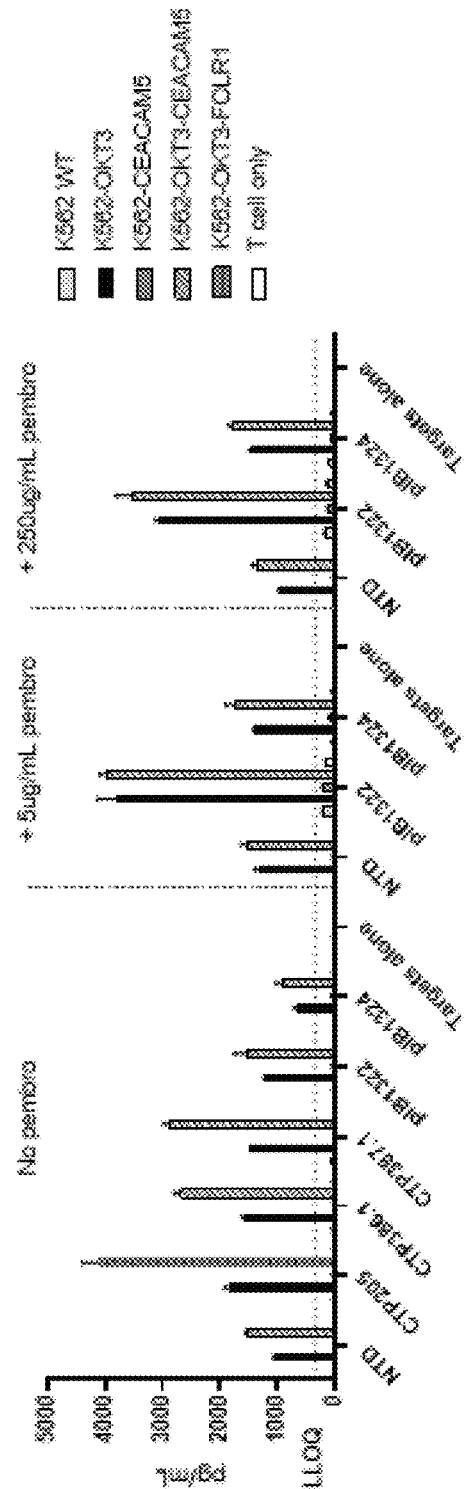
Figure 32F:
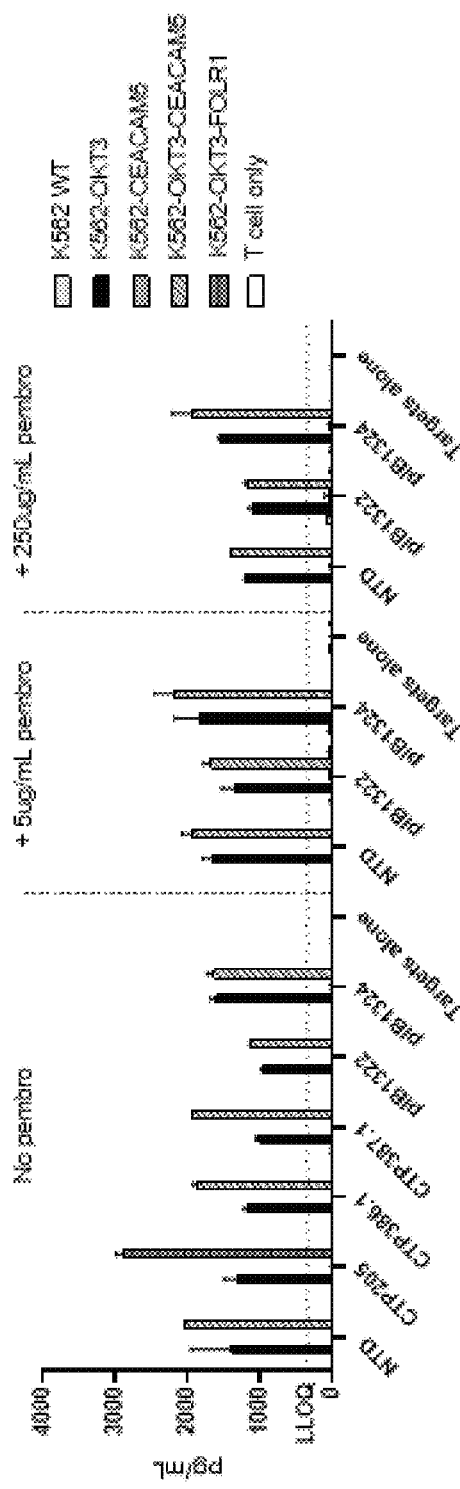
Figure 32G:
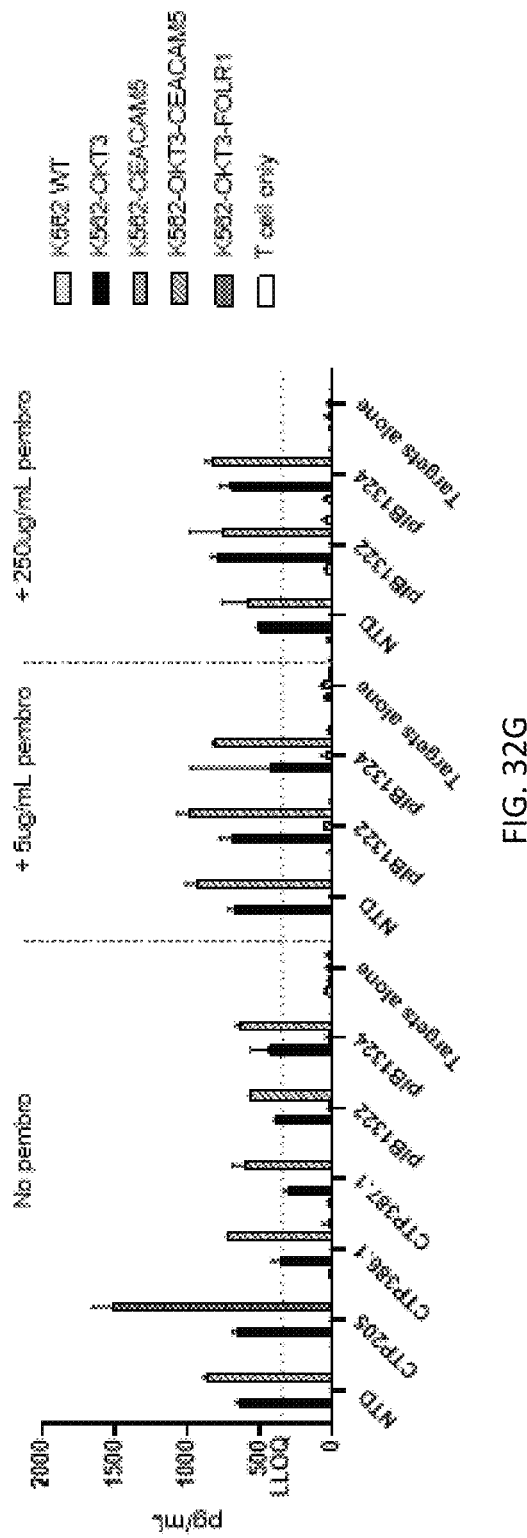
Figure 32H:
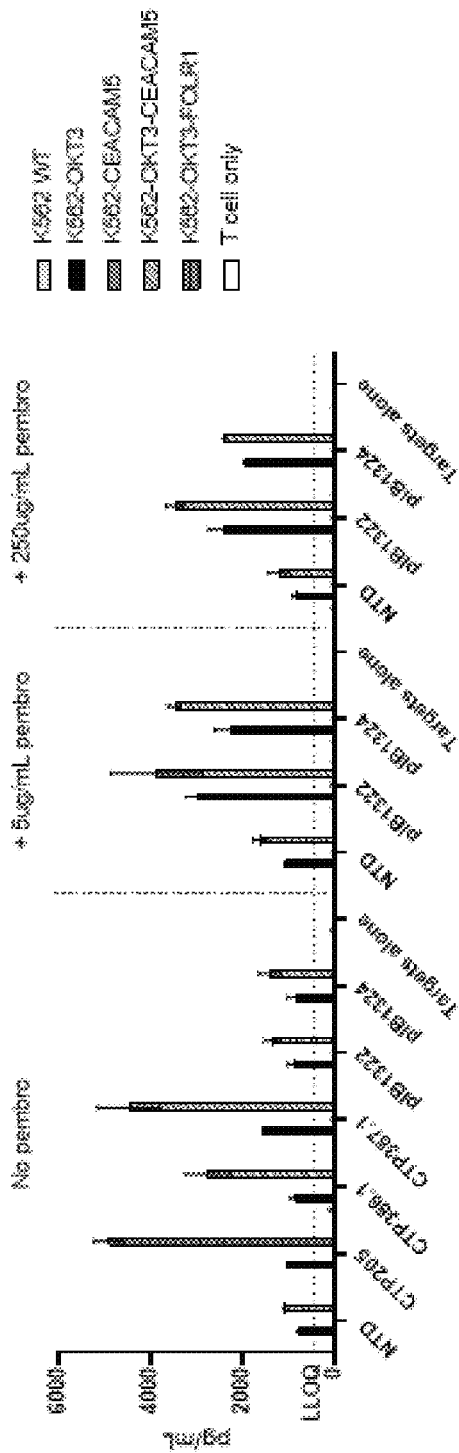

FIG. 32A-32H—depicts the increase in TNFa production (pg/mL) in TIL and K562 cells lines following co-culturing, across the cell types CRC-11974 (FIG. 32A), CRC-11959 (FIG. 32B), NSCLC-9332 (FIG. 32C), NSCLC-9596 (FIG. 32D), Ovarian cells (FIG. 32E), Melanoma-CC60 (FIG. 32F), Melanoma-11909 (FIG. 32G), and Melanoma-17614 (FIG. 32H).

DETAILED DESCRIPTION OF THE INVENTION

Disclosed herein are a variety of engineered proteins. In some embodiments, the engineered protein that has at least 80%, 85%, 90%, 95%, 96%, 97%, 98%, 99%, 100%, or any integer that is between 80 and 100%, identity to SEQ ID NO: 166, and wherein the sequence is not SEQ ID NO: 123. In some embodiments, the engineered protein has at least 70%, 75%, 80%, 85%, 90%, 95%, 96%, 97%, 98%, 99%, 100%, or any integer that is between 70 and 100%, identity to SEQ ID NO: 166. In some embodiments, the engineered protein has an at least 80% identity to SEQ ID NO:166. In some embodiments, the engineered protein has an at least 90% identity to SEQ ID NO:166. In some embodiments, the engineered protein is SEQ ID NO:166 (FIG. 9). In some embodiments, the sequence is at least 80% identical and is not the sequence of SEQ ID NO: 123.

In some embodiments, the engineered protein that has at least 80%, 85%, 90%, 95%, 96%, 97%, 98%, 99%, 100%, or any integer that is between 80 and 100%, identity to SEQ ID NO: 167, and wherein the sequence is not SEQ ID NO: 123. In some embodiments, the engineered protein that has at least 70%, 75%, 80%, 85%, 90%, 95%, 96%, 97%, 98%, 99%, 100%, or any integer that is between 70 and 100%, identity to SEQ ID NO: 167. In some embodiments, the engineered protein has an at least 80% identity to SEQ ID NO:167. In some embodiments, the engineered protein has an at least 90% identity to SEQ ID NO:167. In some embodiments, the engineered protein is SEQ ID NO:167 (FIG. 10). In some embodiments, the sequence is at least 80% identical, and is not the sequence of SEQ ID NO: 123.

In some embodiments, an engineered protein is provided that has at least 80%, 85%, 90%, 95%, 96%, 97%, 98%, 99%, 100%, or any integer that is between 80 and 100%, identity to SEQ ID NO: 166, and wherein the sequence is not SEQ ID NO: 123.

In some embodiments, an engineered protein is provided that has at least 80%, 85%, 90%, 95%, 96%, 97%, 98%, 99%, 100%, or any integer that is between 80 and 100%, identity to SEQ ID NO: 167, and wherein the sequence is not SEQ ID NO: 123.

In some embodiments, the engineered protein, CoStAR or fusion protein has a general structure as depicted in FIG. 8A.

In some embodiments, the engineered protein CoStAR or fusion protein has a general structure as depicted in FIG. 8B.

In some embodiments, the engineered protein CoStAR or fusion protein comprises at least one sequence depicted in FIG. 8C.

In some embodiments, the arrangement in FIG. 8A is an embodiment separate from the embodiments in FIG. 8B and/or 8C. In some embodiments, the arrangement in FIG. 8B is an embodiment separate from the embodiments in FIG. 8C and/or 8A. In some embodiments, the arrangement in FIG. 8C is an embodiment separate from the embodiments in FIG. 8A and/or 8B (thus, the sequence itself is envisioned, in some embodiments, as the entirety of the engineered protein). In some embodiments, FIG. 8B depicts some embodiments that are a subset of FIG. 8C. In some embodiments, FIG. 8C depicts some embodiments that are a subset of FIG. 8A and FIG. 8B. Exemplary CDRs are underlined in FIG. 8C (SEQ ID NO: 158 and 160).

In some embodiments, the engineered protein, CoStAR or fusion protein is as depicted in FIG. 9 or 10. Exemplary CDRs are underlined in FIG. 9 and FIG. 10. In some embodiments, the engineered protein, CoStAR or fusion protein is different from other fusion proteins, as shown in FIG. 11. In some embodiments, the engineered protein, CoStAR or fusion protein can lack a tag component and/or a section of CD28.

In some embodiments, the engineered protein comprises a binding domain. In some embodiments, the engineered protein comprises a CD28 domain. In some embodiments, the engineered protein comprises a CD40 domain. In some embodiments, the engineered protein comprises 1, 2, or all 3 of a binding domain, a CD28 domain, and/or a CD40 domain.

In some embodiments, the engineered protein comprises a signal peptide sequence. The term "signal peptide" is given its usual scientific meaning, and thus refers a short peptide that functions in translocating the rest of the attached protein. "Signal peptide" thus may also be called a signal sequence, targeting signal, localization signal, localization sequence, transit peptide, leader sequence or leader peptide. It will be understood that the signal peptide may be any peptide with the function of signaling for the attached peptide to be translocated to the plasma membrane of a cell. In some embodiments, the signal peptide sequence has at least 80%, 85%, 90%, 95%, 96%, 97%, 98%, 99%, 100%, or any integer that is between 80 and 100%, identity to the amino acid sequence of SEQ ID NO: 157.

In some embodiments, the binding domain comprises 1, 2, or all 3 of a VL sequence, a VH sequence, and/or an at least one linker. In some embodiments, the at least one linker has at least 80%, 85%, 90%, 95%, 96%, 97%, 98%, 99%, 100%, or any integer that is between 80 and 100%, identity to the amino acid sequence of SEQ ID NO: 159 or 161. In some embodiments, the binding domain comprises two linker sequences. In some embodiments, the two linker sequences have at least 80%, 85%, 90%, 95%, 96%, 97%, 98%, 99%, 100%, or any integer that is between 80 and 100%, identity to amino acid sequences SEQ ID NO: 159 and SEQ ID NO: 161, respectively.

In some embodiments, the VL sequence has at least 80%, 85%, 90%, 95%, 96%, 97%, 98%, 99%, 100%, or any integer that is between 80 and 100%, identity to the amino acid sequence of SEQ ID NO: 158. In some embodiments, the VH sequence has at least 80%, 85%, 90%, 95%, 96%, 97%, 98%, 99%, 100%, or any integer that is between 80 and 100%, identity to the amino acid sequence of SEQ ID NO: 160. In some embodiments, all 3 of the heavy chain CDRs and/or all three of the light chain CDRs within the VH and VL are identical to the heavy and/or light chain CDRs contained within SEQ ID NOs: 158 and 160. In some embodiments, 1, 2, 3, 4, 5 or 6 of the CDRs have 1, 2, 3, 4 or more point mutations. In some embodiments, 1, 2, 3, 4, 5, or 6 CDRs are 70, 80, 85, 90, 95, 96, 97, 98, 99 or 100% identical to the corresponding CDRs within SEQ ID NOs: 158 and/or 160.

In some embodiments, the protein comprises 1, 2, 3, 4, 5, or all 6 CDR sequence(s) selected from the group consisting of:

```
                                    (SEQ ID NO: 168)
            QASQSLSNLLA, (SEQ ID NO: 169)
            GASNLES, (SEQ ID NO: 170)
            QGGHYSGL, (SEQ ID NO: 171)
            TNDMN, (SEQ ID NO: 172)
            VIYSDDTPDYATWAKG,
            and/or (SEQ ID NO: 173)
            GHYDSAVYAYALNI.
```

In some embodiments, the binding domain and CD28 domain are connected by an at least one linker. In some embodiments, 1, 2, 3, 4, 5 or 6 of the CDRs have 1, 2, 3, 4, or more point mutations. In some embodiments, 1, 2, 3, 4, 5, or 6 CDRs are 70, 80, 85, 90, 95, 96, 97, 98, 99 or 100% identical to the CDRs.

Also disclosed herein is an engineered protein comprising an amino acid sequence that is at least 80%, 85%, 90%, 95%, 96%, 97%, 98%, 99%, 100%, or any integer that is between 80 and 100%, identical to the amino acid sequence of SEQ ID NO: 166 or 167.

In some embodiments, an engineered protein is provided that comprises an amino acid sequence that is at least 80% identical to the amino acid sequence of SEQ ID NO: 166 or 167, wherein the amino acid sequence does not include at least one of:

QKLISEEDLE (SEQ ID NO: 174)

or

LVKQSPMLVAYDNAVNLSCKYSYNLFSREFRASLHKGLDSAVEVCVVYGN YSQQLQVYSKTGFNCDGKLGNESVTFYLQNLYVNQTDIYFCKI. (SEQ ID NO: 175)

In some embodiments, the CD40 domain has at least 80%, 85%, 90%, 95%, 96%, 97%, 98%, 99%, 100%, or any integer that is between 80 and 100%, identity to the amino acid sequence of SEQ ID NO: 165. In some embodiments, the CD28 domain comprises a CD28 transmembrane domain. In some embodiments, the CD28 transmembrane domain has at least 80%, 85%, 90%, 95%, 96%, 97%, 98%, 99%, 100%, or any integer that is between 80 and 100%, identity to SEQ ID NO: 163. In some embodiments, the CD28 domain comprises a CD28 extracellular domain. In some embodiments, the CD28 extracellular domain has at least 80%, 85%, 90%, 95%, 96%, 97%, 98%, 99%, 100%, or any integer that is between 80 and 100%, identity to SEQ ID NO: 162. In some embodiments, the CD28 domain comprises a CD28 intracellular domain. In some embodiments, the CD28 intracellular domain has at least 80%, 85%, 90%, 95%, 96%, 97%, 98%, 99%, 100%, or any integer that is between 80 and 100%, identity to SEQ ID NO: 164.

In some embodiments, the the amino acid sequence and/or fusion protein and/or engineered protein does not include at least one of:

QKLISEEDLE (SEQ ID NO: 174)

or

LVKQSPMLVAYDNAVNLSCKYSYNLFSREFRASLHKGLDSAVEVCVVYGN YSQQLQVYSKTGFNCDGKLGNESVTFYLQNLYVNQTDIYFCKI. (SEQ ID NO: 175)

In some embodiments, the engineered protein lacks both of

QKLISEEDLE (SEQ ID NO: 174)

and

LVKQSPMLVAYDNAVNLSCKYSYNLFSREFRASLHKGLDSAVEVCVVYGN YSQQLQVYSKTGFNCDGKLGNESVTFYLQNLYVNQTDIYFCKI. (SEQ ID NO: 175)

In some embodiments, the engineered protein comprises a sequence that is at least 80%, 85%, 90%, 95%, 96%, 97%, 98%, 99%, 100%, or any integer that is between 80 and 100%, identical to SEQ ID NO: 157.

In some embodiments, the engineered protein comprises a sequence that is at least 80%, 85%, 90%, 95%, 96%, 97%, 98%, 99%, 100%, or any integer that is between 80 and 100%, identical to SEQ ID NO: 158.

In some embodiments, the engineered protein comprises a sequence that is at least 80%, 85%, 90%, 95%, 96%, 97%, 98%, 99%, 100%, or any integer that is between 80 and 100%, identical to SEQ ID NO: 159.

In some embodiments, the engineered protein comprises a sequence that is at least 80%, 85%, 90%, 95%, 96%, 97%, 98%, 99%, 100%, or any integer that is between 80 and 100%, identical to SEQ ID NO: 160.

In some embodiments, the engineered protein comprises a sequence that is at least 80%, 85%, 90%, 95%, 96%, 97%, 98%, 99%, 100%, or any integer that is between 80 and 100%, identical to SEQ ID NO: 161.

In some embodiments, the engineered protein comprises a sequence that is at least 80%, 85%, 90%, 95%, 96%, 97%, 98%, 99%, 100%, or any integer that is between 80 and 100%, identical to SEQ ID NO: 162.

In some embodiments, the engineered protein comprises a sequence that is at least 80%, 85%, 90%, 95%, 96%, 97%, 98%, 99%, 100%, or any integer that is between 80 and 100%, identical to SEQ ID NO: 163.

In some embodiments, the engineered protein comprises a sequence that is at least 80%, 85%, 90%, 95%, 96%, 97%, 98%, 99%, 100%, or any integer that is between 80 and 100%, identical to SEQ ID NO: 164.

In some embodiments, the engineered protein comprises a sequence that is at least 80%, 85%, 90%, 95%, 96%, 97%, 98%, 99%, 100%, or any integer that is between 80 and 100%, identical to SEQ ID NO: 165.

In some embodiments, the engineered protein comprises 1, 2, 3, 4, 5, 6, 7, 8, and/or 9 sequence(s) that have at least 80% identity to SEQ ID NOS: 157-165, respectively. In some embodiments, the engineered protein comprises 1, 2, 3, 4, 5, 6, 7, 8, and/or 9 sequence(s) that have at least 90% identity to SEQ ID NOS: 157-165, respectively. In some embodiments, the engineered protein comprises 1, 2, 3, 4, 5, 6, 7, 8, and/or 9 sequence(s) that have at least 95% identity to SEQ ID NOS: 157-165, respectively. In some embodiments, the engineered protein comprises 1, 2, 3, 4, 5, 6, 7, 8, and/or 9 sequence(s) that have at least 98% identity to SEQ ID NOS: 157-165, respectively. In some embodiments, the engineered protein comprises 1, 2, 3, 4, 5, 6, 7, 8, and/or 9 sequence(s) selected from the group consisting of: SEQ ID NOS: 157-165.

Also disclosed herein is a CoStAR. In some embodiments, the CoStAR comprises an optional signal peptide, a binding domain, wherein the binding domain binds to an anti-pembrolizumab antibody or binding fragment thereof, a CD28 domain, and a CD40 domain, wherein the signal peptide is optionally linked to the binding domain, wherein the binding domain is linked to the CD28 domain, wherein the CD28 domain is linked to the CD40 domain, and wherein the CoStAR comprises an amino acid sequence that: i) lacks at least one of:

QKLISEEDLE (SEQ ID NO: 174)

or

LVKQSPMLVAYDNAVNLSCKYSYNLFSREFRASLHKGLDSAVEVCVVYGN YSQQLQVYSKTGFNCDGKLGNESVTFYLQNLYVNQTDIYFCKI; (SEQ ID NO: 175)

ii) has an amino acid sequence that is greater than 95% identical to SEQ ID NO: 166 or 167; iii) has an amino acid sequence that is greater than 80% identical to SEQ ID NO: 166 or 167 and is not SEQ ID NO: 123; or iv) any combination of i-iv.

Also disclosed herein is a fusion protein. In some embodiments, the fusion protein comprises a means for binding to an antibody that binds to pembrolizumab, a CD28 domain, and a CD40 domain, wherein the means for binding to an antibody is linked to a CD28 domain, wherein the CD28 domain is linked to the CD40 domain, and wherein the fusion protein comprises an amino acid sequence that: i) lacks at least one of:

QKLISEEDLE (SEQ ID NO: 174)

or

LVKQSPMLVAYDNAVNLSCKYSYNLFSREFRASLHKGLDSAVEVCVVYGN YSQQLQVYSKTGFNCDGKLGNESVTFYLQNLYVNQTDIYFCKI; (SEQ ID NO: 175) ii)

has an amino acid sequence that is greater than 95% identical to SEQ ID NO: 166 or 167; iii) has an amino acid sequence that is greater than 80% identical to SEQ ID NO: 166 or 167 and is not SEQ ID NO: 123; or iv) any combination of i-iv. In some embodiments, the means for binding to pembrolizumab is an anti-pembrolizumab antibody. In some embodiments, the anti-pembrolizumab antibody is In some embodiments, the binding domain or the means for binding to an antibody that binds to pembrolizumab comprises: 1, 2, 3, 4, 5, or all 6 CDR sequence(s) selected from the group consisting of:

QASQSLSNLLA, (SEQ ID NO: 168)

GASNLES, (SEQ ID NO: 169)

QGGHYSGL, (SEQ ID NO: 170)

TNDMN, (SEQ ID NO: 171)

VIYSDDTPDYATWAKG, (SEQ ID NO: 172)
and/or

GHYDSAVYAYALNI. (SEQ ID NO: 173)

In some embodiments, 1, 2, 3, 4, 5 or 6 of the CDRs have 1, 2, 3, 4, or more point mutations. In some embodiments, 1, 2, 3, 4, 5, or 6 CDRs are 70, 80, 85, 90, 95, 96, 97, 98, 99 or 100% identical to the CDRs.

In some embodiments, the CD28 domain comprises: SEQ ID Nos: 162, 163, and 164, or a sequence that is at least 80%, 85%, 90%, 95%, 96%, 97%, 98%, 99%, 100%, or any integer that is between 80 and 100%, identical thereto. In some embodiments, the CD40 domain comprises: SEQ ID No: 165, or a sequence that is at least 80%, 85%, 90%, 95%, 96%, 97%, 98%, 99%, 100%, or any integer that is between 80 and 100%, identical thereto.

Also disclosed herein is a fusion protein comprising the amino acid sequence of SEQ ID NO: 166. In some embodiments, the fusion protein comprises a sequence that is at least 80%, 85%, 90%, 95%, 96%, 97%, 98%, 99%, 100%, or any integer that is between 80 and 100%, identical to SEQ ID NO: 166. Also disclosed herein is a fusion protein comprising the amino acid sequence of SEQ ID NO: 167. In some embodiments, the fusion protein comprises a sequence that is at least 80%, 85%, 90%, 95%, 96%, 97%, 98%, 99%, 100%, or any integer that is between 80 and 100%, identical to SEQ ID NO: 167.

Also disclosed herein is a nucleic acid which encodes a protein of any one of the embodiments of the present application.

Also disclosed herein is a vector which comprises a nucleic acid of any one of the embodiments of the present application.

Also disclosed herein is a cell which expresses a protein of any one of the embodiments of the present application.

Also disclosed herein is a cell which expresses at least two proteins of any one of the embodiments of the present application.

Also disclosed herein is a method of making the cell of any one of the embodiments of the present application which comprises the step of transducing or transfecting a cell with a vector of any one of the embodiments of the present application.

Also disclosed herein is a method for preparing a population of cells that express a protein of any one of the embodiments of the present application, comprising detecting expression of the protein on the surface of cells transfected or transduced with a vector according to any one of the embodiments of the present application and selecting cells which are identified as expressing the protein.

Also disclosed herein is a cell population produced by the method of any one of the methods disclosed in the present application.

Also disclosed herein is a cell population which is enriched for cell expression a protein of any one of the embodiments of the present application.

Also disclosed herein is a method for treating a disease in a subject in need thereof, which comprises the step of administering the cell of any one of the embodiments of the present application, or the cell population of any one of the embodiments of the present application, to the subject.

As used herein, "full length protein" or "full length receptor" refers to a receptor protein, such as, for example, a CD40 receptor protein. The term "full length" encompasses receptor proteins lacking up to about 5 or up to 10 amino acids, for example 1, 2, 3, 4, 5, 6, 7, 8, 9, or 10 amino acids, at the N-terminal of the mature receptor protein once its signal peptide has been cleaved. For instance, while a specific cleavage site of a receptors N-terminal signal peptide may be defined, variability in exact point of cleavage has been observed. The term "full length" does not imply presence or absence of amino acids of the receptors N-terminal signal peptide. In one embodiment, the term "full length" (e.g. a full length CD28 or a full length CD40 intracellular domain, according to certain aspects of the invention) encompasses mature receptor proteins (e.g. CD28 according to certain aspects of the invention) lacking the N terminal signal peptide lacking up to about 5, for example 1, 2, 3, 4, 5, or up to 10 amino acids at the N-terminal of the mature receptor protein once its signal peptide has been cleaved. As mentioned above, a "full length" CD28 receptor or other receptor or TCR clustering domain according to the various aspects of the invention does not include the signal peptide and may lack up to about 5, for example 1, 2, 3, 4, 5, or up to 10 amino acids at the N-terminal of the mature receptor protein (e.g. N terminal residues N, K, I, L and/or V). This is shown in the exemplary fusions, e.g. SEQ ID Nos. 4-12 (note that these may lack up to about 5, for example 1, 2, 3, 4, 5, or up to 10 amino acids at the N-terminal of the mature receptor protein as shown in the boxed region).

The chimeric protein of the present invention may comprise a TCR clustering domain as well as a signaling domain that advantageously may comprise a CD40 intracellular domain.

The term "T cell receptor," or "TCR," refers to a heterodimeric receptor composed of αβ or γδ chains that pair on the surface of a T cell. Each α, β, γ, and δ chain is composed of two Ig-like domains: a variable domain (V) that confers antigen recognition through the complementarity determining regions (CDR), followed by a constant domain I that is anchored to cell membrane by a connecting peptide and a transmembralTM) region. The TM region associates with the invariant subunits of the CD3 signaling apparatus. Each of the V domains has three CDRs. These CDRs interact with a complex between an antigenic peptide bound to a protein encoded by the major histocompatibility complex (pMHC) (Davis and Bjorkman (1988) Nature, 334, 395-402; Davis et al. (1998) Annu Rev Immunol, 16, 523-544; Murphy (2012), xix, 868 p.).

Costimulatory receptor proteins useful in the chimeric proteins of the invention include, without limitation, CD2, CD9, CD26, CD27, CD28, CD29, CD38, CD40, CD43, CD46, CD49d, CD55, CD73, CD81, CD82, CD99, CD100, CD134 (OX40), CD137 (41BB), CD150 (SLAM), CD270 (HVEM), CD278 (ICOS), CD357 (GITR), or EphB6, which in their natural form comprise extracellular ligand binding domains and intracellular signal transducing domains. For example, CD2 is characterized as a cell adhesion molecule found on the surface of T cells and is capable of initiating intracellular signals necessary for T cell activation. CD27 is characterized as a type II transmembrane glycoprotein belonging to the TNFR superfamily (TNFRSF) whose expression on B cells is induced by antigen-receptor activation in B cells. CD28 is one of the proteins on T cells and is the receptor for CD80 (B7.1) and CD86 (B7.2) ligands on antigen-presenting cells. CD137 (4-1BB) ligand is found on most leukocytes and on some non-immune cells. OX40 ligand is expressed on many antigen-presenting cells such as DC2s (dendritic cells), macrophages, and B lymphocytes. In one embodiment, the costimulatory receptor protein is full length CD28 as defined herein.

CD40 is a member of the tumor necrosis factor receptor (TNFR) superfamily and several isoforms are generated by alternative splicing. Its ligand, CD154 (also called CD40L) is a protein that is primarily expressed on activated T cells. For reference, the human CD40 isoform 1 protein sequence is set forth in GenBank accession No. NP_001241.1, including signal peptide (amino acids 1-20), transmembrane domain (amino acids 194-215), and cytoplasmic domain (amino acids 216-277)(SEQ ID NO:22). CD40 receptor signaling involves adaptor proteins including but not limited to TNF receptor-associated factors (TRAF), and the cytoplasmic domain comprises signaling components, including but not limited to an SH3 motif (KPTNKAPH), TRAF2 motif (PKQE, PVQE, SVQE), TRAF6 motif (QEPQEINFP) and PKA motif (KKPTNKA, SRISVQE). Further motifs for binding to TRAF1, TRAF2, TRAF3, and TRAF5 comprise the major consensus sequence (P/S/A/T)X(Q/E)E or minor consensus sequence PXQXXD and can be identified in or obtained from, without limitation, TNFR family members such as CD30, Ox40, 4-1BB, and the EBV oncoprotein LMP1. (See, e.g., Ye, H et al., *The Structural Basis for the Recognition of Diverse Receptor Sequences by TRAF2*. Molecular Cell, 1999; 4(3):321-30. doi: 10.1016/S1097-2765(00)80334-2; Park H H, *Structure of TRAF Family: Current Understanding of Receptor Recognition*. Front. Immunol. 2018; 9:1999. doi: 10.3389/fimmu.2018.01999).

Examples disclosed herein demonstrate operation of CD40 as a signaling domain and further that cytokine and chemokine expression profiles are altered by signaling domain selection. In this regard, the CD40 signaling domains of the invention provide distinct and overlapping responses induced by the different factor binding sites. (See, e.g., Ahonen, C L et al., *The CD40-TRAF6 axis controls affinity maturation and the generation of long-lived plasma cells*. Nat Immunol. 2002; 3: 451-456; Mackey M F et al., *Distinct contributions of different CD40 TRAF binding sites to CD154-induced dendritic cell maturation and IL-12 secretion*. Eur J Immunol. 2003; 33: 779-789; Mukundan L et al., *TNF receptor-associated factor 6 is an essential mediator of CD40-activated proinflammatory pathways in monocytes and macrophages*. J Immunol. 2005; 174: 1081-1090.

In some embodiments, a chimeric protein of the invention comprises substantially all of a CD40 costimulatory domain. In some embodiments, a chimeric protein of the invention comprises two or more CD40 costimulatory domains. In some embodiments, a chimeric protein of the invention comprises a CD40 costimulatory domain signaling component or motif, including but not limited to an SH3 motif (KPTNKAPH), TRAF2 motif (PKQE, PVQE, SVQE), TRAF3 motif, TRAF6 motif (QEPQEINFP) or PKA motif (KKPTNKA, SRISVQE) as well as two or more, or three or more, or four or more such components of motifs, which can be in multiple copies and arranged in any order. In some embodiments, a chimeric protein of the invention comprises a CD40 costimulatory domain and a CD40 costimulatory domain signaling component or motif.

In some embodiments, selection of one or more costimulatory domain signaling component or motif is guided by the cell in which the chimeric protein is to be expressed and/or a desired costimulatory activity more closely identified with a signaling component or motif, or avoidance of a costimulatory activity more closely identified with a signaling component or motif.

In some embodiments, a chimeric protein signaling domain comprises, in addition to a CD40 costimulatory domain or signaling component or motif thereof, or two or more such domains or components or motifs or combinations thereof, an additional full length costimulatory domain or signaling component thereof from, without limitation, CD2, CD9, CD26, CD27, CD28, CD29, CD38, CD40, CD43, CD46, CD49d, CD55, CD73, CD81, CD82, CD99, CD100, CD134 (OX40), CD137 (41BB), CD150 (SLAM), CD270 (HVEM), CD278 (ICOS), CD357 (GITR), or EphB6, For reference, the human CD28 protein sequence is set forth in GenBank accession No. NP_006130.1, including signal peptide (amino acids 1-18), extracellular domain (amino acids 19-152), transmembrane domain (amino acids 153-179) and cytoplasmic domain (amino acids 180-200). The extracellular domain includes an immunoglobulin type domain (amino acids 21-136) which contains amino acids with compose the antigen binding site and amino acids that form the homodimer interface. The extracellular domain includes several asparagine residues which may be glycosylated, and the intracellular domain comprises serine and tyrosine residues, which may be phosphorylated.

For reference, the human CD8 alpha chain protein sequence is set forth by GenBank accession No. NP_001139345.1, including signal peptide (amino acids 1-21), extracellular domain (amino acids 22-182), transmembrane domain (amino acids 183-203), and cytoplasmic domain (amino acids 204-235). The extracellular domain includes an immunoglobulin type domain (amino acids 28-128) which contains amino acids with compose the antigen binding site and amino acids that form the homodimer interface. The extracellular domain includes several asparagine residues which may be glycosylated, and the intracellular domain comprises serine and tyrosine residues, which may be phosphorylated.

For reference, the human IgG4 constant region sequence is set forth in UniProtKB/Swiss-Prot: accession No. P01861.1, including CH1 (amino acids 1-98), hinge (amino acids 99-110), CH2 (amino acids 111-220), CH3 (amino acids 221-327). The CH2 region includes asparagine at amino acid 177, which is the glycosylated and associated with Fc receptor and antibody-dependent cell-mediated cytotoxicity (ADCC).

For reference, the protein sequence of human CD137 (41BB), another TNFR superfamily member, is set forth by GenBank accession No. NP_001552.2, including signal peptide (amino acids 1-23), extracellular domain (amino acids 24-186), transmembrane domain (amino acids 187-213), and cytoplasmic domain (amino acids 214-255).

For reference, the human CD134 (OX40) protein sequence is set forth by GenBank accession No. NP_003318.1, including signal peptide (amino acids 1-28), extracellular domain (amino acids 29-214), transmembrane domain (amino acids 215-235), and cytoplasmic domain (amino acids 236-277). This receptor has been shown to activate NF-kappaB through its interaction with adaptor proteins TRAF2 and TRAF5 and studies suggest that this receptor promotes expression of apoptosis inhibitors BCL2 and BCL21L1/BCL2-XL.

The human T-cell surface antigen CD2 has at least two isoforms. For reference, the human CD2 isoform1 protein sequence is set forth by NP_001315538.1, including signal peptide (amino acids 1-24), extracellular domain (amino acids 25-235), transmembrane domain (amino acids 236-261), and cytoplasmic domain (amino acids 262-377). The human CD2 isoform2 protein sequence is set forth by NP_001758.2

For reference, the human CD357 (GITR) isoform-1 protein sequence is set forth by GenBank accession No. NP_004186.1, including signal peptide (amino acids 1-25), extracellular domain (amino acids 26-162), transmembrane domain (amino acids 163-183), and cytoplasmic domain (amino acids 184-241).

For reference, the human CD29 (beta1 integrin) protein sequence is set forth by GenBank accession No. NP_596867, including signal peptide (amino acids 1-20), extracellular domain (amino acids 21-728), transmembrane domain (amino acids 729-751), and cytoplasmic domain (amino acids 752-798).

The human CD150 (SLAM) protein sequence has at several isoforms. In addition to the transmembrane form of CD150 (mCD150), cells of hematopoietic lineage express mRNA encoding the secreted form of CD150 (sCD150), which lacks the entire transmembrane region of 30 amino acids. For reference, human SLAM isoform b is set forth by GenBank accession No. NP_003028.1, including signal peptide (amino acids 1-20), extracellular domain (amino acids 21-237), transmembrane domain (amino acids 238-258), and cytoplasmic domain (amino acids 259-335). Human SLAM isoform a is set forth by GenBank accession No. NP_001317683.1.

In embodiments of the invention, a chimeric protein may be expressed alone under the control of a promoter in a therapeutic population of cells that have therapeutic activity, for example, Tumor Infiltrating Lymphocytes (TILs). Alternatively, the chimeric protein may be expressed along with a therapeutic transgene such as a chimeric antigen receptor (CAR) and/or T-cell Receptor (TCR). Suitable TCRs and CARs are well known in the literature, for example HLA-A*02-NYESO-1 specific TCRs (Rapoport et al. Nat Med 2015) or anti-CD19scFv.CD3ζ fusion CARs (Kochenderfer et al. J Clin Oncol 2015) which have been successfully used to treat Myeloma or B-cell malignancies respectively. The chimeric proteins described herein may be expressed with any known CAR or TCR thus providing the cell with a regulatable growth switch to allow cell expansion in-vitro or in-vivo, and a conventional activation mechanism in the form of the TCR or CAR for anti-cancer activity. Thus the invention provides a cell for use in adoptive cell therapy comprising a chimeric protein as described herein and a TCR and/or CAR that specifically binds to a tumor associated antigen. An exemplary chimeric protein comprising CD28 includes an extracellular antigen binding domain and an extracellular, transmembrane and intracellular signaling domain.

A chimeric protein of the invention optionally comprises a spacer region between the TCR clustering domain and the costimulatory receptor. As used herein, the term "spacer" refers to the extracellular structural region of a chimeric protein that separates the TCR clustering domain from the signaling domain of the chimeric protein. In some embodiments long spacers are employed, for example to target membrane-proximal epitopes or glycosylated antigens (see Guest R. D. et al. The role of extracellular spacer regions in the optimal design of chimeric immune receptors: evaluation of four different scFvs and antigens. J. Immunother. 2005; 28:203-211; Wilkie S. et al., Retargeting of human T cells to tumor-associated MUC1: the evolution of a chimeric antigen receptor. J. Immunol. 2008; 180:4901-4909). In other embodiments, chimeric proteins bear short spacers, for example to target membrane distal epitopes (see Hudecek M. et al., Receptor affinity and extracellular domain modifications affect tumor recognition by ROR1-specific chimeric antigen receptor T cells. Clin. Cancer Res. 2013; 19:3153-3164; Hudecek M. et a127acarbazine27nalling extracellular spacer domain of chimeric antigen receptors is decisive for in vivo antitumor activity. Cancer Immunol. Res. 2015; 3:125-135). In some embodiments, the spacer comprises all or part of or is derived from an IgG hinge, including but not limited to IgG1, IgG2, or IgG4. By "derived from an Ig hinge" is meant a spacer comprising insertions, deletions, or mutations in an IgG hinge. In some embodiments, a spacer can comprise all or part of one or more antibody constant domains, such as but not limited to CH2 and/or CH3 domains. In some embodiments, in a spacer comprising all or part of a CH2 domain, the CH2 domain is modified so as not to bind to an Fc receptor. For example, Fc receptor binding in myeloid cells has been found to impair CAR T cell functionality. In some embodiments, the spacer comprises all or part of an Ig-like hinge from CD28, CD8, or other protein comprising a hinge region. In some embodiments of the invention that comprise a spacer, the spacer is from 1 and 50 amino acids in length.

In some embodiments, the chimeric protein extracellular domain comprises a linker. Linkers comprise short runs of amino acids used to connect domains, for example a binding domain with a spacer or transmembrane domain. In order for there to be flexibility to bind ligand, a ligand binding domain will usually be connected to a spacer or a transmembrane domain by flexible linker comprising from about 5 to 25 amino acids, such as, for example,

AAAGSGGSG or

GGGGSGGGGSGGGGS.

In some embodiments, a chimeric protein comprises a TCR clustering domain joined directly to a signaling domain by a linker, and without a spacer. In some embodiments, a chimeric protein comprises a binding domain joined directly to a transmembrane by a spacer and without a linker.

As discussed above, in some embodiments, a chimeric protein comprises a full length primary costimulatory receptor which can comprise an extracellular ligand binding and intracellular signaling portion of, without limitation, CD2, CD9, CD26, CD27, CD28, CD29, CD38, CD40, CD43, CD46, CD49d, CD55, CD73, CD81, CD82, CD99, CD100, CD134 (OX40), CD137 (41BB), CD150 (SLAM), CD270 (HVEM), CD278 (ICOS), CD357 (GITR), or EphB6. In other embodiments, the chimeric protein, for instance may comprise an extracellular ligand binding domain of one of the aforementioned proteins and an intracellular signaling domain of another of the aforementioned proteins. In some embodiments, the signaling portion of the chimeric protein comprises a single signaling domain. In other embodiments, the signaling portion of the chimeric protein comprises a second intracellular signaling domain such as but not limited to: CD2, CD27, CD28, CD40, CD134 (OX40), CD137 (4-1BB), CD150 (SLAM). In some embodiments, the first and second intracellular signaling domains are the same. In other embodiments, the first and second intracellular signaling domains are different. In some embodiments, the costimulatory receptor is capable of dimerization. Without being bound by theory, it is thought that chimeric proteins dimerize or associate with other accessory molecules for signal initiation. In some embodiments, chimeric proteins dimerize or associate with accessory molecules through transmembrane domain interactions. In some embodiments, dimerization or association with accessory molecules is assisted by costimulatory receptor interactions in the intracellular portion, and/or the extracellular portion of the costimulatory receptor.

Although the main function of the transmembrane is to anchor the chimeric protein in the T cell membrane, in some embodiments, the transmembrane domain influences chimeric protein function. In some embodiments, the transmembrane domain is comprised by the full length primary costimulatory receptor domain. In embodiments of the invention wherein the chimeric protein construct comprises an extracellular domain of one receptor and an intracellular signaling domain of a second receptor, the transmembrane domain can be that of the extracellular domain or the intracellular domain. In some embodiments, the transmembrane domain is from CD4, CD8α, CD28, or ICOS. Gueden et al. associated use of the ICOS transmembrane domain with increased CART cell persistence and overall anti-tumor efficacy (Guedan S. et al., Enhancing CART cell persistence through ICOS and 4-1BB costimulation. JCI Insight. 2018; 3:96976). In an embodiment, the transmembrane domain comprises a hydrophobic α helix that spans the cell membrane.

In some embodiments, amino acid sequence variants of the TCR clustering domain or other moieties provided herein are contemplated. For example, it may be desirable to improve the binding affinity and/or other biological properties of the moiety. Amino acid sequence variants of an antibody moiety may be prepared by introducing appropriate modifications into the nucleotide sequence encoding the clustering moiety, or by peptide synthesis. Such modifications include, for example, deletions from, and/or insertions into and/or substitutions of residues within the amino acid sequences of the antibody moiety. Any combination of deletion, insertion, and substitution can be made to arrive at the final construct, provided that the final construct possesses the desired characteristics.

In some embodiments, TCR clustering domain moieties comprising one or more amino acid substitutions, deletions, or insertions are provided. Amino acid substitutions may be introduced into a binding domain of interest and the products screened for a desired activity, e.g., retained/improved clustering or decreased immunogenicity. In some embodiments, amino acid substitutions may be introduced into one or more of the primary co-stimulatory receptor domain (extracellular or intracellular), secondary costimulatory receptor domain, or extracellular co-receptor domain. Accordingly, the invention encompasses chimeric proteins and component parts particularly disclosed herein as well as variants thereof, i.e. chimeric proteins and component parts having at least 75%, at least 80%, at least 85%, at least 87%, at least 90%, at least 91%, at least 92%, at least 93%, at least 94%, at least 95%, at least 96%, at least 97%, at least 98%, at least 99% sequence identity to the amino acid sequences particularly disclosed herein. The terms "percent similarity," "percent identity," and "percent homology" when referring to a particular sequence are used as set forth in the University of Wisconsin GCG software program BestFit. Other algorithms may be used, e.g. BLAST, psiBLAST or TBLASTN (which use the method of Altschul et al. (1990) J. Mol. Biol. 215: 405-410), FASTA (which uses the method of Pearson and Lipman (1988) PNAS USA 85: 2444-2448).

Particular amino acid sequence variants may differ from a reference sequence by insertion, addition, substitution or deletion of 1 amino acid, 2, 3, 4, 5-10, 10-20 or 20-30 amino acids. In some embodiments, a variant sequence may comprise the reference sequence with 1, 2, 3, 4, 5, 6, 7, 8, 9, 10 or more residues inserted, deleted or substituted. For example, 5, 10, 15, up to 20, up to 30 or up to 40 residues may be inserted, deleted or substituted.

In some preferred embodiments, a variant may differ from a reference sequence by 1, 2, 3, 4, 5, 6, 7, 8, 9, 10 or more conservative substitutions. Conservative substitutions involve the replacement of an amino acid with a different amino acid having similar properties. For example, an aliphatic residue may be replaced by another aliphatic residue, a non-polar residue may be replaced by another non-polar residue, an acidic residue may be replaced by another acidic residue, a basic residue may be replaced by another basic residue, a polar residue may be replaced by another polar residue or an aromatic residue may be replaced by another aromatic residue. Conservative substitutions may, for example, be between amino acids within the following groups:

Conservative substitutions are shown in Table 1 below.

TABLE 1

| Original Residue | Exemplary Substitutions | Preferred Substitutions |
| --- | --- | --- |
| IArg (R) | Lys; Gln; Asn | Lys |
| Asn (N) | Gln; His; Asp; Lys; Arg | Gln |
| Asp (D) | Glu; AsnIu | |
| Cys (C) | Ser; Ala | Ser |
| Gln (Q) | Asn; I | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucinne; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped into different classes according to common side-chain properties: a. hydrophobic: Norleucine, Met, Ala, Val, Leu, Ile; b. neutral hydrophilic: Cys, Ser, Thr, Asn, Gln; c. acidic: Asp, Glu; d. basic: His, Lys, Arg; e. residues that influence chain orientation: Gly, Pro; aromatic: Trp, Tyr, Phe. Non-conservative substitutions will entail exchanging a member of one of these classes for another class.

The cells used in the present invention may be any lymphocyte that is useful in adoptive cell therapy, such as a T-cell or a natural killer (NK) cell, an NKT cell, a gamma/delta T-cell or T regulatory cell. The cells may be allogeneic or autologous to the patient.

T cells or T lymphocytes are a type of lymphocyte that have a central role in cell-mediated immunity. They can be distinguished from other lymphocytes, such as B cells and natural killer cells (NK cells), by the presence of a T-cell receptor (TCR) on the cell surface. There are various types of T cell, as summarized below. Cytotoxic T cells (TC cells, or CTLs) destroy virally infected cells and tumor cells, and are also implicated in transplant rejection. CTLs express the CD8 molecule at their surface.

These cells recognize their targets by binding to antigen associated with MHC class I, which is present on the surface of all nucleated cells. Through IL-10, adenosine and other molecules secreted by regulatory T cells, the CD8+ cells can be inactivated to an anergic state, which prevent autoimmune diseases such as experimental autoimmune encephalomyelitis.

Memory T cells are a subset of antigen-specific T cells that persist long-term after an infection has resolved. They quickly expand to large numbers of effector T cells upon re-exposure to their cognate antigen, thus providing the imm"ne sys"em with "memory" against past infections. Memory T cells comprise three subtypes: central memory T cells (TCM cells) and two types of effector memory T cells (TEM cells and TEMRA cells). Memory cells may be either CD4+ or CD8+. Memory T cells typically express the cell surface protein CD45RO. Regulatory T cells (Treg cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus.

Two major classes of CD4+ Treg cells have been described—naturally occurring Treg cells and adaptive Treg cells. Naturally occurring Treg cells (also known as CD4$^+$CD25$^+$FoxP3$^+$Treg cells) arise in the thymus and have been linked to interactions between developing T cells with both myeloid (CD11c$^+$) and plasmacytoid (CD123$^+$) dendritic cells that have been activated with TSLP. Naturally occurring Treg cells can be distinguished from other T cells by the presence of an intracellular molecule called FoxP3. Adaptive Treg cells (also known as Tr1 cells or Th3 cells) may originate during a normal immune response.

Natural Killer Cells (or NK cells) are a type of cytolytic cell which form part of the innate immune system. NK cells provide rapid responses to innate signals from virally infected cells in an MHC independent manner. NK cells (belonging to the group of innate lymphoid cells) are defined as large granular lymphocytes (LGL) and constitute the third kind of cells differentiated from the common lymphoid progenitor generating B and T lymphocytes.

In some embodiments, therapeutic cells of the invention comprise autologous cells engineered to express a chimeric protein. In some embodiments, therapeutic cells of the invention comprise allogeneic cells engineered to express a chimeric protein. Autologous cells expressing chimeric proteins may be advantageous in avoiding graft-versus-host disease (GVHD) due to TCR-mediated recognition of recipient alloantigens.

An aspect of the invention provides a nucleic acid sequence of the invention, encoding any of the chimeric proteins, polypeptides, or proteins described herein (including functional portions and functional variants thereof). As used herein, the terms "polynucleotide", "nucleotide", and "nucleic acid" are intended to be synonymous with each other. It will be understood by a skilled person that numerous different polynucleotides and nucleic acids can encode the same polypeptide as a result of the degeneracy of the genetic code. In addition, it is to be understood that skilled persons may, using routine techniques, make nucleotide substitutions that do not affect the polypeptide sequence encoded by the polynucleotides described here to reflect the codon usage of any particular host organism in which the polypeptides are to be expressed, e.g. codon optimization. Nucleic acids according to the invention may comprise DNA or RNA. They may be single stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine'chains at' the 3' and/or 5' ends of the molecule. For the purposes of the present invention, it is to be understood that the polynucleotides may be modified by any method available in the art. Such modifications may be carried out in order to enhance the in vivo activity or life span of polynucleotides of interest.

The terms "variant", "homologue" or "derivative" in relation to a nucleotide sequence include any substitution of, variation of, modification of, replacement of, deletion of or addition of one (or more) nucleic acid from or to the sequence.

The nucleic acid sequence may encode the protein sequence shown as SEQ ID NO:2 or a variant thereof. The nucleotide sequence may comprise a codon optimized nucleic acid sequence shown engineered for expression in human cells.

The invention also provides a nucleic acid sequence which comprises a nucleic acid sequence encoding a chimeric protein and a further nucleic acid sequence encoding a T-cell receptor (TCR) and/or chimeric antigen receptor (CAR).

The nucleic acid sequences may be joined by a sequence allowing co-expression of the two or more nucleic acid sequences. For example, the construct may comprise an internal promoter, an internal ribosome entry sequence (IRES) sequence or a sequence encoding a cleavage site. The cleavage site may be self-cleaving, such that when the polypeptide is produced, it is immediately cleaved into the discrete proteins without the need for any external cleavage activity. Various self-cleaving sites are known, including the Foot- and Mouth disease virus (FMDV) and the 2A self-cleaving peptide. The co-expressing sequence may be an internal ribosome entry sequence (IRES). The co-expressing sequence may be an internal promoter.

In an aspect, the present invention provides a vector which comprises a nucleic acid sequence or nucleic acid construct of the invention.

Such a vector may be used to introduce the nucleic acid sequence(s) or nucleic acid construct(s) into a host cell so that it expresses one or more chimeric protein(s) according to the first aspect of the invention and, optionally, one or more other proteins of interest (POI), for example a TCR or a CAR. The vector may, for example, be a plasmid or a viral vector, such as a retroviral vector or a lentiviral vector, or a transposon-based vector or synthetic mRNA.

The nucleic acids of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties.

Vectors derived from retroviruses, such as the lentivirus, are suitable tools to achieve long-term gene transfer since they allow long-term, stable integration of a transgene or transgenes and its propagation in daughter cells. The vector may be capable of transfecting or transducing a lymphocyte including a T cell or an NK cell. The present invention also provides vectors in which a nucleic acid of the present invention is inserted. The expression of natural or synthetic nucleic acids encoding a chimeric protein, and optionally a TCR or CAR is typically achieved by operably linking a nucleic acid encoding the chimeric protein and TCR/CAR polypeptide or portions thereof to one or more promoters, and incorporating the construct into an expression vector.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, MSCV promoter, MND promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter.

The vectors can be suitable for replication and integration in eukaryotic cells. Typical cloning vectors contain transcription and translation terminators, initiation sequences, and promoters useful for regulation of the expression of the desired nucleic acid sequence. Viral vector technology is well known in the art and is described, for example, in Sambrook et al. (2001, Molecular Cloning: A Laboratory Manual, Cold Spring Harbor Laboratory, New York), and in other virology and molecular biology manuals, see also, WO 01/96584; WO 01/29058; and U.S. Pat. No. 6,326,193). In some embodiments, the constructs expressed are as shown in SEQ ID NOS:32-65 and 67-79. In some embodiments the nucleic acids are multi-cistronic constructs that permit the expression of multiple transgenes (e.g., chimeric protein and a TCR and/or CAR etc.) under the control of a single promoter. In some embodiments, the transgenes (e.g., chimeric protein and a TCR and/or CAR etc.) are separated by a self-cleaving 2A peptide. Examples of 2A peptides useful in the nucleic acid constructs of the invention include F2A, P2A, T2A and E2A. In other embodiments of the invention, the nucleic acid construct of the invention is a multi-cistronic construct comprising two promoters; one promoter driving the expression of chimeric protein and the other promoter driving the expression of the TCR or CAR. In some embodiments, the dual promoter constructs of the invention are uni-directional. In other embodiments, the dual promoter constructs of the invention are bi-directional. In order to assess the expression of the chimeric protein polypeptide or portions thereof, the expression vector to be introduced into a cell can also contain either a selectable marker gene or a reporter gene or both to facilitate identification and selection of expressing cells from the population of cells sought to be transfected or transduced through viral vectors.

Prior to expansion and genetic modification, a source of cells (e.g., immune effector cells, e.g., T cells or NK cells) is obtained from a subject. The term "subject" is intended to include living organisms in which an immune response can be elicited (e.g., mammals). Examples of subjects include humans, dogs, cats, mice, rats, and transgenic species thereof. T cells can be obtained from a number of sources, including peripheral blood mononuclear cells, bone marrow, lymph node tissue, cord blood, thymus tissue, tissue from a site of infection, ascites, pleural effusion, spleen tissue, and tumors.

In one aspect, T cells are isolated from peripheral blood lymphocytes by lysing the red blood cells and depleting the monocytes, for example, by centrifugation through a PERCOLL™ gradient or by counterflow centrifugal elutriation.

In another aspect, Tumor infiltrating cells (TILs) are isolated and/or expanded from a tumor, for example by a fragmented, dissected, or enzyme digested tumor biopsy or mass.

A specific subpopulation of T cells, such as CD3+, CD28+, CD4+, CD8+, CD45RA+, and CD45RO+T cells, can be further isolated by positive or negative selection techniques. For example, in one aspect, T cells are isolated by incubation with anti-CD3/anti-CD28-conjugated beads, such as DYNABEADS® M-450 CD3/CD28 T, for a time period sufficient for positive selection of the desired T cells.

In one aspect, the time period is about 30 minutes. In a further aspect, the time period ranges from 30 minutes to 36 hours or longer and all integer values there between. In a further aspect, the time period is at least 1, 2, 3, 4, 5, or 6 hours. In yet another preferred aspect, the time period is 10 to 24 hours. In one aspect, the incubation time period is 24 hours. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain aspects, it may be desirable to perform the selection procedure and use" the "unselected" cells in the activation and exp"nsion proc"ss. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD16, HLA-DR, and CD8. In certain aspects, it may be desirable to enrich for or positively select for regulatory T cells which typically express CD4+, CD25+, CD62Lhi, GITR+, CD137, PD1, TIM3, LAG-3, CD150 and FoxP3+. Alternatively, in certain aspects, T regulatory cells are depleted by anti-CD25 conjugated beads or other similar method of selection.

The methods described herein can include, e.g., selection of a specific subpopulation of immune effector cells, e.g., T cells, that are a T regulatory cell-depleted population, CD25+ depleted cells, using, e.g., a negative selection technique, e.g., described herein. Preferably, the population of T regulatory depleted cells contains less than 30%, 25%, 20%, 15%, 10%, 5%, 4%, 3%, 2%, 1% of CD25+ cells.

A specific subpopulation of chimeric protein effector cells that specifically bind to a target antigen can be enriched for by positive selection techniques. For example, in some embodiments, effector cells are enriched for by incubation with target antigen-conjugated beads for a time period sufficient for positive selection of the desired abTCR effector cells. In some embodiments, the time period is about 30 minutes. In some embodiments, the time period ranges from 30 minutes to 36 hours or longer (including all ranges between these values). In some embodiments, the time period is at least one, 2, 3, 4, 5, or 6 hours. In some embodiments, the time period is 10 to 24 hours. In some embodiments, the incubation time period is 24 hours. For isolation of effector cells present at low levels in the heterogeneous cell population, use of longer incubation times, such as 24 hours, can increase cell yield. Longer incubation times may be used to isolate effector cells in any situation where there are few effector cells as compared to other cell types. The skilled artisan would recognize that multiple rounds of selection can also be used in the context of this invention.

T cells for stimulation can also be frozen after a washing step. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In embodiments described herein, the immune effector cell can be an allogeneic immune effector cell, e.g., T cell or NK cell.

A T cell described herein can be, e.g., engineered such that it does not express a functional HLA on its surface. For example, a T cell described herein, can be engineered such that cell surface expression HLA, e.g., HLA class 1 and/or HLA class II, is downregulated. In some aspects, downregulation of HLA may be accomplished by reducing or eliminating expression of beta-2 microglobulin (B2M).

In some embodiments, the T cell can lack a functional TCR and a functional HLA, e.g., HLA class I and/or HLA class II. Modified T cells that lack expression of a functional TCR and/or HLA can be obtained by any suitable means, including a knock out or knock down of one or more subunit of TCR or HLA. For example, the T cell can include a knock down of TCR and/or HLA using siRNA, shRNA, clustered regularly interspaced short palindromic repeats (CRISPR) transcription-activator like effector nuclease (TALEN), or zinc finger endonuclease (ZFN).

In some embodiments, the allogeneic cell can be a cell which does not expresses or expresses at low levels an inhibitory molecule, e.g. a cell engineered by any method described herein. For example, the cell can be a cell that does not express or expresses at low levels an inhibitory molecule, e.g., that can decrease the ability of a chimeric protein-expressing cell to mount an immune effector response. Examples of inhibitory molecules include PD1, PD-L1, PD-L2, CTLA4, TIM3, CEACAM (e.g., CEACAM-1, CEACAM-3 and/or CEACAM-5), LAGS, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, Ga19, adenosine, and TGFR beta. Inhibition of an inhibitory molecule, e.g., by inhibition at the DNA, RNA or protein level, can optimize a CAR-expressing cell performance. In embodiments, an inhibitory nucleic acid, e.g., an inhibitory nucleic acid, e.g., a dsRNA, e.g., an siRNA or shRNA, a clustered regularly interspaced short palindromic repeats (CRISPR), a transcription-activator like effector nuclease (TALEN), or a zinc finger endonuclease (ZFN), e.g., as described herein, can be used.

T cells may be activated and expanded generally using methods as described, for example, in U.S. Pat. Nos. 6,352,694; 6,534,055; 6,905,680; 6,692,964; 5,858,358; 6,887, 466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention may be expanded by contact with a surface having attached thereto an agent that stimulates a CD3/TCR complex associated signal and a ligand that stimulates a costimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody can be used. Examples of an anti-CD28 antibody include 9.3, B-T3, XR-CD28 (Diaclone, Besancon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol Meth. 227(1-2):53-63, 1999).

In some embodiments, expansion can be performed using flasks or containers, or gas-permeable containers known by those of skill in the art and can proceed for 7 days, 8 days, 9 days, 10 days, 11 days, 12 days, 13 days, or 14 days, about 7 days to about 14 days, about 8 days to about 14 days, about 9 days to about 14 days, about 10 days to about 14 days, about 11 days to about 14 days, about 12 days to about 14 days, or about 13 days to about 14 days. In some embodiments, the second TIL expansion can proceed for about 14 days.

In some embodiments, the expansion can be performed using non-specific T-cell receptor stimulation in the presence of interleukin-2 (IL-2) or interleukin-15 (IL-15). The non-specific T-cell receptor stimulus can include, for example, an anti-CD3 antibody, such as about 30 ng/ml of OKT3, a mouse monoclonal anti-CD3 antibody (commercially available from Ortho-McNeil, Raritan, N.J. or Miltenyi Biotech, Auburn, Calif.) or UHCT-1 (commercially available from BioLegend, San Diego, Calif., USA). Chimeric protein cells can be expanded in vitro by including one or more antigens, including antigenic portions thereof, such as epitope(s), of a cancer, which can be optionally expressed from a vector, such as a human leukocyte antigen A2 (HLA-A2) binding peptide, e.g., 0.3.mu.M MART-1:26-35 (27L) or gp100:209-217 (210M), optionally in the presence of a T-cell growth factor, such as 300 IU/mL IL-2 or IL-15. Other suitable antigens may include, e.g., NY-ESO-1, TRP-1, TRP-2, tyrosinase cancer antigen, MAGE-A3, SSX-2, and VEGFR2, or antigenic portions thereof. Chimeric protein cells may also be rapidly expanded by re-stimulation with the same antigen(s) of the cancer pulsed onto HLA-A2-expressing antigen-presenting cells. Alternatively, the chimeric protein cells can be further stimulated with, e.g., example, irradiated, autologous lymphocytes or with irradiated HLA-A2+ allogeneic lymphocytes and IL-2. In some embodiments, the stimulation occurs as part of the expansion. In some embodiments, the expansion occurs in the presence of irradiated, autologous lymphocytes or with irradiated HLA-A2+ allogeneic lymphocytes and IL-2.

In some embodiments, the cell culture medium comprises IL-2. In some embodiments, the cell culture medium comprises about 1000 IU/mL, about 1500 IU/mL, about 2000 IU/mL, about 2500 IU/mL, about 3000 IU/mL, about 3500 IU/mL, about 4000 IU/mL, about 4500 IU/mL, about 5000 IU/mL, about 5500 IU/mL, about 6000 IU/mL, about 6500 IU/mL, about 7000 IU/mL, about 7500 IU/mL, or about 8000 IU/mL, or between 1000 and 2000 IU/mL, between 2000 and 3000 IU/mL, between 3000 and 4000 IU/mL, between 4000 and 5000 IU/mL, between 5000 and 6000 IU/mL, between 6000 and 7000 IU/mL, between 7000 and 8000 IU/mL, or between 8000 IU/mL of IL-2.

In some embodiments, the cell culture medium comprises OKT3 antibody. In some embodiments, the cell culture medium comprises about 0.1 ng/mL, about 0.5 ng/mL, about 1 ng/mL, about 2.5 ng/mL, about 5 ng/mL, about 7.5 ng/mL, about 10 ng/mL, about 15 ng/mL, about 20 ng/mL, about 25 ng/mL, about 30 ng/mL, about 35 ng/mL, about 40 ng/mL, about 50 ng/mL, about 60 ng/mL, about 70 ng/mL, about 80 ng/mL, about 90 ng/mL, about 100 ng/mL, about 200 ng/mL, about 500 ng/mL, about 1 μg/mL or between 0.1 ng/mL and 1 ng/mL, between 1 ng/mL and 5 ng/mL, between 5 ng/mL and 10 ng/mL, between 10 ng/mL and 20 ng/mL, between 20 ng/mL and 30 ng/mL, between 30 ng/mL and 40 ng/mL, between 40 ng/mL and 50 ng/mL, or between 50 ng/mL and 100 ng/mL of OKT3 antibody.

In some embodiments, a combination of IL-2, IL-7, IL-15, and/or IL-21 are employed as a combination during the expansion. In some embodiments, IL-2, IL-7, IL-15, and/or IL-21 as well as any combinations thereof can be included during the expansion. In some embodiments, a combination of IL-2, IL-15, and IL-21 are employed as a combination during the expansion. In some embodiments, IL-2, IL-15, and IL-21 as well as any combinations thereof can be included.

In some embodiments, the expansion can be conducted in a supplemented cell culture medium comprising IL-2, OKT-3, and antigen-presenting feeder cells.

In some embodiments, the expansion culture media comprises about 500 IU/mL of IL-15, about 400 IU/mL of IL-15, about 300 IU/mL of IL-15, about 200 IU/mL of IL-15, about 180 IU/mL of IL-15, about 160 IU/mL of IL-15, about 140 IU/mL of IL-15, about 120 IU/mL of IL-15, or about 100 IU/mL of IL-15, or about 500 IU/mL of IL-15 to about 100 IU/mL of IL-15, or about 400 IU/mL of IL-15 to about 100 IU/mL of IL-15 or about 300 IU/mL of IL-15 to about 100 IU/mL of IL-15 or about 200 IU/mL of IL-15, or about 180 IU/mL of IL-15.

In some embodiments, the expansion culture media comprises about 20 IU/mL of IL-21, about 15 IU/mL of IL-21, about 12 IU/mL of IL-21, about 10 IU/mL of IL-21, about 5 IU/mL of IL-21, about 4 IU/mL of IL-21, about 3 IU/mL of IL-21, about 2 IU/mL of IL-21, about 1 IU/mL of IL-21, or about 0.5 IU/mL of IL-21, or about 20 IU/mL of IL-21 to about 0.5 IU/mL of IL-21, or about 15 IU/mL of IL-21 to about 0.5 IU/mL of IL-21, or about 12 IU/mL of IL-21 to about 0.5 IU/mL of IL-21, or about 10 IU/mL of IL-21 to about 0.5 IU/mL of IL-21, or about 5 IU/mL of IL-21 to about 1 IU/mL of IL-21, or about 2 IU/mL of IL-21. In some embodiments, the cell culture medium comprises about 1 IU/mL of IL-21, or about 0.5 IU/mL of IL-21.

In some embodiments the antigen-presenting feeder cells (APCs) are PBMCs. In an embodiment, the ratio of chimeric protein cells to PBMCs and/or antigen-presenting cells in the expansion is about 1 to 25, about 1 to 50, about 1 to 100, about 1 to 125, about 1 to 150, about 1 to 175, about 1 to 200, about 1 to 225, about 1 to 250, about 1 to 275, about 1 to 300, about 1 to 325, about 1 to 350, about 1 to 375, about 1 to 400, or about 1 to 500, or between 1 to 50 and 1 to 300, or between 1 to 100 and 1 to 200.

In certain aspects, the primary stimulatory signal and the costimulatory signal for the T cell may be provided by different protocols. For example, the agents providing each signal may be in solution or coupled to a surface. When coupled to a surface, the agents may be coupled to the same su"fac" (i.e., in "cis" formation) or to separate sur"aces" i.e., in "trans" formation). Alternatively, one agent may be coupled to a surface and the other agent in solution. In one aspect, the agent providing the costimulatory signal is bound to a cell surface and the agent providing the primary activation signal is in solution or coupled to a surface. In certain aspects, both agents can be in solution. In one aspect, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one aspect, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the costimulatory signal is an anti-CD28 antibody or antigen-binding fragment thereof; and both agents are co-immobilized to the same bead in equivalent molecular amounts. In one aspect, a 1:1 ratio of each antibody bound to the beads for CD4+ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular aspect an increase of from about 1 to about 3 fold is observed as compared to the expansion observed using a ratio of 1:1. In one aspect, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain aspects of the invention, the ratio of anti CD28 antibody to anti CD3 antibody bound to the beads is greater than 2:1. In one particular aspect, a 1:100 CD3:CD28 ratio of antibody bound to beads is used. In one aspect, a 1:75 CD3:CD28 ratio of antibody bound to beads is used. In a further aspect, a 1:50 CD3:CD28 ratio of antibody bound to beads is used. In one aspect, a 1:30 CD3:CD28 ratio of antibody bound to beads is used. In one preferred aspect, a 1:10 CD3:CD28 ratio of antibody bound to beads is used. In one aspect, a 1:3 CD3:CD28 ratio of antibody bound to the beads is used. In yet one aspect, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain aspects the ratio of cells to particles ranges from 1:100 to 100:1 and any integer values in-between and in further aspects the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one aspect, a ratio of particles to cells of 1:1 or less is used. In one particular aspect, a preferred particle: cell ratio is 1:5. In further aspects, the ratio of particles to cells can be varied depending on the day of stimulation. For example, in one aspect, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular aspect, the ratio of particles to cells is 1:1 on the first day of stimulation and adjusted to 1:5 on the third and fifth days of stimulation. In one aspect, particles are added on a daily or every other day basis to a final ratio of 1:1 on the first day, and 1:5 on the third and fifth days of stimulation. In one aspect, the ratio of particles to cells is 2:1 on the first day of stimulation and adjusted to 1:10 on the third and fifth days of stimulation. In one aspect, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type. In one aspect, the most typical ratios for use are in the neighborhood of 1:1, 2:1 and 3:1 on the first day.

In further aspects of the present invention, the cells, such as T cells, are combined with agent-coated beads, the beads and the cells are subsequently separated, and then the cells are cultured. In an alternative aspect, prior to culture, the agent-coated beads and cells are not separated but are cultured together. In a further aspect, the beads and cells are first concentrated by application of a force, such as a magnetic force, resulting in increased ligation of cell surface markers, thereby inducing cell stimulation.

Viral- and non-viral-based genetic engineering tools can be used to generate chimeric protein cells, including without limitation T cells, NK cells resulting in permanent or transient expression of therapeutic genes. Retrovirus-based gene delivery is a mature, well-characterized technology, which has been used to permanently integrate CARs into the host cell genome (Scholler J., e.g. Decade-long safety and function of retroviral-modified chimeric antigen receptor T cells. Sci. Transl. Med. 2012; 4:132ra53; Rosenberg S. A. et al., Gene transfer into humans—immunotherapy of patients with advanced melanoma, using tumor-infiltrating lymphocytes modified by retroviral gene transduction. N. Engl. J. Med.

Non-viral DNA transfection methods can also be used. For example, Singh et al describes use of the Sleeping Beauty (SB) transposon system developed to engineer CAR T cells (Singh H., et al., Redirecting specificity of T-cell populations for CD19 using the Sleeping Beauty system. Cancer Res. 2008; 68:2961-2971) and is being used in clinical trials (see e.g., ClinicalTrials.gov: NCT00968760 and NCT01653717). The same technology is applicable to engineer chimeric protein cells.

Multiple SB enzymes have been used to deliver transgenes. Mates describes a hyperactive transposase (SB100X) with approximately 100-fold enhancement in efficiency when compared to the first-generation transposase. SB100× supported 35-50% stable gene transfer in human CD34(+) cells enriched in hematopoietic stem or progenitor cells.

(Mates L. et al., Molecular evolution of a novel hyperactive Sleeping Beauty transposase enables robust stable gene transfer in vertebrates. Nat. Genet. 2009; 41:753-761) and multiple transgenes can be delivered from multicistronic single plasmids (e.g., Thokala R. et al., Redirecting specificity of T cells using the Sleeping Beauty system to express chimeric antigen receptors by mix-and-matching of VL and VH domains targeting cD123+ tumors. PLoS ONE. 2016; 11:e0159477) or multiple plasmids (e.g., Hurton L. V. et al., Tethered IL-15 augments antitumor activity and promotes a stem-cell memory subset in tumor-specific T cells. Proc. Natl. Acad. Sci. USA. 2016; 113:E7788-E7797). Such systems are used with chimeric proteins of the invention.

Morita et al, describes the piggyBac transposon system to integrate larger transgenes (Morita D. et al., Enhanced expression of anti-CD19 chimeric antigen receptor in piggyBac transposon-engineered T cells. Mol. Ther. Methods Clin. Dev. 2017; 8:131-140) Nakazawa et al. describes use of the system to generate EBV-specific cytotoxic T-cells expressing HER2-specific chimeric antigen receptor (Nakazawa Y et al, PiggyBac-mediated cancer immunotherapy using EBV-specific cytotoxic T-cells expressing HER2-specific chimeric antigen receptor. Mol. Ther. 2011; 19:2133-2143). Manuri et al used the system to generate CD-19 specific T cells (Manuri P. V. R. et al., piggyBac transposon/transposase system to generate CD19-specific T cells for the treatment of B-lineage malignancies. Hum. Gene Ther. 2010; 21:427-437).

Transposon technology is easy and economical. One potential drawback is the longer expansion protocols currently employed may result in T cell differentiation, impaired activity and poor persistence of the infused cells. Monjezi et al describe development minicircle vectors that minimize these difficulties through higher efficiency integrations (Monjezi R. et al., Enhanced CAR T-cell engineering using non-viral Sleeping Beauty transposition from minicircle vectors. Leukemia. 2017; 31:186-194). These transposon technologies can be used for chimeric proteins of the invention.

The present invention also relates to a pharmaceutical composition containing a vector or a chimeric protein expressing cell of the invention together with a pharmaceutically acceptable carrier, diluent or excipient, and optionally one or more further pharmaceutically active polypeptides and/or compounds.

In some embodiments, a pharmaceutical composition is provided comprising a chimeric protein described above and a pharmaceutically acceptable carrier. In some embodiments, a pharmaceutical composition is provided comprising a nucleic acid encoding a chimeric protein according to any of the embodiments described above and a pharmaceutically acceptable carrier. In some embodiments, a pharmaceutical composition is provided comprising an effector cell expressing a chimeric protein described above and a pharmaceutically acceptable carrier. Such a formulation may, for example, be in a form suitable for intravenous infusion.

As used herein, by "pharmaceutically acceptable" or "pharmacologically compatible" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

An aspect of the invention provides a population of modified T cells expressing a recombinant chimeric protein. A suitable population may be produced by a method described above.

The population of modified T cells may be for use as a medicament. For example, a population of modified T cells as described herein may be used in cancer immunotherapy therapy, for example adoptive T cell therapy.

Other aspects of the invention provide the use of a population of modified T cells as described herein for the manufacture of a medicament for the treatment of cancer, a population of modified T cells as described herein for the treatment of cancer, and a method of treatment of cancer may comprise administering a population of modified T cells as described herein to an individual in need thereof.

The population of modified T cells may be autologous i.e. the modified T cells were originally obtained from the same individual to whom they are subsequently administered (i.e. the donor and recipient individual are the same). A suitable population of modified T cells for administration to the individual may be produced by a method comprising providing an initial population of T cells obtained from the individual, modifying the T cells to express a cAMP PDE or fragment thereof and an antigen receptor which binds specifically to cancer cells in the individual, and culturing the modified T cells.

The population of modified T cells may be allogeneic i.e. the modified T cells were originally obtained from a different individual to the individual to whom they are subsequently administered (i.e. the donor and recipient individual are different). The donor and recipient individuals may be HLA matched to avoid GVHD and other undesirable immune effects. A suitable population of modified T cells for administration to a recipient individual may be produced by a method comprising providing an initial population of T cells obtained from a donor individual, modifying the T cells to express a chimeric protein which binds specifically to cancer cells in the recipient individual, and culturing the modified T cells.

Following administration of the modified T cells, the recipient individual may exhibit a T cell mediated immune response against cancer cells in the recipient individual. This may have a beneficial effect on the cancer condition in the individual.

Cancer conditions may be characterized by the abnormal proliferation of malignant cancer cells and may include leukaemias, such as AML, CML, ALL and CLL, lymphomas, such as Hodgkin lymphoma, non-Hodgkin lymphoma and multiple myeloma, and solid cancers such as sarcomas, skin cancer, melanoma, bladder cancer, brain cancer, breast cancer, uterus cancer, ovary cancer, prostate cancer, lung cancer, colorectal cancer, cervical cancer, liver cancer, head and neck cancer, oesophageal cancer, pancreas cancer, renal cancer, adrenal cancer, stomach cancer, testicular cancer, cancer of the gall bladder and biliary tracts, thyroid cancer, thymus cancer, cancer of bone, and cerebral cancer, as well as cancer of unknown primary (CUP).

Cancer cells within an individual may be immunologically distinct from normal somatic cells in the individual (i.e. the cancerous tumor may be immunogenic). For example, the cancer cells may be capable of eliciting a systemic immune response in the individual against one or more antigens expressed by the cancer cells. The tumor antigens that elicit the immune response may be specific to cancer cells or may be shared by one or more normal cells in the individual.

An individual suitable for treatment as described above may be a mammal, such as a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orangutan, gibbon), or a human.

In preferred embodiments, the individual is a human. In other preferred embodiments, non-human mammals, especially mammals that are conventionally used as models for demonstrating therapeutic efficacy in humans (e.g. murine, primate, porcine, canine, or rabbit animals) may be employed.

The term "therapeutically effective amount" refers to an amount of a chimeric protein or composition comprising a chimeric protein as disclosed herei", eff"ctive to "treat" a disease or disorder in an individual. In the case of cancer, the therapeutically effective amount of a chimeric protein or composition comprising a chimeric protein as disclosed herein can reduce the number of cancer cells; reduce the tumor size or weight; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent a chimeric protein or composition comprising a chimeric protein as disclosed herein can prevent growth and/or kill existing cancer cells, it can be cytostatic and/or cytotoxic. In some embodiments, the therapeutically effective amount is a growth inhibitory amount. In some embodiments, the therapeutically effective amount is an amount that improves progression free survival of a patient. In the case of infectious disease, such as viral infection, the therapeutically effective amount of a chimeric protein or composition comprising a chimeric protein as disclosed herein can reduce the number of cells infected by the pathogen; reduce the production or release of pathogen-derived antigens; inhibit (i.e., slow to some extent and preferably stop) spread of the pathogen to uninfected cells; and/or relieve to some extent one or more symptoms associated with the infection. In some embodiments, the therapeutically effective amount is an amount that extends the survival of a patient.

Cells, including T and NK cells, expressing chimeric proteins for use in the methods of the present may either be created ex vivo eithe' from a patient's own peripheral blood (autologous), or in the setting of a haematopoietic stem cell transplant from donor peripheral blood (allogenic), or peripheral blood from an unconnected donor (allogenic). Alternatively, T-cells or NK cells may be derived from ex-vivo differentiation of inducible progenitor cells or embryonic progenitor cells to T-cells or NK cells. In these instances, T-cells expressing a chimeric protein and, optionally, a CAR and/or TCR, are generated by introducing DNA or RNA coding for the chimeric protein and, optionally, a CAR and/or TCR, by one of many means including transduction with a viral vector, transfection with DNA or RNA.

T or NK cells expressing a chimeric protein of the present invention and, optionally, expressing a TCR and/or CAR may be used for the treatment of haematological cancers or solid tumors.

A method for the treatment of disease relates to the therapeutic use of a vector or cell, including a T or NK cell, of the invention. In this respect, the vector, or T or NK cell may be administered to a subject having an existing disease or condition in order to lessen, reduce or improve at least one symptom associated with the disease and/or to slow down, reduce or block the progression of the disease. The method of the invention may cause or promote T-cell mediated killing of cancer cells. The vector, or T or NK cell according to the present invention may be administered to a patient with one or more additional therapeutic agents. The one or more additional therapeutic agents can be co-administered to the patient. By "co-administering" is meant administering one or more additional therapeutic agents and the vector, or T or NK cell of the present invention sufficiently close in time such that the vector, or T or NK cell can enhance the effect of one or more additional therapeutic agents, or vice versa. In this regard, the vectors or cells can be administered first and the one or more additional therapeutic agents can be administered second, or vice versa. Alternatively, the vectors or cells and the one or more additional therapeutic agents can be administered simultaneously. One co-administered therapeutic agent that may be useful is IL-2, as this is currently used in existing cell therapies to boost the activity of administered cells. However, IL-2 treatment is associated with toxicity and tolerability issues.

In some embodiments, the addition of the engineered protein to a subject induces cytokine secretion. In some embodiments, the addition of CoStAR to a subject induces cytokine secretion. In some embodiments, the cytokine secretion lowers cytokine levels in the subject, including but not limited to IL-2. In some embodiments, the cytokine secretion following CoStAR exposure results in no detectable IL-2 in the subject. In some embodiments, the addition of the engineered protein to a subject reduces or eliminates the need for administration of exogenous IL-2. In some embodiments, the addition of the CoStAR to a subject reduces or eliminates the need for administration of exogenous IL-2.

In some embodiments, other mechanisms of action are involved in the killing of tumor cells apart from the direct effect of CoStAR. In some embodiments, secretion of cytokines and/or proliferation are evaluated. In some embodiments, tumor cell killing potency is characterized by flow cytometry to enumerate T cells and target cells and plate-based fluorescence or luminescence to measure percent killing. In some embodiments, cytokine secretion potency is characterized at the single cell level by flow cytometry and ELISA/MSD to characterize the population. In some embodiments, proliferation potency is determined by flow cytometry to characterize the population. In some embodiments, TIL potency may be determined by additional analytes, memory phenotype, cytotoxicity using cell lines, cytotoxicity using a patient specific tumor, a cytokine panel, cell proliferation and/or cellular composition.

As mentioned, for administration to a patient, the chimeric protein effector cells can be allogeneic or autologous to the patient. In some embodiments, allogeneic cells are further genetically modified, for example by gene editing, so as to minimize or prevent GVHD and/or a patient's immune response against the chimeric protein cells.

The chimeric protein effector cells are used to treat cancers and neoplastic diseases associated with a target antigen. Cancers and neoplastic diseases that may be treated using any of the methods described herein include tumors that are not vascularized, or not yet substantially vascularized, as well as vascularized tumors. The cancers may comprise non-solid tumors (such as hematological tumors, for example, leukemias and lymphomas) or may comprise solid tumors. Types of cancers to be treated with the chimeric protein effector cells of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, l'mphoma, Hodgkin's dise'se, non-Hodgkin's lymphoma (indolent and high grade forms), multiple myeloma, plasmacyt'ma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include adrenocortical carcinoma, cholangiocarcinoma, fibrosarcoma, myxosarcoma, liposarcoma, chondrosarcoma, osteosarcoma, and other sarcomas, synovioma, mes'thelioma, Ewing's tumor, leiomyosarcoma, rhabdomyosarcoma, colon carcinoma, stomach cancer, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, thyroid cancer (e.g., medullary thyroid carcinoma and papillary thyroid carcinoma), pheochromocytomas sebaceous gland carcinoma, papillary carcinoma, papillary adenocarcinomas, medullary carcinoma, bronchogenic carcinoma, renal cell carcinoma, hepatoma, bile duct carcinoma, chorio'arcinoma, Wilms' tumor, cervical cancer (e.g., cervical carcinoma and pre-invasive cervical dysplasia), colorectal cancer, cancer of the anus, anal canal, or anorectum, vaginal cancer, cancer of the vulva (e.g., squamous cell carcinoma, intraepithelial carcinoma, adenocarcinoma, and fibrosarcoma), penile cancer, oropharyngeal cancer, esophageal cancer, head cancers (e.g., squamous cell carcinoma), neck cancers (e.g., squamous cell carcinoma), testicular cancer (e.g., seminoma, teratoma, embryonal carcinoma, teratocarcinoma, choriocarcinoma, sarcoma, Leydig cell tumor, fibroma, fibroadenoma, adenomatoid tumors, and lipoma), bladder carcinoma, kidney cancer, melanoma, cancer of the uterus (e.g., endometrial carcinoma), urothelial cancers (e.g., squamous cell carcinoma, transitional cell carcinoma, adenocarcinoma, ureter cancer, and urinary bladder cancer), and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

When "an immunologically effective amount," "an anti-tumor effective amount," "a tumor-inhibiting effective amount," or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, in some instances $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988).

A chimeric protein-expressing cell described herein may be used in combination with other known agents and therapie". Administered" "in combination", as used herein, means that two (or more) different treatments are delivered to the subject during the cours' of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referr"d to herein"s "s"multaneous" or "con"urrent delivery". In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

A chimeric protein-expressing cell described herein and the at least one additional therapeutic agent can be administered simultaneously, in the same or in separate compositions, or sequentially. For sequential administration, the CAR-expressing cell described herein can be administered first, and the additional agent can be administered second, or the order of administration can be reversed.

The chimeric protein therapy and/or other therapeutic agents, procedures or modalities can be administered during periods of active disorder, or during a period of remission or less active disease. The chimeric protein therapy can be administered before the other treatment, concurrently with the treatment, post-treatment, or during remission of the disorder.

When administered in combination, the therapy and the additional agent (e.g., second or third agent), or all, can be administered in an amount or dose that is higher, lower or the same than the amount or dosage of each agent used individually, e.g., as a monotherapy. In some embodiments, the administered amount or dosage of the chimeric protein therapy, the additional agent (e.g., second or third agent), or all, is lower (e.g., at least 20%, at least 30%, at least 40%, or at least 50%) than the amount or dosage of each agent used individually, e.g., as a monotherapy. In other embodiments, the amount or dosage of the chimeric protein therapy, the additional agent (e.g., second or third agent), or all, that results in a desired effect (e.g., treatment of cancer) is lower (e.g., at least 20%, at least 30%, at least 40%, or at least 50% lower) than the amount or dosage of each agent used individually, e.g., as a monotherapy, required to achieve the same therapeutic effect.

In further aspects, a chimeric protein-expressing cell described herein may be used in a treatment regimen in combination with surgery, chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludarabine, cyclosporin, FK506, rapamycin, mycophenolic acid, steroids, FR901228, cytokines, and irradiation, peptide vaccine, such as that described in Izumoto et al. 2008 J Neurosurg 108:963-971.

In certain instances, compounds of the present invention are combined with other therapeutic agents, such as other anti-cancer agents, anti-allergic agents, anti-nausea agents (or anti-emetics), pain relievers, cytoprotective agents, and combinations thereof.

In one embodiment, a chimeric protein-expressing cell described herein can be used in combination with a chemotherapeutic agent. Exemplary chemotherapeutic agents include an anthracycline (e.g., doxorubicin (e.g., liposomal doxorubicin)), a vinca alkaloid (e.g., vinblastine, vincristine, vindesine, vinorelbine), an alkylating agent (e.g., cy53acarbazineide, decarbazine, melphalan, ifosfamide, temozolomide), an immune cell antibody (e.g., alemtuzamab, gemtuzumab, rituximab, ofatumumab, tositumomab, brentuximab), an antimetabolite (including, e.g., folic acid antagonists, pyrimidine analogs, purine analogs and adenosine deaminase inhibitors (e.g., fludarabine)), an mTOR inhibitor, a TNFR glucocorticoid induced TNFR related protein (GITR) agonist, a proteasome inhibitor (e.g., aclacinomycin A, gliotoxin or bortezomib), an immunomodulator such as thalidomide or a thalidomide derivative (e.g., lenalidomide).

General Chemotherapeutic agents considered for use in combination therapies include busulfan (Myleran®), busulfan injection (Busulfex®), cladribine (Leustatin®), cyclophosphamide (Cytoxan® or Neosar®), cytarabine, cytosine arabinoside (Cytosar-U®), cytarabine liposome injection (DepoCyt®), daunorubicin hydrochloride (Cerubidine®), daunorubicin citrate liposome injection (DaunoXome®), dexamethasone, doxorubicin hydrochloride (Adriamycin®, Rubex®), etoposide (Vepesid®), fludarabine phosphate (Fludara®), hydroxyurea (Hydrea®), Idarubicin (Idamycin®), mitoxantrone (Novantrone®), Gemtuzumab Ozogamicin (Mylotarg®).

In embodiments, general chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

Treatments can be evaluated, for example, by tumor regression, tumor weight or size shrinkage, time to progression, duration of survival, progression free survival, overall response rate, duration of response, quality of life, protein expression and/or activity. Approaches to determining efficacy of the therapy can be employed, including for example, measurement of response through radiological imaging.

TCR Incorporated Antigen Agnostic Receptors (TIAARs)

Table 2 provides exemplary, non-limiting examples of components of TCR incorporated antigen agnostic receptors (TIAARs) of the invention. Table 3 shows exemplary arrangements of the components.

TABLE 2

TCR incorporated antigen agnostic receptor (TIAAR) components

| Code | Signal peptide | Tag | ECD_TMD | ICD | Costim |
|---|---|---|---|---|---|
| pIB1026 | CD3D | Myc | CD3D | N/A | CD28-CD40 |
| pIB1027 | CD3E | FLAG | CD3E | N/A | CD28-CD40 |
| pIB1028 | CD3G | Myc | CD3G | N/A | CD28-CD40 |
| pIB1029 | CD3Z | Myc IC | CD3Z | N/A | CD28-CD40 |
| pIB1030 | CD8A | Myc | hTRDC | N/A | CD28-CD40 |
| pIB1031 | CD8A | FLAG | hTRGC1 | N/A | CD28-CD40 |
| pIB1032 | CD8A | Myc | mTRAC | N/A | CD28-CD40 |
| pIB1033 | CD8A | FLAG | mTRBC1 | N/A | CD28-CD40 |
| pIB1046 | CD8A x2 | Myc and FLAG | hTRDC_hTRGC1 | N/A | CD28-CD40 |
| pIB1047 | CD8A x2 | Myc and FLAG | mTRAC_mTRBC1 | N/A | CD28-CD40 |
| pIB1048 | CD3D and CD3E | Myc and FLAG | CD3D_CD3E | N/A | CD28-CD40 |
| pIB1049 | CD3G and CD3E | Myc and FLAG | CD3G_CD3E | N/A | CD28-CD40 |

TABLE 2-continued

TCR incorporated antigen agnostic receptor (TIAAR) components

| Code | Signal peptide | Tag | ECD_TMD | ICD | Costim |
|---|---|---|---|---|---|
| pIB1050 | CD3D and CD3E | Myc and FLAG | CD3D_CD3E | CD3D_CD3E | CD28-CD40 |
| pIB1051 | CD3D and CD3E | Myc and FLAG | CD3D_CD3E | CD3D_CD3E | N/A |
| pIB1052 | CD3D and CD3E | Myc and FLAG | CD3D_CD3E | N/A | N/A |
| pIB1053 | CD3G and CD3E | Myc and FLAG | CD3G_CD3E | CD3G_CD3E | CD28-CD40 |
| pIB1054 | CD3G and CD3E | Myc and FLAG | CD3G_CD3E | CD3G_CD3E | N/A |
| pIB1055 | CD3G and CD3E | Myc and FLAG | CD3G_CD3E | N/A | N/A |
| pIB1056 | CD3Z | Myc IC | CD3Z | CD3Z | CD28-CD40 |
| pIB1057 | CD3Z | Myc IC | CD3Z | CD3Z | N/A |
| pIB1058 | CD3Z | Myc IC | CD3Z | N/A | N/A |
| pIB1059 | CD3Z | Myc IC | CD3Z | CD3Z (x2) | CD28-CD40 |
| pIB1060 | CD3Z | Myc IC | CD3Z | CD3Z (x2) | N/A |
| pIB1061 | CD3Z | Myc IC | CD3Z | CD3Z (x2) | CD28-CD40 (swaped) |
| pIB1062 | CD3Z | Myc IC | CD3Z | CD3Z | CD28-CD40 (swaped) |
| pIB1063 | CD80 | Myc | CD80 | CD80 | N/A |
| pIB1064 | no signal peptide | Myc IC | N/A | Lck | N/A |
| pIB1065 | no signal peptide | Myc IC | N/A | Lck (Y505F) | N/A |
| pIB1066 | CD80 | Myc | CD80 | Lck | N/A |
| pIB1067 | CD80 | Myc | CD80 | Lck | CD28-CD40 |
| pIB1068 | CD80 | Myc | CD80 | CD80_Lck (Y505F) | N/A |
| pIB1069 | CD80 | Myc | CD80 | CD80_Lck (Y505F) | CD28-CD40 |
| pIB1070 | CD8A | Myc | LAT | LAT | N/A |
| pIB1071 | CD8A | Myc | LAT | LAT | CD28-CD40 |
| pIB1072 | CD4 | Myc | CD4 | CD4 | CD28-CD40 |
| pIB1073 | CD4 | Myc | CD4 | CD4 | CD28-CD40 |
| pIB1074 | CD8A and CD8B | Myc and FLAG | CD8A and CD8B | CD8A and CD8B | N/A |
| pIB1075 | CD8A and CD8B | Myc and FLAG | CD8A and CD8B | CD8A and CD8B | CD28-CD40 |

TABLE 3

TCR incorporated antigen agnostic receptors (TIAARs)

| Code | Description |
|---|---|
| pIB1026 | CD3D_CD3D_CD28CD40 |
| pIB1027 | CD3E_CD3E_CD28CD40 |
| pIB1028 | CD3G_CD3G_CD28CD40 |
| pIB1029 | CD3Z_CD3Z_CD28CD40_Myc |
| pIB1030 | CD8A_hTRDC_CD28CD40 |
| pIB1031 | CD8A_hTRGC1_CD28CD40 |
| pIB1032 | CD8A_mTRAC_CD28CD40 |
| pIB1033 | CD8A_mTRBC1_CD28CD40 |
| pIB1046 | CD8A_hTRDC_CD28CD40-T2A-CD8a_hTRGC1_CD28CD40 |
| pIB1047 | CD8A_mTRAC_CD28CD40-T2A-CD8A_mTRBC1_CD28CD40 |
| pIB1048 | CD3D_CD3D_CD28CD40-T2A-CD3E_CD3E_CD28CD40 |
| pIB1049 | CD3G_CD3G_CD28CD40-T2A-CD3E_CD3E_CD28CD40 |
| pIB1050 | CD3D_CD3D_CD3D (ICD)_CD28CD40-T2A-CD3E_CD3E_CD3E (ICD)_CD28CD40 |
| pIB1051 | CD3D_CD3D_CD3D ICD-T2A-CD3E_CD3E_CD3E ICD |
| pIB1052 | CD3D_CD3D (control)-T2A-CD3E_CD3E (control) |
| pIB1053 | CD3G_CD3G_CD3G (ICD)_CD28CD40-T2A-CD3E_CD3E_CD3E (ICD)_CD28CD40 |
| pIB1054 | CD3G_CD3G_CD3G ICD-T2A-CD3E_CD3E_CD3E ICD |
| pIB1055 | CD3G_CD3G (control)-T2A-CD3E_CD3E (control) |
| pIB1056 | CD3z _CD3z_CD3z ICD _CD28CD40_Myc |
| pIB1057 | CD3z _CD3z_CD3z ICD_Myc |
| pIB1058 | CD3z _CD3z (control) |
| pIB1059 | CD3Z_CD3Z_CD3Z ICD (duplicating CD3z endodomain-6 ITAMs)_CD28CD40_Myc |

TABLE 3-continued

TCR incorporated antigen agnostic receptors (TIAARs)

| Code | Description |
|---|---|
| pIB1060 | CD3Z_CD3Z_CD3Z ICD (duplicating CD3z endodomain-6 ITAMs)_Myc |
| pIB1061 | CD3Z_CD3Z_CD28CD40_CD3Z (6 ITAMs)_Myc |
| pIB1062 | CD3Z_CD3Z_CD28CD40_CD3Z ICD_Myc |
| pIB1063 | CD80 (control) |
| pIB1064 | Lck (control) |
| pIB1065 | Lck (Y505F) (control) |
| pIB1066 | CD80_Lck |
| pIB1067 | CD80_Lck_CD28CD40 |
| pIB1068 | CD80_Lck (Y505F) |
| pIB1069 | CD80_Lck (Y505F)_CD28CD40 |
| pIB1070 | LAT (control) |
| pIB1071 | LAT_C28CD40 |
| pIB1072 | CD4 control |
| pIB1073 | CD4_CD28_CD40 |
| pIB1074 | CD8 control |
| pIB1075 | CD8_CD28_CD40 |

Constitutive Costimulatory Proteins

Table 4 provides exemplary, non-limiting examples of components of constitutive costimulatory proteins of the invention. Table 5 shows the exemplary arrangements of the components.

TABLE 4

Constitutively stimulating antigen agnostic receptor (C-SAAR) components

| Code | Signal peptide | Tag | ECD_TMD | Costim |
|---|---|---|---|---|
| pIB1076 | CD8A | Myc | LZ (cFos)_EGFR | CD28-CD40 |
| pIB1077 | CD8A | Myc | LZ (cFos)_CD28 | CD28-CD40 |
| pIB1078 | CD8A | Myc | LZ (cJun)_EGFR | CD28-CD40 |
| pIB1079 | CD8A | Myc | LZ (cJun)_CD28 | CD28-CD40 |
| pIB1080 | CD8A | Myc | LZ (c/EBP)_EGFR | CD28-CD40 |
| pIB1081 | CD8A | Myc | LZ (c/EBP)_CD28 | CD28-CD40 |
| pIB1103 | GpA | Myc | GpA ECD_TMD | CD28-CD40 |
| pIB1104 | GpA | Myc | GpA TMD | CD28-CD40 |
| pIB1105 | EPOR | Myc | EPOR ECD_TMD | CD28-CD40 |
| pIB1106 | EPOR | Myc | EPOR TMD | CD28-CD40 |
| pIB1107 | TPOR | Myc | TPOR ECD_TMD | CD28-CD40 |
| pIB1108 | TPOR | Myc | TPOR TMD | CD28-CD40 |
| pIB1109 | TPOR | Myc | TPOR ECD_TMD (S505N) | CD28-CD40 |
| pIB1110 | TPOR | Myc | TPOR TMD (S505N) | CD28-CD40 |
| pIB1111 | TPOR | Myc | TPOR ECD_TMD (W515K) | CD28-CD40 |
| pIB1112 | TPOR | Myc | TPOR TMD (W515K) | CD28-CD40 |
| pIB1113 | TPOR | Myc | TPOR ECD_TMD (H499L) | CD28-CD40 |
| pIB1114 | TPOR | Myc | TPOR TMD (H499L) | CD28-CD40 |
| pIB1115 | TPOR | Myc | TPOR ECD_TMD (S505N-W515K) | CD28-CD40 |
| pIB1116 | TPOR | Myc | TPOR TMD (S505N-W515K) | CD28-CD40 |
| pIB1117 | TPOR | Myc | TPOR ECD_TMD (H499Y-S505N) | CD28-CD40 |
| pIB1118 | TPOR | Myc | TPOR TMD (H499Y-S505N) | CD28-CD40 |
| pIB1119 | TPOR | Myc | TPOR ECD_TMD (L498W-H499C) | CD28-CD40 |
| pIB1120 | TPOR | Myc | TPOR TMD (L498W-H499C) | CD28-CD40 |
| pIB1025 | CD8a | Myc | CD28 | CD28-CD40 |
| pIB1179 | CD8a | N/A | IgG1 + CD28TM | CD28-CD40 |
| pIB1180 | CD8a | N/A | IgG1mut + CD28TM | CD28-CD40 |
| pIB1181 | CD8a | N/A | IgG2 + CD28TM | CD28-CD40 |
| pIB1182 | CD8a | N/A | IgG3 + CD28TM | CD28-CD40 |
| pIB1183 | CD8a | N/A | IgG4 + CD28TM | CD28-CD40 |
| pIB1184 | CD8a | N/A | IgG4mut + CD28TM | CD28-CD40 |
| pIB1185 | CD8a | N/A | IgG1 + CD28 stalk/TM | CD28-CD40 |
| pIB1186 | CD8a | N/A | IgG1mut + CD28 stalk/TM | CD28-CD40 |
| pIB1187 | CD8a | N/A | IgG2 + CD28 stalk/TM | CD28-CD40 |
| pIB1188 | CD8a | N/A | IgG3 + CD28 stalk/TM | CD28-CD40 |
| pIB1189 | CD8a | N/A | IgG4 + CD28 stalk/TM | CD28-CD40 |
| pIB1190 | CD8a | N/A | IgG4mut + CD28 stalk/TM | CD28-CD40 |

TABLE 5

C-SAAR Proteins

| Code | Description |
|---|---|
| pIB1076 | LZ (cFos)-EGFRTM/JMD-CD28-CD40 |
| pIB1077 | LZ (cFos)-CD28TM-CD28-CD40 |
| pIB1078 | LZ (cJun)-EGFRTM/JMD-CD28-CD40 |
| pIB1079 | LZ (cJun)-CD28TM-CD28-CD40 |
| pIB1080 | LZ (c/EBP)-EGFRTM/JMD-CD28-CD40 |
| pIB1081 | LZ (c/EBP)-CD28TM-CD28-CD40 |
| pIB1103 | GpA ECD-TMD-CD28-CD40 |
| pIB1104 | GpA TMD-CD28-CD40 |
| pIB1105 | EpoR ECD-TMD-CD28-CD40 |
| pIB1106 | EpoR TMD-CD28-CD40 |
| pIB1107 | TPO ECD-TPO (WT) TMD-CD28-CD40 |
| pIB1108 | TPO (WT) TMD-CD28-CD40 |
| pIB1109 | TPO ECD-TPO (S505N) TMD-CD28-CD40 |
| pIB1110 | TPO (S505N) TMD-CD28-CD40 |

TABLE 5-continued

C-SAAR Proteins

| Code | Description |
|---|---|
| pIB1111 | TPO ECD-TPO (W515K) TMD-CD28-CD40 |
| pIB1112 | TPO (W515K) TMD-CD28-CD40 |
| pIB1113 | TPO ECD-TPO (H499L) TMD-CD28-CD40 |
| pIB1114 | TPO (H499L) TMD-CD28-CD40 |
| pIB1115 | TPO ECD-TPO (S505N-W515K) TMD-CD28-CD40 |
| pIB1116 | TPO (S505N-W515K) TMD-CD28-CD40 |
| pIB1117 | TPO ECD-TPO (H499Y-S505N) TMD-CD28-CD40 |
| pIB1118 | TPO (H499Y-S505N) TMD-CD28-CD40 |
| pIB1119 | TPO ECD-TPO (L498W-H499C) TMD-CD28-CD40 |
| pIB1120 | TPO (L498W-H499C) TMD-CD28-CD40 |
| pIB1025 | CD28 TM_CD28_CD40 |
| pIB1179 | IICH2CH3)-CD28(TM)-CD28(CoStim)-CD40(CoStim) |
| pIB1180 | IgG1ICH3, mutant)-CD28(TM)-CD28(CoStim)-CD40(CoStim) |
| IIB1182 | IgG3(CH2CH3)-CD28(TM)-CD28(CoStim)-CD40(CoI) |
| IpIB1184 | IgG4(CH2CH3, mutant)-CD28(TM)-CD28(CoStim)-CD40(CoStim) |
| pIB1185 | IgG1(CH2CH3)-CD28(Stalk + TM)-CD28(CoStim)-CD40(CoStim) |
| pIB1186 | IgG1(CH2CH3, mutant)-CD28(Stalk + TM)-CD28(CoStim)-CD40(CoStim) |
| pIB1187 | IgG2(CH2CH3)-CD28(Stalk + TM)-CD28(CoStim)-CD40(CoStim) |
| pIB1188 | IgG3(CH2CH3)-CD28(Stalk + TM)-CD28(CoStim)-CD40(CoStim) |
| pIB1189 | IgG4(CH2CH3)-CD28(Stalk + TM)-CD28(CoStim)-CD40(CoStim) |
| pIB1190 | IgG4(CH2CH3, mutant)-CD28(Stalk + TM)-CD28(CoStim)-CD40(CoStim) |

Inducible Costimulatory Receptors

Table 6 provides exemplary, non-limiting examples of inducible costimulatory receptors of the invention. Table 7 shows exemplary arrangements of the components.

TABLE 6

Inducible costimulatory protein components

| Code | Signal peptide | Tag | ECD_TMD | ICD | Costim |
|---|---|---|---|---|---|
| pIB1082 | EGFR | Myc | EGFR | N/A | CD28-CD40 |
| pIB1083 | EGFR | Myc | EGFR (domain IV) | N/A | CD28-CD40 |
| pIB1084 | EGFR | Myc | EGFR (623-668) | N/A | CD28-CD40 |
| pIB1085 | Her2 | Myc | Her2 | N/A | CD28-CD40 |
| pIB1086 | Her2 | Myc | Her2 (V659E) | N/A | CD28-CD40 |
| pIB1087 | Her2 | Myc | Her2 (V660D) | N/A | CD28-CD40 |
| pIB1088 | Her2 | Myc | Her2 (V660R) | N/A | CD28-CD40 |
| pIB1089 | Her2 | Myc | Her2 domain IV_TMD | N/A | CD28-CD40 |
| pIB1090 | Her2 | Myc | Her2 domain IV_TMD (V659E) | N/A | CD28-CD40 |
| pIB1091 | Her2 | Myc | Her2 domain IV_TMD (G660D) | N/A | CD28-CD40 |
| pIB1092 | Her2 | Myc | Her2 domain IV_TMD (G660R) | N/A | CD28-CD40 |
| pIB1093 | Her2 | Myc | Her2 TMD | N/A | CD28-CD40 |
| pIB1094 | Her2 | Myc | Her2 TMD (V659E) | N/A | CD28-CD40 |
| pIB1095 | Her2 | Myc | Her2 TMD (G660D) | N/A | CD28-CD40 |
| pIB1096 | Her2 | Myc | Her2 TMD (G660R) | N/A | CD28-CD40 |
| pIB1097 | CD8A | Myc | A30514 VH_VL | N/A | CD28-CD40 |
| pIB1098 | CD8A | Myc | A30514 VL_VH | N/A | CD28-CD40 |
| pIB1099 | CD8A | Myc | A30523 VH_VL | N/A | CD28-CD40 |
| pIB1100 | CD8A | Myc | A30523 VL_VH | N/A | CD28-CD40 |
| pIB1101 | CD8A | Myc | A30633 VH_VL | N/A | CD28-CD40 |
| pIB1102 | CD8A | Myc | A30633 VL_VH | N/A | CD28-CD40 |

TABLE 7

Inducible costimulatory proteins

| Code | GOI description |
|---|---|
| pIB1082 | WT EGFR ECD-EGFRTM/JMD-CD28-CD40 |
| pIB1083 | domain IV-EGFRTM/JMD-CD28-CD40 |
| pIB1084 | EGFRTM/JMD-CD28-CD40 (control) |
| pIB1085 | Her 2 (Domain 1 to IV)-TMD/JMD-CD28-CD40 |
| pIB1086 | Her 2 (Domain 1 to IV)-TMD (V659E)/JMD-CD28-CD40 |
| pIB1087 | Her 2 (Domain 1 to IV)-TMD (G660D)/JMD-CD28-CD40 |
| pIB1088 | Her 2 (Domain 1 to IV)-TMD (G660R)/JMD-CD28-CD40 |
| pIB1089 | Her 2 (Domain IV)-TMD/JMD-CD28-CD40 |
| pIB1090 | Her 2 (Domain IV)-TMD (V659E)/JMD-CD28-CD40 |
| pIB1091 | Her 2 (Domain IV)-TMD (G660D)/JMD-CD28-CD40 |
| pIB1092 | Her 2 (Domain IV)-TMD (G660R)/JMD-CD28-CD40 |
| pIB1093 | Her 2 TMD/JMD-CD28-CD40 |
| pIB1094 | Her 2 TMD (V659E)/JMD-CD28-CD40 |
| pIB1095 | Her 2 TMD (G660D)/JMD-CD28-CD40 |
| pIB1096 | Her 2 TMD (G660R)/JMD-CD28-CD40 |

TABLE 7-continued

Inducible costimulatory proteins

| Code | GOI description |
| --- | --- |
| pIB1097 | Anti-ID1 VH-VL (A30514-pembrolizumab)-CD28TMD CD28-CD40 |
| pIB1098 | Anti-ID1 VL-VH (A30514-pembrolizumab)-CD28TMD CD28-CD40 |
| pIB1099 | Anti-ID2 Vh-VL (A30523-pembrolizumab)-CD28TMD CD28-CD40 |
| pIB1100 | Anti-ID2 VL-Vh (A30523-pembrolizumab)-CD28TMD CD28-CD40 |
| pIB1101 | Anti-ID3 Vh-VL (A30633-pembrolizumab)-CD28TMD CD28-CD40 |
| pIB1102 | Anti-ID3 VL-VH (A30633-pembrolizumab)-CD28TMD CD28-CD40 |

The following sequences in the below table include complete components and are non-limiting. Components may include a signal peptide (SP), a TCR clustering domain (CD) and/or a signaling domain (SD). It will be understood that whereas certain proteins may comprise N-terminal signal peptides when expressed, those signal peptides are cleaved and may be imprecisely cleaved when the proteins are expressed, and that the resulting proteins from which signal peptides are removed comprise binding domains having variation of up to about five amino acids in the location of the N-terminal amino acid.

TABLE 8

TCR costimulation construct examples

```
SEQ ID NO: 1
Component:    SP CD3D_
Sequence:     MEHSTFLSGL VLATLLSQVS P

SEQ ID NO: 2
Component:    CD CD3D_
Sequence:     FKIPIEELED RVFVNCNTSI TWVEGTVGTL LSDITRLDLG KRILDPRGIY
              RCNGTDIYKD KESTVQVHYR MCQSCVELDP ATVAGIIVTD VIATLLLALG
              VFCFA SEQ ID NO: 3
Component:    SD CD28CD40
Sequence:     RSKRSRLLHS DYMNMTPRRP GPTRKHYQPY APPRDFAAYR SKKVAKKPTN
              KAPHPKQEPQ EINFPDDLPG SNTAAPVQET LHGCQPVTQE DGKESRISVQ
              ERQ SEQ ID NO: 4
Full length:  CD3D_CD3D_CD28CD40
Sequence:     MEHSTFLSGL VLATLLSQVS PFKIPIEELE DRVFVNCNTS ITWVEGTVGT
              LLSDITRLDL GKRILDPRGI YRCNGTDIYK DKESTVQVHY RMCQSCVELD
              PATVAGIIVT DVIATLLLAL GVFCFARSKR SRLLHSDYMN MTPRRPGPTR
              KHYQPYAPPR DFAAYRSKKV AKKPTNKAPH PKQEPQEINF PDDLPGSNTA
              APVQETLHGC QPVTQEDGKE SRISVQERQ SEQ ID NO: 5
Component:    SP CD3E_
Sequence:     MQSGTHWRVL GLCLLSVGVW GQ SEQ ID NO: 6
Component:    CD CD3E_
Sequence:     DGNEEMGGIT QTPYKVSISG TTVILTCPQY PGSEILWQHN DKNIGGDEDD
              KNIGSDEDHL SLKEFSELEQ SGYYVCYPRG SKPEDANFYL YLRARVCENC
              MEMDVMSVAT IVIVDICITG GLLLLVYYWS SEQ ID NO: 7
Component:    SD CD28CD40
Sequence:     RSKRSRLLHS DYMNMTPRRP GPTRKHYQPY APPRDFAAYR SKKVAKKPTN
              KAPHPKQEPQ EINFPDDLPG SNTAAPVQET LHGCQPVTQE DGKESRISVQ
              ERQ SEQ ID NO: 8
Full length:  CD3E_CD3E_CD28CD40
Sequence:     MQSGTHWRVL GLCLLSVGVW GQDGNEEMGG ITQTPYKVSI SGTTVILTCPQ
              YPGSEILWQH NDKNIGGDED DKNIGSDEDH LSLKEFSELE QSGYYVCYPRG
              SKPEDANFYL YLRARVCENC MEMDVMSVAT IVIVDICITG GLLLLVYYWSR
              SKRSRLLHSD YMNMTPRRPG PTRKHYQPYA PPRDFAAYRS KKVAKKPTNKA
              PHPKQEPQEI NFPDDLPGSN TAAPVQETLH GCQPVTQEDG KESRISVQERQ SEQ ID NO: 9
Component:    SP CD3G_
Sequence:     MEQGKGLAVL ILAIILLQGT LA
```

TABLE 8-continued

TCR costimulation construct examples

SEQ ID NO: 10
Component: CD CD3G_
Sequence: QSIKGNHLVK VYDYQEDGSV LLTCDAEAKN ITWFKDGKMI GFLTEDKKKW
NLGSNAKDPR GMYQCKGSQN KSKPLQVYYR MCQNCIELNA ATISGFLFAE
IVSIFVLAVG VYFIA SEQ ID NO: 11
Component: SD CD28CD40
Sequence: RSKRSRLLHS DYMNMTPRRP GPTRKHYQPY APPRDFAAYR SKKVAKKPTN
KAPHPKQEPQ EINFPDDLPG SNTAAPVQET LHGCQPVTQE DGKESRISVQ
ERQ SEQ ID NO: 12
Full length: CD3G_CD3G_CD28CD40
Sequence: MEQGKGLAVL ILAIILLQGT LAQSIKGNHL VKVYDYQEDG SVLLTCDAEA
KNITWFKDGK MIGFLTEDKK KWNLGSNAKD PRGMYQCKGS QNKSKPLQVY
YRMCQNCIEL NAATISGFLF AEIVSIFVLA VGVYFIARSK RSRLLHSDYM
NMTPRRPGPT RKHYQPYAPP RDFAAYRSKK VAKKPTNKAP HPKQEPQEIN
FPDDLPGSNT AAPVQETLHG CQPVTQEDGK ESRISVQERQ SEQ ID NO: 13
Component: SP CD3Z_
Sequence: MKWKALFTAA ILQAQLPITE A SEQ ID NO: 14
Component: CD CD3Z_
Sequence: QSFGLLDPKL CYLLDGILFI YGVILTALFL SEQ ID NO: 15
Component: SD CD28CD40
Sequence: RSKRSRLLHS DYMNMTPRRP GPTRKHYQPY APPRDFAAYR SKKVAKKPTN
KAPHPKQEPQ EINFPDDLPG SNTAAPVQET LHGCQPVTQE DGKESRISVQ
ERQ SEQ ID NO: 16
Full length: CD3Z_CD3Z_CD28CD40
Sequence: MKWKALFTAA ILQAQLPITE AQSFGLLDPK LCYLLDGILF IYGVILTALF
LRSKRSRLLH SDYMNMTPRR PGPTRKHYQP YAPPRDFAAY RSKKVAKKPT
NKAPHPKQEP QEINFPDDLP GSNTAAPVQE TLHGCQPVTQ EDGKESRISV
QERQ SEQ ID NO: 17
Component: SP CD8A_
Sequence: MALPVTALLL PLALLLHAAR P SEQ ID NO: 18
Component: CD TRDC_
Sequence: SQPHTKPSVF VMKNGTNVAC LVKEFYPKDI RINLVSSKKI TEFDPAIVIS
PSGKYNAVKL GKYEDSNSVT CSVQHDNKTV HSTDFEVKTD STDHVKPKET
ENTKQPSKSC HKPKAIVHTE KVNMMSLTVL GLRMLFAKTV AVNFLLTAKL
FFL SEQ ID NO: 19
Component: SD CD28CD40
Sequence: RSKRSRLLHS DYMNMTPRRP GPTRKHYQPY APPRDFAAYR SKKVAKKPTN
KAPHPKQEPQ EINFPDDLPG SNTAAPVQET LHGCQPVTQE DGKESRISVQ
ERQ SEQ ID NO: 20
Full length: CD8A_TRDC_CD28CD40
Sequence: MALPVTALLL PLALLLHAAR PSQPHTKPSV FVMKNGTNVA CLVKEFYPKD
IRINLVSSKK ITEFDPAIVI SPSGKYNAVK LGKYEDSNSV TCSVQHDNKT
VHSTDFEVKT DSTDHVKPKE TENTKQPSKS CHKPKAIVHT EKVNMMSLTV
LGLRMLFAKT VAVNFLLTAK LFFLRSKRSR LLHSDYMNMT PRRPGPTRKH
YQPYAPPRDF AAYRSKKVAK KPTNKAPHPK QEPQEINFPD DLPGSNTAAP
VQETLHGCQP VTQEDGKESR ISVQERQ SEQ ID NO: 21
Component: SP CD8A_
Sequence: MALPVTALLL PLALLLHAAR P SEQ ID NO: 22
Component: CD TRGC1_
Sequence: DKQLDADVSP KPTIFLPSIA ETKLQKAGTY LCLLEKFFPD VIKIHWQEKK
SNTILGSQEG NTMKTNDTYM KFSWLTVPEK SLDKEHRCIV RHENNKNGVD
QEIIFPPIKT DVITMDPKDN CSKDANDTLL LQLTNTSAYY MYLLLLLKSV
VYFAIITCCL L TABLE 8-continued TCR costimulation construct examples SEQ ID NO: 23
Component: SD CD28CD40
Sequence:
RSKRSRLLHS DYMNMTPRRP GPTRKHYQPY APPRDFAAYR SKKVAKKPTN
KAPHPKQEPQ EINFPDDLPG SNTAAPVQET LHGCQPVTQE DGKESRISVQ
ERQ SEQ ID NO: 24
Full length: CD8A_TRGC1_CD28CD40
Sequence:
MALPVTALLL PLALLLHAAR PDKQLDADVS PKPTIFLPSI AETKLQKAGT
YLCLLEKFFP DVIKIHWQEK KSNTILGSQE GNTMKTNDTY MKFSWLTVPE
KSLDKEHRCI VRHENNKNGV DQEIIFPPIK TDVITMDPKD NCSKDANDTL
LLQLTNTSAY YMYLLLLLKS VVYFAIITCC LLRSKRSRLL HSDYMNMTPR
RPGPTRKHYQ PYAPPRDFAA YRSKKVAKKP TNKAPHPKQE PQEINFPDDL
PGSNTAAPVQ ETLHGCQPVT QEDGKESRIS VQERQ SEQ ID NO: 25
Component: SP CD8A_
Sequence:
MALPVTALLL PLALLLHAAR P SEQ ID NO: 26
Component: CD TRAC_
Sequence:
IQNPEPAVYQ LKDPRSQDST LCLFTDFDSQ INVPKTMESG TFITDKCVLD
MKAMDSKSNG AIAWSNQTSF TCQDIFKETN ATYPSSDVPC DATLTEKSFE
TDMNLNFQNL LVIVLRILLL KVAGFNLLMT LRLWSS SEQ ID NO: 27
Component: SD CD28CD40
Sequence:
RSKRSRLLHS DYMNMTPRRP GPTRKHYQPY APPRDFAAYR SKKVAKKPTN
KAPH PKQEP QEINFPDDLP GSNTAAPVQE TLHGCQPVTQ EDGKESRISV
QERQ SEQ ID NO: 28
Full length: CD8A_TRAC_CD28CD40
Sequence:
MALPVTALLL PLALLLHAAR PIQNPEPAVY QLKDPRSQDS TLCLFTDFDS
QINVPKTMES GTFITDKCVL DMKAMDSKSN GAIAWSNQTS FTCQDIFKET
NATYPSSDVP CDATLTEKSF ETDMNLNFQN LLVIVLRILL LKVAGFNLLM
TLRLWSSRSK RSRLLHSDYM NMTPRRPGPT RKHYQPYAPP RDFAAYRSKK
VAKKPTNKAP HPKQEPQEIN FPDDLPGSNT AAPVQETLHG CQPVTQEDGK
ESRISVQERQ SEQ ID NO: 29
Component: SP CD8A_
Sequence:
MALPVTALLL PLALLLHAAR P SEQ ID NO: 30
Component: CD TRBC1_
Sequence:
VLTPPKVSLF EPSKAEIANK QKATLVCLAR GFFPDHVELS WWVNGKEVHS
GVCTDPQAYK ESNYSYCLSS RLRVSATFWH NPRNHFRCQV QFHGLSEEDK
WPEGSPKPVT QNISAEAWGR ADCGITSASY QQGVLSATIL YEILLGKATL
YAVLVSTLVV MAMVKRKNS SEQ ID NO: 31
Component: SD CD28CD40
Sequence:
RSKRSRLLHS DYMNMTPRRP GPTRKHYQPY APPRDFAAYR SKKVAKKPTN
KAPHPKQEPQ EINFPDDLPG SNTAAPVQET LHGCQPVTQE DGKESRISVQ
ERQ SEQ ID NO: 32
Full length: CD8A_TRBC1_CD28CD40
Sequence:
MALPVTALLL PLALLLHAAR PVLTPPKVSL FEPSKAEIAN KQKATLVCLA
RGFFPDHVEL SWWVNGKEVH SGVCTDPQAY KESNYSYCLS SRLRVSATFW
HNPRNHFRCQ VQFHGLSEED KWPEGSPKPV TQNISAEAWG RADCGITSAS
YQQGVLSATI LYEILLGKAT LYAVLVSTLV VMAMVKRKNS RSKRSRLLHS
DYMNMTPRRP GPTRKHYQPY APPRDFAAYR SKKVAKKPTN KAPHPKQEPQ
EINFPDDLPG SNTAAPVQET LHGCQPVTQE DGKESRISVQ ERQ SEQ ID NO: 33
vector clone: pIB1001
Sequence
MALPVTALLL PLALLLHAAR PEQKLISEED LQVQLVQSGA EVKKPGASVK
VSCKASGYTF TSYWMNWVRQ APGQGLEWMG RIDPYDSETH
YAQKLQGRVT
MTTDTSTSTA YMELRSLRSD DTAVYYCARG GYDFDVGTLY WFFDVWGQGT
TVTVSSGGGG SGGGGSGGGG SDIQMTQSPS SLSASVGDRV TITCRASENI
YSYLAWYQQK PGKAPKLLIY NAKTLAEGVP SRFSGSGSGT DFTLTISSLQ
PEDFATYYCQ HHYGTPRTFG GGTKVEIKAA AGSGGSGILV KQSPMLVAYD
NAVNLSCKYS YNLFSREFRA SLHKGLDSAV EVCVVYGNYS QQLQVYSKTG
FNCDGKLGNE SVTFYLQNLY VNQTDIYFCK IEVMYPPPYL DNEKSNGTII

TABLE 8-continued

TCR costimulation construct examples

```
               HVKGKHLCPS PLFPGPSKPF WVLVVVGGVL ACYSLLVTVA FIIFWVRSKR
               SRLLHSDYMN MTPRRPGPTR KHYQPYAPPR DFAAYRSKKV AKKPTNKAPH
               PKQEPQEINF PDDLPGSNTA APVQETLHGC QPVTQEDGKE SRISVQERQ

SEQ ID NO: 34
vector clone: pIB1002
Sequence:      MALPVTALLL PLALLLHAAR PEQKLISEED LDIQMTQSPS SLSASVGDRV
               TITCRASENI YSYLAWYQQK PGKAPKLLIY NAKTLAEGVP SRFSGSGSGT
               DFTLTISSLQ PEDFATYYCQ HHYGTPRTFG GGTKVEIKGG GGSGGGGSGG
               GGSQVQLVQS GAEVKKPGAS VKVSCKASGY TFTSYWMNWV
               RQAPGQGLEW
               MGRIDPYDSE THYAQKLQGR VTMTTDTSTS TAYMELRSLR SDDTAVYYCA
               RGGYDFDVGT LYWFFDVWGQ GTTVTVSSAA AGSGGSGILV KQSPMLVAYD
               NAVNLSCKYS YNLFSREFRA SLHKGLDSAV EVCVVYGNYS QQLQVYSKTG
               FNCDGKLGNE SVTFYLQNLY VNQTDIYFCK IEVMYPPPYL DNEKSNGTII
               HVKGKHLCPS PLFPGPSKPF WVLVVVGGVL ACYSLLVTVA FIIFWVRSKR
               SRLLHSDYMN MTPRRPGPTR KHYQPYAPPR DFAAYRSKKV AKKPTNKAPH
               PKQEPQEINF PDDLPGSNTA APVQETLHGC QPVTQEDGKE SRISVQERQ SEQ ID NO: 35
vector clone: pIB1003
Sequence:      MALPVTALLL PLALLLHAAR PEQKLISEED LQVQLVESGG GVVQPGRSLR
               LSCAASGFTF SSYDMHWVRQ APGKGLEWVA VIWYDGSNKY YADSVKGRFT
               ISRDNSKNTL YLQMNSLRAE DTAVYYCARG SGNWGFFDYW GQGTLVTVSS
               GGGGSGGGGS GGGGSDIQMT QSPSSLSASV GDRVTITCRA SQGISRWLAW
               YQQKPEKAPK SLIYAASSLQ SGVPSRFSGS GSGTDFTLTI SSLQPEDFAT
               YYCQQYNTYP RTFGQGTKVE IKAAAGSGGS GILVKQSPML VAYDNAVNLS
               CKYSYNLFSR EFRASLHKGL DSAVEVCVVY GNYSQQLQVY SKTGFNCDGK
               LGNESVTFYL QNLYVNQTDI YFCKIEVMYP PPYLDNEKSN GTIIHVKGKH
               LCPSPLFPGP SKPFWVLVVV GGVLACYSLL VTVAFIIFWV RSKRSRLLHS
               DYMNMTPRRP GPTRKHYQPY APPRDFAAYR SKKVAKKPTN KAPHPKQEPQ
               EINFPDDLPG SNTAAPVQET LHGCQPVTQE DGKESRISVQ ERQ SEQ ID NO: 36
vector clone: pIB1004
Sequence:      MALPVTALLL PLALLLHAAR PEQKLISEED LDIQMTQSPS SLSASVGDRV
               TITCRASQGI SRWLAWYQQK PEKAPKSLIY AASSLQSGVP SRFSGSGSGT
               DFTLTISSLQ PEDFATYYCQ QYNTYPRTFG QGTKVEIKGG GGSGGGGSGG
               GGSQVQLVES GGGVVQPGRS LRLSCAASGF TFSSYDMHWV RQAPGKGLEW
               VAVIWYDGSN KYYADSVKGR FTISRDNSKN TLYLQMNSLR AEDTAVYYCA
               RGSGNWGFFD YWGQGTLVTV SSAAAGSGGS GILVKQSPML VAYDNAVNLS
               CKYSYNLFSR EFRASLHKGL DSAVEVCVVY GNYSQQLQVY SKTGFNCDGK
               LGNESVTFYL QNLYVNQTDI YFCKIEVMYP PPYLDNEKSN GTIIHVKGKH
               LCPSPLFPGP SKPFWVLVVV GGVLACYSLL VTVAFIIFWV RSKRSRLLHS
               DYMNMTPRRP GPTRKHYQPY APPRDFAAYR SKKVAKKPTN KAPHPKQEPQ
               EINFPDDLPG SNTAAPVQET LHGCQPVTQE DGKESRISVQ ERQ SEQ ID NO: 37
vector clone: pIB1005
Sequence:      MALPVTALLL PLALLLHAAR PEQKLISEED LQVQLQQWGA GLLKPSETLS
               LTCAVYGGSF SGYYWSWIRQ SPEGLEWIGE INHGGYVTYN PSLESRVTIS
               VDTSKNQFSL KLSSVTAADT AVYYCARDYG PGNYDWYFDL WGRGTLVTVS
               SGGGGSGGGG SGGGGSEIVL TQSPATLSLS PGERATLSCR ASQSVSSYLA
               WYQQKPGQAP RLLIYDASNR ATGIPARFSG SGSGTDFTLT ISSLEPEDFA
               VYYCQQRSNW PPALTFGGGT KVEIKRAAAG SGGSGILVKQ SPMLVAYDNA
               VNLSCKYSYN LFSREFRASL HKGLDSAVEV CVVYGNYSQQ LQVYSKTGFN
               CDGKLGNESV TFYLQNLYVN QTDIYFCKIE VMYPPPYLDN EKSNGTIIHV
               KGKHLCPSPL FPGPSKPFWV LVVVGGVLAC YSLLVTVAFI IFWVRSKRSR
               LLHSDYMNMT PRRPGPTRKH YQPYAPPRDF AAYRSKKVAK KPTNKAPHPK
               QEPQEINFPD DLPGSNTAAP VQETLHGCQP VTQEDGKESR ISVQERQ SEQ ID NO: 38
vector clone : pIB1006
Sequence:      MALPVTALLL PLALLLHAAR PEQKLISEED LEIVLTQSPA TLSLSPGERA
               TLSCRASQSV SSYLAWYQQK PGQAPRLLIY DASNRATGIP ARFSGSGSGT
               DFTLTISSLE PEDFAVYYCQ QRSNWPPALT FGGGTKVEIK RGGGGSGGGG
               SGGGGSQVQL QQWGAGLLKP SETLSLTCAV YGGSFSGYYW SWIRQSPEGL
               EWIGEINHGG YVTYNPSLES RVTISVDTSK NQFSLKLSSV TAADTAVYYC
               ARDYGPGNYD WYFDLWGRGT LVTVSSAAAG SGGSGILVKQ SPMLVAYDNA
               VNLSCKYSYN LFSREFRASL HKGLDSAVEV CVVYGNYSQQ LQVYSKTGFN
               CDGKLGNESV TFYLQNLYVN QTDIYFCKIE VMYPPPYLDN EKSNGTIIHV
               KGKHLCPSPL FPGPSKPFWV LVVVGGVLAC YSLLVTVAFI IFWVRSKRSR
               LLHSDYMNMT PRRPGPTRKH YQPYAPPRDF AAYRSKKVAK KPTNKAPHPK
               QEPQEINFPD DLPGSNTAAP VQETLHGCQP VTQEDGKESR ISVQERQ
```

TABLE 8-continued

TCR costimulation construct examples

SEQ ID NO: 39
vector clone: pIB1007
Sequence:
MALPVTALLL PLALLLHAAR PEQKLISEED LQVTLRESGP ALVKPTQTLT
LTCTFSGFSL STSGMGVGWI RQPPGKALEW LAHIWWDDDK YYNPSLKSRL
TISKDTSKNQ VVLTMTNMDP VDTATYYCAR TRRYFPPAYW GQGTLVTVSS
GGGGSGGGGS GGGGSEIVMT QSPATLSVSP GERATLSCKA SQNVGTNVAW
YQQKPGQAPR LLIYSASYRY SGIPARFSGS GSGTEFTLTI SSLQSEDFAV
YYCQQYNTDP LTFGGGTKVE IKAAAGSGGS GILVKQSPML VAYDNAVNLS
CKYSYNLFSR EFRASLHKGL DSAVEVCVVY GNYSQQLQVY SKTGFNCDGK
LGNESVTFYL QNLYVNQTDI YFCKIEVMYP PPYLDNEKSN GTIIHVKGKH
LCPSPLFPGP SKPFWVLVVV GGVLACYSLL VTVAFIIFWV RSKRSRLLHS
DYMNMTPRRP GPTRKHYQPY APPRDFAAYR SKKVAKKPTN KAPHPKQEPQ
EINFPDDLPG SNTAAPVQET LHGCQPVTQE DGKESRISVQ ERQ SEQ ID NO: 40
vector clone: pIB1008
Sequence:
MALPVTALLL PLALLLHAAR PEQKLISEED LEIVMTQSPA TLSVSPGERA
TLSCKASQNV GTNVAWYQQK PGQAPRLLIY SASYRYSGIP ARFSGSGSGT
EFTLTISSLQ SEDFAVYYCQ QYNTDPLTFG GGTKVEIKGG GGSGGGGSGG
GGSQVTLRES GPALVKPTQT LTLTCTFSGF SLSTSGMGVG WIRQPPGKAL
EWLAHIWWDD DKYYNPSLKS RLTISKDTSK NQVVLTMTNM DPVDTATYYC
ARTRRYFPPA YWGQGTLVTV SSAAGSGGS GILVKQSPML VAYDNAVNLS
CKYSYNLFSR EFRASLHKGL DSAVEVCVVY GNYSQQLQVY SKTGFNCDGK
LGNESVTFYL QNLYVNQTDI YFCKIEVMYP PPYLDNEKSN GTIIHVKGKH
LCPSPLFPGP SKPFWVLVVV GGVLACYSLL VTVAFIIFWV RSKRSRLLHS
DYMNMTPRRP GPTRKHYQPY APPRDFAAYR SKKVAKKPTN KAPHPKQEPQ
EINFPDDLPG SNTAAPVQET LHGCQPVTQE DGKESRISVQ ERQ SEQ ID NO: 41
vector clone: pIB1009
Sequence:
MALPVTALLL PLALLLHAAR PEQKLISEED LQVQLVQSGV EVKKPGASVK
VSCKASGYTF TNYYMYWVRQ APGQGLEWMG GINPSNGGTN FNEKFKNRVT
LTTDSSTTTA YMELKSLQFD DTAVYYCARR DYRFDMGFDY WGQGTTVTVS
SGGGGSGGGG SGGGGSEIVL TQSPATLSLS PGERATLSCR ASKGVSTSGY
SYLHWYQQKP GQAPRLLIYL ASYLESGVPA RFSGSGSGTD FTLTISSLEP
EDFAVYYCQH SRDLPLTFGG GTKVEIKRAA AGSGGSGILV KQSPMLVAYD
NAVNLSCKYS YNLFSREFRA SLHKGLDSAV EVCVVYGNYS QQLQVYSKTG
FNCDGKLGNE SVTFYLQNLY VNQTDIYFCK IEVMYPPPYL DNEKSNGTII
HVKGKHLCPS PLFPGPSKPF WVLVVVGGVL ACYSLLVTVA FIIFWVRSKR
SRLLHSDYMN MTPRRPGPTR KHYQPYAPPR DFAAYRSKKV AKKPTNKAPH
PKQEPQEINF PDDLPGSNTA APVQETLHGC QPVTQEDGKE SRISVQERQ SEQ ID NO: 42
vector clone: pIB1010
Sequence:
MALPVTALLL PLALLLHAAR PEQKLISEED LEIVLTQSPA TLSLSPGERA
TLSCRASKGV STSGYSYLHW YQQKPGQAPR LLIYLASYLE SGVPARFSGS
GSGTDFTLTI SSLEPEDFAV YYCQHSRDLP LTFGGGTKVE IKRGGGGSGG
GGSGGGGSQV QLVQSGVEVK KPGASVKVSC KASGYTFTNY
YMYWVRQAPG
QGLEWMGGIN PSNGGTNFNE KFKNRVTLTT DSSTTTAYME LKSLQFDDTA
VYYCARRDYR FDMGFDYWGQ GTTVTVSSAA AGSGGSGILV KQSPMLVAYD
NAVNLSCKYS YNLFSREFRA SLHKGLDSAV EVCVVYGNYS QQLQVYSKTG
FNCDGKLGNE SVTFYLQNLY VNQTDIYFCK IEVMYPPPYL DNEKSNGTII
HVKGKHLCPS PLFPGPSKPF WVLVVVGGVL ACYSLLVTVA FIIFWVRSKR
SRLLHSDYMN MTPRRPGPTR KHYQPYAPPR DFAAYRSKKV AKKPTNKAPH
PKQEPQEINF PDDLPGSNTA APVQETLHGC QPVTQEDGKE SRISVQERQ SEQ ID NO: 43
vector clone: pIB1011
Sequence:
MALPVTALLL PLALLLHAAR PEQKLISEED LEVQLVESGG GLVQPGGSLR
LSCAASGFTF SDSWIHWVRQ APGKGLEWVA WISPYGGSTY YADSVKGRFT
ISADTSKNTA YLQMNSLRAE DTAVYYCARR HWPGGFDYWG QGTLVTVSSG
GGGSGGGGSG GGGSDIQMTQ SPSSLSASVG DRVTITCRAS QDVSTAVAWY
QQKPGKAPKL LIYSASFLYS GVPSRFSGSG SGTDFTLTIS SLQPEDFATY
YCQQYLHPA TFGQGTKVEI KRAAAGSGGS GILVKQSPML VAYDNAVNLS
CKYSYNLFSR EFRASLHKGL DSAVEVCVVY GNYSQQLQVY SKTGFNCDGK
LGNESVTFYL QNLYVNQTDI YFCKIEVMYP PPYLDNEKSN GTIIHVKGKH
LCPSPLFPGP SKPFWVLVVV GGVLACYSLL VTVAFIIFWV RSKRSRLLHS
DYMNMTPRRP GPTRKHYQPY APPRDFAAYR SKKVAKKPTN KAPHPKQEPQ
EINFPDDLPG SNTAAPVQET LHGCQPVTQE DGKESRISVQ ERQ SEQ ID NO: 44
vector clone: pIB1012
Sequence:
MALPVTALLL PLALLLHAAR PEQKLISEED LDIQMTQSPS SLSASVGDRV
TITCRASQDV STAVAWYQQK PGKAPKLLIY SASFLYSGVP SRFSGSGSGT
DFTLTISSLQ PEDFATYYCQ QYLYHPATFG QGTKVEIKRG GGSGGGGSG
GGGSEVQLVE SGGGLVQPGG SLRLSCAASG FTFSDSWIHW VRQAPGKGLE TABLE 8-continued TCR costimulation construct examples

```
                WVAWISPYGG STYYADSVKG RFTISADTSK NTAYLQMNSL RAEDTAVYYC
                ARRHWPGGFD YWGQGTLVTV SSAAAGSGGS GILVKQSPML VAYDNAVNLS
                CKYSYNLFSR EFRASLHKGL DSAVEVCVVY GNYSQQLQVY SKTGFNCDGK
                LGNESVTFYL QNLYVNQTDI YFCKIEVMYP PPYLDNEKSN GTIIHVKGKH
                LCPSPLFPGP SKPFWVLVVV GGVLACYSLL VTVAFIIFWV RSKRSRLLHS
                DYMNMTPRRP GPTRKHYQPY APPRDFAAYR SKKVAKKPTN KAPHPKQEPQ
                EINFPDDLPG SNTAAPVQET LHGCQPVTQE DGKESRISVQ ERQ
```

SEQ ID NO: 45
vector clone: pIB1013
Sequence:
```
                MALPVTALLL PLALLLHAAR PEQKLISEED LQVQLVQSGA EVKKPGASVK
                VSCKASGYTF TNYWIGWVKQ APGQGLEWIG YLYPGGLYTN YNEKFKGKAT
                MTADTSTNTA YMELSSLRSE DTAVYYCARY RDYDYAMDYW GQGTLVTVSS
                GGGGSGGGGS GGGGSDVVMT QTPLSLPVTL GQPASISCKS TKSLLNSDGF
                TYLGWCLQKP GQSPQLLIYL VSNRFSGVPD RFSGSGSGTD FTLKISRVEA
                EDVGVYYCFQ SNYLPLTFGQ GTKLEIKRAA AGSGGSGILV KQSPMLVAYD
                NAVNLSCKYS YNLFSREFRA SLHKGLDSAV EVCVVYGNYS QQLQVYSKTG
                FNCDGKLGNE SVTFYLQNLY VNQTDIYFCK IEVMYPPPYL DNEKSNGTII
                HVKGKHLCPS PLFPGPSKPF WVLVVVGGVL ACYSLLVTVA FIIFWVRSKR
                SRLLHSDYMN MTPRRPGPTR KHYQPYAPPR DFAAYRSKKV AKKPTNKAPH
                PKQEPQEINF PDDLPGSNTA APVQETLHGC QPVTQEDGKE SRISVQERQ
```

SEQ ID NO: 46
vector clone: pIB1014
Sequence:
```
                MALPVTALLL PLALLLHAAR PEQKLISEED LDVVMTQTPL SLPVTLGQPA
                SISCKSTKSL LNSDGFTYLG WCLQKPGQSP QLLIYLVSNR FSGVPDRFSG
                SGSGTDFTLK ISRVEAEDVG VYYCFQSNYL PLTFGQGTKL EIKRGGGGSG
                GGGSGGGGSQ VQLVQSGAEV KKPGASVKVS CKASGYTFTN YWIGWVKQAP
                GQGLEWIGYL YPGGLYTNYN EKFKGKATMT ADTSTNTAYM ELSSLRSEDT
                AVYYCARYRD YDYAMDYWGQ GTLVTVSSAA AGSGGSGILV
                KQSPMLVAYD
                NAVNLSCKYS YNLFSREFRA SLHKGLDSAV EVCVVYGNYS QQLQVYSKTG
                FNCDGKLGNE SVTFYLQNLY VNQTDIYFCK IEVMYPPPYL DNEKSNGTII
                HVKGKHLCPS PLFPGPSKPF WVLVVVGGVL ACYSLLVTVA FIIFWVRSKR
                SRLLHSDYMN MTPRRPGPTR KHYQPYAPPR DFAAYRSKKV AKKPTNKAPH
                PKQEPQEINF PDDLPGSNTA APVQETLHGC QPVTQEDGKE SRISVQERQ
```

SEQ ID NO: 47
vector clone: pIB1015
Sequence:
```
                MALPVTALLL PLALLLHAAR PEQKLISEED LQVQLQESGP GLVKPSQTLS
                LTCAVYGGSF SSGYWNWIRK HPGKGLEYIG YISYNGITYH NPSLKSRITI
                NRDTSKNQYS LQLNSVTPED TAVYYCARYK YDYDGGHAMD
                YWGQGTLVTV
                SSGGGGSGGG GSGGGGSDIQ MTQSPSSLSA SVGDRVTITC RASQDISNYL
                NWYQQKPGKA PKLLIYYTSK LHSGVPSRFS GSGSGTDYTL TISSLQPEDF
                ATYYCQQGSA LPWTFGQGTK VEIKAAGSG GSGILVKQSP MLVAYDNAVN
                LSCKYSYNLF SREFRASLHK GLDSAVEVCV VYGNYSQQLQ VYSKTGFNCD
                GKLGNESVTF YLQNLYVNQT DIYFCKIEVM YPPPYLDNEK SNGTIIHVKG
                KHLCPSPLFP GPSKPFWVLV VVGGVLACYS LLVTVAFIIF WVRSKRSRLL
                HSDYMNMTPR RPGPTRKHYQ PYAPPRDFAA YRSKKVAKKP TNKAPHPKQE
                PQEINFPDDL PGSNTAAPVQ ETLHGCQPVT QEDGKESRIS VQERQ
```

SEQ ID NO: 48
vector clone: pIB1016
Sequence:
```
                MALPVTALLL PLALLLHAAR PEQKLISEED LDIQMTQSPS SLSASVGDRV
                TITCRASQDI SNYLNWYQQK PGKAPKLLIY YTSKLHSGVP SRFSGSGSGT
                DYTLTISSLQ PEDFATYYCQ QGSALPWTFG QGTKVEIKGG GGSGGGGSGG
                GGSQVQLQES GPGLVKPSQT LSLTCAVYGG SFSSGYWNWI RKHPGKGLEY
                IGYISYNGIT YHNPSLKSRI TINRDTSKNQ YSLQLNSVTP EDTAVYYCAR
                YKYDYDGGHA MDYWGQGTLV TVSSAAAGSG GSGILVKQSP
                MLVAYDNAVN
                LSCKYSYNLF SREFRASLHK GLDSAVEVCV VYGNYSQQLQ VYSKTGFNCD
                GKLGNESVTF YLQNLYVNQT DIYFCKIEVM YPPPYLDNEK SNGTIIHVKG
                KHLCPSPLFP GPSKPFWVLV VVGGVLACYS LLVTVAFIIF WVRSKRSRLL
                HSDYMNMTPR RPGPTRKHYQ PYAPPRDFAA YRSKKVAKKP TNKAPHPKQE
                PQEINFPDDL PGSNTAAPVQ ETLHGCQPVT QEDGKESRIS VQERQ
```

SEQ ID NO: 49
vector clone: pIB1017
Sequence:
```
                MALPVTALLL PLALLLHAAR PEQKLISEED LQVQLVESGG GVVQPGRSLR
                LSCAASGFTF SSYTMHWVRQ APGKGLEWVT FISYDGNNKY YADSVKGRFT
                ISRDNSKNTL YLQMNSLRAE DTAIYYCART GWLGPFDYWG QGTLVTVSSG
                GGGSGGGGSG GGGSEIVLTQ SPGTLSLSPG ERATLSCRAS QSVGSSYLAW
                YQQKPGQAPR LLIYGAFSRA TGIPDRFSGS GSGTDFTLTI SRLEPEDFAV
```

TABLE 8-continued

TCR costimulation construct examples

```
                YYCQQYGSSP WTFGQGTKVE IKAAAGSGGS GILVKQSPML VAYDNAVNLS
                CKYSYNLFSR EFRASLHKGL DSAVEVCVVY GNYSQQLQVY SKTGFNCDGK
                LGNESVTFYL QNLYVNQTDI YFCKIEVMYP PPYLDNEKSN GTIIHVKGKH
                LCPSPLFPGP SKPFWVLVVV GGVLACYSLL VTVAFIIFWV RSKRSRLLHS
                DYMNMTPRRP GPTRKHYQPY APPRDFAAYR SKKVAKKPTN KAPHPKQEPQ
                EINFPDDLPG SNTAAPVQET LHGCQPVTQE DGKESRISVQ ERQ

SEQ ID NO: 50
vector clone:  pIB1018
Sequence:      MALPVTALLL PLALLLHAAR PEQKLISEED LEIVLTQSPG TLSLSPGERA
               TLSCRASQSV GSSYLAWYQQ KPGQAPRLLI YGAFSRATGI PDRFSGSGSG
               TDFTLTISRL EPEDFAVYYC QQYGSSPWTF GQGTKVEIKG GGGSGGGGSG
               GGGSQVQLVE SGGGVVQPGR SLRLSCAASG FTFSSYTMHW VRQAPGKGLE
               WVTFISYDGN NKYYADSVKG RFTISRDNSK NTLYLQMNSL RAEDTAIYYC
               ARTGWLGPFD YWGQGTLVTV SSAAGSGGS GILVKQSPML VAYDNAVNLS
               CKYSYNLFSR EFRASLHKGL DSAVEVCVVY GNYSQQLQVY SKTGFNCDGK
               LGNESVTFYL QNLYVNQTDI YFCKIEVMYP PPYLDNEKSN GTIIHVKGKH
               LCPSPLFPGP SKPFWVLVVV GGVLACYSLL VTVAFIIFWV RSKRSRLLHS
               DYMNMTPRRP GPTRKHYQPY APPRDFAAYR SKKVAKKPTN KAPHPKQEPQ
               EINFPDDLPG SNTAAPVQET LHGCQPVTQE DGKESRISVQ ERQ SEQ ID NO: 51
vector clone:  pIB1019
Sequence:      MALPVTALLL PLALLLHAAR PEQKLISEED LEVQLVESGG GVVRPGGSLR
               LSCVASGVTF DDYGMSWVRQ APGKGLEWVS GINWNGGDTD YSDSVKGRFT
               ISRDNAKNSL YLQMNSLRAE DTALYYCARD FYGSGSYYHV PFDYWGQGIL
               VTVSSGGGGS GGGGSGGGGS EIVLTQSPGT LSLSPGERAT LSCRASQSVS
               RSYLAWYQQK RGQAPRLLIY GASSRATGIP DRFSGDGSGT DFTLSISRLE
               PEDFAVYYCH QYDMSPFTFG PGTKVDIKAA AGSGGSGILV KQSPMLVAYD
               NAVNLSCKYS YNLFSREFRA SLHKGLDSAV EVCVVYGNYS QQLQVYSKTG
               FNCDGKLGNE SVTFYLQNLY VNQTDIYFCK IEVMYPPPYL DNEKSNGTII
               HVKGKHLCPS PLFPGPSKPF WVLVVVGGVL ACYSLLVTVA FIIFWVRSKR
               SRLLHSDYMN MTPRRPGPTR KHYQPYAPPR DFAAYRSKKV AKKPTNKAPH
               PKQEPQEINF PDDLPGSNTA APVQETLHGC QPVTQEDGKE SRISVQERQ SEQ ID NO: 52
vector clone:  pIB1020
Sequence:      MALPVTALLL PLALLLHAAR PEQKLISEED LEIVLTQSPG TLSLSPGERA
               TLSCRASQSV SRSYLAWYQQ KRGQAPRLLI YGASSRATGI PDRFSGDGSG
               TDFTLSISRL EPEDFAVYYC HQYDMSPFTF GPGTKVDIKG GGGSGGGGSG
               GGGSEVQLVE SGGGVVRPGG SLRLSCVASG VTFDDYGMSW VRQAPGKGLE
               WVSGINWNGG DTDYSDSVKG RFTISRDNAK NSLYLQMNSL RAEDTALYYC
               ARDFYGSGSY YHVPFDYWGQ GILVTVSSAA AGSGGSGILV KQSPMLVAYD
               NAVNLSCKYS YNLFSREFRA SLHKGLDSAV EVCVVYGNYS QQLQVYSKTG
               FNCDGKLGNE SVTFYLQNLY VNQTDIYFCK IEVMYPPPYL DNEKSNGTII
               HVKGKHLCPS PLFPGPSKPF WVLVVVGGVL ACYSLLVTVA FIIFWVRSKR
               SRLLHSDYMN MTPRRPGPTR KHYQPYAPPR DFAAYRSKKV AKKPTNKAPH
               PKQEPQEINF PDDLPGSNTA APVQETLHGC QPVTQEDGKE SRISVQERQ SEQ ID NO: 53
vector clone:  pIB1021
Sequence:      MALPVTALLL PLALLLHAAR PEQKLISEED LQVQLVESGG GVVQPGRSLR
               LSCAASGFSF SSTYVCWVRQ APGKGLEWIA CIYTGDGTNY SASWAKGRFT
               ISKDSSKNTV YLQMNSLRAE DTAVYFCARP DITYGFAINF WGPGTLVTVS
               SGGGGSGGGG SGGGGSDIQM TQSPSSLSAS VGDRVTIKCQ ASQSISSRLA
               WYQQKPGKPP KLLIYRASTL ASGVPSRFSG SGSGTDFTLT ISSLQPEDVA
               TYYCQCTGYG ISWPIGGGTK VEIKAAAGSG GSGILVKQSP MLVAYDNAVN
               LSCKYSYNLF SREFRASLHK GLDSAVEVCV VYGNYSQQLQ VYSKTGFNCD
               GKLGNESVTF YLQNLYVNQT DIYFCKIEVM YPPPYLDNEK SNGTIIHVKG
               KHLCPSPLFP GPSKPFWVLV VGGVLACYS LLVTVAFIIF WVRSKRSRLL
               HSDYMNMTPR RPGPTRKHYQ PYAPPRDFAA YRSKKVAKKP TNKAPHPKQE
               PQEINFPDDL PGSNTAAPVQ ETLHGCQPVT QEDGKESRIS VQERQ SEQ ID NO: 54
vector clone:  pIB1022
Sequence:      MALPVTALLL PLALLLHAAR PEQKLISEED LDIQMTQSPS SLSASVGDRV
               TIKCQASQSI SSRLAWYQQK PGKPPKLLIY RASTLASGVP SRFSGSGSGT
               DFTLTISSLQ PEDVATYYCQ CTGYGISWPI GGGTKVEIKG GGGSGGGGSG
               GGGSQVQLVE SGGGVVQPGR SLRLSCAASG FSFSSTYVCW VRQAPGKGLE
               WIACIYTGDG TNYSASWAKG RFTISKDSSK NTVYLQMNSL RAEDTAVYFC
               ARPDITYGFA INFWGPGTLV TVSSAAGSGG GSGILVKQSP MLVAYDNAVN
               LSCKYSYNLF SREFRASLHK GLDSAVEVCV VYGNYSQQLQ VYSKTGFNCD
               GKLGNESVTF YLQNLYVNQT DIYFCKIEVM YPPPYLDNEK SNGTIIHVKG
               KHLCPSPLFP GPSKPFWVLV VGGVLACYS LLVTVAFIIF WVRSKRSRLL
               HSDYMNMTPR RPGPTRKHYQ PYAPPRDFAA YRSKKVAKKP TNKAPHPKQE
               PQEINFPDDL PGSNTAAPVQ ETLHGCQPVT QEDGKESRIS VQERQ
```

TABLE 8-continued

TCR costimulation construct examples

SEQ ID NO: 55
vector clone: pIB1023
Sequence:
MALPVTALLL PLALLLHAAR PEQKLISEED LQVQLVQSGA EVKKPGASVK
VSCKASGYTF TGYYMHWVRQ APGQGLEWMG WINPDSGGTN YAQKFQGRVT
MTRDTSISTA YMELNRLRSD DTAVYYCARD QPLGYCTNGV CSYFDYWGQG
TLVTVSSGGG GSGGGGSGGG GSDIQMTQSP SSVSASVGDR VTITCRASQG
IYSWLAWYQQ KPGKAPNLLI YTASTLQSGV PSRFSGSGSG TDFTLTISSL
QPEDFATYYC QQANIFPLTF GGGTKVEIKA AAGSGGSGIL VKQSPMLVAY
DNAVNLSCKY SYNLFSREFR ASLHKGLDSA VEVCVVYGNY SQQLQVYSKT
GFNCDGKLGN ESVTFYLQNL YVNQTDIYFC KIEVMYPPPY LDNEKSNGTI
IHVKGKHLCP SPLFPGPSKP FWVLVVVGGV LACYSLLVTV AFIIFWVRSK
RSRLLHSDYM NMTPRRPGPT RKHYQPYAPP RDFAAYRSKK VAKKPTNKAP
HPKQEPQEIN FPDDLPGSNT AAPVQETLHG CQPVTQEDGK ESRISVQERQ SEQ ID NO: 56
vector clone: pIB1024
Sequence:
MALPVTALLL PLALLLHAAR PEQKLISEED LDIQMTQSPS SVSASVGDRV
TITCRASQGI YSWLAWYQQK PGKAPNLLIY TASTLQSGVP SRFSGSGSGT
DFTLTISSLQ PEDFATYYCQ QANIFPLTFG GGTKVEIKGG GGSGGGGSGG
GGSQVQLVQS GAEVKKPGAS VKVSCKASGY TFTGYYMHWV RQAPGQGLEW
MGWINPDSGG TNYAQKFQGR VTMTRDTSIS TAYMELNRLR SDDTAVYYCA
RDQPLGYCTN GVCSYFDYWG QGTLVTVSSA AAGSGGSGIL VKQSPMLVAY
DNAVNLSCKY SYNLFSREFR ASLHKGLDSA VEVCVVYGNY SQQLQVYSKT
GFNCDGKLGN ESVTFYLQNL YVNQTDIYFC KIEVMYPPPY LDNEKSNGTI
IHVKGKHLCP SPLFPGPSKP FWVLVVVGGV LACYSLLVTV AFIIFWVRSK
RSRLLHSDYM NMTPRRPGPT RKHYQPYAPP RDFAAYRSKK VAKKPTNKAP
HPKQEPQEIN FPDDLPGSNT AAPVQETLHG CQPVTQEDGK ESRISVQERQ SEQ ID NO: 57
vector clone: pIB1025
Sequence:
MALPVTALLL PLALLLHAAR PEQKLISEED LILVKQSPML VAYDNAVNLS
CKYSYNLFSR EFRASLHKGL DSAVEVCVVY GNYSQQLQVY SKTGFNCDGK
LGNESVTFYL QNLYVNQTDI YFCKIEVMYP PPYLDNEKSN GTIIHVKGKH
LCPSPLFPGP SKPFWVLVVV GGVLACYSLL VTVAFIIFWV RSKRSRLLHS
DYMNMTPRRP GPTRKHYQPY APPRDFAAYR SKKVAKKPTN KAPHPKQEPQ
EINFPDDLPG SNTAAPVQET LHGCQPVTQE DGKESRISVQ ERQ SEQ ID NO: 58
vector clone: pIB1026
Sequence:
MEHSTFLSGL VLATLLSQVS PEQKLISEED LFKIPIEELE DRVFVNCNTS
ITWVEGTVGT LLSDITRLDL GKRILDPRGI YRCNGTDIYK DKESTVQVHY
RMCQSCVELD PATVAGIIVT DVIATLLLAL GVFCFARSKR SRLLHSDYMN
MTPRRPGPTR KHYQPYAPPR DFAAYRSKKV AKKPTNKAPH PKQEPQEINF
PDDLPGSNTA APVQETLHGC QPVTQEDGKE SRISVQERQ SEQ ID NO: 59
vector clone: pIB1027
Sequence:
MQSGTHWRVL GLCLLSVGVW GQDYKDDDDK DGNEEMGGIT QTPYKVSISG
TTVILTCPQY PGSEILWQHN DKNIGGDEDD KNIGSDEDHL SLKEFSELEQ
SGYYVCYPRG SKPEDANFYL YLRARVCENC MEMDVMSVAT IVIVDICITG
GLLLLVYYWS RSKRSRLLHS DYMNMTPRRP GPTRKHYQPY APPRDFAAYR
SKKVAKKPTN KAPHPKQEPQ EINFPDDLPG SNTAAPVQET LHGCQPVTQE
DGKESRISVQ ERQ SEQ ID NO: 60
vector clone: pIB1028
Sequence:
MEQGKGLAVL ILAIILLQGT LAEQKLISEE DLQSIKGNHL VKVYDYQEDG
SVLLTCDAEA KNITWFKDGK MIGFLTEDKK KWNLGSNAKD PRGMYQCKGS
QNKSKPLQVY YRMCQNCIEL NAATISGFLF AEIVSIFVLA VGVYFIARSK
RSRLLHSDYM NMTPRRPGPT RKHYQPYAPP RDFAAYRSKK VAKKPTNKAP
HPKQEPQEIN FPDDLPGSNT AAPVQETLHG CQPVTQEDGK ESRISVQERQ SEQ ID NO: 61
vector clone: pIB1029
Sequence:
MKWKALFTAA ILQAQLPITE AQSFGLLDPK LCYLLDGILF IYGVILTALF
LRSKRSRLLH SDYMNMTPRR PGPTRKHYQP YAPPRDFAAY RSKKVAKKPT
NKAPHPKQEP QEINFPDDLP GSNTAAPVQE TLHGCQPVTQ EDGKESRISV
QERQEQKLIS EEDL SEQ ID NO: 62
vector clone: pIB1030
Sequence:
MALPVTALLL PLALLLHAAR PEQKLISEED LSQPHTKPSV FVMKNGTNVA
CLVKEFYPKD IRINLVSSKK ITEFDPAIVI SPSGKYNAVK LGKYEDSNSV
TCSVQHDNKT VHSTDFEVKT DSTDHVKPKE TENTKQPSKS CHKPKAIVHT TABLE 8-continued TCR costimulation construct examples

```
                    EKVNMMSLTV LGLRMLFAKT VAVNFLLTAK LFFLRSKRSR LLHSDYMNMT
                    PRRPGPTRKH YQPYAPPRDF AAYRSKKVAK KPTNKAPHPK QEPQEINFPD
                    DLPGSNTAAP VQETLHGCQP VTQEDGKESR ISVQERQ

SEQ ID NO: 63
vector clone:      pIB1031
Sequence:
                   MALPVTALLL PLALLLHAAR PDYKDDDDKD KQLDADVSPK PTIFLPSIAE
                   TKLQKAGTYL CLLEKFFPDV IKIHWQEKKS NTILGSQEGN TMKTNDTYMK
                   FSWLTVPEKS LDKEHRCIVR HENNKNGVDQ EIIFPPIKTD VITMDPKDNC
                   SKDANDTLLL QLTNTSAYYM YLLLLLKSVV YFAIITCCLL RSKRSRLLHS
                   DYMNMTPRRP GPTRKHYQPY APPRDFAAYR SKKVAKKPTN KAPHPKQEPQ
                   EINFPDDLPG SNTAAPVQET LHGCQPVTQE DGKESRISVQ ERQ SEQ ID NO: 64
vector clone:      pIB1032
Sequence:
                   MALPVTALLL PLALLLHAAR PEQKLISEED LIQNPEPAVY QLKDPRSQDS
                   TLCLFTDFDS QINVPKTMES GTFITDKCVL DMKAMDSKSN GAIAWSNQTS
                   FTCQDIFKET NATYPSSDVP CDATLTEKSF ETDMNLNFQN LLVIVLRILL
                   LKVAGFNLLM TLRLWSSRSK RSRLLHSDYM NMTPRRPGPT RKHYQPYAPP
                   RDFAAYRSKK VAKKPTNKAP HPKQEPQEIN FPDDLPGSNT AAPVQETLHG
                   CQPVTQEDGK ESRISVQERQ SEQ ID NO: 65
vector clone:      pIB1033
Sequence:
                   MALPVTALLL PLALLLHAAR PDYKDDDDKV LTPPKVSLFE PSKAEIANKQ
                   KATLVCLARG FFPDHVELSW WVNGKEVHSG VCTDPQAYKE SNYSYCLSSR
                   LRVSATFWHN PRNHFRCQVQ FHGLSEEDKW PEGSPKPVTQ NISAEAWGRA
                   DCGITSASYQ QGVLSATILY EILLGKATLY AVLVSTLVVM AMVKRKNSRS
                   KRSRLLHSDY MNMTPRRPGP TRKHYQPYAP PRDFAAYRSK KVAKKPTNKA
                   PHPKQEPQEI NFPDDLPGSN TAAPVQETLH GCQPVTQEDG KESRISVQER
                   Q SEQ ID NO: 66
vector clone:      pIB1046
Sequence:
                   MALPVTALLL PLALLLHAAR PEQKLISEED LSQPHTKPSV FVMKNGTNVA
                   CLVKEFYPKD IRINLVSSKK ITEFDPAIVI SPSGKYNAVK LGKYEDSNSV
                   TCSVQHDNKT VHSTDFEVKT DSTDHVKPKE TENTKQPSKS CHKPKAIVHT
                   EKVNMMSLTV LGLRMLFAKT VAVNFLLTAK LFFLRSKRSR LLHSDYMNMT
                   PRRPGPTRKH YQPYAPPRDF AAYRSKKVAK KPTNKAPHPK QEPQEINFPD
                   DLPGSNTAAP VQETLHGCQP VTQEDGKESR ISVQERQRAK RGSGEGRGSL
                   LTCGDVEENP GPMALPVTAL LLPLALLLHA ARPDYKDDDD KDKQLDADVS
                   PKPTIFLPSI AETKLQKAGT YLCLLEKFFP DVIKIHWQEK KSNTILGSQE
                   GNTMKTNDTY MKFSWLTVPE KSLDKEHRCI VRHENNKNGV DQEIIFPPIK
                   TDVITMDPKD NCSKDANDTL LLQLTNTSAY YMYLLLLLKS VVYFAIITCC
                   LLRSKRSRLL HSDYMNMTPR RPGPTRKHYQ PYAPPRDFAA YRSKKVAKKP
                   TNKAPHPKQE PQEINFPDDL PGSNTAAPVQ ETLHGCQPVT QEDGKESRIS
                   VQERQ SEQ ID NO: 67
vector clone:      pIB1047
Sequence:
                   MALPVTALLL PLALLLHAAR PEQKLISEED LIQNPEPAVY QLKDPRSQDS
                   TLCLFTDFDS QINVPKTMES GTFITDKCVL DMKAMDSKSN GAIAWSNQTS
                   FTCQDIFKET NATYPSSDVP CDATLTEKSF ETDMNLNFQN LLVIVLRILL
                   LKVAGFNLLM TLRLWSSRSK RSRLLHSDYM NMTPRRPGPT RKHYQPYAPP
                   RDFAAYRSKK VAKKPTNKAP HPKQEPQEIN FPDDLPGSNT AAPVQETLHG
                   CQPVTQEDGK ESRISVQERQ RAKRGSGEGR GSLLTCGDVE ENPGPMALPV
                   TALLLPLALL LHAARPDYKD DDDKVLTPPK VSLFEPSKAE IANKQKATLV
                   CLARGFFPDH VELSWWVNGK EVHSGVCTDP QAYKESNYSY CLSSRLRVSA
                   TFWHNPRNHF RCQVQFHGLS EEDKWPEGSP KPVTQNISAE AWGRADCGIT
                   SASYQQGVLS ATILYEILLG KATLYAVLVS TLVVMAMVKR KNSRSKRSRL
                   LHSDYMNMTP RRPGPTRKHY QPYAPPRDFA AYRSKKVAKK PTNKAPHPKQ
                   EPQEINFPDD LPGSNTAAPV QETLHGCQPV TQEDGKESRI SVQERQ SEQ ID NO: 68
vector clone:      pIB1048
Sequence:
                   MEHSTFLSGL VLATLLSQVS PEQKLISEED LFKIPIEELE DRVFVNCNTS
                   ITWVEGTVGT LLSDITRLDL GKRILDPRGI YRCNGTDIYK DKESTVQVHY
                   RMCQSCVELD PATVAGIIVT DVIATLLLAL GVFCFARSKR SRLLHSDYMN
                   MTPRRPGPTR KHYQPYAPPR DFAAYRSKKV AKKPTNKAPH PKQEPQEINF
                   PDDLPGSNTA APVQETLHGC QPVTQEDGKE SRISVQERQR AKRGSGEGRG
                   SLLTCGDVEE NPGPMQSGTH WRVLGLCLLS VGVWGQDYKD
                   DDDKDGNEEM
                   GGITQTPYKV SISGTTVILT CPQYPGSEIL WQHNDKNIGG DEDDKNIGSD
                   EDHLSLKEFS ELEQSGYYVC YPRGSKPEDA NFYLYLRARV CENCMEMDVM
                   SVATIVIVDI CITGGLLLLV YYWSRSKRSR LLHSDYMNMT PRRPGPTRKH
                   YQPYAPPRDF AAYRSKKVAK KPTNKAPHPK QEPQEINFPD DLPGSNTAAP
                   VQETLHGCQP VTQEDGKESR ISVQERQ
```

TABLE 8-continued

TCR costimulation construct examples

SEQ ID NO: 69
vector clone: pIB1049
Sequence:
MEQGKGLAVL ILAIILLQGT LAEQKLISEE DLQSIKGNHL VKVYDYQEDG
SVLLTCDAEA KNITWFKDGK MIGFLTEDKK KWNLGSNAKD PRGMYQCKGS
QNKSKPLQVY YRMCQNCIEL NAATISGFLF AEIVSIFVLA VGVYFIARSK
RSRLLHSDYM NMTPRRPGPT RKHYQPYAPP RDFAAYRSKK VAKKPTNKAP
HPKQEPQEIN FPDDLPGSNT AAPVQETLHG CQPVTQEDGK ESRISVQERQ
RAKRGSGMQS GTHWRVLGLC LLSVGVWGQD YKDDDDKDGN
EEMGGITQTP
YKVSISGTTV ILTCPQYPGS EILWQHNDKN IGGDEDDKNI GSDEDHLSLK
EFSELEQSGY YVCYPRGSKP EDANFYLYLR ARVCENCMEM DVMSVATIVI
VDICITGGLL LLVYYWSRSK RSRLLHSDYM NMTPRRPGPT RKHYQPYAPP
RDFAAYRSKK VAKKPTNKAP HPKQEPQEIN FPDDLPGSNT AAPVQETLHG
CQPVTQEDGK ESRISVQERQ SEQ ID NO: 70
vector clone: pIB1050
Sequence:
MEHSTFLSGL VLATLLSQVS PEQKLISEED LFKIPIEELE DRVFVNCNTS
ITWVEGTVGT LLSDITRLDL GKRILDPRGI YRCNGTDIYK DKESTVQVHY
RMCQSCVELD PATVAGIIVT DVIATLLLAL GVFCFAGHET GRLSGAADTQ
ALLRNDQVYQ PLRDRDDAQY SHLGGNWARN KRSKRSRLLH SDYMNMTPRR
PGPTRKHYQP YAPPRDFAAY RSKKVAKKPT NKAPHPKQEP QEINFPDDLP
GSNTAAPVQE TLHGCQPVTQ EDGKESRISV QERQRAKRGS GEGRGSLLTC
GDVEENPGPM QSGTHWRVLG LCLLSVGVWG QDYKDDDDKD
GNEEMGGITQ
TPYKVSISGT TVILTCPQYP GSEILWQHND KNIGGDEDDK NIGSDEDHLS
LKEFSELEQS GYYVCYPRGS KPEDANFYLY LRARVCENCM EMDVMSVATI
VIVDICITGG LLLLVYYWSK NRKAKAKPVT RGAGAGGRQR GQNKERPPPV
PNPDYEPIRK GQRDLYSGLN QRRIRSKRSR LLHSDYMNMT PRRPGPTRKH
YQPYAPPRDF AAYRSKKVAK KPTNKAPHPK QEPQEINFPD DLPGSNTAAP
VQETLHGCQP VTQEDGKESR ISVQERQ SEQ ID NO: 71
vector clone: pIB1051
Sequence:
MEHSTFLSGL VLATLLSQVS PEQKLISEED LFKIPIEELE DRVFVNCNTS
ITWVEGTVGT LLSDITRLDL GKRILDPRGI YRCNGTDIYK DKESTVQVHY
RMCQSCVELD PATVAGIIVT DVIATLLLAL GVFCFAGHET GRLSGAADTQ
ALLRNDQVYQ PLRDRDDAQY SHLGGNWARN KRAKRGSGEG RGSLLTCGDV
EENPGPMQSG THWRVLGLCL LSVGVWGQDY KDDDDKDGNE EMGGITQTPY
KVSISGTTVI LTCPQYPGSE ILWQHNDKNI GGDEDDKNIG SDEDHLSLKE
FSELEQSGYY VCYPRGSKPE DANFYLYLRA RVCENCMEMD VMSVATIVIV
DICITGGLLL LVYYWSKNRK AKAKPVTRGA GAGGRQRGQN KERPPPVPNP
DYEPIRKGQR DLYSGLNQRR I SEQ ID NO: 72
vector clone: pIB1052
Sequence:
MEHSTFLSGL VLATLLSQVS PEQKLISEED LFKIPIEELE DRVFVNCNTS
ITWVEGTVGT LLSDITRLDL GKRILDPRGI YRCNGTDIYK DKESTVQVHY
RMCQSCVELD PATVAGIIVT DVIATLLLAL GVFCFARAKR GSGEGRGSLL
TCGDVEENPG PMQSGTHWRV LGLCLLSVGV WGQDYKDDDD
KDGNEEMGGI
TQTPYKVSIS GTTVILTCPQ YPGSEILWQH NDKNIGGDED DKNIGSDEDH
LSLKEFSELE QSGYYVCYPR GSKPEDANFY LYLRARVCEN CMEMDVMSVA
TIVIVDICIT GGLLLLVYYW S SEQ ID NO: 73
vector clone: pIB1053
Sequence:
MEQGKGLAVL ILAIILLQGT LAEQKLISEE DLQSIKGNHL VKVYDYQEDG
SVLLTCDAEA KNITWFKDGK MIGFLTEDKK KWNLGSNAKD PRGMYQCKGS
QNKSKPLQVY YRMCQNCIEL NAATISGFLF AEIVSIFVLA VGVYFIAGQD
GVRQSRASDK QTLLPNDQLY QPLKDREDDQ YSHLQGNQLR RNRSKRSRLL
HSDYMNMTPR RPGPTRKHYQ PYAPPRDFAA YRSKKVAKKP TNKAPHPKQE
PQEINFPDDL PGSNTAAPVQ ETLHGCQPVT QEDGKESRIS VQERQRAKRG
SGEGRGSLLT CGDVEENPGP MQSGTHWRVL GLCLLSVGVW GQDYKDDDDK
DGNEEMGGIT QTPYKVSISG TTVILTCPQY PGSEILWQHN DKNIGGDEDD
KNIGSDEDHL SLKEFSELEQ SGYYVCYPRG SKPEDANFYL YLRARVCENC
MEMDVMSVAT IVIVDICITG GLLLLVYYWS KNRKAKAKPV TRGAGAGGRQ
RGQNKERPPP VPNPDYEPIR KGQRDLYSGL NQRRIRSKRS RLLHSDYMNM
TPRRPGPTRK HYQPYAPPRD FAAYRSKKVA KKPTNKAPHP QEPQEINFP
DDLPGSNTAA PVQETLHGCQ PVTQEDGKES RISVQERQ SEQ ID NO: 74
vector clone: pIB1054
Sequence:
MEQGKGLAVL ILAIILLQGT LAEQKLISEE DLQSIKGNHL VKVYDYQEDG
SVLLTCDAEA KNITWFKDGK MIGFLTEDKK KWNLGSNAKD PRGMYQCKGS
QNKSKPLQVY YRMCQNCIEL NAATISGFLF AEIVSIFVLA VGVYFIAGQD
GVRQSRASDK QTLLPNDQLY QPLKDREDDQ YSHLQGNQLR RNRAKRGSGE
GRGSLLTCGD VEENPGPMQS GTHWRVLGLC LLSVGVWGQD TABLE 8-continued TCR costimulation construct examples

|  | YKDDDDKDGN<br>EEMGGITQTP YKVSISGTTV ILTCPQYPGS EILWQHNDKN IGGDEDDKNI<br>GSDEDHLSLK EFSELEQSGY YVCYPRGSKP EDANFYLYLR ARVCENCMEM<br>DVMSVATIVI VDICITGGLL LLVYYWSKNR KAKAKPVTRG AGAGGRQRGQ<br>NKERPPPVPN PDYEPIRKGQ RDLYSGLNQR RI |

SEQ ID NO: 75
vector clone: pIB1055
Sequence:
MEQGKGLAVL ILAIILLQGT LAEQKLISEE DLQSIKGNHL VKVYDYQEDG
SVLLTCDAEA KNITWFKDGK MIGFLTEDKK KWNLGSNAKD PRGMYQCKGS
QNKSKPLQVY YRMCQNCIEL NAATISGFLF AEIVSIFVLA VGVYFIARAK
RGSGEGRGSL LTCGDVEENP GPMQSGTHWR VLGLCLLSVG VWGQDYKDDD
DKDGNEEMGG ITQTPYKVSI SGTTVILTCP QYPGSEILWQ HNDKNIGGDE
DDKNIGSDED HLSLKEFSEL EQSGYYVCYP RGSKPEDANF YLYLRARVCE
NCMEMDVMSV ATIVIVDICI TGGLLLLVYY WS SEQ ID NO: 76
vector clone: pIB1056
Sequence:
MKWKALFTAA ILQAQLPITE AQSFGLLDPK LCYLLDGILF IYGVILTALF
LRVKFSRSAD APAYQQGQNQ LYNELNLGRR EEYDVLDKRR GRDPEMGGKP
QRRKNPQEGL YNELQKDKMA EAYSEIGMKG ERRRGKGHDG LYQGLSTATK
DTYDALHMQA LPPRRSKRSR LLHSDYMNMT PRRPGPTRKH YQPYAPPRDF
AAYRSKKVAK KPTNKAPHPK QEPQEINFPD DLPGSNTAAP VQETLHGCQP
VTQEDGKESR ISVQERQEQK LISEEDL SEQ ID NO: 78
vector clone: pIB1057
Sequence:
MKWKALFTAA ILQAQLPITE AQSFGLLDPK LCYLLDGILF IYGVILTALF
LRVKFSRSAD APAYQQGQNQ LYNELNLGRR EEYDVLDKRR GRDPEMGGKP
QRRKNPQEGL YNELQKDKMA EAYSEIGMKG ERRRGKGHDG LYQGLSTATK
DTYDALHMQA LPPREQKLIS EEDL SEQ ID NO: 79
vector clone: pIB1058
Sequence:
MKWKALFTAA ILQAQLPITE AQSFGLLDPK LCYLLDGILF IYGVILTALF
LEQKLISEED L SEQ ID NO: 80
vector clone: pIB1059
Sequence:
MKWKALFTAA ILQAQLPITE AQSFGLLDPK LCYLLDGILF IYGVILTALF
LRVKFSRSAD APAYQQGQNQ LYNELNLGRR EEYDVLDKRR GRDPEMGGKP
QRRKNPQEGL YNELQKDKMA EAYSEIGMKG ERRRGKGHDG LYQGLSTATK
DTYDALHMQA LPPRRVKFSR SADAPAYQQG QNQLYNELNL GRREEYDVLD
KRRGRDPEMG GKPQRRKNPQ EGLYNELQKD KMAEAYSEIG MKGERRRGKG
HDGLYQGLST ATKDTYDALH MQALPPRRSK RSRLLHSDYM NMTPRRPGPT
RKHYQPYAPP RDFAAYRSKK VAKKPTNKAP HPKQEPQEIN FPDDLPGSNT
AAPVQETLHG CQPVTQEDGK ESRISVQERQ EQKLISEEDL SEQ ID NO: 81
vector clone: pIB1060
Sequence:
MKWKALFTAA ILQAQLPITE AQSFGLLDPK LCYLLDGILF IYGVILTALF
LRVKFSRSAD APAYQQGQNQ LYNELNLGRR EEYDVLDKRR GRDPEMGGKP
QRRKNPQEGL YNELQKDKMA EAYSEIGMKG ERRRGKGHDG LYQGLSTATK
DTYDALHMQA LPPRRVKFSR SADAPAYQQG QNQLYNELNL GRREEYDVLD
KRRGRDPEMG GKPQRRKNPQ EGLYNELQKD KMAEAYSEIG MKGERRRGKG
HDGLYQGLST ATKDTYDALH MQALPPREQK LISEEDL SEQ ID NO: 82
vector clone: pIB1061
Sequence:
MKWKALFTAA ILQAQLPITE AQSFGLLDPK LCYLLDGILF IYGVILTALF
LRSKRSRLLH SDYMNMTPRR PGPTRKHYQP YAPPRDFAAY RSKKVAKKPT
NKAPHPKQEP QEINFPDDLP GSNTAAPVQE TLHGCQPVTQ EDGKESRISV
QERQRVKFSR SADAPAYQQG QNQLYNELNL GRREEYDVLD KRRGRDPEMG
GKPQRRKNPQ EGLYNELQKD KMAEAYSEIG MKGERRRGKG HDGLYQGLST
ATKDTYDALH MQALPPRRVK FSRSADAPAY QQGQNQLYNE LNLGRREEYD
VLDKRRGRDP EMGGKPQRRK NPQEGLYNEL QKDKMAEAYS EIGMKGERRR
GKGHDGLYQG LSTATKDTYD ALHMQALPPR EQKLISEEDL SEQ ID NO: 83
vector clone: pIB1062
Sequence:
MKWKALFTAA ILQAQLPITE AQSFGLLDPK LCYLLDGILF IYGVILTALF
LRSKRSRLLH SDYMNMTPRR PGPTRKHYQP YAPPRDFAAY RSKKVAKKPT
NKAPHPKQEP QEINFPDDLP GSNTAAPVQE TLHGCQPVTQ EDGKESRISV
QERQRVKFSR SADAPAYQQG QNQLYNELNL GRREEYDVLD KRRGRDPEMG
GKPQRRKNPQ EGLYNELQKD KMAEAYSEIG MKGERRRGKG HDGLYQGLST
ATKDTYDALH MQALPPREQK LISEEDL TABLE 8-continued TCR costimulation construct examples SEQ ID NO: 84
vector clone: pIB1063
Sequence:
MGHTRRQGTS PSKCPYLNFF QLLVLAGLSH FCSGEQKLIS EEDLVIHVTK
EVKEVATLSC GHNVSVEELA QTRIYWQKEK KMVLTMMSGD MNIWPEYKNR
TIFDITNNLS IVILALRPSD EGTYECVVLK YEKDAFKREH LAEVTLSVKA
DFPTPSISDF EIPTSNIRRI ICSTSGGFPE PHLSWLENGE ELNAINTTVS
QDPETELYAV SSKLDFNMTT NHSFMCLIKY GHLRVNQTFN WNTTKQEHFP
DNLLPSWAIT LISVNGIFVI CCL SEQ ID NO: 85
vector clone: pIB1064
Sequence:
MGCGCSSHPE DDWMENIDVC ENCHYPIVPL DGKGTLLIRN GSEVRDPLVT
YEGSNPPASP LQDNLVIALH SYEPSHDGDL GFEKGEQLRI LEQSGEWWKA
QSLTTGQEGF IPFNFVAKAN SLEPEPWFFK NLSRKDAERQ LLAPGNTHGS
FLIRESESTA GSFSLSVRDF DQNQGEVVKH YKIRNLDNGG FYISPRITFP
GLHELVRHYT NASDGLCTRL SRPCQTQKPQ KPWWEDEWEV PRETLKLVER
LGAGQFGEVW MGYYNGHTKV AVKSLKQGSM SPDAFLAEAN
LMKQLQHQRL
VRLYAVVTQE PIYIITEYME NGSLVDFLKT PSGIKLTINK LLDMAAQIAE
GMAFIEERNY IHRDLRAANI LVSDTLSCKI ADFGLARLIE DNEYTAREGA
KFPIKWTAPE AINYGTFTIK SDVWSFGILL TEIVTHGRIP YPGMTNPEVI
QNLERGYRMV RPDNCPEELY QLMRLCWKER PEDRPTFDYL RSVLEDFFTA
TEGQYQPQPE QKLISEEDL SEQ ID NO: 86
vector clone: pIB1065
Sequence:
MGCGCSSHPE DDWMENIDVC ENCHYPIVPL DGKGTLLIRN GSEVRDPLVT
YEGSNPPASP LQDNLVIALH SYEPSHDGDL GFEKGEQLRI LEQSGEWWKA
QSLTTGQEGF IPFNFVAKAN SLEPEPWFFK NLSRKDAERQ LLAPGNTHGS
FLIRESESTA GSFSLSVRDF DQNQGEVVKH YKIRNLDNGG FYISPRITFP
GLHELVRHYT NASDGLCTRL SRPCQTQKPQ KPWWEDEWEV PRETLKLVER
LGAGQFGEVW MGYYNGHTKV AVKSLKQGSM SPDAFLAEAN
LMKQLQHQRL
VRLYAVVTQE PIYIITEYME NGSLVDFLKT PSGIKLTINK LLDMAAQIAE
GMAFIEERNY IHRDLRAANI LVSDTLSCKI ADFGLARLIE DNEYTAREGA
KFPIKWTAPE AINYGTFTIK SDVWSFGILL TEIVTHGRIP YPGMTNPEVI
QNLERGYRMV RPDNCPEELY QLMRLCWKER PEDRPTFDYL RSVLEDFFTA
TEGQFQPQPE QKLISEEDL SEQ ID NO: 87
vector clone: pIB1066
Sequence:
MGHTRRQGTS PSKCPYLNFF QLLVLAGLSH FCSGEQKLIS EEDLVIHVTK
EVKEVATLSC GHNVSVEELA QTRIYWQKEK KMVLTMMSGD MNIWPEYKNR
TIFDITNNLS IVILALRPSD EGTYECVVLK YEKDAFKREH LAEVTLSVKA
DFPTPSISDF EIPTSNIRRI ICSTSGGFPE PHLSWLENGE ELNAINTTVS
QDPETELYAV SSKLDFNMTT NHSFMCLIKY GHLRVNQTFN WNTTKQEHFP
DNLLPSWAIT LISVNGIFVI CCLGCGCSSH PEDDWMENID VCENCHYPIV
PLDGKGTLLI RNGSEVRDPL VTYEGSNPPA SPLQDNLVIA LHSYEPSHDG
DLGFEKGEQL RILEQSGEWW KAQSLTTGQE GFIPFNFVAK ANSLEPEPWF
FKNLSRKDAE RQLLAPGNTH GSFLIRESES TAGSFSLSVR DFDQNQGEVV
KHYKIRNLDN GGFYISPRIT FPGLHELVRH YTNASDGLCT RLSRPCQTQK
PQKPWWEDEW EVPRETLKLV ERLGAGQFGE VWMGYYNGHT
KVAVKSLKQG
SMSPDAFLAE ANLMKQLQHQ RLVRLYAVVT QEPIYIITEY MENGSLVDFL
KTPSGIKLTI NKLLDMAAQI AEGMAFIEER NYIHRDLRAA NILVSDTLSC
KIADFGLARL IEDNEYTARE GAKFPIKWTA PEAINYGTFT IKSDVWSFGI
LLTEIVTHGR IPYPGMTNPE VIQNLERGYR MVRPDNCPEE LYQLMRLCWK
ERPEDRPTFD YLRSVLEDFF TATEGQYQPQ P SEQ ID NO: 88
vector clone: pIB1067
Sequence:
MGHTRRQGTS PSKCPYLNFF QLLVLAGLSH FCSGEQKLIS EEDLVIHVTK
EVKEVATLSC GHNVSVEELA QTRIYWQKEK KMVLTMMSGD MNIWPEYKNR
TIFDITNNLS IVILALRPSD EGTYECVVLK YEKDAFKREH LAEVTLSVKA
DFPTPSISDF EIPTSNIRRI ICSTSGGFPE PHLSWLENGE ELNAINTTVS
QDPETELYAV SSKLDFNMTT NHSFMCLIKY GHLRVNQTFN WNTTKQEHFP
DNLLPSWAIT LISVNGIFVI CCLGCGCSSH PEDDWMENID VCENCHYPIV
PLDGKGTLLI RNGSEVRDPL VTYEGSNPPA SPLQDNLVIA LHSYEPSHDG
DLGFEKGEQL RILEQSGEWW KAQSLTTGQE GFIPFNFVAK ANSLEPEPWF
FKNLSRKDAE RQLLAPGNTH GSFLIRESES TAGSFSLSVR DFDQNQGEVV
KHYKIRNLDN GGFYISPRIT FPGLHELVRH YTNASDGLCT RLSRPCQTQK
PQKPWWEDEW EVPRETLKLV ERLGAGQFGE VWMGYYNGHT
KVAVKSLKQG
SMSPDAFLAE ANLMKQLQHQ RLVRLYAVVT QEPIYIITEY MENGSLVDFL
KTPSGIKLTI NKLLDMAAQI AEGMAFIEER NYIHRDLRAA NILVSDTLSC
KIADFGLARL IEDNEYTARE GAKFPIKWTA PEAINYGTFT IKSDVWSFGI
LLTEIVTHGR IPYPGMTNPE VIQNLERGYR MVRPDNCPEE LYQLMRLCWK TABLE 8-continued TCR costimulation construct examples

```
                    ERPEDRPTFD YLRSVLEDFF TATEGQYQPQ PRSKRSRLLH SDYMNMTPRR
                    PGPTRKHYQP YAPPRDFAAY RSKKVAKKPT NKAPHPKQEP QEINFPDDLP
                    GSNTAAPVQE TLHGCQPVTQ EDGKESRISV QERQ

SEQ ID NO: 89
vector clone:      pIB1068
Sequence:
                    MGHTRRQGTS PSKCPYLNFF QLLVLAGLSH FCSGEQKLIS EEDLVIHVTK
                    EVKEVATLSC GHNVSVEELA QTRIYWQKEK KMVLTMMSGD MNIWPEYKNR
                    TIFDITNNLS IVILALRPSD EGTYECVVLK YEKDAFKREH LAEVTLSVKA
                    DFPTPSISDF EIPTSNIRRI ICSTSGGFPE PHLSWLENGE ELNAINTTVS
                    QDPETELYAV SSKLDFNMTT NHSFMCLIKY GHLRVNQTFN WNTTKQEHFP
                    DNLLPSWAIT LISVNGIFVI CCLGCGCSSH PEDDWMENID VCENCHYPIV
                    PLDGKGTLLI RNGSEVRDPL VTYEGSNPPA SPLQDNLVIA LHSYEPSHDG
                    DLGFEKGEQL RILEQSGEWW KAQSLTTGQE GFIPFNFVAK ANSLEPEPWF
                    FKNLSRKDAE RQLLAPGNTH GSFLIRESES TAGSFSLSVR DFDQNQGEVV
                    KHYKIRNLDN GGFYISPRIT FPGLHELVRH YTNASDGLCT RLSRPCQTQK
                    PQKPWWEDEW EVPRETLKLV ERLGAGQFGE VWMGYYNGHT
                    KVAVKSLKQG
                    SMSPDAFLAE ANLMKQLHQQ RLVRLYAVVT QEPIYIITEY MENGSLVDFL
                    KTPSGIKLTI NKLLDMAAQI AEGMAFIEER NYIHRDLRAA NILVSDTLSC
                    KIADFGLARL IEDNEYTARE GAKFPIKWTA PEAINYGTFT IKSDVWSFGI
                    LLTEIVTHGR IPYPGMTNPE VIQNLERGYR MVRPDNCPEE LYQLMRLCWK
                    ERPEDRPTFD YLRSVLEDFF TATEGQFQPQ P SEQ ID NO: 90
vector clone:      pIB1069
Sequence:
                    MGHTRRQGTS PSKCPYLNFF QLLVLAGLSH FCSGEQKLIS EEDLVIHVTK
                    EVKEVATLSC GHNVSVEELA QTRIYWQKEK KMVLTMMSGD MNIWPEYKNR
                    TIFDITNNLS IVILALRPSD EGTYECVVLK YEKDAFKREH LAEVTLSVKA
                    DFPTPSISDF EIPTSNIRRI ICSTSGGFPE PHLSWLENGE ELNAINTTVS
                    QDPETELYAV SSKLDFNMTT NHSFMCLIKY GHLRVNQTFN WNTTKQEHFP
                    DNLLPSWAIT LISVNGIFVI CCLGCGCSSH PEDDWMENID VCENCHYPIV
                    PLDGKGTLLI RNGSEVRDPL VTYEGSNPPA SPLQDNLVIA LHSYEPSHDG
                    DLGFEKGEQL RILEQSGEWW KAQSLTTGQE GFIPFNFVAK ANSLEPEPWF
                    FKNLSRKDAE RQLLAPGNTH GSFLIRESES TAGSFSLSVR DFDQNQGEVV
                    KHYKIRNLDN GGFYISPRIT FPGLHELVRH YTNASDGLCT RLSRPCQTQK
                    PQKPWWEDEW EVPRETLKLV ERLGAGQFGE VWMGYYNGHT
                    KVAVKSLKQG
                    SMSPDAFLAE ANLMKQLHQQ RLVRLYAVVT QEPIYIITEY MENGSLVDFL
                    KTPSGIKLTI NKLLDMAAQI AEGMAFIEER NYIHRDLRAA NILVSDTLSC
                    KIADFGLARL IEDNEYTARE GAKFPIKWTA PEAINYGTFT IKSDVWSFGI
                    LLTEIVTHGR IPYPGMTNPE VIQNLERGYR MVRPDNCPEE LYQLMRLCWK
                    ERPEDRPTFD YLRSVLEDFF TATEGQFQPQ PRSKRSRLLH SDYMNMTPRR
                    PGPTRKHYQP YAPPRDFAAY RSKKVAKKPT NKAPHPKQEP QEINFPDDLP
                    GSNTAAPVQE TLHGCQPVTQ EDGKESRISV QERQ SEQ ID NO: 91
vector clone:      pIB1070
Sequence:
                    MALPVTALLL PLALLLHAAR PEQKLISEED LMEEAILVPC VLGLLLLPIL
                    AMLMALCVHC HRLPGSYDST SSDSLYPRGI QFKRPHTVAP WPPAYPPVTS
                    YPPLSQPDLL PIPRSPQPLG GSHRTPSSRR DSDGANSVAS YENEGASGIR
                    GAQAGWGVWG PSWTRLTPVS LPPEPACEDA DEDEDDYHNP GYLVVLPDST
                    PATSTAAPSA PALSTPGIRD SAFSMESIDD YVNVPESGES AEASLDGSRE
                    YVNVSQELHP GAAKTEPAAL SSQEAEEVEE EGAPDYENLQ ELN SEQ ID NO: 92
vector clone:      pIB1071
Sequence:
                    MALPVTALLL PLALLLHAAR PEQKLISEED LMEEAILVPC VLGLLLLPIL
                    AMLMALCVHC HRLPGSYDST SSDSLYPRGI QFKRPHTVAP WPPAYPPVTS
                    YPPLSQPDLL PIPRSPQPLG GSHRTPSSRR DSDGANSVAS YENEGASGIR
                    GAQAGWGVWG PSWTRLTPVS LPPEPACEDA DEDEDDYHNP GYLVVLPDST
                    PATSTAAPSA PALSTPGIRD SAFSMESIDD YVNVPESGES AEASLDGSRE
                    YVNVSQELHP GAAKTEPAAL SSQEAEEVEE EGAPDYENLQ ELNRSKRSRL
                    LHSDYMNMTP RRPGPTRKHY QPYAPPRDFA AYRSKKVAKK PTNKAPHPKQ
                    EPQEINFPDD LPGSNTAAPV QETLHGCQPV TQEDGKESRI SVQERQ SEQ ID NO: 93
vector clone:      pIB1072
Sequence:
                    MNRGVPFRHL LLVLQLALLP AATQGEQKLI SEEDLKKVVL GKKGDTVELT
                    CTASQKKSIQ FHWKNSNQIK ILGNQGSFLT KGPSKLNDRA DSRRSLWDQG
                    NFPLIIKNLK IEDSDTYICE VEDQKEEVQL LVFGLTANSD THLLQGQSLT
                    LTLESPPGSS PSVQCRSPRG KNIQGGKTLS VSQLELQDSG TWTCTVLQNQ
                    KKVEFKIDIV VLAFQKASSI VYKKEGEQVE FSFPLAFTVE KLTGSGELWW
                    QAERASSSKS WITFDLKNKE VSVKRVTQDP KLQMGKKLPL HLTLPQALPQ
                    YAGSGNLTLA LEAKTGKLHQ EVNLVVMRAT QLQKNLTCEV WGPTSPKLML
                    SLKLENKEAK VSKREKAVWV LNPEAGMWQC LLSDSGQVLL ESNIKVLPTW
                    STPVQPMALI VLGGVAGLLL FIGLGIFFCV RCRHRRRQAE RMSQIKRLLS
                    EKKTCQCPHR FQKTCSPI
```

TABLE 8-continued

TCR costimulation construct examples

SEQ ID NO: 94
vector clone: pIB1073
Sequence:
MNRGVPFRHL LLVLQLALLP AATQGEQKLI SEEDLKKVVL GKKGDTVELT
CTASQKKSIQ FHWKNSNQIK ILGNQGSFLT KGPSKLNDRA DSRRSLWDQG
NFPLIIKNLK IEDSDTYICE VEDQKEEVQL LVFGLTANSD THLLQGQSLT
LTLESPPGSS PSVQCRSPRG KNIQGGKTLS VSQLELQDSG TWTCTVLQNQ
KKVEFKIDIV VLAFQKASSI VYKKEGEQVE FSFPLAFTVE KLTGSGELWW
QAERASSSKS WITFDLKNKE VSVKRVTQDP KLQMGKKLPL HLTLPQALPQ
YAGSGNLTLA LEAKTGKLHQ EVNLVVMRAT QLQKNLTCEV WGPTSPKLML
SLKLENKEAK VSKREKAVWV LNPEAGMWQC LLSDSGQVLL ESNIKVLPTW
STPVQPMALI VLGGVAGLLL FIGLGIFFCV RCRHRRRQAE RMSQIKRLLS
EKKTCQCPHR FQKTCSPIRS KRSRLLHSDY MNMTPRRPGP TRKHYQPYAP
PRDFAAYRSK KVAKKPTNKA PHPKQEPQEI NFPDDLPGSN TAAPVQETLH
GCQPVTQEDG KESRISVQER Q SEQ ID NO: 95
vector clone: pIB1074
Sequence:
MALPVTALLL PLALLLHAAR PEQKLISEED LSQFRVSPLD RTWNLGETVE
LKCQVLLSNP TSGCSWLFQP RGAAASPTFL LYLSQNKPKA AEGLDTQRFS
GKRLGDTFVL TLSDFRRENE GYYFCSALSN SIMYFSHFVP VFLPAKPTTT
PAPRPPTPAP TIASQPLSLR PEACRPAAGG AVHTRGLDFA CDIYIWAPLA
GTCGVLLLSL VITLYCNHRN RRRVCKCPRP VVKSGDKPSL SARYVRAKRG
SGEGRGSLLT CGDVEENPGP MRPRLWLLLA AQLTVLHGNS VDYKDDDDKL
QQTPAYIKVQ TNKMVMLSCE AKISLSNMRI YWLRQRQAPS SDSHHEFLAL
WDSAKGTIHG EEVEQEKIAV FRDASRFILN LTSVKPEDSG IYFCMIVGSP
ELTFGKGTQL SVVDFLPTTA QPTKKSTLKK RVCRLPRPET QKGPLCSPIT
LGLLVAGVLV LLVSLGVAIH LCCRRRRARL RFMKQFYK SEQ ID NO: 96
vector clone: pIB1075
Sequence:
MALPVTALLL PLALLLHAAR PEQKLISEED LSQFRVSPLD RTWNLGETVE
LKCQVLLSNP TSGCSWLFQP RGAAASPTFL LYLSQNKPKA AEGLDTQRFS
GKRLGDTFVL TLSDFRRENE GYYFCSALSN SIMYFSHFVP VFLPAKPTTT
PAPRPPTPAP TIASQPLSLR PEACRPAAGG AVHTRGLDFA CDIYIWAPLA
GTCGVLLLSL VITLYCNHRN RRRVCKCPRP VVKSGDKPSL SARYVRSKRS
RLLHSDYMNM TPRRPGPTRK HYQPYAPPRD FAAYRSKKVA KKPTNKAPHP
KQEPQEINFP DDLPGSNTAA PVQETLHGCQ PVTQEDGKES RISVQERQRA
KRGSGEGRGS LLTCGDVEEN PGPMRPRLWL LLAAQLTVLH GNSVDYKDDD
DKLQQTPAYI KVQTNKMVML SCEAKISLSN MRIYWLRQRQ APSSDSHHEF
LALWDSAKGT IHGEEVEQEK IAVFRDASRF ILNLTSVKPE DSGIYFCMIV
GSPELTFGKG TQLSVVDFLP TTAQPTKKST LKKRVCRLPR PETQKGPLCS
PITLGLLVAG VLVLLVSLGV AIHLCCRRRR ARLRFMKQFY KRSKRSLLH
SDYMNMTPRR PGPTRKHYQP YAPPRDFAAY RSKKVAKKPT NKAPHPKQEP
QEINFPDDLP GSNTAAPVQE TLHGCQPVTQ EDGKESRISV QERQ SEQ ID NO: 97
vector clone: pIB1076
Sequence:
MALPVTALLL PLALLLHAAR PEQKLISEED LELTDTLQAE TDQLEDEKSA
LQTEIANLLK EKEKLEFILA AHNCTYGCTG PGLEGCPTNG PKIPSIATGM
VGALLLLLVV ALGIGLFMRS KRSRLLHSDY MNMTPRRPGP TRKHYQPYAP
PRDFAAYRSK KVAKKPTNKA PHPKQEPQEI NFPDDLPGSN TAAPVQETLH
GCQPVTQEDG KESRISVQER Q SEQ ID NO: 98
vector clone: pIB1077
Sequence:
MALPVTALLL PLALLLHAAR PEQKLISEED LELTDTLQAE TDQLEDEKSA
LQTEIANLLK EKEKLEFILA AHFWVLVVVG GVLACYSLLV TVAFIIFWVR
SKRSRLLHSD YMNMTPRRPG PTRKHYQPYA PPRDFAAYRS KKVAKKPTNK
APHPKQEPQE INFPDDLPGS NTAAPVQETL HGCQPVTQED GKESRISVQE
RQ SEQ ID NO: 99
vector clone: pIB1078
Sequence:
MALPVTALLL PLALLLHAAR PEQKLISEED LLEEKVKTLK AQNSELASTA
NMLREQVAQL NCTYGCTGPG LEGCPTNGPK IPSIATGMVG ALLLLLVVAL
GIGLFMRSKR SRLLHSDYMN MTPRRPGPTR KHYQPYAPPR DFAAYRSKKV
AKKPTNKAPH PKQEPQEINF PDDLPGSNTA APVQETLHGC QPVTQEDGKE
SRISVQERQ SEQ ID NO: 100
vector clone: pIB1079
Sequence:
MALPVTALLL PLALLLHAAR PEQKLISEED LLEEKVKTLK AQNSELASTA
NMLREQVAQL FWVLVVVGGV LACYSLLVTV AFIIFWVRSK RSRLLHSDYM
NMTPRRPGPT RKHYQPYAPP RDFAAYRSKK VAKKPTNKAP HPKQEPQEIN
FPDDLPGSNT AAPVQETLHG CQPVTQEDGK ESRISVQERQ TABLE 8-continued TCR costimulation construct examples SEQ ID NO: 101
vector clone: pIB1080
Sequence:
MALPVTALLL PLALLLHAAR PEQKLISEED LETQHKVLEL TAENERLQKK
VEQLSRELST NCTYGCTGPG LEGCPTNGPK IPSIATGMVG ALLLLLVVAL
GIGLFMRSKR SRLLHSDYMN MTPRRPGPTR KHYQPYAPPR DFAAYRSKKV
AKKPTNKAPH PKQEPQEINF PDDLPGSNTA APVQETLHGC QPVTQEDGKE
SRISVQERQ SEQ ID NO: 102
vector clone: pIB1081
Sequence:
MALPVTALLL PLALLLHAAR PEQKLISEED LETQHKVLEL TAENERLQKK
VEQLSRELST FWVLVVVGGV LACYSLLVTV AFIIFWVRSK RSRLLHSDYM
NMTPRRPGPT RKHYQPYAPP RDFAAYRSKK VAKKPTNKAP HPKQEPQEIN
FPDDLPGSNT AAPVQETLHG CQPVTQEDGK ESRISVQERQ SEQ ID NO: 103
vector clone: pIB1082
Sequence:
MRPSGTAGAA LLALLAALCP ASRAEQKLIS EEDLLEEKKV CQGTSNKLTQ
LGTFEDHFLS LQRMFNNCEV VLGNLEITYV QRNYDLSFLK TIQEVAGYVL
IALNTVERIP LENLQIIRGN MYYENSYALA VLSNYDANKT GLKELPMRNL
QEILHGAVRF SNNPALCNVE SIQWRDIVSS DFLSNMSMDF QNHLGSCQKC
DPSCPNGSCW GAGEENCQKL TKIICAQQCS GRCRGKSPSD CCHNQCAAGC
TGPRESDCLV CRKFRDEATC KDTCPPLMLY NPTTYQMDVN PEGKYSFGAT
CVKKCPRNYV VTDHGSCVRA CGADSYEMEE DGVRKCKKCE GPCRKVCNGI
GIGEFKDSLS INATNIKHFK NCTSISGDLH ILPVAFRGDS FTHTPPLDPQ
ELDILKTVKE ITGFLLIQAW PENRTDLHAF ENLEIIRGRT KQHGQFSLAV
VSLNITSLGL RSLKEISDGD VIISGNKNLC YANTINWKKL FGTSGQKTKI
ISNRGENSCK ATGQVCHALC SPEGCWGPEP RDCVSCRNVS RGRECVDKCN
LLEGEPREFV ENSECIQCHP ECLPQAMNIT CTGRGPDNCI QCAHYIDGPH
CVKTCPAGVM GENNTLVWKY ADAGHVCHLC HPNCTYGCTG PGLEGCPTNG
PKIPSIATGM VGALLLLLVV ALGIGLFMRS KRSRLLHSDY MNMTPRRPGP
TRKHYQPYAP PRDFAAYRSK VAKKPTNKA PHPKQEPQEI NFPDDLPGSN
TAAPVQETLH GCQPVTQEDG KESRISVQER Q SEQ ID NO: 104
vector clone: pIB1083
Sequence:
MRPSGTAGAA LLALLAALCP ASRAEQKLIS EEDLGTSGQK TKIISNRGEN
SCKATGQVCH ALCSPEGCWG PEPRDCVSCR NVSRGRECVD KCNLLEGEPR
EFVENSECIQ CHPECLPQAM NITCTGRGPD NCIQCAHYID GPHCVKTCPA
GVMGENNTLV WKYADAGHVC HLCHPNCTYG CTGPGLEGCP TNGPKIPSIA
TGMVGALLLL LVVALGIGLF MRSKRSRLLH SDYMNMTPRR PGPTRKHYQP
YAPPRDFAAY RSKKVAKKPT NKAPHPKQEP QEINFPDDLP GSNTAAPVQE
TLHGCQPVTQ EDGKESRISV QERQ SEQ ID NO: 105
vector clone: pIB1084
Sequence:
MRPSGTAGAA LLALLAALCP ASRAEQKLIS EEDLNCTYGC TGPGLEGCPT
NGPKIPSIAT GMVGALLLLL VVALGIGLFM RSKRSRLLHS DYMNMTPRRP
GPTRKHYQPY APPRDFAAYR SKKVAKKPTN KAPHPKQEPQ EINFPDDLPG
SNTAAPVQET LHGCQPVTQE DGKESRISVQ ERQ SEQ ID NO: 106
vector clone: pIB1085
Sequence:
MELAALCRWG LLLALLPPGA ASEQKLISEE DLTQVCTGTD MKLRLPASPE
THLDMLRHLY QGCQVVQGNL ELTYLPTNAS LSFLQDIQEV QGYVLIAHNQ
VRQVPLQRLR IVRGTQLFED NYALAVLDNG DPLNNTTPVT GASPGGLREL
QLRSLTEILK GGVLIQRNPQ LCYQDTILWK DIFHKNNQLA LTLIDTNRSR
ACHPCSPMCK GSRCWGESSE DCQSLTRTVC AGGCARCKGP LPTDCCHEQC
AAGCTGPKHS DCLACLHFNH SGICELHCPA LVTYNTDTFE SMPNPEGRYT
FGASCVTACP YNYLSTDVGS CTLVCPLHNQ EVTAEDGTQR CEKCSKPCAR
VCYGLGMEHL REVRAVTSAN IQEFAGCKKI FGSLAFLPES FDGDPASNTA
PLQPEQLQVF ETLEEITGYL YISAWPDSLP DLSVFQNLQV IRGRILHNGA
YSLTLQGLGI SWLGLRSLRE LGSGLALIHH NTHLCFVHTV PWDQLFRNPH
QALLHTANRP EDECVGEGLA CHQLCARGHC WGPGPTQCVN CSQFLRGQEC
VEECRVLQGL PREYVNARHC LPCHPECPQ NGSVTCFGPE ADQCVACAHY
KDPPFCVARC PSGVKPDLSY MPIWKFPDEE GACQPCPINC THSCVDLDDK
GCPAEQRASP LTSIISAVVG ILLVVVLGVV FGILIRSKRS RLLHSDYMNM
TPRRPGPTRK HYQPYAPPRD FAAYRSKKVA KKPTNKAPHP KQEPQEINFP
DDLPGSNTAA PVQETLHGCQ PVTQEDGKES RISVQERQ SEQ ID NO: 107
vector clone: pIB1086
Sequence:
MELAALCRWG LLLALLPPGA ASEQKLISEE DLTQVCTGTD MKLRLPASPE
THLDMLRHLY QGCQVVQGNL ELTYLPTNAS LSFLQDIQEV QGYVLIAHNQ
VRQVPLQRLR IVRGTQLFED NYALAVLDNG DPLNNTTPVT GASPGGLREL
QLRSLTEILK GGVLIQRNPQ LCYQDTILWK DIFHKNNQLA LTLIDTNRSR
ACHPCSPMCK GSRCWGESSE DCQSLTRTVC AGGCARCKGP LPTDCCHEQC TABLE 8-continued TCR costimulation construct examples

```
                AAGCTGPKHS DCLACLHFNH SGICELHCPA LVTYNTDTFE SMPNPEGRYT
                FGASCVTACP YNYLSTDVGS CTLVCPLHNQ EVTAEDGTQR CEKCSKPCAR
                VCYGLGMEHL REVRAVTSAN IQEFAGCKKI FGSLAFLPES FDGDPASNTA
                PLQPEQLQVF ETLEEITGYL YISAWPDSLP DLSVFQNLQV IRGRILHNGA
                YSLTLQGLGI SWLGLRSLRE LGSSGLALIHH NTHLCFVHTV PWDQLFRNPH
                QALLHTANRP EDECVGEGLA CHQLCARGHC WGPGPTQCVN CSQFLRGQEC
                VEECRVLQGL PREYVNARHC LPCHPECQPQ NGSVTCFGPE ADQCVACAHY
                KDPPFCVARC PSGVKPDLSY MPIWKFPDEE GACQPCPINC THSCVDLDDK
                GCPAEQRASP LTSIISAVEG ILLVVVLGVV FGILIRSKRS RLLHSDYMNM
                TPRRPGPTRK HYQPYAPPRD FAAYRSKKVA KKPTNKAPHP KQEPQEINFP
                DDLPGSNTAA PVQETLHGCQ PVTQEDGKES RISVQERQ
```

SEQ ID NO: 108
vector clone:  pIB1087
Sequence:
```
                MELAALCRWG LLLALLPPGA ASEQKLISEE DLTQVCTGTD MKLRLPASPE
                THLDMLRHLY QGCQVVQGNL ELTYLPTNAS LSFLQDIQEV QGYVLIAHNQ
                VRQVPLQRLR IVRGTQLFED NYALAVLDNG DPLNNTTPVT GASPGGLREL
                QLRSLTEILK GGVLIQRNPQ LCYQDTILWK DIFHKNNQLA LTLIDTNRSR
                ACHPCSPMCK GSRCWGESSE DCQSLTRTVC AGGCARCKGP LPTDCCHEQC
                AAGCTGPKHS DCLACLHFNH SGICELHCPA LVTYNTDTFE SMPNPEGRYT
                FGASCVTACP YNYLSTDVGS CTLVCPLHNQ EVTAEDGTQR CEKCSKPCAR
                VCYGLGMEHL REVRAVTSAN IQEFAGCKKI FGSLAFLPES FDGDPASNTA
                PLQPEQLQVF ETLEEITGYL YISAWPDSLP DLSVFQNLQV IRGRILHNGA
                YSLTLQGLGI SWLGLRSLRE LGSSGLALIHH NTHLCFVHTV PWDQLFRNPH
                QALLHTANRP EDECVGEGLA CHQLCARGHC WGPGPTQCVN CSQFLRGQEC
                VEECRVLQGL PREYVNARHC LPCHPECQPQ NGSVTCFGPE ADQCVACAHY
                KDPPFCVARC PSGVKPDLSY MPIWKFPDEE GACQPCPINC THSCVDLDDK
                GCPAEQRASP LTSIISAVVD ILLVVVLGVV FGILIRSKRS RLLHSDYMNM
                TPRRPGPTRK HYQPYAPPRD FAAYRSKKVA KKPTNKAPHP KQEPQEINFP
                DDLPGSNTAA PVQETLHGCQ PVTQEDGKES RISVQERQ
```

SEQ ID NO: 109
vector clone:  pIB1088
Sequence:
```
                MELAALCRWG LLLALLPPGA ASEQKLISEE DLTQVCTGTD MKLRLPASPE
                THLDMLRHLY QGCQVVQGNL ELTYLPTNAS LSFLQDIQEV QGYVLIAHNQ
                VRQVPLQRLR IVRGTQLFED NYALAVLDNG DPLNNTTPVT GASPGGLREL
                QLRSLTEILK GGVLIQRNPQ LCYQDTILWK DIFHKNNQLA LTLIDTNRSR
                ACHPCSPMCK GSRCWGESSE DCQSLTRTVC AGGCARCKGP LPTDCCHEQC
                AAGCTGPKHS DCLACLHFNH SGICELHCPA LVTYNTDTFE SMPNPEGRYT
                FGASCVTACP YNYLSTDVGS CTLVCPLHNQ EVTAEDGTQR CEKCSKPCAR
                VCYGLGMEHL REVRAVTSAN IQEFAGCKKI FGSLAFLPES FDGDPASNTA
                PLQPEQLQVF ETLEEITGYL YISAWPDSLP DLSVFQNLQV IRGRILHNGA
                YSLTLQGLGI SWLGLRSLRE LGSSGLALIHH NTHLCFVHTV PWDQLFRNPH
                QALLHTANRP EDECVGEGLA CHQLCARGHC WGPGPTQCVN CSQFLRGQEC
                VEECRVLQGL PREYVNARHC LPCHPECQPQ NGSVTCFGPE ADQCVACAHY
                KDPPFCVARC PSGVKPDLSY MPIWKFPDEE GACQPCPINC THSCVDLDDK
                GCPAEQRASP LTSIISAVVR ILLVVVLGVV FGILIRSKRS RLLHSDYMNM
                TPRRPGPTRK HYQPYAPPRD FAAYRSKKVA KKPTNKAPHP KQEPQEINFP
                DDLPGSNTAA PVQETLHGCQ PVTQEDGKES RISVQERQ
```

SEQ ID NO: 110
vector clone:  pIB1089
Sequence:
```
                MELAALCRWG LLLALLPPGA ASEQKLISEE DLQLCARGHC WGPGPTQCVN
                CSQFLRGQEC VEECRVLQGL PREYVNARHC LPCHPECQPQ NGSVTCFGPE
                ADQCVACAHY KDPPFCVARC PSGVKPDLSY MPIWKFPDEE GACQPCPINC
                THSCVDLDDK GCPAEQRASP LTSIISAVVG ILLVVVLGVV FGILIRSKRS
                RLLHSDYMNM TPRRPGPTRK HYQPYAPPRD FAAYRSKKVA KKPTNKAPHP
                KQEPQEINFP DDLPGSNTAA PVQETLHGCQ PVTQEDGKES RISVQERQ
```

SEQ ID NO: 111
vector clone:  pIB1090
Sequence:
```
                MELAALCRWG LLLALLPPGA ASEQKLISEE DLQLCARGHC WGPGPTQCVN
                CSQFLRGQEC VEECRVLQGL PREYVNARHC LPCHPECQPQ NGSVTCFGPE
                ADQCVACAHY KDPPFCVARC PSGVKPDLSY MPIWKFPDEE GACQPCPINC
                THSCVDLDDK GCPAEQRASP LTSIISAVEG ILLVVVLGVV FGILIRSKRS
                RLLHSDYMNM TPRRPGPTRK HYQPYAPPRD FAAYRSKKVA KKPTNKAPHP
                KQEPQEINFP DDLPGSNTAA PVQETLHGCQ PVTQEDGKES RISVQERQ
```

SEQ ID NO: 112
vector clone:  pIB1091
Sequence:
```
                MELAALCRWG LLLALLPPGA ASEQKLISEE DLQLCARGHC WGPGPTQCVN
                CSQFLRGQEC VEECRVLQGL PREYVNARHC LPCHPECQPQ NGSVTCFGPE
                ADQCVACAHY KDPPFCVARC PSGVKPDLSY MPIWKFPDEE GACQPCPINC
                THSCVDLDDK GCPAEQRASP LTSIISAVVD ILLVVVLGVV FGILIRSKRS
                RLLHSDYMNM TPRRPGPTRK HYQPYAPPRD FAAYRSKKVA KKPTNKAPHP
                KQEPQEINFP DDLPGSNTAA PVQETLHGCQ PVTQEDGKES RISVQERQ
```

TABLE 8-continued

TCR costimulation construct examples

SEQ ID NO: 113
vector clone: pIB1092
Sequence:
MELAALCRWG LLLALLPPGA ASEQKLISEE DLQLCARGHC WGPGPTQCVN
CSQFLRGQEC VEECRVLQGL PREYVNARHC LPCHPECQPQ NGSVTCFGPE
ADQCVACAHY KDPPFCVARC PSGVKPDLSY MPIWKFPDEE GACQPCPINC
THSCVDLDDK GCPAEQRASP LTSIISAVVR ILLVVVLGVV FGILIRSKRS
RLLHSDYMNM TPRRPGPTRK HYQPYAPPRD FAAYRSKKVA KKPTNKAPHP
KQEPQEINFP DDLPGSNTAA PVQETLHGCQ PVTQEDGKES RISVQERQ SEQ ID NO: 114
vector clone: pIB1093
Sequence:
MELAALCRWG LLLALLPPGA ASEQKLISEE DLSIISAVVG ILLVVVLGVV
FGILIRSKRS RLLHSDYMNM TPRRPGPTRK HYQPYAPPRD FAAYRSKKVA
KKPTNKAPHP KQEPQEINFP DDLPGSNTAA PVQETLHGCQ PVTQEDGKES
RISVQERQ SEQ ID NO: 115
vector clone: pIB1094
Sequence:
MELAALCRWG LLLALLPPGA ASEQKLISEE DLSIISAVEG ILLVVVLGVV
FGILIRSKRS RLLHSDYMNM TPRRPGPTRK HYQPYAPPRD FAAYRSKKVA
KKPTNKAPHP KQEPQEINFP DDLPGSNTAA PVQETLHGCQ PVTQEDGKES
RISVQERQ SEQ ID NO: 116
vector clone: pIB1095
Sequence:
MELAALCRWG LLLALLPPGA ASEQKLISEE DLSIISAVVD ILLVVVLGVV
FGILIRSKRS RLLHSDYMNM TPRRPGPTRK HYQPYAPPRD FAAYRSKKVA
KKPTNKAPHP KQEPQEINFP DDLPGSNTAA PVQETLHGCQ PVTQEDGKES
RISVQERQ SEQ ID NO: 117
vector clone: pIB1096
Sequence:
MELAALCRWG LLLALLPPGA ASEQKLISEE DLSIISAVVR ILLVVVLGVV
FGILIRSKRS RLLHSDYMNM TPRRPGPTRK HYQPYAPPRD FAAYRSKKVA
KKPTNKAPHP KQEPQEINFP DDLPGSNTAA PVQETLHGCQ PVTQEDGKES
RISVQERQ SEQ ID NO: 118
vector clone: pIB1097
Sequence:
MALPVTALLL PLALLLHAAR PEQKLISEED LQEQLVESGG RLVTPGTPLT
LTCTASGFSL GSDFMSWVRQ APGKGLEWIG YIDPRSDIPY YASWAKGRFT
ISKTSTTVDL KITSPTTEDT ATYFCARDLN AGYFNGIFYI WGPGTLVTVS
SGGGGSGGGG SGGGGSELVM TQTPSSVSAA VGDTVTINCQ ASETVATLLA
WYQQKPGQPP KLLIYGASNL ESGVPSRFRG SGSGTEFTLT ISGMKAEDAA
TYYCQYGYIS TGSNTFGAGT NVEIKAAAGS GGSGILVKQS PMLVAYDNAV
NLSCKYSYNL FSREFRASLH KGLDSAVEVC VVYGNYSQQL QVYSKTGFNC
DGKLGNESVT FYLQNLYVNQ TDIYFCKIEV MYPPPYLDNE KSNGTIIHVK
GKHLCPSPLF PGPSKPFWVL VVVGGVLACY SLLVTVAFII FWVRSKRSRL
LHSDYMNMTP RRPGPTRKHY QPYAPPRDFA AYRSKKVAKK PTNKAPHPKQ
EPQEINFPDD LPGSNTAAPV QETLHGCQPV TQEDGKESRI SVQERQ SEQ ID NO: 119
vector clone: pIB1098
Sequence:
MALPVTALLL PLALLLHAAR PEQKLISEED LELVMTQTPS SVSAAVGDTV
TINCQASETV ATLLAWYQQK PGQPPKLLIY GASNLESGVP SRFRGSGSGT
EFTLTISGMK AEDAATYYCQ YGYISTGSNT FGAGTNVEIK GGGGSGGGGS
GGGGSQEQLV ESGGRLVTPG TPLTLTCTAS GFSLGSDFMS WVRQAPGKGL
EWIGYIDPRS DIPYYASWAK GRFTISKTST TVDLKITSPT TEDTATYFCA
RDLNAGYFNG IFYIWGPGTL VTVSSAAAGS GGSGILVKQS PMLVAYDNAV
NLSCKYSYNL FSREFRASLH KGLDSAVEVC VVYGNYSQQL QVYSKTGFNC
DGKLGNESVT FYLQNLYVNQ TDIYFCKIEV MYPPPYLDNE KSNGTIIHVK
GKHLCPSPLF PGPSKPFWVL VVVGGVLACY SLLVTVAFII FWVRSKRSRL
LHSDYMNMTP RRPGPTRKHY QPYAPPRDFA AYRSKKVAKK PTNKAPHPKQ
EPQEINFPDD LPGSNTAAPV QETLHGCQPV TQEDGKESRI SVQERQ SEQ ID NO: 120
vector clone: pIB1099
Sequence:
MALPVTALLL PLALLLHAAR PEQKLISEED LQEQLVESGG RLVTPGTPLT
LTCTASGFSL GSDFMSWVRQ APGKGLEWIG YIDPRSDIPY YASWAKGRFT
ISKTSTTVDL KITSPTTEDT ATYFCARDLN AGYFNGIFYI WGPGTLVTVS
SGGGGSGGGG SGGGGSELDM TQTPSSTSEP VGGTVTINCQ ASQTISSYLS
WYQQKPGHPP KLLIYDASDL ASGVPSRFSG SRSGTQFTLT ISGVQCDDAA
TYYCLGVYDY RSDDGAAFGG GTELEILAAA GSGGSGILVK QSPMLVAYDN
AVNLSCKYSY NLFSREFRAS LHKGLDSAVE VCVVYGNYSQ QLQVYSKTGF
NCDGKLGNES VTFYLQNLYV NQTDIYFCKI EVMYPPPYLD NEKSNGTIIH TABLE 8-continued TCR costimulation construct examples

```
                   VKGKHLCPSP LFPGPSKPFW VLVVVGGVLA CYSLLVTVAF IIFWVRSKRS
                   RLLHSDYMNM TPRRPGPTRK HYQPYAPPRD FAAYRSKKVA KKPTNKAPHP
                   KQEPQEINFP DDLPGSNTAA PVQETLHGCQ PVTQEDGKES RISVQERQ

SEQ ID NO: 121
vector clone:      pIB1100
Sequence:          MALPVTALLL PLALLLHAAR PEQKLISEED LELDMTQTPS STSEPVGGTV
                   TINCQASQTI SSYLSWYQQK PGHPPKLLIY DASDLASGVP SRFSGSRSGT
                   QFTLTISGVQ CDDAATYYCL GVYDYRSDDG AAFGGGTELE ILGGGGSGGG
                   GSGGGGSQEQ LVESGGRLVT PGTPLTLTCT ASGFSLSDF MSWVRQAPGK
                   GLEWIGYIDP RSDIPYYASW AKGRFTISKT STTVDLKITS PTTEDTATYF
                   CARDLNAGYF NGIFYIWGPG TLVTVSSAAA GSGGSGILVK QSPMLVAYDN
                   AVNLSCKYSY NLFSREFRAS LHKGLDSAVE VCVVYGNYSQ QLQVYSKTGF
                   NCDGKLGNES VTFYLQNLYV NQTDIYFCKI EVMYPPPYLD NEKSNGTIIH
                   VKGKHLCPSP LFPGPSKPFW VLVVVGGVLA CYSLLVTVAF IIFWVRSKRS
                   RLLHSDYMNM TPRRPGPTRK HYQPYAPPRD FAAYRSKKVA KKPTNKAPHP
                   KQEPQEINFP DDLPGSNTAA PVQETLHGCQ PVTQEDGKES RISVQERQ SEQ ID NO: 122
vector clone:      pIB1101
Sequence:          MALPVTALLL PLALLLHAAR PEQKLISEED LQSLEESGGR LVTPGTPLTL
                   TCTVSGFSLS TNDMNWVRQA PGKGLEWIGV IYSDDTPDYA TWAKGRFTIS
                   RTSTTVDLKI TSPTTEDTAT YFCARGHYDS AVYAYALNIW GPGTLVTVSS
                   GGGGSGGGGS GGGGSELVMT QTPSSVSAAV GGTVTITCQA SQSLSNLLAW
                   YQQKPGQPPK LLIYGASNLE SGVPSRFRGS GSGTDFTLTI SGMKAEDAAT
                   YYCQGGHYSG LTFGNGTNVE IKAAAGSGGS GILVKQSPML VAYDNAVNLS
                   CKYSYNLFSR EFRASLHKGL DSAVEVCVVY GNYSQQLQVY SKTGFNCDGK
                   LGNESVTFYL QNLYVNQTDI YFCKIEVMYP PPYLDNEKSN GTIIHVKGKH
                   LCPSPLFPGP SKPFWVLVVV GGVLACYSLL VTVAFIIFWV RSKRSRLLHS
                   DYMNMTPRRP GPTRKHYQPY APPRDFAAYR SKKVAKKPTN KAPHPKQEPQ
                   EINFPDDLPG SNTAAPVQET LHGCQPVTQE DGKESRISVQ ERQ SEQ ID NO: 123
vector clone:      pIB1102
Sequence:          MALPVTALLL PLALLLHAAR PEQKLISEED LELVMTQTPS SVSAAVGGTV
                   TITCQASQSL SNLLAWYQQK PGQPPKLLIY GASNLESGVP SRFRGSGSGT
                   DFTLTISGMK AEDAATYYCQ GGHYSGLTFG NGTNVEIKGG GGSGGGGSGG
                   GGSQSLEESG GRLVTPGTPL TLTCTVSGFS LSTNDMNWVR QAPGKGLEWI
                   GVIYSDDTPD YATWAKGRFT ISRTSTTVDL KITSPTTEDT ATYFCARGHY
                   DSAVYAYALN IWGPGTLVTV SSAAGSGGS GILVKQSPML VAYDNAVNLS
                   CKYSYNLFSR EFRASLHKGL DSAVEVCVVY GNYSQQLQVY SKTGFNCDGK
                   LGNESVTFYL QNLYVNQTDI YFCKIEVMYP PPYLDNEKSN GTIIHVKGKH
                   LCPSPLFPGP SKPFWVLVVV GGVLACYSLL VTVAFIIFWV RSKRSRLLHS
                   DYMNMTPRRP GPTRKHYQPY APPRDFAAYR SKKVAKKPTN KAPHPKQEPQ
                   EINFPDDLPG SNTAAPVQET LHGCQPVTQE DGKESRISVQ ERQ SEQ ID NO: 124
vector clone:      pIB1103
Sequence:          MYGKIIFVLL LSEIVSISAE QKLISEEDLS TTGVAMHTS TSSSVTKSYI
                   SSQTNDTHKR DTYAATPRAH EVSEISVRTV YPPEEETGER VQLAHHFSEP
                   EITLIIFGVM AGVIGTILLI SYGRSKRSRL LHSDYMNMTP RRPGPTRKHY
                   QPYAPPRDFA AYRSKKVAKK PTNKAPHPKQ EPQEINFPDD LPGSNTAAPV
                   QETLHGCQPV TQEDGKESRI SVQERQ SEQ ID NO: 125
vector clone:      pIB1104
Sequence:          MYGKIIFVLL LSEIVSISAE QKLISEEDLI TLIIFGVMAG VIGTILLISY
                   GRSKRSRLLH SDYMNMTPRR PGPTRKHYQP YAPPRDFAAY RSKKVAKKPT
                   NKAPHPKQEP QEINFPDDLP GSNTAAPVQE TLHGCQPVTQ EDGKESRISV
                   QERQ SEQ ID NO: 126
vector clone:      pIB1105
Sequence:          MDHLGASLWP QVGSLCLLLA GAAWEQKLIS EEDLAPPPNL PDPKFESKAA
                   LLAARGPEEL LCFTERLEDL VCFWEEAASA GVGPGNYSFS YQLEDEPWKL
                   CRLHQAPTAR GAVRFWCSLP TADTSSFVPL ELRVTAASGA PRYHRVIHIN
                   EVVLLDAPVG LVARLADESG HVVLRWLPPP ETPMTSHIRY EVDVSAGNGA
                   GSVQRVEILE GRTECVLSNL RGRTRYTFAV RARMAEPSFG GFWSAWSEPV
                   SLLTPSDLDP LILTLSLILV VILVLLTVLA LLSRSKRSRL LHSDYMNMTP
                   RRPGPTRKHY QPYAPPRDFA AYRSKKVAKK PTNKAPHPKQ EPQEINFPDD
                   LPGSNTAAPV QETLHGCQPV TQEDGKESRI SVQERQ SEQ ID NO: 127
vector clone:      pIB1106
Sequence:          MDHLGASLWP QVGSLCLLLA GAAWEQKLIS EEDLLILTLS LILVVILVLL
                   TVLALLSRSK RSRLLHSDYM NMTPRRPGPT RKHYQPYAPP RDFAAYRSKK
                   VAKKPTNKAP HPKQEPQEIN FPDDLPGSNT AAPVQETLHG CQPVTQEDGK
                   ESRISVQERQ
```

TABLE 8-continued

TCR costimulation construct examples

SEQ ID NO: 128
vector clone: pIB1107
Sequence:
MPSWALFMVT SCLLLAPQNL AQVSSEQKLI SEEDLQDVSL LASDSEPLKC
FSRTFEDLTC FWDEEEAAPS GTYQLLYAYP REKPRACPLS SQSMPHFGTR
YVCQFPDQEE VRLFFPLHLW VKNVFLNQTR TQRVLFVDSV GLPAPPSIIK
AMGGSQPGEL QISWEEPAPE ISDFLRYELR YGPRDPKNST GPTVIQLIAT
ETCCPALQRP HSASALDQSP CAQPTMPWQD GPKQTSPSRE ASALTAEGGS
CLISGLQPGN SYWLQLRSEP DGISLGGSWG SWSLPVTVDL PGDAVALGLQ
CFTLDLKNVT CQWQQQDHAS SQGFFYHSRA RCCPRDRYPI WENCEEEEKT
NPGLQTPQFS RCHFKSRNDS IIHILVEVTT APGTVHSYLG SPFWIHQAVR
LPTPNLHWRE ISSGHLELEW QHPSSWAAQE TCYQLRYTGE GHQDWKVLEP
PLGARGGTLE LRPRSRYRLQ LRARLNGPTY QGPWSSWSDP TRVETATETA
WISLVTALHL VLGLSAVLGL LLLRWRSKRS RLLHSDYMNM TPRRPGPTRK
HYQPYAPPRD FAAYRSKKVA KKPTNKAPHP KQEPQEINFP DDLPGSNTAA
PVQETLHGCQ PVTQEDGKES RISVQERQ SEQ ID NO: 129
vector clone: pIB1108
Sequence:
MPSWALFMVT SCLLLAPQNL AQVSSEQKLI SEEDLISLVT ALHLVLGLSA
VLGLLLLRWR SKRSRLLHSD YMNMTPRRPG PTRKHYQPYA PPRDFAAYRS
KKVAKKPTNK APHPKQEPQE INFPDDLPGS NTAAPVQETL HGCQPVTQED
GKESRISVQE RQ SEQ ID NO: 130
vector clone: pIB1109
Sequence:
MPSWALFMVT SCLLLAPQNL AQVSSEQKLI SEEDLQDVSL LASDSEPLKC
FSRTFEDLTC FWDEEEAAPS GTYQLLYAYP REKPRACPLS SQSMPHFGTR
YVCQFPDQEE VRLFFPLHLW VKNVFLNQTR TQRVLFVDSV GLPAPPSIIK
AMGGSQPGEL QISWEEPAPE ISDFLRYELR YGPRDPKNST GPTVIQLIAT
ETCCPALQRP HSASALDQSP CAQPTMPWQD GPKQTSPSRE ASALTAEGGS
CLISGLQPGN SYWLQLRSEP DGISLGGSWG SWSLPVTVDL PGDAVALGLQ
CFTLDLKNVT CQWQQQDHAS SQGFFYHSRA RCCPRDRYPI WENCEEEEKT
NPGLQTPQFS RCHFKSRNDS IIHILVEVTT APGTVHSYLG SPFWIHQAVR
LPTPNLHWRE ISSGHLELEW QHPSSWAAQE TCYQLRYTGE GHQDWKVLEP
PLGARGGTLE LRPRSRYRLQ LRARLNGPTY QGPWSSWSDP TRVETATETA
WISLVTALHL VLGLNAVLGL LLLRWRSKRS RLLHSDYMNM TPRRPGPTRK
HYQPYAPPRD FAAYRSKKVA KKPTNKAPHP KQEPQEINFP DDLPGSNTAA
PVQETLHGCQ PVTQEDGKES RISVQERQ SEQ ID NO: 131
vector clone: pIB1110
Sequence:
MPSWALFMVT SCLLLAPQNL AQVSSEQKLI SEEDLISLVT ALHLVLGLNA
VLGLLLLRWR SKRSRLLHSD YMNMTPRRPG PTRKHYQPYA PPRDFAAYRS
KKVAKKPTNK APHPKQEPQE INFPDDLPGS NTAAPVQETL HGCQPVTQED
GKESRISVQE RQ SEQ ID NO: 132
vector clone: pIB1111
Sequence:
MPSWALFMVT SCLLLAPQNL AQVSSEQKLI SEEDLQDVSL LASDSEPLKC
FSRTFEDLTC FWDEEEAAPS GTYQLLYAYP REKPRACPLS SQSMPHFGTR
YVCQFPDQEE VRLFFPLHLW VKNVFLNQTR TQRVLFVDSV GLPAPPSIIK
AMGGSQPGEL QISWEEPAPE ISDFLRYELR YGPRDPKNST GPTVIQLIAT
ETCCPALQRP HSASALDQSP CAQPTMPWQD GPKQTSPSRE ASALTAEGGS
CLISGLQPGN SYWLQLRSEP DGISLGGSWG SWSLPVTVDL PGDAVALGLQ
CFTLDLKNVT CQWQQQDHAS SQGFFYHSRA RCCPRDRYPI WENCEEEEKT
NPGLQTPQFS RCHFKSRNDS IIHILVEVTT APGTVHSYLG SPFWIHQAVR
LPTPNLHWRE ISSGHLELEW QHPSSWAAQE TCYQLRYTGE GHQDWKVLEP
PLGARGGTLE LRPRSRYRLQ LRARLNGPTY QGPWSSWSDP TRVETATETA
WISLVTALHL VLGLSAVLGL LLLRKRSKRS RLLHSDYMNM TPRRPGPTRK
HYQPYAPPRD FAAYRSKKVA KKPTNKAPHP KQEPQEINFP DDLPGSNTAA
PVQETLHGCQ PVTQEDGKES RISVQERQ SEQ ID NO: 133
vector clone: pIB1112
Sequence:
MPSWALFMVT SCLLLAPQNL AQVSSEQKLI SEEDLISLVT ALHLVLGLSA
VLGLLLLRKR SKRSRLLHSD YMNMTPRRPG PTRKHYQPYA PPRDFAAYRS
KKVAKKPTNK APHPKQEPQE INFPDDLPGS NTAAPVQETL HGCQPVTQED
GKESRISVQE RQ SEQ ID NO: 134
vector clone: pIB1113
Sequence:
MPSWALFMVT SCLLLAPQNL AQVSSEQKLI SEEDLQDVSL LASDSEPLKC
FSRTFEDLTC FWDEEEAAPS GTYQLLYAYP REKPRACPLS SQSMPHFGTR
YVCQFPDQEE VRLFFPLHLW VKNVFLNQTR TQRVLFVDSV GLPAPPSIIK
AMGGSQPGEL QISWEEPAPE ISDFLRYELR YGPRDPKNST GPTVIQLIAT
ETCCPALQRP HSASALDQSP CAQPTMPWQD GPKQTSPSRE ASALTAEGGS
CLISGLQPGN SYWLQLRSEP DGISLGGSWG SWSLPVTVDL PGDAVALGLQ

TABLE 8-continued

TCR costimulation construct examples

```
                    CFTLDLKNVT CQWQQQDHAS SQGFFYHSRA RCCPRDRYPI WENCEEEEKT
                    NPGLQTPQFS RCHFKSRNDS IIHILVEVTT APGTVHSYLG SPFWIHQAVR
                    LPTPNLHWRE ISSGHLELEW QHPSSWAAQE TCYQLRYTGE GHQDWKVLEP
                    PLGARGGTLE LRPRSRYRLQ LRARLNGPTY QGPWSSWSDP TRVETATETA
                    WISLVTALLL VLGLSAVLGL LLLRWRSKRS RLLHSDYMNM TPRRPGPTRK
                    HYQPYAPPRD FAAYRSKKVA KKPTNKAPHP KQEPQEINFP DDLPGSNTAA
                    PVQETLHGCQ PVTQEDGKES RISVQERQ

SEQ ID NO: 135
vector clone:       pIB1114
Sequence:           MPSWALFMVT SCLLLAPQNL AQVSSEQKLI SEEDLISLVT ALLLVLGLSA
                    VLGLLLLRWR SKRSRLLHSD YMNMTPRRPG PTRKHYQPYA PPRDFAAYRS
                    KKVAKKPTNK APHPKQEPQE INFPDDLPGS NTAAPVQETL HGCQPVTQED
                    GKESRISVQE RQ SEQ ID NO: 136
vector clone:       pIB1115
Sequence:           MPSWALFMVT SCLLLAPQNL AQVSSEQKLI SEEDLQDVSL LASDSEPLKC
                    FSRTFEDLTC FWDEEEAAPS GTYQLLYAYP REKPRACPLS SQSMPHFGTR
                    YVCQFPDQEE VRLFFPLHLW VKNVFLNQTR TQRVLFVDSV GLPAPPSIIK
                    AMGGSQPGEL QISWEEPAPE ISDFLRYELR YGPRDPKNST GPTVIQLIAT
                    ETCCPALQRP HSASALDQSP CAQPTMPWQD GPKQTSPSRE ASALTAEGGS
                    CLISGLQPGN SYWLQLRSEP DGISLGGSWG SWSLPVTVDL PGDAVALGLQ
                    CFTLDLKNVT CQWQQQDHAS SQGFFYHSRA RCCPRDRYPI WENCEEEEKT
                    NPGLQTPQFS RCHFKSRNDS IIHILVEVTT APGTVHSYLG SPFWIHQAVR
                    LPTPNLHWRE ISSGHLELEW QHPSSWAAQE TCYQLRYTGE GHQDWKVLEP
                    PLGARGGTLE LRPRSRYRLQ LRARLNGPTY QGPWSSWSDP TRVETATETA
                    WISLVTALHL VLGLNAVLGL LLLRKRSKRS RLLHSDYMNM TPRRPGPTRK
                    HYQPYAPPRD FAAYRSKKVA KKPTNKAPHP KQEPQEINFP DDLPGSNTAA
                    PVQETLHGCQ PVTQEDGKES RISVQERQ SEQ ID NO: 137
vector clone:       pIB1116
Sequence:           MPSWALFMVT SCLLLAPQNL AQVSSEQKLI SEEDLISLVT ALHLVLGLNA
                    VLGLLLLRKR SKRSRLLHSD YMNMTPRRPG PTRKHYQPYA PPRDFAAYRS
                    KKVAKKPTNK APHPKQEPQE INFPDDLPGS NTAAPVQETL HGCQPVTQED
                    GKESRISVQE RQ SEQ ID NO: 138
vector clone:       pIB1117
Sequence:           MPSWALFMVT SCLLLAPQNL AQVSSEQKLI SEEDLQDVSL LASDSEPLKC
                    FSRTFEDLTC FWDEEEAAPS GTYQLLYAYP REKPRACPLS SQSMPHFGTR
                    YVCQFPDQEE VRLFFPLHLW VKNVFLNQTR TQRVLFVDSV GLPAPPSIIK
                    AMGGSQPGEL QISWEEPAPE ISDFLRYELR YGPRDPKNST GPTVIQLIAT
                    ETCCPALQRP HSASALDQSP CAQPTMPWQD GPKQTSPSRE ASALTAEGGS
                    CLISGLQPGN SYWLQLRSEP DGISLGGSWG SWSLPVTVDL PGDAVALGLQ
                    CFTLDLKNVT CQWQQQDHAS SQGFFYHSRA RCCPRDRYPI WENCEEEEKT
                    NPGLQTPQFS RCHFKSRNDS IIHILVEVTT APGTVHSYLG SPFWIHQAVR
                    LPTPNLHWRE ISSGHLELEW QHPSSWAAQE TCYQLRYTGE GHQDWKVLEP
                    PLGARGGTLE LRPRSRYRLQ LRARLNGPTY QGPWSSWSDP TRVETATETA
                    WISLVTALYL VLGLNAVLGL LLLRWRSKRS RLLHSDYMNM TPRRPGPTRK
                    HYQPYAPPRD FAAYRSKKVA KKPTNKAPHP KQEPQEINFP DDLPGSNTAA
                    PVQETLHGCQ PVTQEDGKES RISVQERQ SEQ ID NO: 139
vector clone:       pIB1118
Sequence:           MPSWALFMVT SCLLLAPQNL AQVSSEQKLI SEEDLISLVT ALYLVLGLNA
                    VLGLLLLRWR SKRSRLLHSD YMNMTPRRPG PTRKHYQPYA PPRDFAAYRS
                    KKVAKKPTNK APHPKQEPQE INFPDDLPGS NTAAPVQETL HGCQPVTQED
                    GKESRISVQE RQ SEQ ID NO: 140
vector clone:       pIB1119
Sequence:           MPSWALFMVT SCLLLAPQNL AQVSSEQKLI SEEDLQDVSL LASDSEPLKC
                    FSRTFEDLTC FWDEEEAAPS GTYQLLYAYP REKPRACPLS SQSMPHFGTR
                    YVCQFPDQEE VRLFFPLHLW VKNVFLNQTR TQRVLFVDSV GLPAPPSIIK
                    AMGGSQPGEL QISWEEPAPE ISDFLRYELR YGPRDPKNST GPTVIQLIAT
                    ETCCPALQRP HSASALDQSP CAQPTMPWQD GPKQTSPSRE ASALTAEGGS
                    CLISGLQPGN SYWLQLRSEP DGISLGGSWG SWSLPVTVDL PGDAVALGLQ
                    CFTLDLKNVT CQWQQQDHAS SQGFFYHSRA RCCPRDRYPI WENCEEEEKT
                    NPGLQTPQFS RCHFKSRNDS IIHILVEVTT APGTVHSYLG SPFWIHQAVR
                    LPTPNLHWRE ISSGHLELEW QHPSSWAAQE TCYQLRYTGE GHQDWKVLEP
                    PLGARGGTLE LRPRSRYRLQ LRARLNGPTY QGPWSSWSDP TRVETATETA
                    WISLVTAWCL VLGLSAVLGL LLLRWRSKRS RLLHSDYMNM TPRRPGPTRK
                    HYQPYAPPRD FAAYRSKKVA KKPTNKAPHP KQEPQEINFP DDLPGSNTAA
                    PVQETLHGCQ PVTQEDGKES RISVQERQ
```

TABLE 8-continued

TCR costimulation construct examples

SEQ ID NO: 141
vector clone: pIB1120
Sequence:
MPSWALFMVT SCLLLAPQNL AQVSSEQKLI SEEDLISLVT AWCLVLGLSA
VLGLLLLRWR SKRSRLLHSD YMNMTPRRPG PTRKHYQPYA PPRDFAAYRS
KKVAKKPTNK APHPKQEPQE INFPDDLPGS NTAAPVQETL HGCQPVTQED
GKESRISVQE RQ SEQ ID NO: 142
vector clone: pIB1179
Sequence:
MALPVTALLL PLALLLHAAR PEPKSCDKTH TCPPCPAPEL LGGPSVFLFP
PKPKDTLMIS RTPEVTCVVV DVSHEDPEVK FNWYVDGVEV HNAKTKPREE
QYNSTYRVVS VLTVLHQDWL NGKEYKCKVS NKALPAPIEK TISKAKGQPR
EPQVYTLPPS RDELTKNQVS LTCLVKGFYP SDIAVEWESN GQPENNYKTT
PPVLDSDGSF FLYSKLTVDK SRWQQGNVFS CSVMHEALHN HYTQKSLSLS
PGKAAAFWVL VVVGGVLACY SLLVTVAFII FWVRSKRSRL LHSDYMNMTP
RRPGPTRKHY QPYAPPRDFA AYRSKKVAKK PTNKAPHPKQ EPQEINFPDD
LPGSNTAAPV QETLHGCQPV TQEDGKESRI SVQERQ SEQ ID NO: 143
vector clone: pIB1180
Sequence:
MALPVTALLL PLALLLHAAR PAEPKSPDKT HTCPPCPAPP VAGPSVFLFP
PKPKDTLMIA RTPEVTCVVV DVSHEDPEVK FNWYVDGVEV HNAKTKPREE
QYNSTYRVVS VLTVLHQDWL NGKEYKCKVS NKALPAPIEK TISKAKGQPR
EPQVYTLPPS RDELTKNQVS LTCLVKGFYP SDIAVEWESN GQPENNYKTT
PPVLDSDGSF FLYSKLTVDK SRWQQGNVFS CSVMHEALHN HYTQKSLSLS
PGKKDPKFWV LVVVGGVLAC YSLLVTVAFIIFWVRSKRSR LLHSDYMNMT
PRRPGPTRKH YQPYAPPRDF AAYRSKKVAK KPTNKAPHPK QEPQEINFPD
DLPGSNTAAP VQETLHGCQP VTQEDGKESR ISVQERQ SEQ ID NO: 144
vector clone: pIB1181
Sequence:
MALPVTALLL PLALLLHAAR PERKCCVECP PCPAPPVAGP SVFLFPPKPK
DTLMISRTPE VTCVVVDVSH EDPEVQFNWY VDGVEVHNAK TKPREEQFNS
TFRVVSVLTV VHQDWLNGKE YKCKVSNKGL PAPIEKTISK TKGQPREPQV
YTLPPSREEM TKNQVSLTCL VKGFYPSDIS VEWESNGQPE NNYKTTPPML
DSDGSFFLYS KLTVDKSRWQ QGNVFSCSVM HEALHNHYTQ KSLSLSPGKF
WVLVVVGGVL ACYSLLVTVA FIIFWVRSKR SRLLHSDYMN MTPRRPGPTR
KHYQPYAPPR DFAAYRSKKV AKKPTNKAPH PKQEPQEINF PDDLPGSNTA
APVQETLHGC QPVTQEDGKE SRISVQERQ SEQ ID NO: 145
vector clone: pIB1182
Sequence:
MALPVTALLL PLALLLHAAR PELKTPLGDT THTCPRCPEP KSCDTPPPCP
RCPEPKSCDT PPPCPRCPEP KSCDTPPPCP RCPAPELLGG PSVFLFPPKP
KDTLMISRTP EVTCVVVDVS HEDPEVQFKW YVDGVEVHNA KTKPREEQYN
STFRVVSVLT VLHQDWLNGK EYKCKVSNKA LPAPIEKTIS KTKGQPREPQ
VYTLPPSREE MTKNQVSLTC LVKGFYPSDI AVEWESSGQP ENNYTTPPM
LDSDGSFFLY SKLTVDKSRQ QGNIFSCSV MHEALHNRFT QKSLSLSPGK
FWVLVVVGGV LACYSLLVTV AFIIFWVRSK RSRLLHSDYM NMTPRRPGPT
RKHYQPYAPP RDFAAYRSKK VAKKPTNKAP HPKQEPQEIN FPDDLPGSNT
AAPVQETLHG CQPVTQEDGK ESRISVQERQ SEQ ID NO: 146
vector clone: pIB1183
Sequence:
MALPVTALLL PLALLLHAAR PESKYGPPCP SCPAPEFLGG PSVFLFPPKP
KDTLMISRTP EVTCVVVDVS QEDPEVQFNW YVDGVEVHNA KTKPREEQFN
STYRVVSVLT VLHQDWLNGK EYKCKVSNKG LPSSIEKTIS KAKGQPREPQ
VYTLPPSQEE MTKNQVSLTC LVKGFYPSDI AVEWESNGQP ENNYKTTPPV
LDSDGSFFLY SRLTVDKSRW QEGNVFSCSV MHEALHNHYT QKSLSLSLGK
FWVLVVVGGV LACYSLLVTV AFIIFWVRSK RSRLLHSDYM NMTPRRPGPT
RKHYQPYAPP RDFAAYRSKK VAKKPTNKAP HPKQEPQEIN FPDDLPGSNT
AAPVQETLHG CQPVTQEDGK ESRISVQERQ SEQ ID NO: 147
vector clone: pIB1184
Sequence:
MALPVTALLL PLALLLHAAR PESKYGPPCP PCPAPEFEGG PSVFLFPPKP
KDTLMISRTP EVTCVVVDVS QEDPEVQFNW YVDGVEVHNA KTKPREEQFQ
STYRVVSVLT VLHQDWLNGK EYKCKVSNKG LPSSIEKTIS KAKGQPREPQ
VYTLPPSQEE MTKNQVSLTC LVKGFYPSDI AVEWESNGQP ENNYKTTPPV
LDSDGSFFLY SRLTVDKSRW QEGNVFSCSV MHEALHNHYT QKSLSLSLGK
FWVLVVVGGV LACYSLLVTV AFIIFWVRSK RSRLLHSDYM NMTPRRPGPT
RKHYQPYAPP RDFAAYRSKK VAKKPTNKAP HPKQEPQEIN FPDDLPGSNT
AAPVQETLHG CQPVTQEDGK ESRISVQERQ TABLE 8-continued TCR costimulation construct examples SEQ ID NO: 148
vector clone:      pIB1185
Sequence:
MALPVTALLL PLALLLHAAR PEPKSCDKTH TCPPCPAPEL LGGPSVFLFP
PKPKDTLMIS RTPEVTCVVV DVSHEDPEVK FNWYVDGVEV HNAKTKPREE
QYNSTYRVVS VLTVLHQDWL NGKEYKCKVS NKALPAPIEK TISKAKGQPR
EPQVYTLPPS RDELTKNQVS LTCLVKGFYP SDIAVEWESN GQPENNYKTT
PPVLDSDGSF FLYSKLTVDK SRWQQGNVFS CSVMHEALHN HYTQKSLSLS
PGKAAAIEVM YPPPYLDNEK SNGTIIHVKG KHLCPSPLFP GPSKPFWVLV
VVGGVLACYS LLVTVAFIIF WVRSKRSRLL HSDYMNMTPR RPGPTRKHYQ
PYAPPRDFAA YRSKKVAKKP TNKAPHPKQE PQEINFPDDL PGSNTAAPVQ
ETLHGCQPVT QEDGKESRIS VQERQ SEQ ID NO: 149
vector clone:      pIB1186
Sequence:
MALPVTALLL PLALLLHAAR PAEPKSPDKT HTCPPCPAPP VAGPSVFLFP
PKPKDTLMIA RTPEVTCVVV DVSHEDPEVK FNWYVDGVEV HNAKTKPREE
QYNSTYRVVS VLTVLHQDWL NGKEYKCKVS NKALPAPIEK TISKAKGQPR
EPQVYTLPPS RDELTKNQVS LTCLVKGFYP SDIAVEWESN GQPENNYKTT
PPVLDSDGSF FLYSKLTVDK SRWQQGNVFS CSVMHEALHN HYTQKSLSLS
PGKKDPKIEV MYPPPYLDNE KSNGTIIHVK GKHLCPSPLF PGPSKPFWVL
VVVGGVLACY SLLVTVAFII FWVRSKRSRL LHSDYMNMTP RRPGPTRKHY
QPYAPPRDFA AYRSKKVAKK PTNKAPHPKQ EPQEINFPDD LPGSNTAAPV
QETLHGCQPV TQEDGKESRI SVQERQ SEQ ID NO: 150
vector clone:      pIB1187
Sequence:
MALPVTALLL PLALLLHAAR PERKCCVECP PCPAPPVAGP SVFLFPPKPK
DTLMISRTPE VTCVVVDVSH EDPEVQFNWY VDGVEVHNAK TKPREEQFNS
TFRVVSVLTV VHQDWLNGKE YKCKVSNKGL PAPIEKTISK TKGQPREPQV
YTLPPSREEM TKNQVSLTCL VKGFYPSDIS VEWESNGQPE NNYKTTPPML
DSDGSFFLYS KLTVDKSRWQ QGNVFSCSVM HEALHNHYTQ KSLSLSPGKI
EVMYPPPYLD NEKSNGTIIH VKGKHLCPSP LFPGPSKPFW VLVVGGVLA
CYSLLVTVAF IIFWVRSKRS RLLHSDYMNM TPRRPGPTRK HYQPYAPPRD
FAAYRSKKVA KKPTNKAPHP KQEPQEINFP DDLPGSNTAA PVQETLHGCQ
PVTQEDGKES RISVQERQ SEQ ID NO: 151
vector clone:      pIB1188
Sequence:
MALPVTALLL PLALLLHAAR PELKTPLGDT THTCPRCPEP KSCDTPPPCP
RCPEPKSCDT PPPCPRCPEP KSCDTPPPCP RCPAPELLGG PSVFLFPPKP
KDTLMISRTP EVTCVVVDVS HEDPEVQFKW YVDGVEVHNA KTKPREEQYN
STFRVVSVLT VLHQDWLNGK EYKCKVSNKA LPAPIEKTIS KTKGQPREPQ
VYTLPPSREE MTKNQVSLTC LVKGFYPSDI AVEWESSGQP ENNYTTPPM
LDSDGSFFLY SKLTVDKSRW QQGNIFSCSV MHEALHNRFT QKSLSLSPGK
IEVMYPPPYL DNEKSNGTII HVKGKHLCPS PLFPGPSKPF WVLVVGGVL
ACYSLLVTVA FIIFWVRSKR SRLLHSDYMN MTPRRPGPTR KHYQPYAPPR
DFAAYRSKKV AKKPTNKAPH PKQEPQEINF PDDLPGSNTA APVQETLHGC
QPVTQEDGKE SRISVQERQ SEQ ID NO: 152
vector clone:      pIB1189
Sequence:
MALPVTALLL PLALLLHAAR PESKYGPPCP SCPAPEFLGG PSVFLFPPKP
KDTLMISRTP EVTCVVVDVS QEDPEVQFNW YVDGVEVHNA KTKPREEQFN
STYRVVSVLT VLHQDWLNGK EYKCKVSNKG LPSSIEKTIS KAKGQPREPQ
VYTLPPSQEE MTKNQVSLTC LVKGFYPSDI AVEWESNGQP ENNYKTTPPV
LDSDGSFFLY SRLTVDKSRW QEGNVFSCSV MHEALHNHYT QKSLSLSLGK
IEVMYPPPYL DNEKSNGTII HVKGKHLCPS PLFPGPSKPF WVLVVGGVL
ACYSLLVTVA FIIFWVRSKR SRLLHSDYMN MTPRRPGPTR KHYQPYAPPR
DFAAYRSKKV AKKPTNKAPH PKQEPQEINF PDDLPGSNTA APVQETLHGC
QPVTQEDGKE SRISVQERQ SEQ ID NO: 153
vector clone:      pIB1190
Sequence:
MALPVTALLL PLALLLHAAR PESKYGPPCP PCPAPEFEGG PSVFLFPPKP
KDTLMISRTP EVTCVVVDVS QEDPEVQFNW YVDGVEVHNA KTKPREEQFQ
STYRVVSVLT VLHQDWLNGK EYKCKVSNKG LPSSIEKTIS KAKGQPREPQ
VYTLPPSQEE MTKNQVSLTC LVKGFYPSDI AVEWESNGQP ENNYKTTPPV
LDSDGSFFLY SRLTVDKSRW QEGNVFSCSV MHEALHNHYT QKSLSLSLGK
IEVMYPPPYL DNEKSNGTII HVKGKHLCPS PLFPGPSKPF WVLVVGGVL
ACYSLLVTVA FIIFWVRSKR SRLLHSDYMN MTPRRPGPTR KHYQPYAPPR
DFAAYRSKKV AKKPTNKAPH PKQEPQEINF PDDLPGSNTA APVQETLHGC
QPVTQEDGKE SRISVQERQ TABLE 8-continued TCR costimulation construct examples SEQ ID NO: 154
designation    CD40
Sequence       KKVAKKPTNK APHPKQEPQE INFPDDLPGS NTAAPVQETL HGCQPVTQED
               GKESRISVQE RQ SEQ ID NO: 155
designation    CD40_tandem
Sequence       KKVAKKPTNK APHPKQEPQE INFPDDLPGS NTAAPVQETL HGCQPVTQED
               GKESRISVQE RQKKVAKKPT NKAPHPKQEP QEINFPDDLP GSNTAAPVQE
               TLHGCQPVTQ EDGKESRISV QERQ SEQ ID NO: 156
designation    CD40_P227A
Sequence       KKVAKKPTNK AAHPKQEPQE INFPDDLPGS NTAAPVQETL HGCQPVTQED
               GKESRISVQE RQ In some embodiments, any one or more of the arrangements below are contemplated:

1. An engineered protein that has at least 80%, 85%, 90%, 95%, 96%, 97%, 98%, 99%, 100%, or any integer that is between 80 and 100%, identity to SEQ ID NO: 166, and wherein the sequence is not SEQ ID NO: 123.
2. An engineered protein that has at least 80%, 85%, 90%, 95%, 96%, 97%, 98%, 99%, 100%, or any integer that is between 80 and 100%, identity to SEQ ID NO: 167, and wherein the sequence is not SEQ ID NO: 123.
3. The engineered protein of any one of arrangements 1 or 2, further comprising a binding domain, CD28 domain, and CD40 domain.
4. The engineered protein of any one of arrangements 2-3, further comprising a signal peptide sequence.
5. The engineered protein of arrangement 4, wherein the signal peptide sequence has at least 80%, 85%, 90%, 95%, 96%, 97%, 98%, 99%, 100%, or any integer that is between 80 and 100%, identity to the amino acid sequence of SEQ ID NO: 157.
6. The engineered protein of any one of arrangements 3-5, wherein the binding domain comprises a VL sequence, a VH sequence, and an at least one linker.
7. The engineered protein of arrangement 6, wherein the at least one linker has at least 80%, 85%, 90%, 95%, 96%, 97%, 98%, 99%, 100%, or any integer that is between 80 and 100%, identity to the amino acid sequence of SEQ ID NO: 159 or 161.
8. The engineered protein of any one of arrangements 6-7, wherein the binding domain comprises two linker sequences.
9. The engineered protein of arrangement 8, wherein the two linker sequences have at least 80%, 85%, 90%, 95%, 96%, 97%, 98%, 99%, 100%, or any integer that is between 80 and 100%, identity to amino acid sequences SEQ ID NO: 159 and SEQ ID NO: 161, respectively.
10. The engineered protein of any one of arrangements 6-9, wherein the VL sequence has at least 80%, 85%, 90%, 95%, 96%, 97%, 98%, 99%, 100%, or any integer that is between 80 and 100%, identity to the amino acid sequence of SEQ ID NO: 158.
11. The engineered protein of any one of arrangements 6-10, wherein the VH sequence has at least 80%, 85%, 90%, 95%, 96%, 97%, 98%, 99%, 100%, or any integer that is between 80 and 100%, identity to the amino acid sequence of SEQ ID NO: 160.
12. The engineered protein of any one of arrangements 3-11, wherein the CD40 domain has at least 80%, 85%, 90%, 95%, 96%, 97%, 98%, 99%, 100%, or any integer that is between 80 and 100%, identity to the amino acid sequence of SEQ ID NO: 165.
13. The engineered protein of any one of arrangements 3-12, wherein the CD28 domain comprises a CD28 transmembrane domain.
14. The engineered protein of arrangement 13, wherein the CD28 transmembrane domain has at least 80%, 85%, 90%, 95%, 96%, 97%, 98%, 99%, 100%, or any integer that is between 80 and 100%, identity to SEQ ID NO: 163.
15. The engineered protein of any one of arrangements 3-14, wherein the CD28 domain comprises a CD28 extracellular domain.
16. The engineered protein of arrangement 15, wherein the CD28 extracellular domain has at least 80%, 85%, 90%, 95%, 96%, 97%, 98%, 99%, 100%, or any integer that is between 80 and 100%, identity to SEQ ID NO: 162.
17. The engineered protein of any one of arrangements 3-16, wherein the CD28 domain comprises a CD28 intracellular domain.
18. The engineered protein of arrangement 17, wherein the CD28 intracellular domain has at least 80%, 85%, 90%, 95%, 96%, 97%, 98%, 99%, 100%, or any integer that is between 80 and 100%, identity to SEQ ID NO: 164.
19. The engineered protein of any one of arrangements 1-18, wherein the protein further comprises 1, 2, 3, 4, 5, or all 6 CDR sequence(s) selected from the group consisting of:

```
                                        (SEQ ID NO: 168)
QASQSLSNLLA, (SEQ ID NO: 169)
GASNLES, (SEQ ID NO: 170)
QGGHYSGL, (SEQ ID NO: 171)
TNDMN, (SEQ ID NO: 172)
VIYSDDTPDYATWAKG,
``` and/or

```
                                        (SEQ ID NO: 173)
GHYDSAVYAYALNI.
```

20. An engineered protein comprising an amino acid sequence that is at least 80% identical to the amino acid sequence of SEQ ID NO: 166 or 167, wherein the amino acid sequence does not include at least one of:

```
                                           (SEQ ID NO: 174)
        QKLISEEDLE
```
or

```
                                           (SEQ ID NO: 175)
LVKQSPMLVAYDNAVNLSCKYSYNLFSREFRASLHKGLDSAVEVCVVYG
NYSQQLQVYSKTGFNCDGKLGNESVTFYLQNLYVNQTDIYFCKI.
```

21. The engineered protein of arrangement 20, wherein the engineered protein lacks both of

```
                                           (SEQ ID NO: 174)
        QKLISEEDLE
```
and

```
                                           (SEQ ID NO: 175)
LVKQSPMLVAYDNAVNLSCKYSYNLFSREFRASLHKGLDSAVEVCVVYG
NYSQQLQVYSKTGFNCDGKLGNESVTFYLQNLYVNQTDIYFCKI.
```

22. The engineered protein of either of arrangements 20 or 21, wherein SEQ ID NO: 166 or 167 comprises a sequence that is at least 80, 90, 95, 96, 97, 98, 99 or 100% identical to SEQ ID NO: 158.

23. The engineered protein of either of arrangements 20 or 21, wherein SEQ ID NO: 166 or 167 comprises a sequence that is at least 80, 90, 95, 96, 97, 98, 99 or 100% identical to SEQ ID NO: 160.

24. The engineered protein of either of arrangements 23, wherein SEQ ID NO: 166 or 167 comprises a sequence that is at least 80, 90, 95, 96, 97, 98, 99 or 100% identical to SEQ ID NO: 158.

25. The engineered protein of any one of arrangements 20-24, wherein SEQ ID NO: 166 or 167 comprises a sequence that is at least 80, 90, 95, 96, 97, 98, 99 or 100% identical to SEQ ID NO: 162.

26. The engineered protein of any one of arrangements 20-25, wherein SEQ ID NO: 166 or 167 comprises a sequence that is at least 80, 90, 95, 96, 97, 98, 99 or 100% identical to SEQ ID NO: 164.

27. The engineered protein of any one of arrangements 20-26, wherein SEQ ID NO: 166 or 167 comprises a sequence that is at least 80, 90, 95, 96, 97, 98, 99 or 100% identical to SEQ ID NO: 165.

28. The engineered protein of any one of arrangements 20-27, wherein SEQ ID NO: 166 or 167 comprises a sequence that is at least 80, 90, 95, 96, 97, 98, 99 or 100% identical to SEQ ID NO: 163.

29. The engineered protein of any one of arrangements 20-28, wherein SEQ ID NO: 166 or 167 comprises a sequence that is at least 80, 90, 95, 96, 97, 98, 99 or 100% identical to SEQ ID NO: 161.

30. The engineered protein of any one of arrangements 20-29, wherein SEQ ID NO: 166 or 167 comprises a sequence that is at least 80, 90, 95, 96, 97, 98, 99 or 100% identical to SEQ ID NO: 159.

31. The engineered protein of any one of arrangements 20-30, wherein SEQ ID NO: 166 or 167 comprises a sequence that is at least 80, 90, 95, 96, 97, 98, 99 or 100% identical to SEQ ID NO: 157.

32. The engineered protein of any one of arrangements 20-31, wherein SEQ ID NO: 166 or 167 comprises a sequence that is at least 80, 90, 95, 96, 97, 98, 99 or 100% identical to SEQ ID NO: 162.

33. The engineered protein of any one of arrangements 20-32, wherein SEQ ID NO: 166 or 167 comprises 1, 2, 3, 4, 5, 6, 7, and/or all 8 sequence(s) that is/are at least 95% identical to a sequence selected from the group consisting of SEQ ID NOs: 158, 160, 162, 163, 164, and 165.

34. The engineered protein of any one of arrangements 20-33, wherein SEQ ID NO: 166 or 167 comprises a sequence that is more than 98% identical to each of SEQ ID NOs: 158, 160, 162, 163, 164, and 165.

35. A CoStAR comprising:
(a) an optional signal peptide;
(b) a binding domain, wherein the binding domain binds to an anti-pembrolizumab antibody or binding fragment thereof;
(c) a CD28 domain;
(d) a CD40 domain;
wherein a) is optionally linked to b), wherein b) is linked to c), wherein c) is linked to d), and wherein the CoStAR comprises an amino acid sequence that:
i) lacks at least one of:

```
                                           (SEQ ID NO: 174)
        QKLISEEDLE
```
or

```
                                           (SEQ ID NO: 175)
LVKQSPMLVAYDNAVNLSCKYSYNLFSREFRASLHKGLDSAVEVCVVYG
NYSQQLQVYSKTGFNCDGKLGNESVTFYLQNLYVNQTDIYFCKI;
``` ii) has an amino acid sequence that is greater than 95% identical to SEQ ID NO: 166 or 167;
iii) has an amino acid sequence that is greater than 80% identical to SEQ ID NO: 166 or 167 and is not SEQ ID NO: 123; or
iv) any combination of i-iv.

36. A fusion protein comprising:
(a) a means for binding to an antibody that binds to pembrolizumab;
(b) a CD28 domain;
(c) a CD40 domain;
wherein a) is linked to b), wherein b) is linked to c), and wherein the fusion protein comprises an amino acid sequence that:
i) lacks at least one of: or

```
                                           (SEQ ID NO: 174)
        QKLISEEDLE
```
or

```
                                           (SEQ ID NO: 175)
LVKQSPMLVAYDNAVNLSCKYSYNLFSREFRASLHKGLDSAVEVCVVYG
NYSQQLQVYSKTGFNCDGKLGNESVTFYLQNLYVNQTDIYFCKI;
``` ii) has an amino acid sequence that is greater than 95% identical to SEQ ID NO: 166 or 167;
iii) has an amino acid sequence that is greater than 80% identical to SEQ ID NO: 166 or 167 and is not SEQ ID NO: 123; or
iv) any combination of i-iv.

37. The CoStAR or fusion protein of arrangements 35 or 36, wherein the binding domain or the means for binding to an antibody that binds to pembrolizumab comprises: 1, 2, 3, 4, 5, or all 6 CDR sequence(s) selected from the group consisting of:

```
                                 (SEQ ID NO: 168)
QASQSLSNLLA, (SEQ ID NO: 169)
GASNLES, (SEQ ID NO: 170)
QGGHYSGL, (SEQ ID NO: 171)
TNDMN, (SEQ ID NO: 172)
VIYSDDTPDYATWAKG,
``` and/or

```
                                 (SEQ ID NO: 173)
GHYDSAVYAYALNI.
```

38. The CoStAR or fusion protein of one of arrangements 35-37, wherein the CD28 domain comprises: SEQ ID Nos: 162, 163, and 164, or a sequence that is at least 80% or 95, or 98% identical thereto.
39. The CoStAR or fusion protein of one of arrangements 35-38, wherein the CD40 domain comprises: SEQ ID No: 165, or a sequence that is at least 80% or 95, or 98% identical thereto.
40. A fusion protein comprising the amino acid sequence of SEQ ID NO: 166.
41. A fusion protein comprising the amino acid sequence of SEQ ID NO: 167.
42. A nucleic acid which encodes the protein of any one of the preceding arrangements.
43. A vector which comprises the nucleic acid of any one of the preceding arrangements.
44. A cell which expresses the protein of any one of the preceding arrangements.
45. A cell which expresses at least two proteins of any one of the preceding arrangements.
46. A method of making the cell of any one of arrangement 44 or 45, which comprises the step of transducing or transfecting a cell with a vector of arrangement 43.
47. A method for preparing a population of cells that express a protein of any one of arrangements 1 to 41, comprising detecting expression of the protein on the surface of cells transfected or transduced with a vector according to arrangement 43 and selecting cells which are identified as expressing the protein.
48. A cell population produced by the method of arrangement 47.
49. A cell population which is enriched for cell expression a protein of any one of arrangements 1 to 41.
50. A method for treating a disease in a subject in need thereof, which comprises the step of administering the cell of any one of arrangements 44-45 or the cell population of arrangement 48 or 49 to the subject.
51. The engineered protein of any one of arrangements 1-41, wherein the binding domain and CD28 domain are connected by at least one linker.

Although the present invention and its advantages have been described in detail, it should be understood that various changes, substitutions and alterations can be made herein without departing from the spirit and scope of the invention as defined in the appended claims.

EXAMPLES

The present invention will be further illustrated in the following Examples which are given for illustration purposes only and are not intended to limit the invention in any way.

Examples 1

Coculture assay set up. T cells from 2 healthy donors were either modified to express the constructs tested or left non-transduced (NTD) at MOI 10. One day prior to coculture set up, effector T cells were thawed and resuspended at $1 \times 10^6$ cells/mL in T cell media (TCM) without IL2 and incubated overnight at 37° C. with 5% CO2. On the day of coculture, T cells (effectors) and Ba/F3-OKT3 targets were collected and counted using a ViCELL BLU as per manufacturer's instructions. T cells were then cocultured with B a/F3 OKT3 targets at the 10:1, 1:1 and 1:10 E:T (effector: target) ratios overnight. For the inducible costimulatory protein constructs tested (i.e., pIB1097 to pIB1102), an additional set of wells were setup to which 10 μg/mL pembrolizumab was added in addition to Ba/F3 OKT3 targets. Each condition was performed in duplicates. Unstimulated T cells served as negative controls. Two sets of each E:T ratio as well as the T cell only control plates were set up. Brefeldin A was added at 1:1000 dilution to one set of plates to assess cytokine production by intracellular cytokine staining (ICS) using a flow cytometer after overnight co-culture. The second set was incubated for 5 days following which T cell counts and activation marker expression (i.e., 41BB and CD69) was assessed by flow cytometry.

The invention includes modifying components of the TCR complex and associated signaling adaptors (such as, for example, in a TCR incorporated antigen agnostic receptor "TIAAR"), identifying transmembrane domains (TMDs) and modifications that enable constitutive activation of receptors ("constitutive") and utilizing antibodies to induce activation of the receptor ("inducible").

scFV targeting co-stimulatory or inhibitor receptors and ligands. The scFV are derived from antibodies targeting co-stimulatory or inhibitory molecules expressed on immune cells.

TABLE 9

| Signal peptide | Tag | ECD_TMD | ICD | Costim | GOI description |
| --- | --- | --- | --- | --- | --- |
| CD8a | Myc | hZ270_HL | NA | CD28-CD40 | anti-NKG2A blocking |
| CD8a | Myc | hZ270_LH | NA | CD28-CD40 | anti-NKG2A blocking |
| CD8a | Myc | Varlilumab_HL | NA | CD28-CD40 | anti-CD27 agonist |
| CD8a | Myc | Varlilumab_LH | NA | CD28-CD40 | anti-CD27 agonist |
| CD8a | Myc | Urelumab_HL | NA | CD28-CD40 | anti-CD137 agonist |
| CD8a | Myc | Urelumab_LH | NA | CD28-CD40 | anti-CD137 agonist |
| CD8a | Myc | TRX518_HL | NA | CD28-CD40 | anti-GITR agonist |

TABLE 9-continued

| Signal peptide | Tag | ECD_TMD | ICD | Costim | GOI description |
|---|---|---|---|---|---|
| CD8a | Myc | TRX518_LH | NA | CD28-CD40 | anti-GITR agonist |
| CD8a | Myc | Pembroluzimab_HL | NA | CD28-CD40 | anti-PD1 blocking |
| CD8a | Myc | Pembroluzimab_LH | NA | CD28-CD40 | anti-PD1 blocking |
| CD8a | Myc | Atezolizumab_HL | NA | CD28-CD40 | anti-PDL1 blocking |
| CD8a | Myc | Atezolizumab_LH | NA | CD28-CD40 | anti-PDL1 blocking |
| CD8a | Myc | RONK203_HL | NA | CD28-CD40 | anti-FasL blocking |
| CD8a | Myc | RONK203_LH | NA | CD28-CD40 | anti-FasL blocking |
| CD8a | Myc | Tavolimab_HL | NA | CD28-CD40 | anti-OX40 agonist |
| CD8a | Myc | Tavolimab_LH | NA | CD28-CD40 | anti-OX40 agonist |
| CD8a | Myc | Ipilimumab_HL | NA | CD28-CD40 | anti-CTLA4 blocking |
| CD8a | Myc | Ipilimumab_LH | NA | CD28-CD40 | anti-CTLA4 blocking |
| CD8a | Myc | KY1044_HL | NA | CD28-CD40 | anti-ICOS agonist |
| CD8a | Myc | KY1044_LH | NA | CD28-CD40 | anti-ICOS agonist |
| CD8a | Myc | APX005_HL | NA | CD28-CD40 | anti-CD40 agonist |
| CD8a | Myc | APX005_LH | NA | CD28-CD40 | anti-CD40 agonist |
| CD8a | Myc | Selicrelumab_HL | NA | CD28-CD40 | anti-CD40 agonist |
| CD8a | Myc | Selicrelumab_LH | NA | CD28-CD40 | anti-CD40 agonist |

TABLE 10

TIAAR (TCR incorporated) list of constructs

| Code | Concept | Signal peptide | Tag | ECD_TMD | ICD | Costim | GOI description |
|---|---|---|---|---|---|---|---|
| pIB1026 | TIAAR | CD3D | Myc | CD3D | N/A | CD28-CD40 | CD3D_CD3D_CD28CD40 |
| pIB1027 | TIAAR | CD3E | FLAG | CD3E | N/A | CD28-CD40 | CD3E_CD3E_CD28CD40 |
| pIB1028 | TIAAR | CD3G | Myc | CD3G | N/A | CD28-CD40 | CD3G_CD3G_CD28CD40 |
| pIB1029 | TIAAR | CD3Z | Myc IC | CD3Z | N/A | CD28-CD40 | CD3Z_CD3Z_CD28CD40_Myc |
| pIB1030 | TIAAR | CD8A | Myc | hTRDC | N/A | CD28-CD40 | CD8A_hTRDC_CD28CD40 |
| pIB1031 | TIAAR | CD8A | FLAG | hTRGC1 | N/A | CD28-CD40 | CD8A_hTRGC1_CD28CD40 |
| pIB1032 | TIAAR | CD8A | Myc | mTRAC | N/A | CD28-CD40 | CD8A_mTRAC_CD28CD40 |
| pIB1033 | TIAAR | CD8A | FLAG | mTRBC1 | N/A | CD28-CD40 | CD8A_mTRBC1_CD28CD40 |
| pIB1046 | TIAAR | CD8A x2 | Myc and FLAG | hTRDC_hTRGC1 | N/A | CD28-CD40 | CD8A_hTRDC_CD28CD40-T2A-CD8a_hTRGC1_CD28CD40 |
| pIB1047 | TIAAR | CD8A x2 | Myc and FLAG | mTRAC_mTRBC1 | N/A | CD28-CD40 | CD8A_mTRAC_CD28CD40-T2A-CD8A_mTRBC1_CD28CD40 |
| pIB1048 | TIAAR | CD3D and CD3E | Myc and FLAG | CD3D_CD3E | N/A | CD28-CD40 | CD3D_CD3D_CD28CD40-T2A-CD3E_CD3E_CD28CD40 |
| pIB1049 | TIAAR | CD3G and CD3E | Myc and FLAG | CD3G_CD3E | N/A | CD28-CD40 | CD3G_CD3G_CD28CD40-T2A-CD3E_CD3E_CD28CD40 |
| pIB1050 | TIAAR | CD3D and CD3E | Myc and FLAG | CD3D_CD3E | CD3D_CD3E | CD28-CD40 | CD3D_CD3D_CD3D (ICD)_CD28CD40-T2A-CD3E_CD3E_CD3E (ICD)_CD28CD40 |
| pIB1051 | TIAAR | CD3D and CD3E | Myc and FLAG | CD3D_CD3E | CD3D_CD3E | N/A | CD3D_CD3D_CD3D ICD-T2A-CD3E_CD3E_CD3E ICD |
| pIB1052 | TIAAR | CD3D and CD3E | Myc and FLAG | CD3D_CD3E | N/A | N/A | CD3D_CD3D (control)-T2A-CD3E_CD3E (control) |
| pIB1053 | TIAAR | CD3G and CD3E | Myc and FLAG | CD3G_CD3E | CD3G_CD3E | CD28-CD40 | CD3G_CD3G_CD3G (ICD)_CD28CD40-T2A-CD3E_CD3E_CD3E (ICD)_CD28CD40 |
| pIB1054 | TIAAR | CD3G and CD3E | Myc and FLAG | CD3G_CD3E | CD3G_CD3E | N/A | CD3G_CD3G_CD3G ICD-T2A-CD3E_CD3E_CD3E ICD |
| pIB1055 | TIAAR | CD3G and CD3E | Myc and FLAG | CD3G_CD3E | N/A | N/A | CD3G_CD3G (control)-T2A-CD3E_CD3E (control) |
| pIB1056 | TIAAR | CD3Z | Myc IC | CD3Z | CD3Z | CD28-CD40 | CD3z_CD3z_CD3z ICD_CD28CD40_Myc |
| pIB1057 | TIAAR | CD3Z | Myc IC | CD3Z | CD3Z | N/A | CD3z_CD3z_CD3z ICD_Myc |

TABLE 10-continued

TIAAR (TCR incorporated) list of constructs

| Code | Concept | Signal peptide | Tag | ECD_TMD | ICD | Costim | GOI description |
|---|---|---|---|---|---|---|---|
| pIB1058 | TIAAR | CD3Z | Myc IC | CD3Z | N/A | N/A | CD3z_CD3z (control) |
| pIB1059 | TIAAR | CD3Z | Myc IC | CD3Z | CD3Z (x2) | CD28-CD40 | CD3Z_CD3Z_CD3Z ICD (duplicating CD3z endodomain-6 ITAMs) _CD28CD40_Myc |
| pIB1060 | TIAAR | CD3Z | Myc IC | CD3Z | CD3Z (x2) | N/A | CD3Z_CD3Z_CD3Z ICD (duplicating CD3z endodomain-6 ITAMs)_Myc |
| pIB1061 | TIAAR | CD3Z | Myc IC | CD3Z | CD3Z (x2) | CD28-CD40 (swaped) | CD3Z_CD3Z_CD28CD40_CD3Z (6 ITAMs)_Myc |
| pIB1062 | TIAAR | CD3Z | Myc IC | CD3Z | CD3Z | CD28-CD40 (swaped) | CD3Z_CD3Z_CD28CD40_CD3Z ICD_Myc |
| pIB1063 | TIAAR | CD80 | Myc | CD80 | CD80 | N/A | CD80 (control) |
| pIB1064 | TIAAR | no signal peptide | Myc IC | N/A | Lck | N/A | Lck (control) |
| pIB1065 | TIAAR | no signal peptide | Myc IC | N/A | Lck (Y505F) | N/A | Lck (Y505F) (control) |
| pIB1066 | TIAAR | CD80 | Myc | CD80 | Lck | N/A | CD80_Lck |
| pIB1067 | TIAAR | CD80 | Myc | CD80 | Lck | CD28-CD40 | CD80_Lck_CD28CD40 |
| pIB1068 | TIAAR | CD80 | Myc | CD80 | CD80_Lck (Y505F) | N/A | CD80_Lck (Y505F) |
| pIB1069 | TIAAR | CD80 | Myc | CD80 | CD80_Lck (Y505F) | CD28-CD40 | CD80_Lck (Y505F)_CD28CD40 |
| pIB1070 | TIAAR | CD8A | Myc | LAT | LAT | N/A | LAT (control) |
| pIB1071 | TIAAR | CD8A | Myc | LAT | LAT | CD28-CD40 | LAT_C28CD40 |
| pIB1072 | TIAAR | CD4 | Myc | CD4 | CD4 | CD28-CD40 | CD4 control |
| pIB1073 | TIAAR | CD4 | Myc | CD4 | CD4 | CD28-CD40 | CD4_CD28_CD40 |
| pIB1074 | TIAAR | CD8A and CD8B | Myc and FLAG | CD8A and CD8B | CD8A and CD8B | N/A | CD8 control |
| pIB1075 | TIAAR | CD8A and CD8B | Myc and FLAG | CD8A and CD8B | CD8A and CD8B | CD28-CD40 | CD8_CD28_CD40 |

Cytokine production (Bcl-xL, IL2, IFNgamma and TNFalpha) from genetically modified and non-transduced T cells (NTD) after overnight stimulation with either Ba/F3 OKT3 targets or left unstimulated (i.e., T cells only) (FIG. 2). There was increased Bcl-xL, IL2, IFNgamma and TNFalpha production from genetically modified T cells as compared to NTD cells in Donor 1. There was an increase in IFNγ production and comparable or lower levels of Bcl-xL, IL2, IFNgamma and TNFalpha production in genetically modified as compared to NTD cells in Donor 2.

Figure 1A:
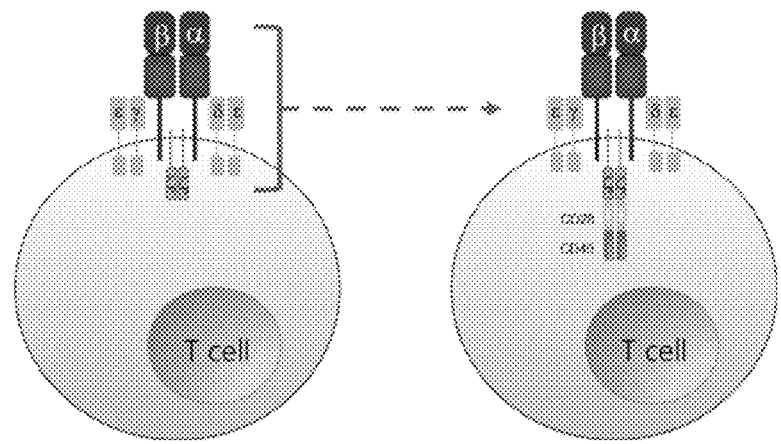
FIG. 1A-1C— Schematic models for universal costimulatory proteins.
Figure 1B:
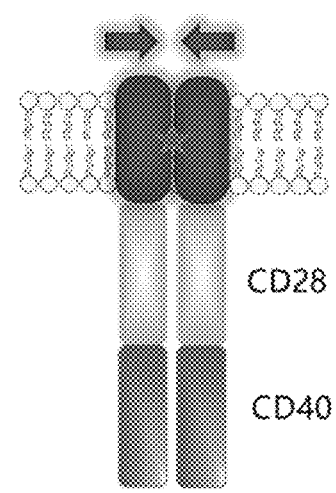
Figure 1C:
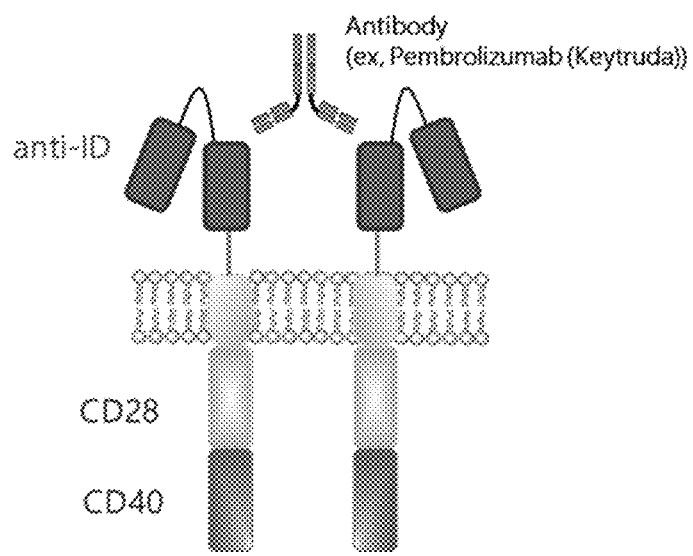
Figure 3A:
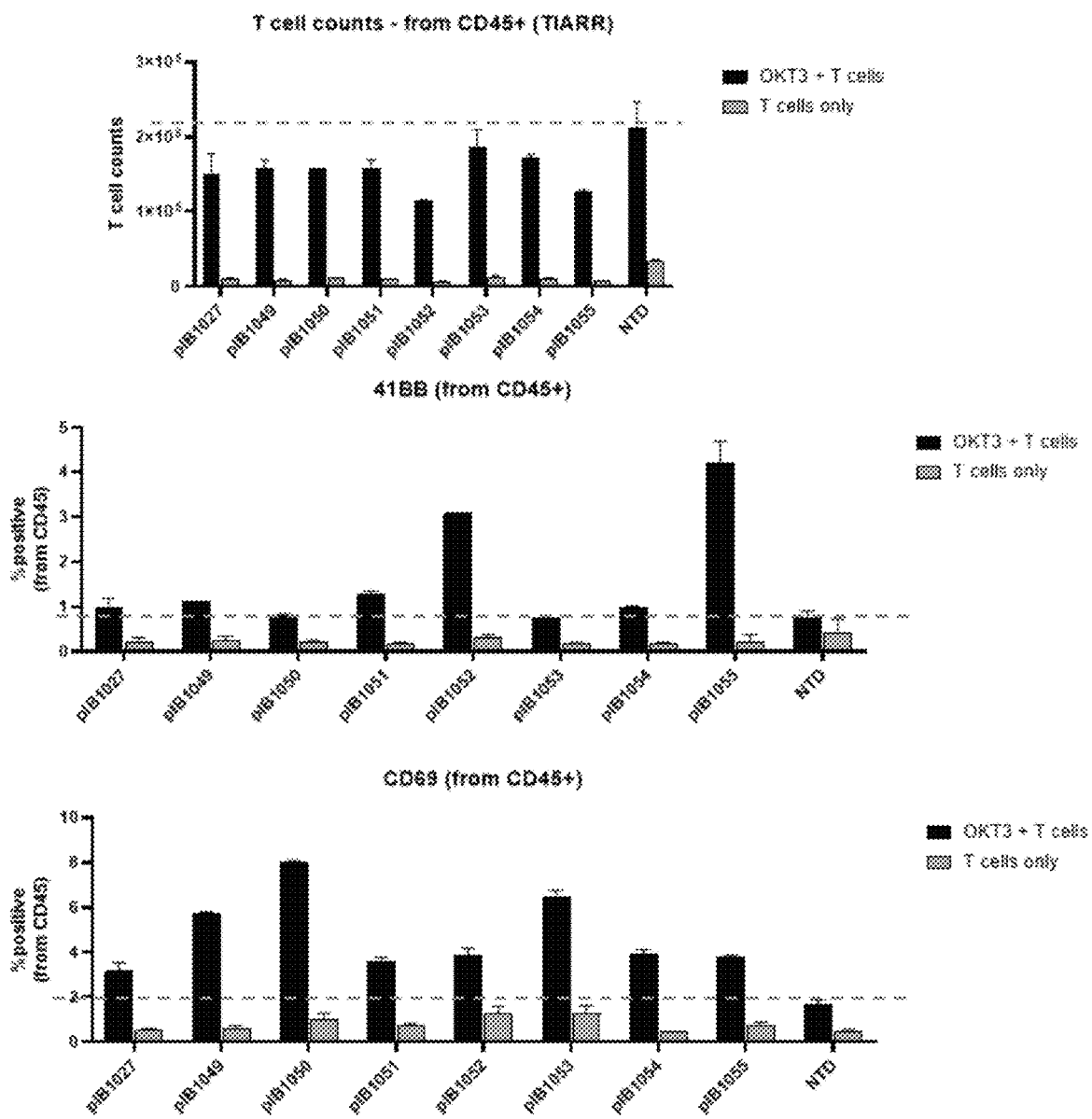
FIGS. 3A-3B—Proliferation and activation marker expression by TIAAR transduced cells. Proliferation (T cell counts) and activation marker expression (41BB and CD69) was determined for genetically modified and non-transduced T cells (NTD) from donor 1 (FIG. 3A) and donor 2 (FIG. 3B) after 5-day co-culture with either Ba/F3 OKT3 targets or left unstimulated (i.e., T cells only).
Figure 3B:
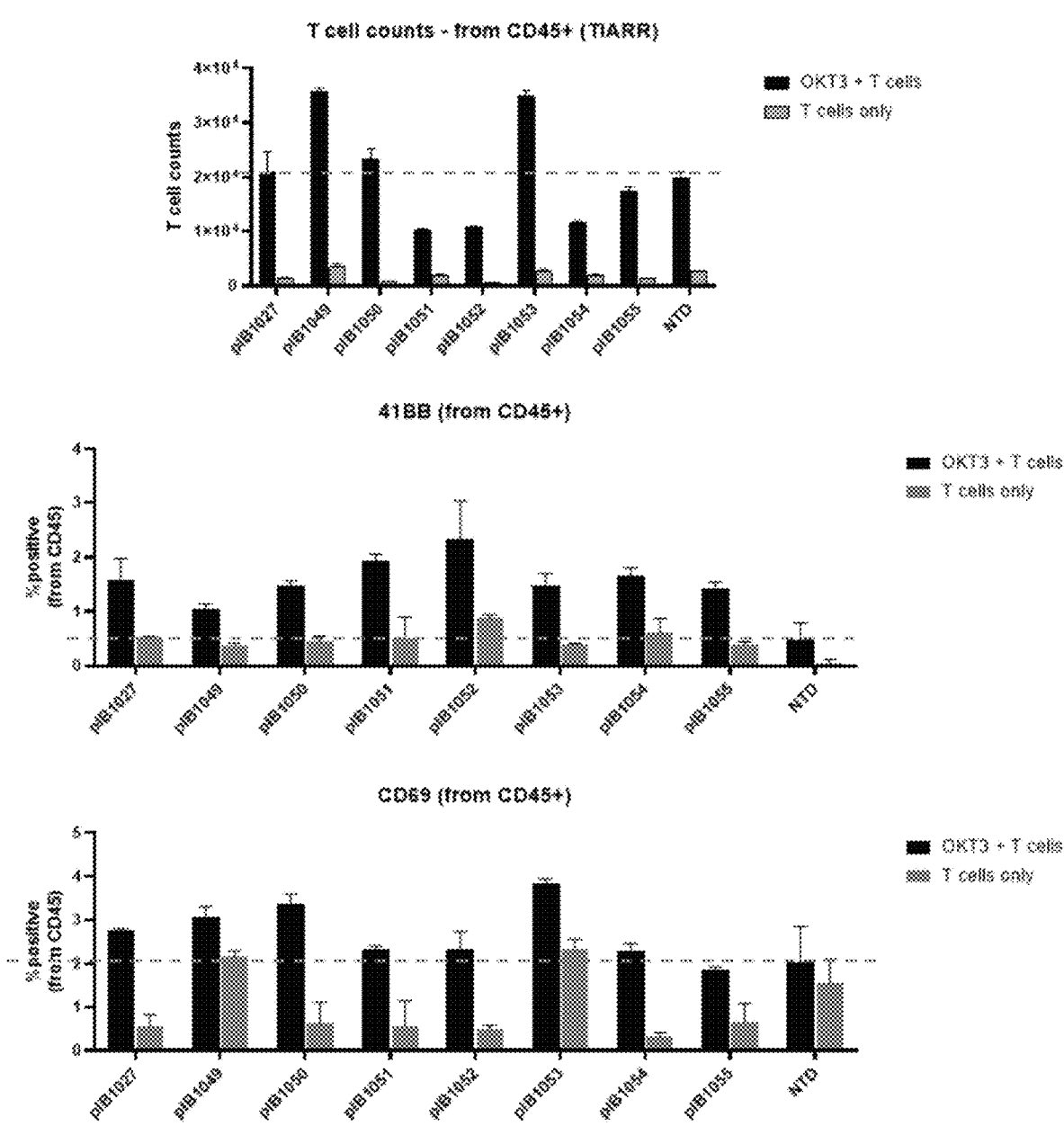

Proliferation (T cell counts from CD45+(TIARR)) and activation marker expression (41BB from CD45+ and CD69 from CD45+) from genetically modified and non-transduced T cells (NTD) after 5-day co-culture with either Ba/F3 OKT3 targets or left unstimulated (i.e., T cells only) (FIGS. 3A-3B). There was decreased T cell counts in genetically modified as compared to NTD cells in Donor 1. There was increased or similar 41BB and CD69 expression in genetically modified as compared to NTD cells in Donor 1. There was increased or similar 41BB and CD69 expression in genetically modified T cells as compared to NTD cells in Donor 1. There was increased T cell counts for 2 modifications tested, and a similar or decreased T cell counts for the remaining genetically modified T cells as compared to NTD cells in Donor 2. There was increased or comparable 41BB and CD169 expression in genetically modified as compared to NTD cells in Donor 2.

TABLE 11

List of constitutive constructs

| Code | Concept | Signal peptide | Tag | ECD_TMD | ICD | Costim | GOI description |
|---|---|---|---|---|---|---|---|
| pIB1076 | C-SAAR | CD8A | Myc | LZ (cFos)_EGFR | N/A | CD28-CD40 | LZ (cFos)-EGFRTM/JMD-CD28-CD40 |
| pIB1077 | C-SAAR | CD8A | Myc | LZ (cFos)_CD28 | N/A | CD28-CD40 | LZ (cFos)-CD28TM-CD28-CD40 |
| pIB1078 | C-SAAR | CD8A | Myc | LZ (cJun)_EGFR | N/A | CD28-CD40 | LZ (cJun)-EGFRTM/JMD-CD28-CD40 |

TABLE 11-continued

List of constitutive constructs

| Code | Concept | Signal peptide | Tag | ECD_TMD | ICD | Costim | GOI description |
|---|---|---|---|---|---|---|---|
| pIB1079 | C-SAAR | CD8A | Myc | LZ (cJun)_CD28 | N/A | CD28-CD40 | LZ (cJun)-CD28TM-CD28-CD40 |
| pIB1080 | C-SAAR | CD8A | Myc | LZ (c/EBP)_EGFR | N/A | CD28-CD40 | LZ (c/EBP)-EGFRTM/JMD-CD28-CD40 |
| pIB1081 | C-SAAR | CD8A | Myc | LZ (c/EBP)_CD28 | N/A | CD28-CD40 | LZ (c/EBP)-CD28TM-CD28-CD40 |
| pIB1103 | C-SAAR | GpA | Myc | GpA ECD_TMD | N/A | CD28-CD40 | GpA ECD-TMD-CD28-CD40 |
| pIB1104 | C-SAAR | GpA | Myc | GpA TMD | N/A | CD28-CD40 | GpA TMD-CD28-CD40 |
| pIB1105 | C-SAAR | EPOR | Myc | EPOR ECD_TMD | N/A | CD28-CD40 | EpoR ECD-TMD-CD28-CD40 |
| pIB1106 | C-SAAR | EPOR | Myc | EPOR TMD | N/A | CD28-CD40 | EpoR TMD-CD28-CD40 |
| pIB1107 | C-SAAR | TPOR | Myc | TPOR ECD_TMD | N/A | CD28-CD40 | TPO ECD-TPO (WT) TMD-CD28-CD40 |
| pIB1108 | C-SAAR | TPOR | Myc | TPOR TMD | N/A | CD28-CD40 | TPO (WT) TMD-CD28-CD40 |
| pIB1109 | C-SAAR | TPOR | Myc | TPOR ECD_TMD (S505N) | N/A | CD28-CD40 | TPO ECD-TPO (S505N) TMD-CD28-CD40 |
| pIB1110 | C-SAAR | TPOR | Myc | TPOR TMD (S505N) | N/A | CD28-CD40 | TPO (S505N) TMD-CD28-CD40 |
| pIB1111 | C-SAAR | TPOR | Myc | TPOR ECD_TMD (W515K) | N/A | CD28-CD40 | TPO ECD-TPO (W515K) TMD-CD28-CD40 |
| pIB1112 | C-SAAR | TPOR | Myc | TPOR TMD (W515K) | N/A | CD28-CD40 | TPO (W515K) TMD-CD28-CD40 |
| pIB1113 | C-SAAR | TPOR | Myc | TPOR ECD_TMD (H499L) | N/A | CD28-CD40 | TPO ECD-TPO (H499L) TMD-CD28-CD40 |
| pIB1114 | C-SAAR | TPOR | Myc | TPOR TMD (H499L) | N/A | CD28-CD40 | TPO (H499L) TMD-CD28-CD40 |
| pIB1115 | C-SAAR | TPOR | Myc | TPOR ECD_TMD (S505N-W515K) | N/A | CD28-CD40 | TPO ECD-TPO (S505N-W515K) TMD-CD28-CD40 |
| pIB1116 | C-SAAR | TPOR | Myc | TPOR TMD (S505N-W515K) | N/A | CD28-CD40 | TPO (S505N-W515K) TMD-CD28-CD40 |
| pIB1117 | C-SAAR | TPOR | Myc | TPOR ECD_TMD (H499Y-S505N) | N/A | CD28-CD40 | TPO ECD-TPO (H499Y-S505N) TMD-CD28-CD40 |
| pIB1118 | C-SAAR | TPOR | Myc | TPOR TMD (H499Y-S505N) | N/A | CD28-CD40 | TPO (H499Y-S505N) TMD-CD28-CD40 |
| pIB1119 | C-SAAR | TPOR | Myc | TPOR ECD_TMD (L498W-H499C) | N/A | CD28-CD40 | TPO ECD-TPO (L498W-H499C) TMD-CD28-CD40 |
| pIB1120 | C-SAAR | TPOR | Myc | TPOR TMD (L498W-H499C) | N/A | CD28-CD40 | TPO (L498W-H499C) TMD-CD28-CD40 |
| pIB1025 | C-SAAR | CD8a | Myc | CD28 | N/A | CD28-CD40 | CD28 TM_CD28_CD40 |
| pIB1179 | C-SAAR | CD8a | N/A | IgG128TM | N/A | CD28-CD40 | IgG1(CH2CH3)-CD28(TM)-CD28(CoStim)-CD40(CoStim) |
| pIB1180 | C-SAAR | CD8a | N/A | IgG1mut + CIM | N/A | CD28-CD40 | IgG1(CH2CH3, mutant)-CD28(TM)-CD28(CoStim)-CD40(CoStim) |
| pIB1181 | C-SAAR | CD8aI | N/A | IgG2 + CD28TM | N/A | CD28-CD40 | IgG2(CH2CH3)-CD28(TM)-CD28(CoStim)-CD40(CoStim) |
| pIB1182 | C-SAAR | I | N/A | IgG3 + CD28TM | N/A | CD28-CD40 | IgG3(CH2CH3)-CD28(TM)-CD28(CoStim)-CD40(CoStim) |
| pIB1183 | C-SICD8a | CD8a | N/A | IgG4 + CD28TM | N/A | CD28-CD40 | IgG4(CH2CH3)-CD28(TM)-CD28(CoStim)-CD40(CoStim) |
| pIB1184 | C-SAAR | CDI/A | N/A | IgG4mut + CD28TM | N/A | CD40 | IgG4(CH2CH3, mutant)-CD28I-CD28(CoStim)-CD40(CoStim) |
| pIB1185 | C-SAAR | CD8a | N/A | IgG1 + CD28 stalk/TM | N/A | CD28-CD40 | IgG1(CH2CH3)-CD28(Stalk + TM)-CD28(CoStim)-CD40(CoStim) |
| pIB1186 | C-SAAR | CD8a | N/A | IgG1mut + CD28 stalk/TM | N/A | CD28-CD40 | IgG1(CH2CH3, mutant)-CD28(Stalk + TM)-CD28(CoStim)-CD40(CoStim) |
| pIB1187 | C-SAAR | CD8a | N/A | IgG2 + CD28 stalk/TM | N/A | CD28-CD40 | IgG2(CH2CH3)-CD28(Stalk + TM)-CD28(CoStim)-CD40(CoStim) |

TABLE 11-continued

List of constitutive constructs

| Code | Concept | Signal peptide | Tag | ECD_TMD | ICD | Costim | GOI description |
|---|---|---|---|---|---|---|---|
| pIB1188 | C-SAAR | CD8a | N/A | IgG3 + CD28 stalk/TM | N/A | CD28-CD40 | IgG3(CH2CH3)-CD28(Stalk + TM)-CD28(CoStim)-CD40(CoStim) |
| pIB1189 | C-SAAR | CD8a | N/A | IgG4 + CD28 stalk/TM | N/A | CD28-CD40 | IgG4(CH2CH3)-CD28(Stalk + TM)-CD28(CoStim)-CD40(CoStim) |
| pIB1190 | C-SAAR | CD8a | N/A | IgG4mut + CD28 stalk/TM | N/A | CD28-CD40 | IgG4(CH2CH3, mutant)-CD28(Stalk + TM)-CD28(CoStim)-CD40(CoStim) |

Cytokine production (Bcl-xL, IL2, IFNgamma and TNFalpha) from genetically modified and non-transduced T cells (NTD) after overnight stimulation with either Ba/F3 OKT3 targets or left unstimulated (i.e., T cells only) (FIG. 4). There was increased or comparable Bcl-xL, IL2, and TNFalpha production and comparable or lower levels of IFNgamma from genetically modified T cells as compared to NTD cells in Donor 1. There was an increase in IFNgamma and IL2 production and comparable or lower levels of Bcl-xL and TNFalpha production in genetically modified as compared to NTD cells in Donor 2.

Figure 5A:
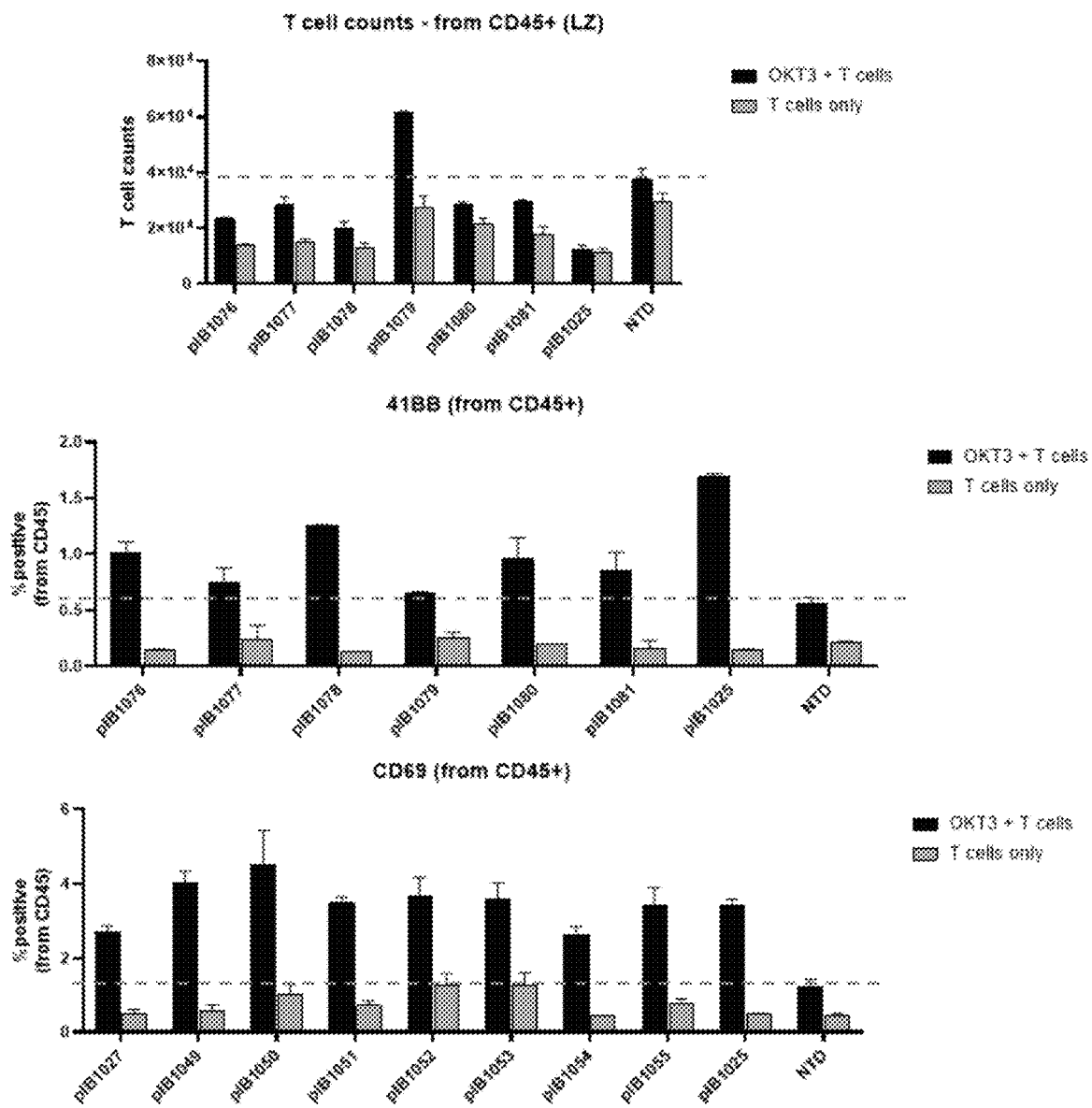
FIGS. 5A-5B—Proliferation and activation marker expression by LZ-CoStAR transduced cells. Proliferation (T cell counts) and activation marker expression (41BB and CD69) was determined for genetically modified and non-transduced T cells (NTD) from donor 1 (FIG. 5A) and donor 2 (FIG. 5B) after 5-day co-culture with either Ba/F3 OKT3 targets or left unstimulated (i.e., T cells only).
Figure 5B:
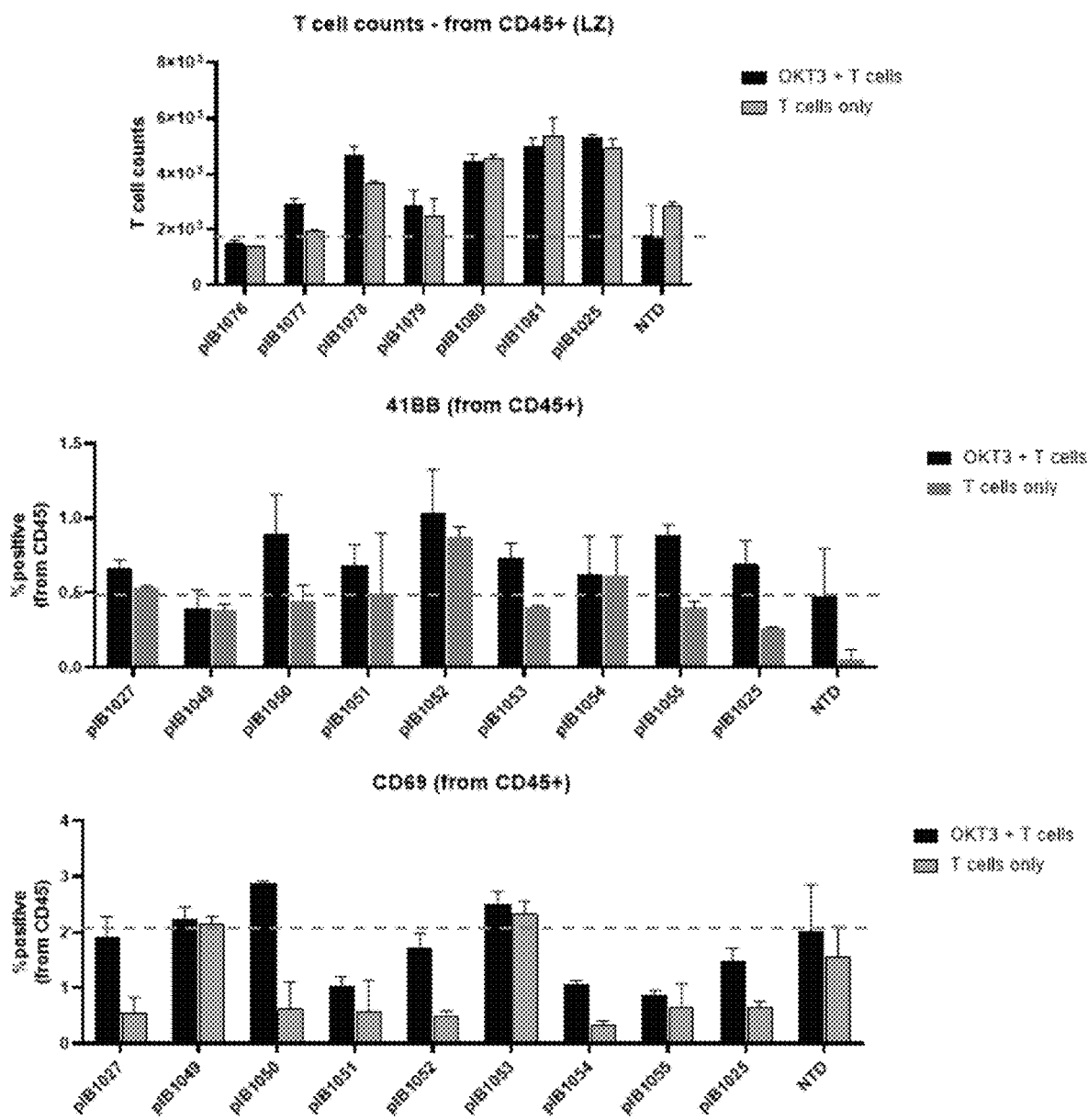

Proliferation (T cell counts from CD45+(LZ)) and activation marker expression (41BB from CD45+ and CD69 from CD45+) from genetically modified and non-transduced T cells (NTD) after 5-day co-culture with either Ba/F3 OKT3 targets or left unstimulated (i.e., T cells only) (FIGS. 5A-5B). There was decreased T cell counts in genetically modified as compared to NTD cells in Donor 1. There was increased 41BB and CD69 expression in genetically modified T cells as compared to NTD cells in Donor 1. There was increased T cell counts as compared to NTD cells in Donor 2, an increase in 41BB expression in genetically modified T cells as compared to NTD cells, and similar or decreased expression of CD169 in genetically modified T cells as compared to NTD cells in Donor 2.

TABLE 12

List of inducible constructs

| Code | Concept | Signal peptide | Tag | ECD_TMD | ICD | Costim | GOI description |
|---|---|---|---|---|---|---|---|
| pIB1082 | Inducible | EGFR | Myc | EGFR | N/A | CD28-CD40 | WT EGFR ECD-EGFRTM/JMD-CD28-CD40 |
| pIB1083 | Inducible | EGFR | Myc | EGFR (domain IV) | N/A | CD28-CD40 | domain IV-EGFRTM/JMD-CD28-CD40 |
| pIB1084 | Inducible | EGFR | Myc | EGFR (623-668) | N/A | CD28-CD40 | EGFRTM/JMD-CD28-CD40 (control) |
| pIB1085 | Inducible | Her2 | Myc | Her2 | N/A | CD28-CD40 | Her 2 (Domain 1 to IV)-TMD/JMD-CD28-CD40 |
| pIB1086 | Inducible | Her2 | Myc | Her2 (V659E) | N/A | CD28-CD40 | Her 2 (Domain 1 to IV)-TMD (V659E)/JMD-CD28-CD40 |
| pIB1087 | Inducible | Her2 | Myc | Her2 (V660D) | N/A | CD28-CD40 | Her 2 (Domain 1 to IV)-TMD (G660D)/JMD-CD28-CD40 |
| pIB1088 | Inducible | Her2 | Myc | Her2 (V660R) | N/A | CD28-CD40 | Her 2 (Domain 1 to IV)-TMD (G660R)/JMD-CD28-CD40 |
| pIB1089 | Inducible | Her2 | Myc | Her2 domain IV_TMD | N/A | CD28-CD40 | Her 2 (Domain IV)-TMD/JMD-CD28-CD40 |
| pIB1090 | Inducible | Her2 | Myc | Her2 domain IV_TMD (V659E) | N/A | CD28-CD40 | Her 2 (Domain IV)-TMD (V659E)/JMD-CD28-CD40 |
| pIB1091 | Inducible | Her2 | Myc | Her2 domain IV_TMD (G660D) | N/A | CD28-CD40 | Her 2 (Domain IV)-TMD (G660D)/JMD-CD28-CD40 |
| pIB1092 | Inducible | Her2 | Myc | Her2 domain IV_TMD (G660R) | N/A | CD28-CD40 | Her 2 (Domain IV)-TMD (G660R)/JMD-CD28-CD40 |
| pIB1093 | Inducible | Her2 | Myc | Her2 TMD | N/A | CD28-CD40 | Her 2 TMD/JMD-CD28-CD40 |
| pIB1094 | Inducible | Her2 | Myc | Her2 TMD (V659E) | N/A | CD28-CD40 | Her 2 TMD (V659E)/JMD-CD28-CD40 |
| pIB1095 | Inducible | Her2 | Myc | Her2 TMD (G660D) | N/A | CD28-CD40 | Her 2 TMD (G660D)/JMD-CD28-CD40 |
| pIB1096 | Inducible | Her2 | Myc | Her2 TMD (G660R) | N/A | CD28-CD40 | Her 2 TMD (G660R)/JMD-CD28-CD40 |
| pIB1097 | Inducible | CD8A | Myc | A30514 VH_VL | N/A | CD28-CD40 | Anti-IDI VH-VL (A30514-pembrolizumab)-CD28TMD CD28-CD40 |

TABLE 12-continued

List of inducible constructs

| Code | Concept | Signal peptide | Tag | ECD_TMD | ICD | Costim | GOI description |
|---|---|---|---|---|---|---|---|
| pIB1098 | Inducible | CD8A | Myc | A30514 VL_VH | N/A | CD28-CD40 | Anti-IDI VL-VH (A30514-pembrolizumab)-CD28TMD CD28-CD40 |
| pIB1099 | Inducible | CD8A | Myc | A30523 VH_VL | N/A | CD28-CD40 | Anti-ID2 Vh-VL (A30523-pembrolizumab)-CD28TMD CD28-CD40 |
| pIB1100 | Inducible | CD8A | Myc | A30523 VL_VH | N/A | CD28-CD40 | Anti-ID2 VL-Vh (A30523-pembrolizumab)-CD28TMD CD28-CD40 |
| pIB1101 | Inducible | CD8A | Myc | A30633 VH_VL | N/A | CD28-CD40 | Anti-ID3 Vh-VL (A30633-pembrolizumab)-CD28TMD CD28-CD40 |
| pIB1102 | Inducible | CD8A | Myc | A30633 VL_VH | N/A | CD28-CD40 | Anti-ID3 VL-VH (A30633-pembrolizumab)-CD28TMD CD28-CD40 |

Cytokine production (Bcl-xL, IL2, IFNg and TNFa) from genetically modified and non-transduced T cells (NTD) after overnight stimulation with either Ba/F3 OKT3 targets or Ba/F3 OKT3 targets with 10 ug/mL pembrolizumab or left unstimulated (i.e., T cells only) (FIG. 6). There was increased or comparable Bcl-xL, IL2, IFNgamma and TNFalpha production from genetically modified T cells in the presence of Ba/F3 OKT3 and pembrolizumab as compared to conditions with Ba/F3 OKT3 stimulation alone and NTD cells in both Donor 1 and Donor 2.

Figure 7A:
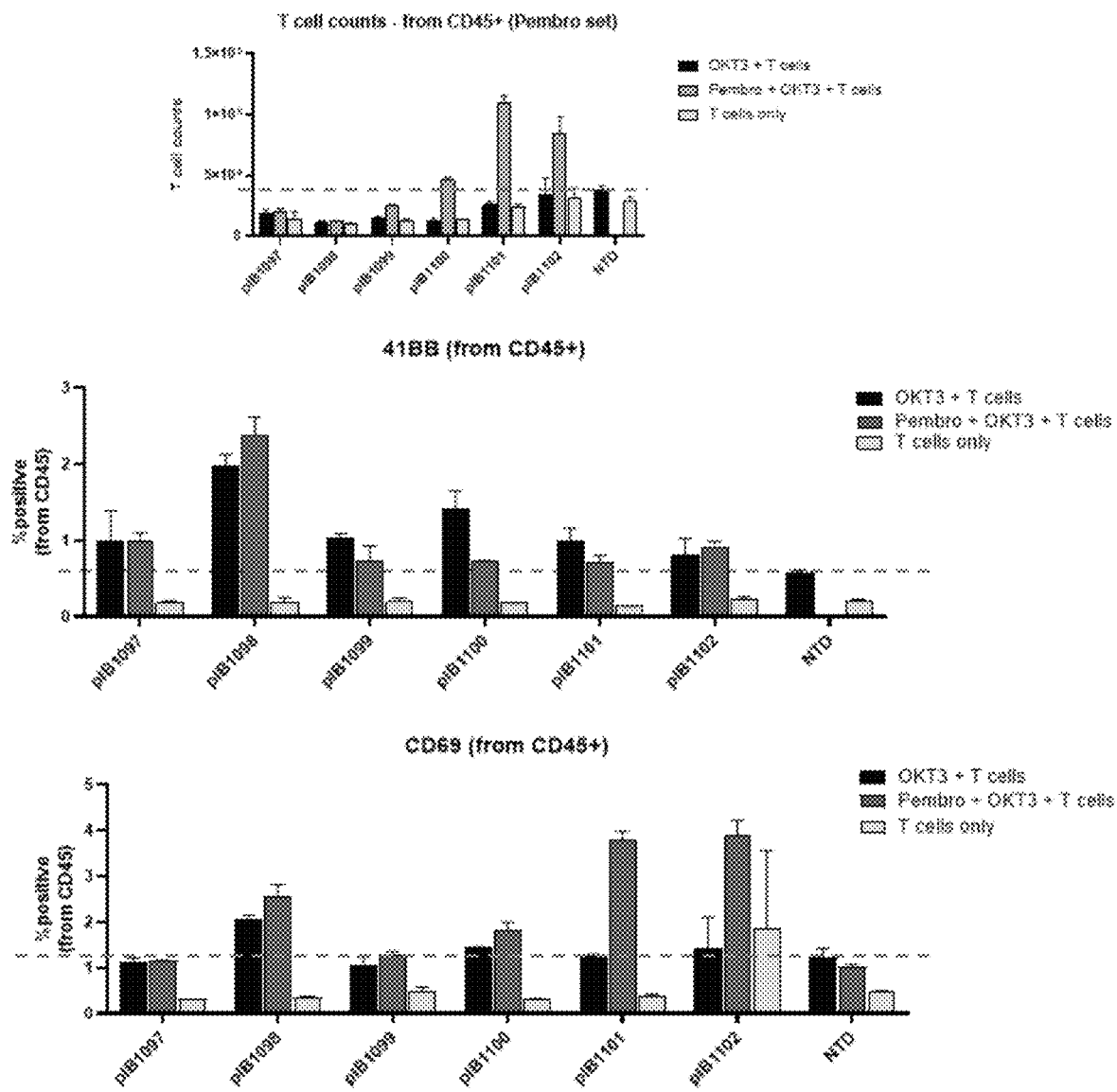
FIGS. 7A-7B—Proliferation and activation marker expression by inducible universal CoStAR transduced cells. Proliferation (T cell counts) and activation marker expression (41BB and CD69) was determined for genetically modified and non-transduced T cells (NTD) from donor 1 (FIG. 7A) and donor 2 (FIG. 7B) after 5-day co-culture with either Ba/F3 OKT3 targets or left unstimulated (i.e., T cells only). The universal CoStAR is inducible by pembrolizumab.
Figure 7B:
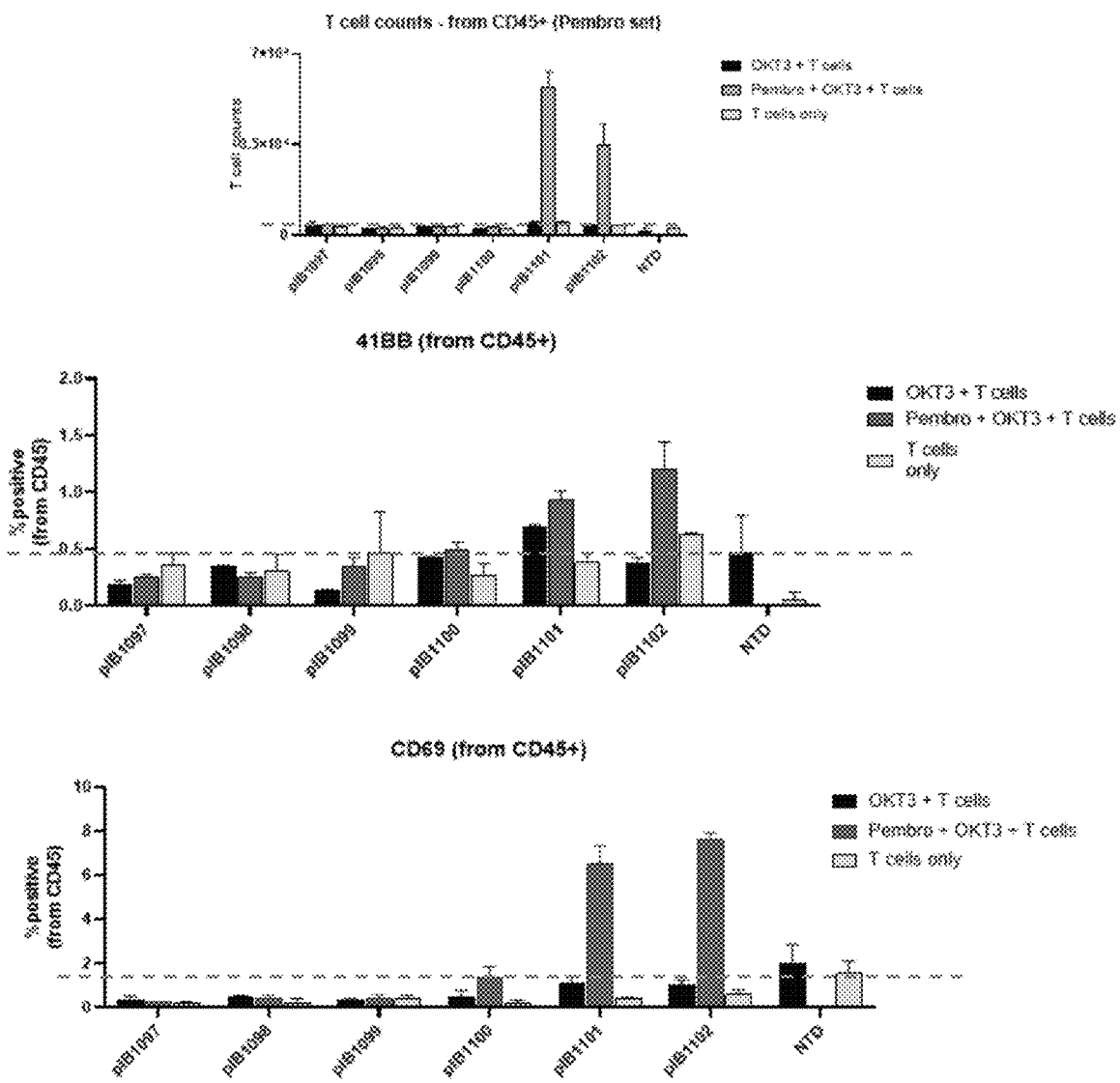

Proliferation (T cell counts from CD45+(Inducible)) and activation marker expression (41BB from CD45+ and CD69 from CD45+) from genetically modified and non-transduced T cells (NTD) after 5-day co-culture with either Ba/F3 OKT3 targets or Ba/F3 OKT3 targets with 10 ug/mL pembrolizumab or left unstimulated (i.e., T cells only) (FIGS. 7A-7B). There was increased, comparable and decreased T cell counts in genetically modified T cells as compared to NTD cells in Donor 1. There was increased or similar 41BB and CD169 expression in genetically modified T cells as compared to NTD cells in Donor 1. There was increased or comparable T cell counts in genetically modified T cells as compared to NTD cells in Donor 2. There was increased, similar and decreased 41BB and CD169 expression in genetically modified cells as compared to NTD cells in Donor 2. Increased T cell counts and activation marker expression in both donors were observed when the genetically modified T cells were stimulated with Ba/F3 OKT3 in the presence of pembrolizumab compared to conditions with Ba/F3 OKT3 stimulation alone as well as NTD cells.

Example 2

Use of Sequences in a Cell System for the Treatment of a Patient

An engineered protein having the sequence of SEQ ID NO: 166 will be transfected into a Tumor Infiltrating Lymphocyte (TIL) cell using standard procedures by incorporating vectors. This cell will then be used to generate a population of TIL cells expressing those proteins. The population will be derived through detecting expression of the protein on the surface of the cells transfected to express the two proteins, and selecting cells which are identified as expressing those proteins. Through this process, the population of cells will be enriched for those expressing the protein. Following enrichment, the TIL cells will be administered at a therapeutic amount to a patient as a therapeutic treatment for cancer.

Example 3

Transduction of CoStAR Constructs into TIL Cells

CoStAR constructs were transduced into TIL cells from tumor digests. The efficiency of CEA or FOLR expression on tumor digests at Day 1 is as shown in FIGS. 20-22, and in Table 13.

TABLE 13

| Tumor type | Construct Name | % CEA from CD45− (FSC-H vs CEA) | % FOLR1 expression (FSC-H vs FOLR1) | % CEA+ % FOLR+ (CEA vs FOLR1) |
|---|---|---|---|---|
| CRC (metastatic) | CRC 11959 | 71.7 | 4.53 | 2.65 |
| CRC (metastatic) | CRC 11974 | 54.6 | 9.9 | 5.31 |
| NSCLC | NSCLC-9332 | 3.88 | 15.3 | 1.56 |
| NSCLC | NSCLC-9596 | 15.1 | 34.8 | 14.7 |
| Ovarian | OV-9662 | 2.03 | 41.3 | 0.93 |
| Melanoma | MEL-CC50 | 1.37 | 0.77 | 0.061 |

TABLE 13-continued

| Tumor type | Construct Name | % CEA from CD45− (FSC-H vs CEA) | % FOLR1 expression (FSC-H vs FOLR1) | % CEA+ % FOLR+ (CEA vs FOLR1) |
|---|---|---|---|---|
| Melanoma | MEL-11909 | 1.26 | 4.53 | 0.25 |
| Melanoma | MEL-17614 | 4.4 | 1.41 | 0.18 |

Figure 12:
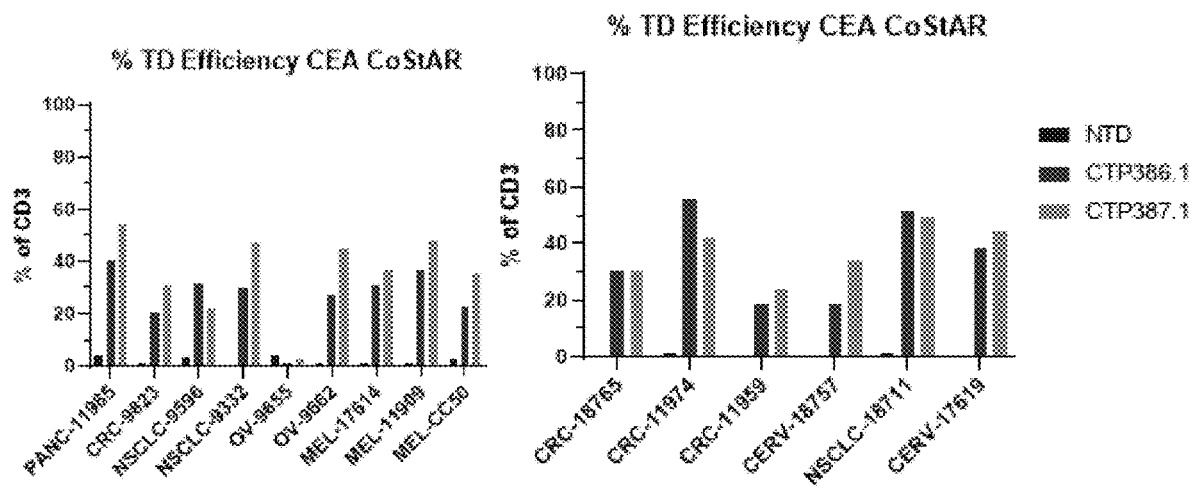
FIG. 12—depicts the transduction efficiency of constructs into TILs after 21 days. Round 1 (left panel) and Round 2

The efficiency of CEA or FOLR expression by Day 21 is as shown in FIGS. 12-14. As can be shown in FIGS. 12-14 and 20-22, the amount of CEA and FOLR expression was significantly higher by 21 days of treatment compared to 1 day of treatment. The transduction was performed using the following materials and methodology:

Methodology: Experimental Outline

On day 1, the tumor digest was thawed (no stimulation) in media 1. There were a total of 15 tumor digests, and comprised pancreatic, CRC, NSCLC, ovarian, melanoma, and cervical tumors (FIG. 18). 0.5-1e6 cells were seeded per condition (6 conditions). Phenotype was recorded were applicable. On days 3 and 4, cells were transduced in media 1 at MOI 10. On day 8, cells were given outgrowth feed, through the addition of 1 mL of media 2 with gentamycin/amphotericin and fresh IL2 (6000 U/mL). On day 10, static REP (G-REX 6) was performed; cells were stimulated with OKT3 (30 ng/mL)+IL2 (3000 U/mL)+irradiated feeders (1:200). On day 15, dynamic REP was performed; cells were transferred to G-REX 6M with 100 mL media 3. On day 18, cells were counted, split as needed, and/or removed 65 mL media and replenished with fresh media 3. On day 21, the REP was ended. This timeline is also schematically depicted in FIG. 19.

Methodology: Media Preparation

TCM base media: GMP/TCM media+25 mM HEPES+25 µM 2-Mercaptoethanol

Media 1: TCM base media+10% FBS, 1× Gentamycin/Amphotericin (500× stock)+50 ug/mL vancomycin+3000 IU/mL IL2

Media 2: TCM base media+10% FBS, 2× Gentamicin/Amphotericin B (500× stock)+100 ug/mL vancomycin+6000 IU/mL IL2

Media 3: TCM base media+8% human AB serum, 3000 IU/mL IL2

Methodology: Detailed Protocol by Day

Day 1: Thaw frozen tumor digest
1. Prepare media 1 as per table in excel sheet. Add 200 uL IL2 to 200 mL of media 1
2. Label a 15 ML conical tube for each tumor digest vial
3. Remove the tumor digest vials from LN, and immediately thaw in 37-degree water bath until small chunks remain.
4. Sterilize the exterior and bring the vials to BSC.
5. Add in 1 ml of pre-warmed media 1 very gently, drop by drop, to each vial.
6. Transfer the total of 2 ml cell suspension from the vial using a 5 ml serological pipette, and add very gently, drop by drop, to the match labeled 15 ml conical tube which contains 2 ml of media 1.
7. Add in 9 ml of pre-warmed media 1 very gently to the cell suspension in the 15 ml conical tube.
8. Centrifuge at 400 g for 10 min.
9. Aspirate off the supernatant carefully without touching the cell pellet.
10. Based on the frozen cell number, resuspend the cells in 5 ml of media 1 gently
11. Count using Vicell and record in excel sheet (1:10 dilution; 30 uL cell suspension in 270 uL media 1)
12. Add 1 mL media and split into 6 conditions
13. Resuspend cells in either 0.5M/mL
14. Seed 0.5M/mL in a 24 well plate or 1M/2 mL in 6 well plate
15. Seed 6 wells for each tumor digest (pIB1322, pIB1324, CTP386.1, CTP387.1, CTP025 and NTD T cells)
16. Add 10 uL/mL amphotericin B only for CRC samples
17. Place plates in incubator
18. Collect cells if available for checking for CEA and FOLR expression on tumor Day 3: TIL Transduction During Outgrowth
1. Prepare required media 1 and add 1 uL/mL IL2 (25 uL IL2 to 25 mL media 1)
2. Dilute the needed volume of LVV in 0.1 mL for 24 well plate or 0.5 ml for 6 well plate with Media 1 in a separate vial for each sample, gently pipette to mix well and add into cell culture.
3. Add equivalent volume of media 1 alone to the nontransduced well.
4. Mix gently and place plate in the incubator.

Day 4: TIL Second Transduction
1. Prepare required media 1 and add 1 uL/mL IL2 (35 uL IL2 to 35 mL media 1)
2. Use the TVC and LVV volume calculation from day 3, dilute the needed volume of LVV in 0.1 ml with Media 1 in a separate vial for each sample
3. Mix gently and place plate in the incubator.

Day 8: Outgrowth Feed
1. Prepare media 2 as per table in the excel sheet. Add 200 uL IL2 to 100 mL media 2.
2. Mix each well
3. Add 1 ml of fresh Media 2 to each well for 6 well plate and 500 uL for 24 well plate
4. Continue the culture to day 10

Day 10: Static REP
1. Prepare media 3 as per table in the excel sheet
2. Collect all conditions
3. Count using Vicell and record in excel sheet
4. Calculate required number of irPBMC feeders needed
   a. Assuming 0.1e6 cells per condition based on cell counts below
   b. At 1:200— will need 12e9 irradiated feeders total
   c. Thaw feeders in media 3 and centrifuge at 300 g×5 mins
   d. Count feeders using Vicell
5. Prepare master mix of media 3+OKT3+IL2 as needed, using the ratios outline in Table 14 below.

TABLE 14

| Reagent | Stock concentration | Per mL of media 4 | Volume needed |
|---|---|---|---|
| Media 3 | NA | 1 mL | 30 mL |
| OKT3 (30 ng/mL or 0.3 uL/mL) | 100 ug/mL | NA | 30 uL (100 ng/mL) |
| IL2 | 3000 U/uL | 1 uL | 30 uL |

6. Add required volumes in the following order to each well of a 6-well G-Rex
   a. Add 30 mL media 4+OKT3+IL2 first to each well
   b. Add irradiated feeders to the bottom of the well
   c. Add TILs gently to the bottom of well
7. Plate an extra well of irradiated feeders alone to monitor and phenotype (seeded in Grex as well)

Day 15: Dynamic REP
1. Collect all cell culture, resuspend wells
2. Count using Vicell and record in excel sheet
3. Transfer 30 mL cell suspension to 6M G-REX and top to 100 ml (ie, add 60 mL media 3+10 mL to rinse the well)
4. Add fresh IL2 (1 uL/mL for 3000 U/mL IL2). Add 100 uL IL2 for each condition Day 18: Dynamic REP Maintenance
1. Take 6M G-REX from incubator
2. Resuspend cells in the wells
3. Count using Vicell and record in excel sheet
4. Either do a media change for cell counts <1e6 cells/mL or split conditions with cell counts >1e6 cells/mL
   Notes:
      a. Let G-Rex sit in Biosafety cabinet for 30 minutes if cells are in suspension or disturbed prior to removing media.
      b. For media change, remove 60 mL media and replenish with 60 mL media 4+IL2
      c. For splitting conditions, transfer 50 mL cell suspension to a second G-REX 6M and make up volume to 100 mL for all conditions.
5. Top wells with media 4 to 100 ml and place in incubator.

Day 21: Harvest
1. Harvest all cells.
2. Centrifuge at 400 g×10 mins
3. Resuspend in 50 mL media 3 and pass through 100 um cell strainer into a fresh 50 mL conical tube
4. Count using Vicell and record in excel sheet
5. Spin down cells at 400 g for 10 min and aspirate off the supernatant.
6. Cryopreserve the cells with CryoStor CS10 and freeze in cryovials.

Example 4

TIL Functional Screening

TIL cells expressing CoStAR constructs then underwent a screen to assess function. The results of this screen are as shown in FIGS. 17A-17B. From the screening, a population of cells were generated that were enriched for CEA and/or FOLR expression. The fraction of anti-CEA, anti-FOLR, and universtal CoStAR cells with positive expression are as shown in FIGS. 23-27. Of these TILS, the CD4/8 ratio was as shown in FIGS. 28A-28D. The methodology for the assay was as follows:

Methodology: Experiment Outline

On day 1, TIL cells were thawed. On day 2, CoStAR-modified TILS were sorted, then ran on fortessa. On day 4, the media change was completed, and the cells were stained and ran on fortessa. On day 6, the TCM media was changed to exclude IL2. On day 7, the co-culture and serial stimulation assay was set up. As can be seen in FIGS. 30A-30H, 31A-31H, and 32A-32H, the co-culture with autologous digest is inconclusive probably due to variability introduced in tumor reactivity of the TILs between different conditions as a result of sorting for CoStAR. Additionally, a higher level of IL2 production observed from both anti-CEA and Universal CoStAR modified TILs in the presence of signal 1+2 in 24-hour co-culture assay. Similar trends observed for IFNg and TNFa. On day 8, the supernatant was collected, and MSD was performed. Cells were then stained to assess the expression of activation markers. An outline of this time is as shown in FIG. 29.

Methodology: TCM Media with IL2

To a bottle of 500 mL RPMI 1640, add: 50 mL FBS, 5 mL pen/strep, 5 mL HEPES, 500 uL 2-mercaptoethanol, and 1 uL/mL of IL-2 stock (3e6 U/mL). The final concentration of the media should be 3000 U/mL.

Methodology: Detailed Protocol by Day

Day 1: Thaw TILS
1) Place vials in water bath
2) Transfer to hood and add cell suspension to 9 mL TCM media
3) Centrifuge at 400 g×5 mins
4) Aspirate
5) Add 5 mL media
6) Count using Vicell
7) Rest cells overnight at 1e6 cells/mL Day 2: Sort CoStAR-modified TILS
1. Collect cells
2. Centrifuge at 400 g×5 mins
3. Aspirate and resuspend in 5 mL media
4. Count using Vicell
5. Prepare buffer (10% FBS+2 mM EDTA), add following to 500 mL of RPMI 1640
   50 mL of fetal bovine serum
   2 mL of 0.5M EDTA
6. Determine cell number, collect cells for LS columns (see "Pre- and Post-sort counts").
7. Centrifuge @ 400×g for 5 minutes, aspirate supernatant. Break pellet.
8. Transfer to 15 mL conical tubes
9. Incubate cells with antibodies as per table
   For CTP205, add 1 uL sol FOLR Fc APC antibody per 1e6 cells
   For pIB1322 and pIB1324, add 10 uL donkey anti-rabbit PE antibody per 1e6 cells
   For CTP386.1 and 387.1, add 2.5 uL CEACAM5-Fc FITC antibody per 1e6 cells
10. Mix well, incubate in the dark @ 4 C for 30 minutes.
11. Wash cells by adding 1-2 mL buffer per 10e6 cells
12. Centrifuge @ 400×g for 5 minutes. Aspirate supernatant.
13. Add 5 mL buffer to wash.
14. Centrifuge @ 400×g for 5 minutes. Aspirate supernatant.
15. Resuspend in 80 uL of buffer 10e6 cells (see table)
16. Add 20 uL of microbeads 10e6 cells (see table)
17. Mix well, incubate for 15 minutes @ 4 C
18. Wash cells by adding 1-2 mL buffer per 10e6 cells
19. Centrifuge @ 400×g for 5 minutes. Aspirate supernatant.
20. Resuspend up to 100e6 cells in 500 uL of buffer.
21. Magnetic separation using LS column
   a) Place LS column on MACS separator.
   b) Rinse with 2 mL buffer. Use column immediately. Rinse column right before adding cell suspension.
   c) Apply cell suspension to column
   d) Wash column 3× with 2 mL of buffer. Collect unlabelled cells that pass through the column
   e) Remove column form separator and place on appropriate tube.
   f) Pipette 5 mL buffer onto column.
   g) Immediately flush by firmly pushing plunger into column.
   h) Centrifuge at 400 g×5 mins
   i) Resuspend in 1 mL (or 5 mL, depending on pellet) TCM media+3000 U/mL IL2
   j) Count on Vicell. (see Pre- and post-sort counts)

k) Add media to maintain cells at 1e6/mL and incubate flasks

Day 4: Complete media change
1. Collect cells in tubes
2. Centrifuge at 400 g×5 mins
3. Aspirate
4. Add TCM media with IL2
5. Count using Vicell
6. Add media to maintain cells at 1e6 cells/mL
7. Collect 0.05 to 0.1e6 cells to run on fortessa-stain with L/D Near Far IR Day 6: Change to media without IL2
8. Collect cells in tubes
9. Centrifuge at 400 g×5 mins
10. Aspirate
11. Add TCM media WITHOUT IL2
12. Count using Vicell
13. Add TCM media WITHOUT IL2 media to maintain cells at 1e6 cells/mL Day 7: Set up co-culture
1. Collect sorted TILs
2. Centrifuge at 400 g×5 mins
3. Aspirate and add 5 mL TCM media without IL2
4. Count using Vicell
5. Collect targets—K562 WT, OKT3, CEACAM5 and OKT3 CEACAM5 and OKT3 FOLR
6. Thaw autologous digest in TCM media without IL2
7. Centrifuge at 400 g×5 mins
8. Aspirate and resuspend in 5 ml TCM media without IL2
9. Count effectors, target cell lines and autologous digest using Vicell
10. Collect 2e6 cells and resuspend in 2 mLs final volume with TCM media without IL2
11. Collect 1e6 targets and resuspend in 10 mLs final volume with TCM media without IL2
12. Collect either 2e6 or 10e6 cells for autologous digest and resuspend in 2 mL TCM media without IL2 (this will be either 1:1 or 1:5 ratio)
13. Plate 50 uL TILs as per plate map
14. Plate 50 uL targets as per plate map.
15. Resuspend targets according to TILs to adjust E:T ratio to 10:1 (this is only for cell lines)
16. Prepare pembro from stock (5 mg/mL) as per table
17. Add 100 uL pembro as per plate map
18. Add 100 uL media to plate 1
19. Make up volume to 200 uL final in all wells. Note that effectors only and target only wells will have 150 uL; add 50 uL media or appropriate pembro concentration depending on plates
20. Add TILs for FMOs
21. Add PBS to empty wells
22. Plate plates in the incubator Example 5

Serial Stimulation Assay of CoStAR-TIL Cells

TIL cells expressing CoStAR constructs then underwent a serial stimulation assay. The results of the stimulation assay are as shown in FIGS. 15A-15E and 16A-16E. As can be seen in those figures, the TILs modified with anti-CEA CoStAR but not Universal CoStAR expanded in a serial stimulation assay comparable to anti-FOLR CoStAR modified TILs. The methodology for the stimulation assay was as follows:

Day 1:
1. Collect effector cells and count using Vicell
2. Thaw targets (irradiated K562 OKT3 CEACAM5 and K562 OKT3 FOLR1) and count using Vicell
3. Record counts in excel sheet and make up volume to 0.2M/ml for each sample
4. Plate 50 uL of effectors (ie, 50K cells) and targets (ie, 10K cells) as per plate map. Note: ADD K562 OKT3 FOLR to control plate
5. Add 100 ul of media into appropriate wells as per plate map
6. Dilute 10 uL of stock pembro in 4.99 ml of fresh media to make 2× concentration for plate 2 (10 ug/ml) and add 100 μl into appropriate wells as per plate map
7. Dilute 0.5 mL of stock pembro in 4.5 ml of fresh media to make 2× concentration for plate 3 (500 ug/ml) and add 100 μl into appropriate wells as per plate map
8. Add 200 uL PBS to wells at the edge of the plates
9. Place the plates into incubator Day 6, 13, 20, 27, and 34: Collect cells for cell count
1. Prepare cell counting by adding 180 μl of media into the Vi-cell 96 well counting plates
2. Resuspend cells in the coculture plates
3. Take 20 μl of resuspended cells and add into the Vi-cell 96 well plates. Refer to "plate map for counting" tab in the excel sheet.
4. Put the coculture plates back into the incubator
5. Count the Vi-cell 96 well plates (1:10 dilution)
6. Put plates back in the incubator Day 7, 14, 21, 28, and 35: re-stimulation of cells with targets
1. Take the cell count files from vi-cell and plug into the excel sheet for calculation
2. Collect 50 uL sample for staining
3. Seal plates with parafilm and spin down the coculture plates at 500 g×5 min
4. Decant the plates inside the biosafety cabinet
5. Resuspend the cells in 50 ul/well of fresh media
6. Prepare pembro and add 100 μl of pembro based on concentration calculation
7. Dilute 12 uL of stock pembro in 6 ml of fresh media to make 2× concentration (10 ug/ml) and add 100 μl into appropriate wells as per plate map
8. Dilute 0.6 mL of stock pembro in 5.4 ml of fresh media to make 2× concentration (500 ug/ml) and add 100 μl into appropriate wells as per plate map
9. Add 100 μl of media into appropriate wells as per plate map
10. Add additional media based on calculation in table
11. Thaw irradiated K562 OKT3 CEACAM5 and K562 OKT3 FOLR targets
12. resuspend target cells at 1M/ml and add target cells based on calculation in table
13. Mix wells and place in incubator
14. Add PBS to empty wells along the edges

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A fusion protein comprising:
(a) a binding domain, wherein the binding domain comprises: an L-CDR1 sequence comprising the amino acid sequence of SEQ ID NO: 168, an L-CDR2 sequence comprising the amino acid sequence of SEQ ID NO: 169, an L-CDR3 sequence comprising the amino acid sequence of SEQ ID NO: 170, an H-CDR1 sequence comprising the amino acid sequence of SEQ ID NO: 171, an H-CDR2 sequence comprising the amino acid sequence of SEQ ID NO: 172, and an H-CDR3 sequence comprising the amino acid sequence of SEQ ID NO: 173;
(b) an amino acid sequence of SEQ ID NO: 162 linked to the binding domain;
(c) an amino acid sequence of SEQ ID NO: 163 linked to (b);
(d) an amino acid sequence of SEQ ID NO: 164 linked to (c); and
(e) an amino acid sequence of SEQ ID NO: 165 linked to (d).

2. The fusion protein of claim 1, wherein the binding domain is capable of binding to pembrolizumab.

3. The fusion protein of claim 1, wherein the binding domain comprises a VL domain comprising the amino acid sequence of SEQ ID NO: 158.

4. The fusion protein of claim 3, wherein the binding domain comprises a VH domain comprising the amino acid sequence of SEQ ID NO: 160.

5. The fusion protein of claim 1, wherein the binding domain comprises a VH domain comprising the amino acid sequence of SEQ ID NO: 160.

6. The fusion protein of claim 1, wherein the fusion protein further comprises a linker between the VL domain and the VH domain, comprising the sequence SEQ ID NO: 159.

7. The fusion protein of claim 1, wherein the binding domain comprises a VH domain, and the VH domain and the amino acid sequence of SEQ ID NO: 162 are connected via a linker comprising SEQ ID NO: 161.

8. A fusion protein comprising the amino acid sequence of SEQ ID NO: 166 or 167.

9. The fusion protein of claim 8, wherein the fusion protein comprises the amino acid sequence of SEQ ID NO: 166.

10. The fusion protein of claim 8, wherein the fusion protein consists essentially of the amino acid sequence of SEQ ID NO: 166.

11. The fusion protein of claim 8, wherein the fusion protein consists of the amino acid sequence of SEQ ID NO: 166.

12. The fusion protein of claim 8, wherein the fusion protein comprises the amino acid sequence of SEQ ID NO: 167.

13. The fusion protein of claim 8, wherein the fusion protein consists essentially of the amino acid sequence of SEQ ID NO: 167.

14. The fusion protein of claim 8, wherein the fusion protein consists of the amino acid sequence of SEQ ID NO: 167.

15. A nucleic acid which encodes a protein comprising the amino acid sequence of SEQ ID NO: 166 or 167.

16. The nucleic acid of claim 15, wherein the protein comprises the amino acid sequence of SEQ ID NO: 166.

17. The nucleic acid of claim 15, wherein the protein consists essentially of the amino acid sequence of SEQ ID NO: 166.

18. The nucleic acid of claim 15, wherein the protein consists of the amino acid sequence of SEQ ID NO: 166.

19. The nucleic acid of claim 15, wherein the protein comprises the amino acid sequence of SEQ ID NO: 167.

20. The nucleic acid of claim 15, wherein the protein consists essentially of the amino acid sequence of SEQ ID NO: 167.

21. The nucleic acid of claim 15, wherein the protein consists of the amino acid sequence of SEQ ID NO: 167.

22. A cell which expresses a protein comprising the amino acid sequence of SEQ ID NO: 166.

23. The cell of claim 22, wherein the protein comprises the amino acid sequence of SEQ ID NO: 166.

24. The cell of claim 22, wherein the protein consists essentially of the amino acid sequence of SEQ ID NO: 166.

25. The cell of claim 22, wherein the protein consists of the amino acid sequence of SEQ ID NO: 166.

* * * * *

SEQUENCE LISTING

```
Sequence total quantity: 175
SEQ ID NO: 1                 moltype = AA  length = 21
FEATURE                      Location/Qualifiers
REGION                       1..21
                             note = synthetic construct
source                       1..21
                             mol_type = protein
                             organism = synthetic construct
SEQUENCE: 1
MEHSTFLSGL VLATLLSQVS P                                             21

SEQ ID NO: 2                 moltype = AA  length = 105
FEATURE                      Location/Qualifiers
REGION                       1..105
                             note = synthetic construct
source                       1..105
                             mol_type = protein
                             organism = synthetic construct
SEQUENCE: 2
FKIPIEELED RVFVNCNTSI TWVEGTVGTL LSDITRLDLG KRILDPRGIY RCNGTDIYKD   60
KESTVQVHYR MCQSCVELDP ATVAGIIVTD VIATLLLALG VFCFA                  105

SEQ ID NO: 3                 moltype = AA  length = 103
FEATURE                      Location/Qualifiers
REGION                       1..103
                             note = synthetic construct
source                       1..103
                             mol_type = protein
                             organism = synthetic construct
SEQUENCE: 3
RSKRSRLLHS DYMNMTPRRP GPTRKHYQPY APPRDFAAYR SKKVAKKPTN KAPHPKQEPQ   60
EINFPDDLPG SNTAAPVQET LHGCQPVTQE DGKESRISVQ ERQ                    103

SEQ ID NO: 4                 moltype = AA  length = 229
FEATURE                      Location/Qualifiers
REGION                       1..229
                             note = synthetic construct
source                       1..229
                             mol_type = protein
                             organism = synthetic construct
SEQUENCE: 4
MEHSTFLSGL VLATLLSQVS PFKIPIEELE DRVFVNCNTS ITWVEGTVGT LLSDITRLDL   60
GKRILDPRGI YRCNGTDIYK DKESTVQVHY RMCQSCVELD PATVAGIIVT DVIATLLLAL   120
GVFCFARSKR SRLLHSDYMN MTPRRPGPTR KHYQPYAPPR DFAAYRSKKV AKKPTNKAPH   180
PKQEPQEINF PDDLPGSNTA APVQETLHGC QPVTQEDGKE SRISVQERQ              229

SEQ ID NO: 5                 moltype = AA  length = 22
FEATURE                      Location/Qualifiers
REGION                       1..22
                             note = synthetic construct
source                       1..22
                             mol_type = protein
                             organism = synthetic construct
SEQUENCE: 5
MQSGTHWRVL GLCLLSVGVW GQ                                            22

SEQ ID NO: 6                 moltype = AA  length = 130
FEATURE                      Location/Qualifiers
REGION                       1..130
                             note = synthetic construct
source                       1..130
                             mol_type = protein
                             organism = synthetic construct
SEQUENCE: 6
DGNEEMGGIT QTPYKVSISG TTVILTCPQY PGSEILWQHN DKNIGGDEDD KNIGSDEDHL   60
SLKEFSELEQ SGYYVCYPRG SKPEDANFYL YLRARVCENC MEMDVMSVAT IVIVDICITG   120
GLLLLVYYWS                                                         130

SEQ ID NO: 7                 moltype = AA  length = 103
FEATURE                      Location/Qualifiers
REGION                       1..103
                             note = synthetic construct
source                       1..103
                             mol_type = protein
                             organism = synthetic construct
SEQUENCE: 7
RSKRSRLLHS DYMNMTPRRP GPTRKHYQPY APPRDFAAYR SKKVAKKPTN KAPHPKQEPQ   60
EINFPDDLPG SNTAAPVQET LHGCQPVTQE DGKESRISVQ ERQ                    103
```

-continued

```
SEQ ID NO: 8              moltype = AA   length = 255
FEATURE                   Location/Qualifiers
REGION                    1..255
                          note = synthetic construct
source                    1..255
                          mol_type = protein
                          organism = synthetic construct
SEQUENCE: 8
MQSGTHWRVL GLCLLSVGVW GQDGNEEMGG ITQTPYKVSI SGTTVILTCP QYPGSEILWQ    60
HNDKNIGGDE DDKNIGSDED HLSLKEFSEL EQSGYYVCYP RGSKPEDANF YLYLRARVCE   120
NCMEMDVMSV ATIVIVDICI TGGLLLLVYY WSRSKRSRLL HSDYMNMTPR RPGPTRKHYQ   180
PYAPPRDFAA YRSKKVAKKP TNKAPHPKQE PQEINFPDDL PGSNTAAPVQ ETLHGCQPVT   240
QEDGKESRIS VQERQ                                                    255

SEQ ID NO: 9              moltype = AA   length = 22
FEATURE                   Location/Qualifiers
REGION                    1..22
                          note = synthetic construct
source                    1..22
                          mol_type = protein
                          organism = synthetic construct
SEQUENCE: 9
MEQGKGLAVL ILAIILLQGT LA                                             22

SEQ ID NO: 10             moltype = AA   length = 115
FEATURE                   Location/Qualifiers
REGION                    1..115
                          note = synthetic construct
source                    1..115
                          mol_type = protein
                          organism = synthetic construct
SEQUENCE: 10
QSIKGNHLVK VYDYQEDGSV LLTCDAEAKN ITWFKDGKMI GFLTEDKKKW NLGSNAKDPR    60
GMYQCKGSQN KSKPLQVYYR MCQNCIELNA ATISGFLFAE IVSIFVLAVG VYFIA        115

SEQ ID NO: 11             moltype = AA   length = 103
FEATURE                   Location/Qualifiers
REGION                    1..103
                          note = synthetic construct
source                    1..103
                          mol_type = protein
                          organism = synthetic construct
SEQUENCE: 11
RSKRSRLLHS DYMNMTPRRP GPTRKHYQPY APPRDFAAYR SKKVAKKPTN KAPHPKQEPQ    60
EINFPDDLPG SNTAAPVQET LHGCQPVTQE DGKESRISVQ ERQ                     103

SEQ ID NO: 12             moltype = AA   length = 154
FEATURE                   Location/Qualifiers
REGION                    1..154
                          note = synthetic construct
source                    1..154
                          mol_type = protein
                          organism = synthetic construct
SEQUENCE: 12
MKWKALFTAA ILQAQLPITE AQSFGLLDPK LCYLLDGILF IYGVILTALF LRSKRSRLLH    60
SDYMNMTPRR PGPTRKHYQP YAPPRDFAAY RSKKVAKKPT NKAPHPKQEP QEINFPDDLP   120
GSNTAAPVQE TLHGCQPVTQ EDGKESRISV QERQ                               154

SEQ ID NO: 13             moltype = AA   length = 21
FEATURE                   Location/Qualifiers
REGION                    1..21
                          note = synthetic construct
source                    1..21
                          mol_type = protein
                          organism = synthetic construct
SEQUENCE: 13
MALPVTALLL PLALLLHAAR P                                              21

SEQ ID NO: 14             moltype = AA   length = 153
FEATURE                   Location/Qualifiers
REGION                    1..153
                          note = synthetic construct
source                    1..153
                          mol_type = protein
                          organism = synthetic construct
SEQUENCE: 14
SQPHTKPSVF VMKNGTNVAC LVKEFYPKDI RINLVSSKKI TEFDPAIVIS PSGKYNAVKL    60
GKYEDSNSVT CSVQHDNKTV HSTDFEVKTD STDHVKPKET ENTKQPSKSC HKPKAIVHTE   120
```

```
KVNMMSLTVL GLRMLFAKTV AVNFLLTAKL FFL                              153

SEQ ID NO: 15           moltype = AA   length = 103
FEATURE                 Location/Qualifiers
REGION                  1..103
                        note = synthetic construct
source                  1..103
                        mol_type = protein
                        organism = synthetic construct
SEQUENCE: 15
RSKRSRLLHS DYMNMTPRRP GPTRKHYQPY APPRDFAAYR SKKVAKKPTN KAPHPKQEPQ  60
EINFPDDLPG SNTAAPVQET LHGCQPVTQE DGKESRISVQ ERQ                   103

SEQ ID NO: 16           moltype = AA   length = 277
FEATURE                 Location/Qualifiers
REGION                  1..277
                        note = synthetic construct
source                  1..277
                        mol_type = protein
                        organism = synthetic construct
SEQUENCE: 16
MALPVTALLL PLALLLHAAR PSQPHTKPSV FVMKNGTNVA CLVKEFYPKD IRINLVSSKK  60
ITEFDPAIVI SPSGKYNAVK LGKYEDSNSV TCSVQHDNKT VHSTDFEVKT DSTDHVKPKE  120
TENTKQPSKS CHKPKAIVHT EKVNMMSLTV LGLRMLFAKT VAVNFLLTAK LFFLRSKRSR  180
LLHSDYMNMT PRRPGPTRKH YQPYAPPRDF AAYRSKKVAK KPTNKAPHPK QEPQEINFPD  240
DLPGSNTAAP VQETLHGCQP VTQEDGKESR ISVQERQ                          277

SEQ ID NO: 17           moltype = AA   length = 21
FEATURE                 Location/Qualifiers
REGION                  1..21
                        note = synthetic construct
source                  1..21
                        mol_type = protein
                        organism = synthetic construct
SEQUENCE: 17
MALPVTALLL PLALLLHAAR P                                           21

SEQ ID NO: 18           moltype = AA   length = 161
FEATURE                 Location/Qualifiers
REGION                  1..161
                        note = synthetic construct
source                  1..161
                        mol_type = protein
                        organism = synthetic construct
SEQUENCE: 18
DKQLDADVSP KPTIFLPSIA ETKLQKAGTY LCLLEKFFPD VIKIHWQEKK SNTILGSQEG  60
NTMKTNDTYM KFSWLTVPEK SLDKEHRCIV RHENNKNGVD QEIIFPPIKT DVITMDPKDN  120
CSKDANDTLL LQLTNTSAYY MYLLLLLKSV VYFAIITCCL L                     161

SEQ ID NO: 19           moltype = AA   length = 103
FEATURE                 Location/Qualifiers
REGION                  1..103
                        note = synthetic construct
source                  1..103
                        mol_type = protein
                        organism = synthetic construct
SEQUENCE: 19
RSKRSRLLHS DYMNMTPRRP GPTRKHYQPY APPRDFAAYR SKKVAKKPTN KAPHPKQEPQ  60
EINFPDDLPG SNTAAPVQET LHGCQPVTQE DGKESRISVQ ERQ                   103

SEQ ID NO: 20           moltype = AA   length = 285
FEATURE                 Location/Qualifiers
REGION                  1..285
                        note = synthetic construct
source                  1..285
                        mol_type = protein
                        organism = synthetic construct
SEQUENCE: 20
MALPVTALLL PLALLLHAAR PDKQLDADVS PKPTIFLPSI AETKLQKAGT YLCLLEKFFP  60
DVIKIHWQEK KSNTILGSQE GNTMKTNDTY MKFSWLTVPE KSLDKEHRCI VRHENNKNGV  120
DQEIIFPPIK TDVITMDPKD NCSKDANDTL LLQLTNTSAY YMYLLLLLKS VVYFAIITCC  180
LLRSKRSRLL HSDYMNMTPR RPGPTRKHYQ PYAPPRDFAA YRSKKVAKKP TNKAPHPKQE  240
PQEINFPDDL PGSNTAAPVQ ETLHGCQPVT QEDGKESRIS VQERQ                 285

SEQ ID NO: 21           moltype = AA   length = 21
FEATURE                 Location/Qualifiers
REGION                  1..21
                        note = synthetic construct
source                  1..21
```

```
                            mol_type = protein
                            organism = synthetic construct
SEQUENCE: 21
MALPVTALLL PLALLLHAAR P                                              21

SEQ ID NO: 22             moltype = AA   length = 136
FEATURE                   Location/Qualifiers
REGION                    1..136
                            note = synthetic construct
source                    1..136
                            mol_type = protein
                            organism = synthetic construct
SEQUENCE: 22
IQNPEPAVYQ LKDPRSQDST LCLFTDFDSQ INVPKTMESG TFITDKCVLD MKAMDSKSNG     60
AIAWSNQTSF TCQDIFKETN ATYPSSDVPC DATLTEKSFE TDMNLNFQNL LVIVLRILLL    120
KVAGFNLLMT LRLWSS                                                   136

SEQ ID NO: 23             moltype = AA   length = 103
FEATURE                   Location/Qualifiers
REGION                    1..103
                            note = synthetic construct
source                    1..103
                            mol_type = protein
                            organism = synthetic construct
SEQUENCE: 23
RSKRSRLLHS DYMNMTPRRP GPTRKHYQPY APPRDFAAYR SKKVAKKPTN KAPHPKQEPQ     60
EINFPDDLPG SNTAAPVQET LHGCQPVTQE DGKESRISVQ ERQ                     103

SEQ ID NO: 24             moltype = AA   length = 260
FEATURE                   Location/Qualifiers
REGION                    1..260
                            note = synthetic construct
source                    1..260
                            mol_type = protein
                            organism = synthetic construct
SEQUENCE: 24
MALPVTALLL PLALLLHAAR PIQNPEPAVY QLKDPRSQDS TLCLFTDFDS QINVPKTMES     60
GTFITDKCVL DMKAMDSKSN GAIAWSNQTS FTCQDIFKET NATYPSSDVP CDATLTEKSF    120
ETDMNLNFQN LLVIVLRILL LKVAGFNLLM TLRLWSSRSK RSRLLHSDYM NMTPRRPGPT    180
RKHYQPYAPP RDFAAYRSKK VAKKPTNKAP HPKQEPQEIN FPDDLPGSNT AAPVQETLHG    240
CQPVTQEDGK ESRISVQERQ                                               260

SEQ ID NO: 25             moltype = AA   length = 21
FEATURE                   Location/Qualifiers
REGION                    1..21
                            note = synthetic construct
source                    1..21
                            mol_type = protein
                            organism = synthetic construct
SEQUENCE: 25
MALPVTALLL PLALLLHAAR P                                              21

SEQ ID NO: 26             moltype = AA   length = 169
FEATURE                   Location/Qualifiers
REGION                    1..169
                            note = synthetic construct
source                    1..169
                            mol_type = protein
                            organism = synthetic construct
SEQUENCE: 26
VLTPPKVSLF EPSKAEIANK QKATLVCLAR GFFPDHVELS WWVNGKEVHS GVCTDPQAYK     60
ESNYSYCLSS RLRVSATFWH NPRNHFRCQV QFHGLSEEDK WPEGSPKPVT QNISAEAWGR    120
ADCGITSASY QQGVLSATIL YEILLGKATL YAVLVSTLVV MAMVKRKNS                169

SEQ ID NO: 27             moltype = AA   length = 103
FEATURE                   Location/Qualifiers
REGION                    1..103
                            note = synthetic construct
source                    1..103
                            mol_type = protein
                            organism = synthetic construct
SEQUENCE: 27
RSKRSRLLHS DYMNMTPRRP GPTRKHYQPY APPRDFAAYR SKKVAKKPTN KAPHPKQEPQ     60
EINFPDDLPG SNTAAPVQET LHGCQPVTQE DGKESRISVQ ERQ                     103

SEQ ID NO: 28             moltype = AA   length = 260
FEATURE                   Location/Qualifiers
REGION                    1..260
                            note = synthetic construct
```

```
source                          1..260
                                mol_type = protein
                                organism = synthetic construct
SEQUENCE: 28
MALPVTALLL PLALLLHAAR PIQNPEPAVY QLKDPRSQDS TLCLFTDFDS QINVPKTMES    60
GTFITDKCVL DMKAMDSKSN GAIAWSNQTS FTCQDIFKET NATYPSSDVP CDATLTEKSF   120
ETDMNLNFQN LLVIVLRILL LKVAGFNLLM TLRLWSSRSK RSRLLHSDYM NMTPRRPGPT   180
RKHYQPYAPP RDFAAYRSKK VAKKPTNKAP HPKQEPQEIN FPDDLPGSNT AAPVQETLHG   240
CQPVTQEDGK ESRISVQERQ                                               260

SEQ ID NO: 29                   moltype = AA  length = 21
FEATURE                         Location/Qualifiers
REGION                          1..21
                                note = synthetic construct
source                          1..21
                                mol_type = protein
                                organism = synthetic construct
SEQUENCE: 29
MALPVTALLL PLALLLHAAR P                                              21

SEQ ID NO: 30                   moltype = AA  length = 169
FEATURE                         Location/Qualifiers
REGION                          1..169
                                note = synthetic construct
source                          1..169
                                mol_type = protein
                                organism = synthetic construct
SEQUENCE: 30
VLTPPKVSLF EPSKAEIANK QKATLVCLAR GFFPDHVELS WWVNGKEVHS GVCTDPQAYK    60
ESNYSYCLSS RLRVSATFWH NPRNHFRCQV QFHGLSEEDK WPEGSPKPVT QNISAEAWGR   120
ADCGITSASY QQGVLSATIL YEILLGKATL YAVLVSTLVV MAMVKRKNS               169

SEQ ID NO: 31                   moltype = AA  length = 103
FEATURE                         Location/Qualifiers
REGION                          1..103
                                note = synthetic construct
source                          1..103
                                mol_type = protein
                                organism = synthetic construct
SEQUENCE: 31
RSKRSRLLHS DYMNMTPRRP GPTRKHYQPY APPRDFAAYR SKKVAKKPTN KAPHPKQEPQ    60
EINFPDDLPG SNTAAPVQET LHGCQPVTQE DGKESRISVQ ERQ                     103

SEQ ID NO: 32                   moltype = AA  length = 293
FEATURE                         Location/Qualifiers
REGION                          1..293
                                note = synthetic construct
source                          1..293
                                mol_type = protein
                                organism = synthetic construct
SEQUENCE: 32
MALPVTALLL PLALLLHAAR PVLTPPKVSL FEPSKAEIAN KQKATLVCLA RGFFPDHVEL    60
SWWVNGKEVH SGVCTDPQAY KESNYSYCLS SRLRVSATFW HNPRNHFRCQ VQFHGLSEED   120
KWPEGSPKPV TQNISAEAWG RADCGITSAS YQQGVLSATI LYEILLGKAT LYAVLVSTLV   180
VMAMVKRKNS RSKRSRLLHS DYMNMTPRRP GPTRKHYQPY APPRDFAAYR SKKVAKKPTN   240
KAPHPKQEPQ EINFPDDLPG SNTAAPVQET LHGCQPVTQE DGKESRISVQ ERQ          293

SEQ ID NO: 33                   moltype = AA  length = 549
FEATURE                         Location/Qualifiers
REGION                          1..547
                                note = synthetic construct
source                          1..549
                                mol_type = protein
                                organism = synthetic construct
SEQUENCE: 33
MALPVTALLL PLALLLHAAR PEQKLISEED LQVQLVQSGA EVKKPGASVK VSCKASGYTF    60
TSYWMNWVRQ APGQGLEWMG RIDPYDSETH YAQKLQGRVT MTTDTSTSTA YMELRSLRSD   120
DTAVYYCARG GYDFDVGTLY WFFDVWGQGT TVTVSSGGGG SGGGGSGGGG SDIQMTQSPS   180
SLSASVGDRV TITCRASENI YSYLAWYQQK PGKAPKLLIY NAKTLAEGVP SRFSGSGSGT   240
DFTLTISSLQ PEDFATYYCQ HHYGTPRTFG GGTKVEIKAA AGSGGGSGILV KQSPMLVAYD   300
NAVNLSCKYS YNLFSREFRA SLHKGLDSAV EVCVVYGNYS QQLQVYSKTG FNCDGKLGNE   360
SVTFYLQNLY VNQTDIYFCK IEVMYPPPYL DNEKSNGTII HVKGKHLCPS PLFPGPSKPF   420
WVLVVVGGVL ACYSLLVTVA FIIFWVRSKR SRLLHSDYMN MTPRRPGPTR KHYQPYAPPR   480
DFAAYRSKKV AKKPTNKAPH PKQEPQEINF PDDLPGSNTA APVQETLHGC QPVTQEDGKE   540
SRISVQERQ                                                           549

SEQ ID NO: 34                   moltype = AA  length = 549
FEATURE                         Location/Qualifiers
REGION                          1..547
```

```
                        note = synthetic construct
source                  1..549
                        mol_type = protein
                        organism = synthetic construct
SEQUENCE: 34
MALPVTALLL PLALLLHAAR PEQKLISEED LDIQMTQSPS SLSASVGDRV TITCRASENI    60
YSYLAWYQQK PGKAPKLLIY NAKTLAEGVP SRFSGSGSGT DFTLTISSLQ PEDFATYYCQ   120
HHYGTPRTFG GGTKVEIKGG GGSGGGGSGG GGSQVQLVQS GAEVKKPGAS VKVSCKASGY   180
TFTSYWMNWV RQAPGQGLEW MGRIDPYDSE THYAQKLQGR VTMTTDTSTS TAYMELRSLR   240
SDDTAVYYCA RGGYDFDVGT LYWFFDVWGQ GTTVTVSSAA AGSGGSGILV KQSPMLVAYD   300
NAVNLSCKYS YNLFSREFRA SLHKGLDSAV EVCVVYGNYS QQLQVYSKTG FNCDGKLGNE   360
SVTFYLQNLY VNQTDIYFCK IEVMYPPPYL DNEKSNGTII HVKGKHLCPS PLFPGPSKPF   420
WVLVVVGGVL ACYSLLVTVA FIIFWVRSKR SRLLHSDYMN MTPRRPGPTR KHYQPYAPPR   480
DFAAYRSKKV AKKPTNKAPH PKQEPQEINF PDDLPGSNTA APVQETLHGC QPVTQEDGKE   540
SRISVQERQ                                                          549

SEQ ID NO: 35           moltype = AA  length = 543
FEATURE                 Location/Qualifiers
REGION                  1..543
                        note = synthetic construct
source                  1..543
                        mol_type = protein
                        organism = synthetic construct
SEQUENCE: 35
MALPVTALLL PLALLLHAAR PEQKLISEED LQVQLVESGG GVVQPGRSLR LSCAASGFTF    60
SSYDMHWVRQ APGKGLEWVA VIWYDGSNKY YADSVKGRFT ISRDNSKNTL YLQMNSLRAE   120
DTAVYYCARG SGNWGFFDYW GQGTLVTVSS GGGGSGGGGS GGGGSDIQMT QSPSSLSASV   180
GDRVTITCRA SQGISRWLAW YQQKPEKAPK SLIYAASSLQ SGVPSRFSGS GSGTDFTLTI   240
SSLQPEDFAT YYCQQYNTYP RTFGQGTKVE IKAAAGSGGS GILVKQSPML VAYDNAVNLS   300
CKYSYNLFSR EFRASLHKGL DSAVEVCVVY GNYSQQLQVY SKTGFNCDGK LGNESVTFYL   360
QNLYVNQTDI YFCKIEVMYP PPYLDNEKSN GTIIHVKGKH LCPSPLFPGP SKPFWVLVVV   420
GGVLACYSLL VTVAFIIFWV RSKRSRLLHS DYMNMTPRRP GPTRKHYQPY APPRDFAAYR   480
SKKVAKKPTN KAPHPKQEPQ EINFPDDLPG SNTAAPVQET LHGCQPVTQE DGKESRISVQ   540
ERQ                                                                543

SEQ ID NO: 36           moltype = AA  length = 543
FEATURE                 Location/Qualifiers
REGION                  1..543
                        note = synthetic construct
source                  1..543
                        mol_type = protein
                        organism = synthetic construct
SEQUENCE: 36
MALPVTALLL PLALLLHAAR PEQKLISEED LDIQMTQSPS SLSASVGDRV TITCRASQGI    60
SRWLAWYQQK PEKAPKSLIY AASSLQSGVP SRFSGSGSGT DFTLTISSLQ PEDFATYYCQ   120
QYNTYPRTFG QGTKVEIKGG GGSGGGGSGG GGSQVQLVES GGGVVQPGRS LRLSCAASGF   180
TFSSYDMHWV RQAPGKGLEW VAVIWYDGSN KYYADSVKGR FTISRDNSKN TLYLQMNSLR   240
AEDTAVYYCA RGSGNWGFFD YWGQGTLVTV SSAAGSGGS GILVKQSPML VAYDNAVNLS   300
CKYSYNLFSR EFRASLHKGL DSAVEVCVVY GNYSQQLQVY SKTGFNCDGK LGNESVTFYL   360
QNLYVNQTDI YFCKIEVMYP PPYLDNEKSN GTIIHVKGKH LCPSPLFPGP SKPFWVLVVV   420
GGVLACYSLL VTVAFIIFWV RSKRSRLLHS DYMNMTPRRP GPTRKHYQPY APPRDFAAYR   480
SKKVAKKPTN KAPHPKQEPQ EINFPDDLPG SNTAAPVQET LHGCQPVTQE DGKESRISVQ   540
ERQ                                                                543

SEQ ID NO: 37           moltype = AA  length = 547
FEATURE                 Location/Qualifiers
REGION                  1..547
                        note = synthetic construct
source                  1..547
                        mol_type = protein
                        organism = synthetic construct
SEQUENCE: 37
MALPVTALLL PLALLLHAAR PEQKLISEED LQVQLQQWGA GLLKPSETLS LTCAVYGGSF    60
SGYYWSWIRQ SPEGLEWIGE INHGGYVTYN PSLESRVTIS VDTSKNQFSL KLSSVTAADT   120
AVYYCARDYG PGNYDWYFDL WGRGTLVTVS SGGGGSGGGG SGGGGSEIVL TQSPATLSLS   180
PGERATLSCR ASQSVSSYLA WYQQKPGQAP RLLIYDASNR ATGIPARFSG SGSGTDFTLT   240
ISSLEPEDFA VYYCQQRSNW PPALTFGGGT KVEIKRAAAG SGGSGILVKQ SPMLVAYDNA   300
VNLSCKYSYN LFSREFRASL HKGLDSAVEV CVVYGNYSQQ LQVYSKTGFN CDGKLGNESV   360
TFYLQNLYVN QTDIYFCKIE VMYPPPYLDN EKSNGTIIHV KGKHLCPSPL FPGPSKPFWV   420
LVVVGGVLAC YSLLVTVAFI IFWVRSKRSR LLHSDYMNMT PRRPGPTRKH YQPYAPPRDF   480
AAYRSKKVAK KPTNKAPHPK QEPQEINFPD DLPGSNTAAP VQETLHGCQP VTQEDGKESR   540
ISVQERQ                                                            547

SEQ ID NO: 38           moltype = AA  length = 547
FEATURE                 Location/Qualifiers
REGION                  1..547
                        note = synthetic construct
source                  1..547
                        mol_type = protein
```

```
                    organism = synthetic construct
SEQUENCE: 38
MALPVTALLL PLALLLHAAR PEQKLISEED LEIVLTQSPA TLSLSPGERA TLSCRASQSV    60
SSYLAWYQQK PGQAPRLLIY DASNRATGIP ARFSGSGSGT DFTLTISSLE PEDFAVYYCQ   120
QRSNWPPALT FGGGTKVEIK RGGGGSGGGG SGGGGSQVQL QQWGAGLLKP SETLSLTCAV   180
YGGSFSGYYW SWIRQSPEGL EWIGEINHGG YVTYNPSLES RVTISVDTSK NQFSLKLSSV   240
TAADTAVYYC ARDYGPGNYD WYFDLWGRGT LVTVSSAAAG SGGGSGILVKQ SPMLVAYDNA  300
VNLSCKYSYN LFSREFRASL HKGLDSAVEV CVVYGNYSQQ LQVYSKTGFN CDGKLGNESV   360
TFYLQNLYVN QTDIYFCKIE VMYPPPYLDN EKSNGTIIHV KGKHLCPSPL FPGPSKPFWV   420
LVVVGGVLAC YSLLVTVAFI IFWVRSKRSR LLHSDYMNMT PRRPGPTRKH YQPYAPPRDF   480
AAYRSKKVAK KPTNKAPHPK QEPQEINFPD DLPGSNTAAP VQETLHGCQP VTQEDGKESR   540
ISVQERQ                                                             547

SEQ ID NO: 39           moltype = AA   length = 543
FEATURE                 Location/Qualifiers
REGION                  1..543
                        note = synthetic construct
source                  1..543
                        mol_type = protein
                        organism = synthetic construct
SEQUENCE: 39
MALPVTALLL PLALLLHAAR PEQKLISEED LQVTLRESGP ALVKPTQTLT LTCTFSGFSL    60
STSGMGVGWI RQPPGKALEW LAHIWWDDDK YYNPSLKSRL TISKDTSKNQ VVLTMTNMDP   120
VDTATYYCAR TRRYFPFAYW GQGTLVTVSS GGGGSGGGGS GGGGSEIVMT QSPATLSVSP   180
GERATLSCKA SQNVGTNVAW YQQKPGQAPR LLIYSASYRY SGIPARFSGS GSGTEFTLTI   240
SSLQSEDFAV YYCQQYNTDP LTFGGGTKVE IKAAAGSGGS IKVQSPML VAYDNAVNLS    300
CKYSYNLFSR EFRASLHKGL DSAVEVCVVY GNYSQQLQVY SKTGFNCDGK LGNESVTFYL   360
QNLYVNQTDI YFCKIEVMYP PPYLDNEKSN GTIIHVKGKH LCPSPLFPGP SKPFWVLVVV   420
GGVLACYSLL VTVAFIIFWV RSKRSRLLHS DYMNMTPRRP GPTRKHYQPY APPRDFAAYR   480
SKKVAKKPTN KAPHPKQEPQ EINFPDDLPG SNTAAPVQET LHGCQPVTQE DGKESRISVQ   540
ERQ                                                                 543

SEQ ID NO: 40           moltype = AA   length = 543
FEATURE                 Location/Qualifiers
REGION                  1..543
                        note = synthetic construct
source                  1..543
                        mol_type = protein
                        organism = synthetic construct
SEQUENCE: 40
MALPVTALLL PLALLLHAAR PEQKLISEED LEIVMTQSPA TLSVSPGERA TLSCKASQNV    60
GTNVAWYQQK PGQAPRLLIY SASYRYSGIP ARFSGSGSGT EFTLTISSLQ SEDFAVYYCQ   120
QYNTDPLTFG GGTKVEIKGG GSGGGGSGGG GGSQVTLRES GPALVKPTQT LTLTCTFSGF   180
SLSTSGMGVG WIRQPPGKAL EWLAHIWWDD DKYYNPSLKS RLTISKDTSK NQVVLTMTNM   240
DPVDTATYYC ARTRRYFPFA YWGQGTLVTV SSAAAGSGGS GILVKQSPML VAYDNAVNLS   300
CKYSYNLFSR EFRASLHKGL DSAVEVCVVY GNYSQQLQVY SKTGFNCDGK LGNESVTFYL   360
QNLYVNQTDI YFCKIEVMYP PPYLDNEKSN GTIIHVKGKH LCPSPLFPGP SKPFWVLVVV   420
GGVLACYSLL VTVAFIIFWV RSKRSRLLHS DYMNMTPRRP GPTRKHYQPY APPRDFAAYR   480
SKKVAKKPTN KAPHPKQEPQ EINFPDDLPG SNTAAPVQET LHGCQPVTQE DGKESRISVQ   540
ERQ                                                                 543

SEQ ID NO: 41           moltype = AA   length = 549
FEATURE                 Location/Qualifiers
REGION                  1..549
                        note = synthetic construct
source                  1..549
                        mol_type = protein
                        organism = synthetic construct
SEQUENCE: 41
MALPVTALLL PLALLLHAAR PEQKLISEED LQVQLVQSGV EVKKPGASVK VSCKASGYTF    60
TNYYMYWVRQ APGQGLEWMG GINPSNGGTN FNEKFKNRVT LTTDSSTTTA YMELKSLQFD   120
DTAVYYCARR DYRFDMGFDY WGQGTTVTVS SGGGGSGGGG SGGGGSEIVL TQSPATLSLS   180
PGERATLSCR ASKGVSTSGY SYLHWYQQKP GQAPRLLIYL ASYLESGVPA RFSGSGSGTD   240
FTLTISSLEP EDFAVYYCQH SRDLPLTFGG GTKVEIKRAA AGSGGSGILV KQSPMLVAYD   300
NAVNLSCKYS YNLFSREFRA SLHKGLDSAV EVCVVYGNYS QQLQVYSKTG FNCDGKLGNE   360
SVTFYLQNLY VNQTDIYFCK IEVMYPPPYL DNEKSNGTII HVKGKHLCPS PLFPGPSKPF   420
WVLVVVGGVL ACYSLLVTVA FIIFWVRSKR SRLLHSDYMN MTPRRPGPTR KHYQPYAPPR   480
DFAAYRSKKV AKKPTNKAPH PKQEPQEINF PDDLPGSNTA APVQETLHGC QPVTQEDGKE   540
SRISVQERQ                                                           549

SEQ ID NO: 42           moltype = AA   length = 549
FEATURE                 Location/Qualifiers
REGION                  1..549
                        note = synthetic construct
source                  1..549
                        mol_type = protein
                        organism = synthetic construct
SEQUENCE: 42
MALPVTALLL PLALLLHAAR PEQKLISEED LEIVLTQSPA TLSLSPGERA TLSCRASKGV    60
```

```
STSGYSYLHW YQQKPGQAPR LLIYLASYLE SGVPARFSGS GSGTDFTLTI SSLEPEDFAV    120
YYCQHSRDLP LTFGGGTKVE IKRGGGGSGG GGSGGGGSQV QLVQSGVEVK KPGASVKVSC    180
KASGYTFTNY YMYWVRQAPG QGLEWMGGIN PSNGGTNFNE KFKNRVTLTT DSSTTTAYME    240
LKSLQFDDTA VYYCARRDYR FDMGFDYWGQ GTTVTVSSAA AGSGGSGILV KQSPMLVAYD    300
NAVNLSCKYS YNLFSREFRA SLHKGLDSAV EVCVVYGNYS QQLQVYSKTG FNCDGKLGNE    360
SVTFYLQNLY VNQTDIYFCK IEVMYPPPYL DNEKSNGTII HVKGKHLCPS PLFPGPSKPF    420
WVLVVVGGVL ACYSLLVTVA FIIFWVRSKR SRLLHSDYMN MTPRRPGPTR KHYQPYAPPR    480
DFAAYRSKKV AKKPTNKAPH PKQEPQEINF PDDLPGSNTA APVQETLHGC QPVTQEDGKE    540
SRISVQERQ                                                           549

SEQ ID NO: 43          moltype = AA  length = 543
FEATURE                Location/Qualifiers
REGION                 1..543
                       note = synthetic construct
source                 1..543
                       mol_type = protein
                       organism = synthetic construct
SEQUENCE: 43
MALPVTALLL PLALLLHAAR PEQKLISEED LEVQLVESGG GLVQPGGSLR LSCAASGFTF     60
SDSWIHWVRQ APGKGLEWVA WISPYGGSTY YADSVKGRFT ISADTSKNTA YLQMNSLRAE    120
DTAVYYCARR HWPGGFDYWG QGTLVTVSSG GGGSGGGGS GGGSDIQMTQ SPSSLSASVG    180
DRVTITCRAS QDVSTAVAWY QQKPGKAPKL LIYSASFLYS GVPSRFSGSG SGTDFTLTIS    240
SLQPEDFATY YCQQYLYHPA TFGQGTKVEI KRAAAGSGGS GILVKQSPML VAYDNAVNLS    300
CKYSYNLFSR EFRASLHKGL DSAVEVCVVY GNYSQQLQVY SKTGFNCDGK LGNESVTFYL    360
QNLYVNQTDI YFCKIEVMYP PPYLDNEKSN GTIIHVKGKH LCPSPLFPGP SKPFWVLVVV    420
GGVLACYSLL VTVAFIIFWV RSKRSRLLHS DYMNMTPRRP GPTRKHYQPY APPRDFAAYR    480
SKKVAKKPTN KAPHPKQEPQ EINFPDDLPG SNTAAPVQET LHGCQPVTQE DGKESRISVQ    540
ERQ                                                                543

SEQ ID NO: 44          moltype = AA  length = 543
FEATURE                Location/Qualifiers
REGION                 1..543
                       note = synthetic construct
source                 1..543
                       mol_type = protein
                       organism = synthetic construct
SEQUENCE: 44
MALPVTALLL PLALLLHAAR PEQKLISEED LDIQMTQSPS SLSASVGDRV TITCRASQDV     60
STAVAWYQQK PGKAPKLLIY SASFLYSGVP SRFSGSGSGT DFTLTISSLQ PEDFATYYCQ    120
QYLYHPATFG QGTKVEIKRG GGGSGGGGSG GGGSEVQLVE SGGGLVQPGG SLRLSCAASG    180
FTFSDSWIHW VRQAPGKGLE WVAWISPYGG STYYADSVKG RFTISADTSK NTAYLQMNSL    240
RAEDTAVYYC ARRHWPGGFD YWGQGTLVTV SSAAGSGGS GILVKQSPML VAYDNAVNLS    300
CKYSYNLFSR EFRASLHKGL DSAVEVCVVY GNYSQQLQVY SKTGFNCDGK LGNESVTFYL    360
QNLYVNQTDI YFCKIEVMYP PPYLDNEKSN GTIIHVKGKH LCPSPLFPGP SKPFWVLVVV    420
GGVLACYSLL VTVAFIIFWV RSKRSRLLHS DYMNMTPRRP GPTRKHYQPY APPRDFAAYR    480
SKKVAKKPTN KAPHPKQEPQ EINFPDDLPG SNTAAPVQET LHGCQPVTQE DGKESRISVQ    540
ERQ                                                                543

SEQ ID NO: 45          moltype = AA  length = 549
FEATURE                Location/Qualifiers
REGION                 1..543
                       note = synthetic construct
source                 1..549
                       mol_type = protein
                       organism = synthetic construct
SEQUENCE: 45
MALPVTALLL PLALLLHAAR PEQKLISEED LQVQLVQSGA EVKKPGASVK VSCKASGYTF     60
TNYWIGWVKQ APGQGLEWIG YLYPGGLYTN YNEKFKGKAT MTADTSTNTA YMELSSLRSE    120
DTAVYYCARY RDYDYAMDYW GQGTLVTVSS GGGGSGGGGS GGGSDVVMT QTPLSLPVTL    180
GQPASISCKS TKSLLNSDGF TYLGWCLQKP GQSPQLLIYL VSNRFSGVPD RFSGSGSGTD    240
FTLKISRVEA EDVGVYYCFQ SNYLPLTFGQ GTKLEIKRAA AGSGGSGILV KQSPMLVAYD    300
NAVNLSCKYS YNLFSREFRA SLHKGLDSAV EVCVVYGNYS QQLQVYSKTG FNCDGKLGNE    360
SVTFYLQNLY VNQTDIYFCK IEVMYPPPYL DNEKSNGTII HVKGKHLCPS PLFPGPSKPF    420
WVLVVVGGVL ACYSLLVTVA FIIFWVRSKR SRLLHSDYMN MTPRRPGPTR KHYQPYAPPR    480
DFAAYRSKKV AKKPTNKAPH PKQEPQEINF PDDLPGSNTA APVQETLHGC QPVTQEDGKE    540
SRISVQERQ                                                           549

SEQ ID NO: 46          moltype = AA  length = 549
FEATURE                Location/Qualifiers
REGION                 1..543
                       note = synthetic construct
source                 1..549
                       mol_type = protein
                       organism = synthetic construct
SEQUENCE: 46
MALPVTALLL PLALLLHAAR PEQKLISEED LDVVMTQTPL SLPVTLGQPA SISCKSTKSL     60
LNSDGFTYLG WCLQKPGQSP QLLIYLVSNR FSGVPDRFSG SGSGTDFTLK ISRVEAEDVG    120
VYYCFQSNYL PLTFGQGTKL EIKRGGGGS GGGSGGGGSQV QLVQSGAEV KKPGASVKVS    180
CKASGYTFTN YWIGWVKQAP GQGLEWIGYL YPGGLYTNYN EKFKGKATMT ADTSTNTAYM    240
```

```
ELSSLRSEDT AVYYCARYRD YDYAMDYWGQ GTLVTVSSAA AGSGGSGILV KQSPMLVAYD   300
NAVNLSCKYS YNLFSREFRA SLHKGLDSAV EVCVVYGNYS QQLQVYSKTG FNCDGKLGNE   360
SVTFYLQNLY VNQTDIYFCK IEVMYPPPYL DNEKSNGTII HVKGKHLCPS PLFPGPSKPF   420
WVLVVVGGVL ACYSLLVTVA FIIFWVRSKR SRLLHSDYMN MTPRRPGPTR KHYQPYAPPR   480
DFAAYRSKKV AKKPTNKAPH PKQEPQEINF PDDLPGSNTA APVQETLHGC QPVTQEDGKE   540
SRISVQERQ                                                          549

SEQ ID NO: 47           moltype = AA  length = 545
FEATURE                 Location/Qualifiers
REGION                  1..545
                        note = synthetic construct
source                  1..545
                        mol_type = protein
                        organism = synthetic construct
SEQUENCE: 47
MALPVTALLL PLALLLHAAR PEQKLISEED LQVQLQESGP GLVKPSQTLS LTCAVYGGSF    60
SSGYWNWIRK HPGKGLEYIG YISYNGITYH NPSLKSRITI NRDTSKNQYS LQLNSVTPED   120
TAVYYCARYK YDYDGGHAMD YWGQGTLVTV SSGGGGSGGG GSGGGGSDIQ MTQSPSSLSA   180
SVGDRVTITC RASQDISNYL NWYQQKPGKA PKLLIYYTSK LHSGVPSRFS GSGSGTDYTL   240
TISSLQPEDF ATYYCQQGSA LPWTFGQGTK VEIKAAGSGG GSGILVKQSP MLVAYDNAVN   300
LSCKYSYNLF SREFRASLHK GLDSAVEVCV VYGNYSQQLQ VYSKTGFNCD GKLGNESVTF   360
YLQNLYVNQT DIYFCKIEVM YPPPYLDNEK SNGTIIHVKG KHLCPSPLFP GPSKPFWVLV   420
VVGGVLACYS LLVTVAFIIF WVRSKRSRLL HSDYMNMTPR RPGPTRKHYQ PYAPPRDFAA   480
YRSKKVAKKP TNKAPHPKQE PQEINFPDDL PGSNTAAPVQ ETLHGCQPVT QEDGKESRIS   540
VQERQ                                                              545

SEQ ID NO: 48           moltype = AA  length = 545
FEATURE                 Location/Qualifiers
REGION                  1..545
                        note = synthetic construct
source                  1..545
                        mol_type = protein
                        organism = synthetic construct
SEQUENCE: 48
MALPVTALLL PLALLLHAAR PEQKLISEED LDIQMTQSPS SLSASVGDRV TITCRASQDI    60
SNYLNWYQQK PGKAPKLLIY YTSKLHSGVP SRFSGSGSGT DYTLTISSLQ PEDFATYYCQ   120
QGSALPWTFG QGTKVEIKGG GSGGGGSGG GGSQVQLQES GPGLVKPSQT LSLTCAVYGG   180
SFSSGYWNWI RKHPGKGLEY IGYISYNGIT YHNPSLKSRI TINRDTSKNQ YSLQLNSVTP   240
EDTAVYYCAR YKYDYDGGHA MDYWGQGTLV TVSSAAGSGG GSGILVKQSP MLVAYDNAVN   300
LSCKYSYNLF SREFRASLHK GLDSAVEVCV VYGNYSQQLQ VYSKTGFNCD GKLGNESVTF   360
YLQNLYVNQT DIYFCKIEVM YPPPYLDNEK SNGTIIHVKG KHLCPSPLFP GPSKPFWVLV   420
VVGGVLACYS LLVTVAFIIF WVRSKRSRLL HSDYMNMTPR RPGPTRKHYQ PYAPPRDFAA   480
YRSKKVAKKP TNKAPHPKQE PQEINFPDDL PGSNTAAPVQ ETLHGCQPVT QEDGKESRIS   540
VQERQ                                                              545

SEQ ID NO: 49           moltype = AA  length = 543
FEATURE                 Location/Qualifiers
REGION                  1..543
                        note = synthetic construct
source                  1..543
                        mol_type = protein
                        organism = synthetic construct
SEQUENCE: 49
MALPVTALLL PLALLLHAAR PEQKLISEED LQVQLVESGG GVVQPGRSLR LSCAASGFTF    60
SSYTMHWVRQ APGKGLEWVT FISYDGNNKY YADSVKGRFT ISRDNSKNTL YLQMNSLRAE   120
DTAIYYCART GWLGPFDYWG QGTLVTVSSG GGGSGGGGSG GGGSEIVLTQ SPGTLSLSPG   180
ERATLSCRAS QSVGSSYLAW YQQKPGQAPR LLIYGAFSRA TGIPDRFSGS GSGTDFTLTI   240
SRLEPEDFAV YYCQQYGSSP WTFGQGTKVE IKAAGSGGS GILVKQSPML VAYDNAVNLS   300
CKYSYNLFSR EFRASLHKGL DSAVEVCVVY GNYSQQLQVY SKTGFNCDGK LGNESVTFYL   360
QNLYVNQTDI YFCKIEVMYP PPYLDNEKSN GTIIHVKGKH LCPSPLFPGP SKPFWVLVVV   420
GGVLACYSLL VTVAFIIFWV RSKRSRLLHS DYMNMTPRRP GPTRKHYQPY APPRDFAAYR   480
SKKVAKKPTN KAPHPKQEPQ EINFPDDLPG SNTAAPVQET LHGCQPVTQE DGKESRISVQ   540
ERQ                                                                543

SEQ ID NO: 50           moltype = AA  length = 543
FEATURE                 Location/Qualifiers
REGION                  1..543
                        note = synthetic construct
source                  1..543
                        mol_type = protein
                        organism = synthetic construct
SEQUENCE: 50
MALPVTALLL PLALLLHAAR PEQKLISEED LEIVLTQSPG TLSLSPGERA TLSCRASQSV    60
GSSYLAWYQQ KPGQAPRLLI YGAFSRATGI PDRFSGSGSG TDFTLTISRL EPEDFAVYYC   120
QQYGSSPWTF GQGTKVEIKG GGGSGGGGSG GGGSQVQLVE SGGGVVQPGR SLRLSCAASG   180
FTFSSYTMHW VRQAPGKGLE WVTFISYDGN NKYYADSVKG RFTISRDNSK NTLYLQMNSL   240
RAEDTAIYYC ARTGWLGPFD YWGQGTLVTV SSAAGSGGGS GILVKQSPML VAYDNAVNLS   300
CKYSYNLFSR EFRASLHKGL DSAVEVCVVY GNYSQQLQVY SKTGFNCDGK LGNESVTFYL   360
QNLYVNQTDI YFCKIEVMYP PPYLDNEKSN GTIIHVKGKH LCPSPLFPGP SKPFWVLVVV   420
```

```
GGVLACYSLL VTVAFIIFWV RSKRSRLLHS DYMNMTPRRP GPTRKHYQPY APPRDFAAYR    480
SKKVAKKPTN KAPHPKQEPQ EINFPDDLPG SNTAAPVQET LHGCQPVTQE DGKESRISVQ    540
ERQ                                                                 543

SEQ ID NO: 51            moltype = AA  length = 549
FEATURE                  Location/Qualifiers
REGION                   1..549
                         note = synthetic construct
source                   1..549
                         mol_type = protein
                         organism = synthetic construct
SEQUENCE: 51
MALPVTALLL PLALLLHAAR PEQKLISEED LEVQLVESGG GVVRPGGSLR LSCVASGVTF    60
DDYGMSWVRQ APGKGLEWVS GINWNGGDTD YSDSVKGRFT ISRDNAKNSL YLQMNSLRAE    120
DTALYYCARD FYGSGSYYHV PFDYWGQGIL VTVSSGGGGS GGGGSGGGGS EIVLTQSPGT    180
LSLSPGERAT LSCRASQSVS RSYLAWYQQK RGQAPRLLIY GASSRATGIP DRFSGDGSGT    240
DFTLSISRLE PEDFAVYYCH QYDMSPFTFG PGTKVDIKAA GGGGSGILV KQSPMLVAYD    300
NAVNLSCKYS YNLFSREFRA SLHKGLDSAV EVCVVYGNYS QQLQVYSKTG FNCDGKLGNE    360
SVTFYLQNLY VNQTDIYFCK IEVMYPPPYL DNEKSNGTII HVKGKHLCPS PLFPGPSKPF    420
WVLVVVGGVL ACYSLLVTVA FIIFWVRSKR SRLLHSDYMN MTPRRPGPTR KHYQPYAPPR    480
DFAAYRSKKV AKKPTNKAPH PKQEPQEINF PDDLPGSNTA APVQETLHGC QPVTQEDGKE    540
SRISVQERQ                                                           549

SEQ ID NO: 52            moltype = AA  length = 549
FEATURE                  Location/Qualifiers
REGION                   1..549
                         note = synthetic construct
source                   1..549
                         mol_type = protein
                         organism = synthetic construct
SEQUENCE: 52
MALPVTALLL PLALLLHAAR PEQKLISEED LEIVLTQSPG TLSLSPGERA TLSCRASQSV    60
SRSYLAWYQQ KRGQAPRLLI YGASSRATGI PDRFSGDGSG TDFTLSISRL EPEDFAVYYC    120
HQYDMSPFTF GPGTKVDIKG GGGSGGGGSG GGGSEVQLVE SGGGVVRPGG SLRLSCVASG    180
VTFDDYGMSW VRQAPGKGLE WVSGINWNGG DTDYSDSVKG RFTISRDNAK NSLYLQMNSL    240
RAEDTALYYC ARDFYGSGSY YHVPPDYWGQ GILVTVSSAA AGSGGGSILV KQSPMLVAYD    300
NAVNLSCKYS YNLFSREFRA SLHKGLDSAV EVCVVYGNYS QQLQVYSKTG FNCDGKLGNE    360
SVTFYLQNLY VNQTDIYFCK IEVMYPPPYL DNEKSNGTII HVKGKHLCPS PLFPGPSKPF    420
WVLVVVGGVL ACYSLLVTVA FIIFWVRSKR SRLLHSDYMN MTPRRPGPTR KHYQPYAPPR    480
DFAAYRSKKV AKKPTNKAPH PKQEPQEINF PDDLPGSNTA APVQETLHGC QPVTQEDGKE    540
SRISVQERQ                                                           549

SEQ ID NO: 53            moltype = AA  length = 545
FEATURE                  Location/Qualifiers
REGION                   1..293
                         note = synthetic construct
source                   1..545
                         mol_type = protein
                         organism = synthetic construct
SEQUENCE: 53
MALPVTALLL PLALLLHAAR PEQKLISEED LQVQLVESGG GVVQPGRSLR LSCAASGFSF    60
SSTYVCWVRQ APGKGLEWIA CIYTGDGTNY SASWAKGRFT ISKDSSKNTV YLQMNSLRAE    120
DTAVYFCARP DITYGFAINF WGPGTLVTVS SGGGGSGGGG SGGGGSDIQM TQSPSSLSAS    180
VGDRVTIKCQ ASQSISSRLA WYQQKPGKPP KLLIYRASTL ASGVPSRFSG SGSGTDFTLT    240
ISSLQPEDVA TYYCQCTGYG ISWPIGGGTK VEIKAAAGSG GGSILVKQSP MLVAYDNAVN    300
LSCKYSYNLF SREFRASLHK GLDSAVEVCV VYGNYSQQLQ VYSKTGFNCD KLGNESVTF    360
YLQNLYVNQT DIYFCKIEVM YPPPYLDNEK SNGTIIHVKG KHLCPSPLFP GPSKPFWVLV    420
VVGGVLACYS LLVTVAFIIF WVRSKRSRLL HSDYMNMTPR RPGPTRKHYQ PYAPPRDFAA    480
YRSKKVAKKP TNKAPHPKQE PQEINFPDDL PGSNTAAPVQ ETLHGCQPVT QEDGKESRIS    540
VQERQ                                                               545

SEQ ID NO: 54            moltype = AA  length = 545
FEATURE                  Location/Qualifiers
REGION                   1..239
                         note = synthetic construct
source                   1..545
                         mol_type = protein
                         organism = synthetic construct
SEQUENCE: 54
MALPVTALLL PLALLLHAAR PEQKLISEED LDIQMTQSPS SLSASVGDRV TIKCQASQSI    60
SSRLAWYQQK PGKPPKLLIY RASTLASGVP SRFSGSGSGT DFTLTISSLQ PEDVATYYCQ    120
CTGYGISWPI GGGTKVEIKG GGGSGGGGSG GGSQVQLVE SGGGVVQPGR SLRLSCAASG    180
FSFSSTYVCW VRQAPGKGLE WIACIYTGDG TNYSASWAKG RFTISKDSSK NTVYLQMNSL    240
RAEDTAVYFC ARPDITYGFA INFWGPGTLV TVSSAAAGSG GGSILVKQSP MLVAYDNAVN    300
LSCKYSYNLF SREFRASLHK GLDSAVEVCV VYGNYSQQLQ VYSKTGFNCD KLGNESVTF    360
YLQNLYVNQT DIYFCKIEVM YPPPYLDNEK SNGTIIHVKG KHLCPSPLFP GPSKPFWVLV    420
VVGGVLACYS LLVTVAFIIF WVRSKRSRLL HSDYMNMTPR RPGPTRKHYQ PYAPPRDFAA    480
YRSKKVAKKP TNKAPHPKQE PQEINFPDDL PGSNTAAPVQ ETLHGCQPVT QEDGKESRIS    540
VQERQ                                                               545
```

```
SEQ ID NO: 55             moltype = AA  length = 550
FEATURE                   Location/Qualifiers
REGION                    1..263
                          note = synthetic construct
source                    1..550
                          mol_type = protein
                          organism = synthetic construct
SEQUENCE: 55
MALPVTALLL PLALLLHAAR PEQKLISEED LQVQLVQSGA EVKKPGASVK VSCKASGYTF    60
TGYYMHWVRQ APGQGLEWMG WINPDSGGTN YAQKFQGRVT MTRDTSISTA YMELNRLRSD   120
DTAVYYCARD QPLGYCTNGV CSYFDYWGQG TLVTVSSGGG GSGGGGSGGG GSDIQMTQSP   180
SSVSASVGDR VTITCRASQG IYSWLAWYQQ KPGKAPNLLI YTASTLQSGV PSRFSGSGSG   240
TDFTLTISSL QPEDFATYYC QQANIFPLTF GGGTKVEIKA AAGSGGSGIL VKQSPMLVAY   300
DNAVNLSCKY SYNLFSREFR ASLHKGLDSA VEVCVVYGNY SQQLQVYSKT GFNCDGKLGN   360
ESVTFYLQNL YVNQTDIYFC KIEVMYPPPY LDNEKSNGTI IHVKGKHLCP SPLFPGPSKP   420
FWVLVVVGGV LACYSLLVTV AFIIFWVRSK RSRLLHSDYM NMTPRRPGPT RKHYQPYAPP   480
RDFAAYRSKK VAKKPTNKAP HPKQEPQEIN FPDDLPGSNT AAPVQETLHG CQPVTQEDGK   540
ESRISVQERQ                                                         550

SEQ ID NO: 56             moltype = AA  length = 550
FEATURE                   Location/Qualifiers
REGION                    1..250
                          note = synthetic construct
source                    1..550
                          mol_type = protein
                          organism = synthetic construct
SEQUENCE: 56
MALPVTALLL PLALLLHAAR PEQKLISEED LDIQMTQSPS SVSASVGDRV TITCRASQGI    60
YSWLAWYQQ PGKAPNLLIY TASTLQSGVP SRFSGSGSGT DFTLTISSLQ PEDFATYYCQ   120
QANIFPLTFG GGTKVEIKGG GGSGGGGSGG GGSQVQLVQS GAEVKKPGAS VKVSCKASGY   180
TFTGYYMHWV RQAPGQGLEW MGWINPDSGG TNYAQKFQGR VTMTRDTSIS TAYMELNRLR   240
SDDTAVYYCA RDQPLGYCTN GVCSYFDYWG QGTLVTVSSA AAGSGGSGIL VKQSPMLVAY   300
DNAVNLSCKY SYNLFSREFR ASLHKGLDSA VEVCVVYGNY SQQLQVYSKT GFNCDGKLGN   360
ESVTFYLQNL YVNQTDIYFC KIEVMYPPPY LDNEKSNGTI IHVKGKHLCP SPLFPGPSKP   420
FWVLVVVGGV LACYSLLVTV AFIIFWVRSK RSRLLHSDYM NMTPRRPGPT RKHYQPYAPP   480
RDFAAYRSKK VAKKPTNKAP HPKQEPQEIN FPDDLPGSNT AAPVQETLHG CQPVTQEDGK   540
ESRISVQERQ                                                         550

SEQ ID NO: 57             moltype = AA  length = 293
FEATURE                   Location/Qualifiers
REGION                    1..164
                          note = synthetic construct
source                    1..293
                          mol_type = protein
                          organism = synthetic construct
SEQUENCE: 57
MALPVTALLL PLALLLHAAR PEQKLISEED LILVKQSPML VAYDNAVNLS CKYSYNLFSR    60
EFRASLHKGL DSAVEVCVVY GNYSQQLQVY SKTGFNCDGK LGNESVTFYL QNLYVNQTDI   120
YFCKIEVMYP PPYLDNEKSN GTIIHVKGKH LCPSPLFPGP SKPFWVLVVV GGVLACYSLL   180
VTVAFIIFWV RSKRSRLLHS DYMNMTPRRP GPTRKHYQPY APPRDFAAYR SKKVAKKPTN   240
KAPHPKQEPQ EINFPDDLPG SNTAAPVQET LHGCQPVTQE DGKESRISVQ ERQ          293

SEQ ID NO: 58             moltype = AA  length = 239
FEATURE                   Location/Qualifiers
REGION                    1..239
                          note = synthetic construct
source                    1..239
                          mol_type = protein
                          organism = synthetic construct
SEQUENCE: 58
MEHSTFLSGL VLATLLSQVS PEQKLISEED LFKIPIEELE DRVFVNCNTS ITWVEGTVGT    60
LLSDITRLDL GKRILDPRGI YRCNGTDIYK DKESTVQVHY RMCQSCVELD PATVAGIIVT   120
DVIATLLLAL GVFCFARSKR SRLLHSDYMN MTPRRPGPTR KHYQPYAPPR DFAAYRSKKV   180
AKKPTNKAPH PKQEPQEINF PDDLPGSNTA APVQETLHGC QPVTQEDGKE SRISVQERQ    239

SEQ ID NO: 59             moltype = AA  length = 263
FEATURE                   Location/Qualifiers
REGION                    1..263
                          note = synthetic construct
source                    1..263
                          mol_type = protein
                          organism = synthetic construct
SEQUENCE: 59
MQSGTHWRVL GLCLLSVGVW GQDYKDDDDK DGNEEMGGIT QTPYKVSISG TTVILTCPQY    60
PGSEILWQHN DKNIGGDEDD KNIGSDEDHL SLKEFSELEQ SGYYVCYPRG SKPEDANFYL   120
YLRARVCENC MEMDVMSVAT IVIVDICITG GLLLLVYYWS RSKRSRLLHS DYMNMTPRRP   180
GPTRKHYQPY APPRDFAAYR SKKVAKKPTN KAPHPKQEPQ EINFPDDLPG SNTAAPVQET   240
LHGCQPVTQE DGKESRISVQ ERQ                                          263
```

```
SEQ ID NO: 60            moltype = AA   length = 250
FEATURE                  Location/Qualifiers
REGION                   1..250
                         note = synthetic construct
source                   1..250
                         mol_type = protein
                         organism = synthetic construct
SEQUENCE: 60
MEQGKGLAVL ILAIILLQGT LAEQKLISEE DLQSIKGNHL VKVYDYQEDG SVLLTCDAEA    60
KNITWFKDGK MIGFLTEDKK KWNLGSNAKD PRGMYQCKGS QNKSKPLQVY YRMCQNCIEL   120
NAATISGFLF AEIVSIFVLA VGVYFIARSK RSRLLHSDYM NMTPRRPGPT RKHYQPYAPP   180
RDFAAYRSKK VAKKPTNKAP HPKQEPQEIN FPDDLPGSNT AAPVQETLHG CQPVTQEDGK   240
ESRISVQERQ                                                         250

SEQ ID NO: 61            moltype = AA   length = 164
FEATURE                  Location/Qualifiers
REGION                   1..164
                         note = synthetic construct
source                   1..164
                         mol_type = protein
                         organism = synthetic construct
SEQUENCE: 61
MKWKALFTAA ILQAQLPITE AQSFGLLDPK LCYLLDGILF IYGVILTALF LRSKRSRLLH    60
SDYMNMTPRR PGPTRKHYQP YAPPRDFAAY RSKKVAKKPT NKAPHPKQEP QEINFPDDLP   120
GSNTAAPVQE TLHGCQPVTQ EDGKESRISV QERQEQKLIS EEDL                    164

SEQ ID NO: 62            moltype = AA   length = 287
FEATURE                  Location/Qualifiers
REGION                   1..287
                         note = synthetic construct
source                   1..287
                         mol_type = protein
                         organism = synthetic construct
SEQUENCE: 62
MALPVTALLL PLALLLHAAR PEQKLISEED LSQPHTKPSV FVMKNGTNVA CLVKEFYPKD    60
IRINLVSSKK ITEFDPAIVI SPSGKYNAVK LGKYEDSNSV TCSVQHDNKT VHSTDFEVKT   120
DSTDHVKPKE TENTKQPSKS CHKPKAIVHT EKVNMMSLTV LGLRMLFAKT VAVNFLLTAK   180
LFFLRSKRSR LLHSDYMNMT PRRPGPTRKH YQPYAPPRDF AAYRSKKVAK KPTNKAPHPK   240
QEPQEINFPD DLPGSNTAAP VQETLHGCQP VTQEDGKESR ISVQERQ                 287

SEQ ID NO: 63            moltype = AA   length = 293
FEATURE                  Location/Qualifiers
REGION                   1..293
                         note = synthetic construct
source                   1..293
                         mol_type = protein
                         organism = synthetic construct
SEQUENCE: 63
MALPVTALLL PLALLLHAAR PDYKDDDDKD KQLDADVSPK PTIFLPSIAE TKLQKAGTYL    60
CLLEKFFPDV IKIHWQEKKS NTILGSQEGN TMKTNDTYMK FSWLTVPEKS LDKEHRCIVR   120
HENNKNGVDQ EIIFPPIKTD VITMDPKDNC SKDANDTLLL QLTNTSAYYM YLLLLLKSVV   180
YFAIITCCLL RSKRSLLHS DYMNMTPRRP GPTRKHYQPY APPRDFAAYR SKKVAKKPTN   240
KAPHPKQEPQ EINFPDDLPG SNTAAPVQET LHGCQPVTQE DGKESRISVQ ERQ          293

SEQ ID NO: 64            moltype = AA   length = 270
FEATURE                  Location/Qualifiers
REGION                   1..270
                         note = synthetic construct
source                   1..270
                         mol_type = protein
                         organism = synthetic construct
SEQUENCE: 64
MALPVTALLL PLALLLHAAR PEQKLISEED LIQNPEPAVY QLKDPRSQDS TLCLFTDFDS    60
QINVPKTMES GTFITDKCVL DMKAMDSKSN GAIAWSNQTS FTCQDIFKET NATYPSSDVP   120
CDATLTEKSF ETDMNLFQN LLVIVLRILL KVAGFNLLM TLRLWSSRSK RSRLLHSDYM   180
NMTPRRPGPT RKHYQPYAPP RDFAAYRSKK VAKKPTNKAP HPKQEPQEIN FPDDLPGSNT   240
AAPVQETLHG CQPVTQEDGK ESRISVQERQ                                   270

SEQ ID NO: 65            moltype = AA   length = 301
FEATURE                  Location/Qualifiers
REGION                   1..301
                         note = synthetic construct
source                   1..301
                         mol_type = protein
                         organism = synthetic construct
SEQUENCE: 65
MALPVTALLL PLALLLHAAR PDYKDDDDKV LTPPKVSLFE PSKAEIANKQ KATLVCLARG    60
FFPDHVELSW WVNGKEVHSG VCTDPQAYKE SNYSYCLSSR LRVSATFWHN PRNHFRCQVQ   120
```

```
FHGLSEEDKW PEGSPKPVTQ NISAEAWGRA DCGITSASYQ QGVLSATILY EILLGKATLY    180
AVLVSTLVVM AMVKRKNSRS KRSRLLHSDY MNMTPRRPGP TRKHYQPYAP PRDFAAYRSK    240
KVAKKPTNKA PHPKQEPQEI NFPDDLPGSN TAAPVQETLH GCQPVTQEDG KESRISVQER    300
Q                                                                  301

SEQ ID NO: 66              moltype = AA  length = 605
FEATURE                    Location/Qualifiers
REGION                     1..605
                           note = synthetic construct
source                     1..605
                           mol_type = protein
                           organism = synthetic construct
SEQUENCE: 66
MALPVTALLL PLALLLHAAR PEQKLISEED LSQPHTKPSV FVMKNGTNVA CLVKEFYPKD    60
IRINLVSSKK ITEFDPAIVI SPSGKYNAVK LGKYEDSNSV TCSVQHDNKT VHSTDFEVKT    120
DSTDHVKPKE TENTKQPSKS CHKPKAIVHT EKVNMMSLTV LGLRMLFAKT VAVNFLLTAK    180
LFFLRSKRSR LLHSDYMNMT PRRPGPTRKH YQPYAPPRDF AAYRSKKVAK KPTNKAPHPK    240
QEPQEINFPD DLPGSNTAAP VQETLHGCQP VTQEDGKESR ISVQERQRAK RGSGEGRGSL    300
LTCGDVEENP GPMALPVTAL LLPLALLLHA ARPDYKDDDD KDKQLDADVS PKPTIFLPSI    360
AETKLQKAGT YLCLLEKFFP DVIKIHWQEK KSNTILGSQE GNTMKTNDTY MKFSWLTVPE    420
KSLDKEHRCI VRHENNKNGV DQEIIFPPIK TDVITMDPKD NCSKDANDTL LLQLTNTSAY    480
YMYLLLLLKS VVYFAIITCC LLRSKRSRLL HSDYMNMTPR RPGPTRKHYQ PYAPPRDFAA    540
YRSKKVAKKP TNKAPHPKQE PQEINFPDDL PGSNTAAPVQ ETLHGCQPVT QEDGKESRIS    600
VQERQ                                                              605

SEQ ID NO: 67              moltype = AA  length = 596
FEATURE                    Location/Qualifiers
REGION                     1..421
                           note = synthetic construct
source                     1..596
                           mol_type = protein
                           organism = synthetic construct
SEQUENCE: 67
MALPVTALLL PLALLLHAAR PEQKLISEED LIQNPEPAVY QLKDPRSQDS TLCLFTDFDS    60
QINVPKTMES GTFITDKCVL DMKAMDSKSN GAIAWSNQTS FTCQDIFKET NATYPSSDVP    120
CDATLTEKSF ETDMNLNFQN LLVIVLRILL LKVAGFNLLM TLRLWSSRSK RSRLLHSDYM    180
NMTPRRPGPT RKHYQPYAPP RDFAAYRSKK VAKKPTNKAP HPKQEPQEIN FPDDLPGSNT    240
AAPVQETLHG CQPVTQEDGK ESRISVQERQ RAKRGSGEGR GSLLTCGDVE ENPGPMALPV    300
TALLLPLALL LHAARPDYKD DDDKVLTPPK VSLFEPSKAE IANKQKATLV CLARGFFPDH    360
VELSWWVNGK EVHSGVCTDP QAYKESNYSY CLSSRLRVSA TFWHNPRNHF RCQVQFHGLS    420
EEDKWPEGSP KPVTQNISAE AWGRADCGIT SASYQQGVLS ATILYEILLG KATLYAVLVS    480
TLVVMAMVKR KNSRSKRSRL LHSDYMNMTP RRPGPTRKHY QPYAPPRDFA AYRSKKVAKK    540
PTNKAPHPKQ EPQEINFPDD LPGSNTAAPV QETLHGCQPV TQEDGKESRI SVQERQ       596

SEQ ID NO: 68              moltype = AA  length = 527
FEATURE                    Location/Qualifiers
REGION                     1..321
                           note = synthetic construct
source                     1..527
                           mol_type = protein
                           organism = synthetic construct
SEQUENCE: 68
MEHSTFLSGL VLATLLSQVS PEQKLISEED LFKIPIEELE DRVFVNCNTS ITWVEGTVGT    60
LLSDITRLDL GKRILDPRGI YRCNGTDIYK DKESTVQVHY RMCQSCVELD PATVAGIIVT    120
DVIATLLLAL GVFCFARSKR SRLLHSDYMN MTPRRPGPTR KHYQPYAPPR DFAAYRSKKV    180
AKKPTNKAPH PKQEPQEINF PDDLPGSNTA APVQETLHGC QPVTQEDGKE SRISVQERQR    240
AKRGSGEGRG SLLTCGDVEE NPGPMQSGTH WRVLGLCLLS VGVWGQDYKD DDDKDGNEEM    300
GGITQTPYKV SISGTTVILT CPQYPGSEIL WQHNDKNIGG DEDDKNIGSD EDHLSLKEFS    360
ELEQSGYYVC YPRGSKPEDA NFYLYLRARV CENCMEMDVM SVATIVIVDI CITGGLLLLV    420
YYWSRSKRSR LLHSDYMNMT PRRPGPTRKH YQPYAPPRDF AAYRSKKVAK KPTNKAPHPK    480
QEPQEINFPD DLPGSNTAAP VQETLHGCQP VTQEDGKESR ISVQERQ                 527

SEQ ID NO: 69              moltype = AA  length = 520
FEATURE                    Location/Qualifiers
REGION                     1..520
                           note = synthetic construct
source                     1..520
                           mol_type = protein
                           organism = synthetic construct
SEQUENCE: 69
MEQGKGLAVL ILAIILLQGT LAEQKLISEE DLQSIKGNHL VKVYDYQEDG SVLLTCDAEA    60
KNITWFKDGK MIGFLTEDKK KWNLGSNAKD PRGMYQCKGS QNKSKPLQVY RMCQNCIEL    120
NAATISGFLF AEIVSIFVLA GVYPIARSK RSRLLHSDYM NMTPRRPGPT RKHYQPYAPP    180
RDFAAYRSKK VAKKPTNKAP HPKQEPQEIN FPDDLPGSNT AAPVQETLHG CQPVTQEDGK    240
ESRISVQERQ RAKRGSGMQS GTHWRVLGLC LLSVGVWGQD YKDDDDKDGN EEMGGITQTP    300
YKVSISGTTV ILTCPQYPGS EILWQHNDKN IGGDEDDKNI GSDEDHLSLK EFSELEQSGY    360
YVCYPRGSKP EDANFYLYLR ARVCENCMEM DVMSVATIVI VDICITGGLL LLVYYWSRSK    420
RSRLLHSDYM NMTPRRPGPT RKHYQPYAPP RDFAAYRSKK VAKKPTNKAP HPKQEPQEIN    480
FPDDLPGSNT AAPVQETLHG CQPVTQEDGK ESRISVQERQ                         520
```

```
SEQ ID NO: 70            moltype = AA   length = 627
FEATURE                  Location/Qualifiers
REGION                   1..432
                         note = synthetic construct
source                   1..627
                         mol_type = protein
                         organism = synthetic construct
SEQUENCE: 70
MEHSTFLSGL VLATLLSQVS PEQKLISEED LFKIPIEELE DRVFVNCNTS ITWVEGTVGT    60
LLSDITRLDL GKRILDPRGI YRCNGTDIYK DKESTVQVHY RMCQSCVELD PATVAGIIVT   120
DVIATLLLAL GVFCFAGHET GRLSGAADTQ ALLRNDQVYQ PLRDRDDAQY SHLGGNWARN   180
KRSKRSRLLH SDYMNMTPRR PGPTRKHYQP YAPPRDFAAY RSKKVAKKPT NKAPHPKQEP   240
QEINFPDDLP GSNTAAPVQE TLHGCQPVTQ EDGKESRISV QERQRAKRGS GEGRGSLLTC   300
GDVEENPGPM QSGTHWRVLG LCLLSVGVWG QDYKDDDDKD GNEEMGGITQ TPYKVSISGT   360
TVILTCPQYP GSEILWQHND KNIGGDEDDK NIGSDEDHLS LKEFSELEQS GYYVCYPRGS   420
KPEDANFYLY LRARVCENCM EMDVMSVATI VIVDICITGG LLLLVYYWSK NRKAKAKPVT   480
RGAGAGGRQR GQNKERPPPV PNPDYEPIRK GQRDLYSGLN QRRIRSKRSR LLHSDYMNMT   540
PRRPGPTRKH YQPYAPPRDF AAYRSKKVAK KPTNKAPHPK QEPQEINFPD DLPGSNTAAP   600
VQETLHGCQP VTQEDGKESR ISVQERQ                                       627

SEQ ID NO: 71            moltype = AA   length = 421
FEATURE                  Location/Qualifiers
REGION                   1..332
                         note = synthetic construct
source                   1..421
                         mol_type = protein
                         organism = synthetic construct
SEQUENCE: 71
MEHSTFLSGL VLATLLSQVS PEQKLISEED LFKIPIEELE DRVFVNCNTS ITWVEGTVGT    60
LLSDITRLDL GKRILDPRGI YRCNGTDIYK DKESTVQVHY RMCQSCVELD PATVAGIIVT   120
DVIATLLLAL GVFCFAGHET GRLSGAADTQ ALLRNDQVYQ PLRDRDDAQY SHLGGNWARN   180
KRAKRGSGEG RGSLLTCGDV EENPGPMQSG THWRVLGLCL LSVGVWGQDY KDDDDKDGNE   240
EMGGITQTPY KVSISGTTVI LTCPQYPGSE ILWQHNDKNI GSDEDHLSLK EFSELEQSGY   300
YVCYPRGSKPE DANFYLYLRA RVCENCMEMD VMSVATIVIV DICITGGLLL             360
LVYYWSKNRK AKAKPVTRGA GAGGRQRGQN KERPPPVPNP DYEPIRKGQR DLYSGLNQRR   420
I                                                                   421

SEQ ID NO: 72            moltype = AA   length = 321
FEATURE                  Location/Qualifiers
REGION                   1..277
                         note = synthetic construct
source                   1..321
                         mol_type = protein
                         organism = synthetic construct
SEQUENCE: 72
MEHSTFLSGL VLATLLSQVS PEQKLISEED LFKIPIEELE DRVFVNCNTS ITWVEGTVGT    60
LLSDITRLDL GKRILDPRGI YRCNGTDIYK DKESTVQVHY RMCQSCVELD PATVAGIIVT   120
DVIATLLLAL GVFCFARAKR GSGEGRGSLL TCGDVEENPG PMQSGTHWRV LGLCLLSVGV   180
WGQDYKDDDD KDGNEEMGGI TQTPYKVSIS GTTVILTCPQ YPGSEILWQH NDKNIGGDED   240
DKNIGSDEDH LSLKEFSELE QSGYYVCYPR GSKPEDANFY LYLRARVCEN CMEMDVMSVA   300
TIVIVDICIT GGLLLLVYYW S                                             321

SEQ ID NO: 73            moltype = AA   length = 638
FEATURE                  Location/Qualifiers
REGION                   1..174
                         note = synthetic construct
source                   1..638
                         mol_type = protein
                         organism = synthetic construct
SEQUENCE: 73
MEQGKGLAVL ILAIILLQGT LAEQKLISEE DLQSIKGNHL VKVYDYQEDG SVLLTCDAEA    60
KNITWFKDGK MIGFLTEDKK KWNLGSNAKD PRGMYQCKGS QNKSKPLQVY YRMCQNCIEL   120
NAATISGFLF AEIVSIFVLA VGVYFIAGQD GVRQSRASDK QTLLPNDQLY QPLKDREDDQ   180
YSHLQGNQLR RNRSKRSRLL HSDYMNMTPR RPGPTRKHYQ PYAPPRDFAA YRSKKVAKKP   240
TNKAPHPKQE PQEINFPDDL PGSNTAAPVQ ETLHGCQPVT QEDGKESRIS VQERQRAKRG   300
SGEGRGSLLT CGDVEENPGP MQSGTHWRVL GLCLLSVGVW GQDYKDDDDK DGNEEMGGIT   360
QTPYKVSISG TTVILTCPQY PGSEILWQHN DKNIGGDEDD KNIGSDEDHL SLKEFSELEQ   420
SGYYVCYPRG SKPEDANFYL YLRARVCENC MEMDVMSVAT IVIVDICITG GLLLLVYYWS   480
KNRKAKAKPV TRGAGAGGRQ RGQNKERPPP VPNPDYEPIR KGQRDLYSGL NQRRIRSKRS   540
RLLHSDYMNM TPRRPGPTRK HYQPYAPPRD FAAYRSKKVA KKPTNKAPHP KQEPQEINFP   600
DDLPGSNTAA PVQETLHGCQ PVTQEDGKES RISVQERQ                           638

SEQ ID NO: 74            moltype = AA   length = 432
FEATURE                  Location/Qualifiers
REGION                   1..61
                         note = synthetic construct
source                   1..432
                         mol_type = protein
```

```
                        organism = synthetic construct
SEQUENCE: 74
MEQGKGLAVL ILAIILLQGT LAEQKLISEE DLQSIKGNHL VKVYDYQEDG SVLLTCDAEA    60
KNITWFKDGK MIGFLTEDKK KWNLGSNAKD PRGMYQCKGS QNKSKPLQVY YRMCQNCIEL   120
NAATISGFLF AEIVSIFVLA VGVYFIAGQD GVRQSRASDK QTLLPNDQLY QPLKDREDDQ   180
YSHLQGNQLR RNRAKRGSGE GRGSLLTCGD VEENPGPMQS GTHWRVLGLC LLSVGVWGQD   240
YKDDDDKDGN EEMGGITQTP YKVSISGTTV ILTCPQYPGS EILWQHNDKN IGGDEDDKNI   300
GSDEDHLSLK EFSELEQSGY YVCYPRGSKP EDANFYLYLR ARVCENCMEM DVMSVATIVI   360
VDICITGLL  LLVYYWSKNR KAKAKPVTRG AGAGGRQRGQ NKERPPPVPN PDYEPIRKGQ   420
RDLYSGLNQR RI                                                       432

SEQ ID NO: 75           moltype = AA  length = 332
FEATURE                 Location/Qualifiers
REGION                  1..332
                        note = synthetic construct
source                  1..332
                        mol_type = protein
                        organism = synthetic construct
SEQUENCE: 75
MEQGKGLAVL ILAIILLQGT LAEQKLISEE DLQSIKGNHL VKVYDYQEDG SVLLTCDAEA    60
KNITWFKDGK MIGFLTEDKK KWNLGSNAKD PRGMYQCKGS QNKSKPLQVY YRMCQNCIEL   120
NAATISGFLF AEIVSIFVLA VGVYFIARAK RGSGEGRGSL LTCGDVEENP GPMQSGTHWR   180
VLGLCLLSVG VWGQDYKDDD DKDGNEEMGG ITQTPYKVSI SGTTVILTCP QYPGSEILWQ   240
HNDKNIGGDE DDKNIGSDED HLSLKEFSEL EQSGYYVCYP RGSKPEDANF YLYLRARVCE   300
NCMEMDVMSV ATIVIVDICI TGGLLLLVYY WS                                 332

SEQ ID NO: 76           moltype = AA  length = 277
FEATURE                 Location/Qualifiers
REGION                  1..277
                        note = synthetic construct
source                  1..277
                        mol_type = protein
                        organism = synthetic construct
SEQUENCE: 76
MKWKALFTAA ILQAQLPITE AQSFGLLDPK LCYLLDGILF IYGVILTALF LRVKFSRSAD    60
APAYQQGQNQ LYNELNLGRR EEYDVLDKRR GRDPEMGGKP QRRKNPQEGL YNELQKDKMA   120
EAYSEIGMKG ERRRGKGHDG LYQGLSTATK DTYDALHMQA LPPRRSKRSR LLHSDYMNMT   180
PRRPGPTRKH YQPYAPPRDF AAYRSKKVAK KPTNKAPHPK QEPQEINFPD DLPGSNTAAP   240
VQETLHGCQP VTQEDGKESR ISVQERQEQK LISEEDL                            277

SEQ ID NO: 77           moltype = AA  length = 390
FEATURE                 Location/Qualifiers
REGION                  1..390
                        note = synthetic construct
source                  1..390
                        mol_type = protein
                        organism = synthetic construct
SEQUENCE: 77
MKWKALFTAA ILQAQLPITE AQSFGLLDPK LCYLLDGILF IYGVILTALF LRSKRSLLH    60
SDYMNMTPRR PGPTRKHYQP YAPPRDFAAY RSKKVAKKPT NKAPHPKQEP QEINFPDDLP   120
GSNTAAPVQE TLHGCQPVTQ EDGKESRISV QERQRVKFSR SADAPAYQQG QNQLYNELNL   180
GRREEYDVLD KRRGRDPEMG GKPQRRKNPQ EGLYNELQKD KMAEAYSEIG MKGERRRGKG   240
HDGLYQGLST ATKDTYDALH MQALPPRRVK FSRSADAPAY QQGQNQLYNE LNLGRREEYD   300
VLDKRRGRDP EMGGKPQRRK NPQEGLYNEL QKDKMAEAYS EIGMKGERRR GKGHDGLYQG   360
LSTATKDTYD ALHMQALPPR EQKLISEEDL                                    390

SEQ ID NO: 78           moltype = AA  length = 174
FEATURE                 Location/Qualifiers
REGION                  1..174
                        note = synthetic construct
source                  1..174
                        mol_type = protein
                        organism = synthetic construct
SEQUENCE: 78
MKWKALFTAA ILQAQLPITE AQSFGLLDPK LCYLLDGILF IYGVILTALF LRVKFSRSAD    60
APAYQQGQNQ LYNELNLGRR EEYDVLDKRR GRDPEMGGKP QRRKNPQEGL YNELQKDKMA   120
EAYSEIGMKG ERRRGKGHDG LYQGLSTATK DTYDALHMQA LPPREQKLIS EEDL          174

SEQ ID NO: 79           moltype = AA  length = 61
FEATURE                 Location/Qualifiers
REGION                  1..61
                        note = synthetic construct
source                  1..61
                        mol_type = protein
                        organism = synthetic construct
SEQUENCE: 79
MKWKALFTAA ILQAQLPITE AQSFGLLDPK LCYLLDGILF IYGVILTALF LEQKLISEED    60
L                                                                    61
```

```
SEQ ID NO: 80             moltype = AA  length = 390
FEATURE                   Location/Qualifiers
REGION                    1..390
                          note = synthetic construct
source                    1..390
                          mol_type = protein
                          organism = synthetic construct
SEQUENCE: 80
MKWKALFTAA ILQAQLPITE AQSFGLLDPK LCYLLDGILF IYGVILTALF LRVKFSRSAD    60
APAYQQGQNQ LYNELNLGRR EEYDVLDKRR GRDPEMGGKP QRRKNPQEGL YNELQKDKMA   120
EAYSEIGMKG ERRRGKGHDG LYQGLSTATK DTYDALHMQA LPPRRVKFSR SADAPAYQQG   180
QNQLYNELNL GRREEYDVLD KRRGRDPEMG GKPQRRKNPQ EGLYNELQKD KMAEAYSEIG   240
MKGERRRGKG HDGLYQGLST ATKDTYDALH MQALPPRRSK RSRLLHSDYM NMTPRRPGPT   300
RKHYQPYAPP RDFAAYRSKK VAKKPTNKAP HPKQEPQEIN FPDDLPGSNT AAPVQETLHG   360
CQPVTQEDGK ESRISVQERQ EQKLISEEDL                                    390

SEQ ID NO: 81             moltype = AA  length = 287
FEATURE                   Location/Qualifiers
REGION                    1..287
                          note = synthetic construct
source                    1..287
                          mol_type = protein
                          organism = synthetic construct
SEQUENCE: 81
MKWKALFTAA ILQAQLPITE AQSFGLLDPK LCYLLDGILF IYGVILTALF LRVKFSRSAD    60
APAYQQGQNQ LYNELNLGRR EEYDVLDKRR GRDPEMGGKP QRRKNPQEGL YNELQKDKMA   120
EAYSEIGMKG ERRRGKGHDG LYQGLSTATK DTYDALHMQA LPPRRVKFSR SADAPAYQQG   180
QNQLYNELNL GRREEYDVLD KRRGRDPEMG GKPQRRKNPQ EGLYNELQKD KMAEAYSEIG   240
MKGERRRGKG HDGLYQGLST ATKDTYDALH MQALPPREQK LISEEDL                 287

SEQ ID NO: 82             moltype = AA  length = 390
FEATURE                   Location/Qualifiers
REGION                    1..390
                          note = synthetic construct
source                    1..390
                          mol_type = protein
                          organism = synthetic construct
SEQUENCE: 82
MKWKALFTAA ILQAQLPITE AQSFGLLDPK LCYLLDGILF IYGVILTALF LRSKRSLLH    60
SDYMNMTPRR PGPTRKHYQP YAPPRDFAAY RSKKVAKKPT NKAPHPKQEP QEINFPDDLP   120
GSNTAAPVQE TLHGCQPVTQ EDGKESRISV QERQRVKFSR SADAPAYQQG QNQLYNELNL   180
GRREEYDVLD KRRGRDPEMG GKPQRRKNPQ EGLYNELQKD KMAEAYSEIG MKGERRRGKG   240
HDGLYQGLST ATKDTYDALH MQALPPRRVK FSRSADAPAY QQGQNQLYNE LNLGRREEYD   300
VLDKRRGRDP EMGGKPQRRK NPQEGLYNEL QKDKMAEAYS EIGMKGERRR GKGHDGLYQG   360
LSTATKDTYD ALHMQALPPR EQKLISEEDL                                    390

SEQ ID NO: 83             moltype = AA  length = 277
FEATURE                   Location/Qualifiers
REGION                    1..277
                          note = synthetic construct
source                    1..277
                          mol_type = protein
                          organism = synthetic construct
SEQUENCE: 83
MKWKALFTAA ILQAQLPITE AQSFGLLDPK LCYLLDGILF IYGVILTALF LRSKRSLLH    60
SDYMNMTPRR PGPTRKHYQP YAPPRDFAAY RSKKVAKKPT NKAPHPKQEP QEINFPDDLP   120
GSNTAAPVQE TLHGCQPVTQ EDGKESRISV QERQRVKFSR SADAPAYQQG QNQLYNELNL   180
GRREEYDVLD KRRGRDPEMG GKPQRRKNPQ EGLYNELQKD KMAEAYSEIG MKGERRRGKG   240
HDGLYQGLST ATKDTYDALH MQALPPREQK LISEEDL                            277

SEQ ID NO: 84             moltype = AA  length = 273
FEATURE                   Location/Qualifiers
REGION                    1..273
                          note = synthetic construct
source                    1..273
                          mol_type = protein
                          organism = synthetic construct
SEQUENCE: 84
MGHTRRQGTS PSKCPYLNFF QLLVLAGLSH FCSGEQKLIS EEDLVIHVTK EVKEVATLSC    60
GHNVSVEELA QTRIYWQKEK KMVLTMMSGD MNIWPEYKNR TIFDITNNLS IVILALRPSD   120
EGTYECVVLK YEKDAFKREH LAEVTLSVKA DFPTPSISDF EIPTSNIRRI ICSTSGGFPE   180
PHLSWLENGE ELNAINTTVS QDPETELYAV SSKLDFNMTT NHSFMCLIKY GHLRVNQTFN   240
WNTTKQEHFP DNLLPSWAIT LISVNGIFVI CCL                                273

SEQ ID NO: 85             moltype = AA  length = 519
FEATURE                   Location/Qualifiers
REGION                    1..519
                          note = synthetic construct
source                    1..519
```

```
                              mol_type = protein
                              organism = synthetic construct
SEQUENCE: 85
MGCGCSSHPE DDWMENIDVC ENCHYPIVPL DGKGTLLIRN GSEVRDPLVT YEGSNPPASP    60
LQDNLVIALH SYEPSHDGDL GFEKGEQLRI LEQSGEWWKA QSLTTGQEGF IPFNFVAKAN   120
SLEPEPWFFK NLSRKDAERQ LLAPGNTHGS FLIRESESTA GSFSLSVRDF DQNQGEVVKH   180
YKIRNLDNGG FYISPRITFP GLHELVRHYT NASDGLCTRL SRPCQTQKPQ KPWWEDEWEV   240
PRETLKLVER LGAGQFGEVW MGYYNGHTKV AVKSLKQGSM SPDAFLAEAN LMKQLQHQRL   300
VRLYAVVTQE PIYIITEYME NGSLVDFLKT PSGIKLTINK LLDMAAQIAE GMAFIEERNY   360
IHRDLRAANI LVSDTLSCKI ADFGLARLIE DNEYTAREGA KFPIKWTAPE AINYGTFTIK   420
SDVWSFGILL TEIVTHGRIP YPGMTNPEVI QNLERGYRMV RPDNCPEELY QLMRLCWKER   480
PEDRPTFDYL RSVLEDFFTA TEGQYQPQPE QKLISEEDL                          519

SEQ ID NO: 86                 moltype = AA   length = 519
FEATURE                       Location/Qualifiers
REGION                        1..293
                              note = synthetic construct
source                        1..519
                              mol_type = protein
                              organism = synthetic construct
SEQUENCE: 86
MGCGCSSHPE DDWMENIDVC ENCHYPIVPL DGKGTLLIRN GSEVRDPLVT YEGSNPPASP    60
LQDNLVIALH SYEPSHDGDL GFEKGEQLRI LEQSGEWWKA QSLTTGQEGF IPFNFVAKAN   120
SLEPEPWFFK NLSRKDAERQ LLAPGNTHGS FLIRESESTA GSFSLSVRDF DQNQGEVVKH   180
YKIRNLDNGG FYISPRITFP GLHELVRHYT NASDGLCTRL SRPCQTQKPQ KPWWEDEWEV   240
PRETLKLVER LGAGQFGEVW MGYYNGHTKV AVKSLKQGSM SPDAFLAEAN LMKQLQHQRL   300
VRLYAVVTQE PIYIITEYME NGSLVDFLKT PSGIKLTINK LLDMAAQIAE GMAFIEERNY   360
IHRDLRAANI LVSDTLSCKI ADFGLARLIE DNEYTAREGA KFPIKWTAPE AINYGTFTIK   420
SDVWSFGILL TEIVTHGRIP YPGMTNPEVI QNLERGYRMV RPDNCPEELY QLMRLCWKER   480
PEDRPTFDYL RSVLEDFFTA TEGQFQPQPE QKLISEEDL                          519

SEQ ID NO: 87                 moltype = AA   length = 781
FEATURE                       Location/Qualifiers
REGION                        1..396
                              note = synthetic construct
source                        1..781
                              mol_type = protein
                              organism = synthetic construct
SEQUENCE: 87
MGHTRRQGTS PSKCPYLNFF QLLVLAGLSH FCSGEQKLIS EEDLVIHVTK EVKEVATLSC    60
GHNVSVEELA QTRIYWQKEK KMVLTMMSGD MNIWPEYKNR TIFDITNNLS IVILALRPSD   120
EGTYECVVLK YEKDAFKREH LAEVTLSVKA DFPTPSISDF EIPTSNIRRI ICSTSGGFPE   180
PHLSWLENGE ELNAINTTVS QDPETELYAV SSKLDFNMTT NHSFMCLIKY GHLRVNQTFN   240
WNTTKQEHFP DNLLPSWAIT LISVNGIFVI CCLGCGCSSH PEDDWMENID VCENCHYPIV   300
PLDGKGTLLI RNGSEVRDPL VTYEGSNPPA SPLQDNLVIA LHSYEPSHDG DLGFEKGEQL   360
RILEQSGEWW KAQSLTTGQE GFIPFNFVAK ANSLEPEPWF FKNLSRKDAE RQLLAPGNTH   420
GSFLIRESES TAGSFSLSVR DFDQNQGEVV KHYKIRNLDN GGFYISPRIT FPGLHELVRH   480
YTNASDGLCT RLSRPCQTQK PQKPWWEDEW EVPRETLKLV ERLGAGQFGE VWMGYYNGHT   540
KVAVKSLKQG SMSPDAFLAE ANLMKQLQHQ RLVRLYAVVT QEPIYIITEY MENGSLVDFL   600
KTPSGIKLTI NKLLDMAAQI AEGMAFIEER NYIHRDLRAA NILVSDTLSC KIADFGLARL   660
IEDNEYTARE GAKFPIKWTA PEAINYGTFT IKSDVWSFGI LLTEIVTHGR IPYPGMTNPE   720
VIQNLERGYR MVRPDNCPEE LYQLMRLCWK ERPEDRPTFD YLRSVLEDFF TATEGQYQPQ   780
P                                                                  781

SEQ ID NO: 88                 moltype = AA   length = 884
FEATURE                       Location/Qualifiers
REGION                        1..468
                              note = synthetic construct
source                        1..884
                              mol_type = protein
                              organism = synthetic construct
SEQUENCE: 88
MGHTRRQGTS PSKCPYLNFF QLLVLAGLSH FCSGEQKLIS EEDLVIHVTK EVKEVATLSC    60
GHNVSVEELA QTRIYWQKEK KMVLTMMSGD MNIWPEYKNR TIFDITNNLS IVILALRPSD   120
EGTYECVVLK YEKDAFKREH LAEVTLSVKA DFPTPSISDF EIPTSNIRRI ICSTSGGFPE   180
PHLSWLENGE ELNAINTTVS QDPETELYAV SSKLDFNMTT NHSFMCLIKY GHLRVNQTFN   240
WNTTKQEHFP DNLLPSWAIT LISVNGIFVI CCLGCGCSSH PEDDWMENID VCENCHYPIV   300
PLDGKGTLLI RNGSEVRDPL VTYEGSNPPA SPLQDNLVIA LHSYEPSHDG DLGFEKGEQL   360
RILEQSGEWW KAQSLTTGQE GFIPFNFVAK ANSLEPEPWF FKNLSRKDAE RQLLAPGNTH   420
GSFLIRESES TAGSFSLSVR DFDQNQGEVV KHYKIRNLDN GGFYISPRIT FPGLHELVRH   480
YTNASDGLCT RLSRPCQTQK PQKPWWEDEW EVPRETLKLV ERLGAGQFGE VWMGYYNGHT   540
KVAVKSLKQG SMSPDAFLAE ANLMKQLQHQ RLVRLYAVVT QEPIYIITEY MENGSLVDFL   600
KTPSGIKLTI NKLLDMAAQI AEGMAFIEER NYIHRDLRAA NILVSDTLSC KIADFGLARL   660
IEDNEYTARE GAKFPIKWTA PEAINYGTFT IKSDVWSFGI LLTEIVTHGR IPYPGMTNPE   720
VIQNLERGYR MVRPDNCPEE LYQLMRLCWK ERPEDRPTFD YLRSVLEDFF TATEGQYQPQ   780
PRSKRSLLH SDYMNMTPRR PGPTRKHYQP YAPPRDFAAY RSKKVAKKPT NKAPHPKQEP    840
QEINFPDDLP GSNTAAPVQE TLHGCPVTQ EDGKESRISV QERQ                    884

SEQ ID NO: 89                 moltype = AA   length = 781
```

```
FEATURE                 Location/Qualifiers
REGION                  1..571
                        note = synthetic construct
source                  1..781
                        mol_type = protein
                        organism = synthetic construct
SEQUENCE: 89
MGHTRRQGTS PSKCPYLNFF QLLVLAGLSH FCSGEQKLIS EEDLVIHVTK EVKEVATLSC    60
GHNVSVEELA QTRIYWQKEK KMVLTMMSGD MNIWPEYKNR TIFDITNNLS IVILALRPSD   120
EGTYECVVLK YEKDAFKREH LAEVTLSVKA DFPTPSISDF EIPTSNIRRI ICSTSGGFPE   180
PHLSWLENGE ELNAINTTVS QDPETELYAV SSKLDFNMTT NHSFMCLIKY GHLRVNQTFN   240
WNTTKQEHFP DNLLPSWAIT LISVNGIFVI CCLGCGCSSH PEDDWMENID VCENCHYPIV   300
PLDGKGTLLI RNGSEVRDPL VTYEGSNPPA SPLQDNLVIA LHSYEPSHDG DLGFEKGEQL   360
RILEQSGEWW KAQSLTTGQE GFIPFNFVAK ANSLEPEPWF FKNLSRKDAE RQLLAPGNTH   420
GSFLIRESES TAGSFSLSVR DFDQNQGEVV KHYKIRNLDN GGFYISPRIT FPGLHELVRH   480
YTNASDGLCT RLSRPCQTQK PQKPWWEDEW EVPRETLKLV ERLGAGQFGE VWMGYYNGHT   540
KVAVKSLKQG SMSPDAFLAE ANLMKQLQHQ RLVRLYAVVT QEPIYIITEY MENGSLVDFL   600
KTPSGIKLTI NKLLDMAAQI AEGMAFIEER NYIHRDLRAA NILVSDTLSC KIADFGLARL   660
IEDNEYTARE GAKFPIKWTA PEAINYGTFT IKSDVWSFGI LLTEIVTHGR IPYPGMTNPE   720
VIQNLERGYR MVRPDNCPEE LYQLMRLCWK ERPEDRPTFD YLRSVLEDFF TATEGQFQPQ   780
P                                                                  781

SEQ ID NO: 90           moltype = AA  length = 884
FEATURE                 Location/Qualifiers
REGION                  1..488
                        note = synthetic construct
source                  1..884
                        mol_type = protein
                        organism = synthetic construct
SEQUENCE: 90
MGHTRRQGTS PSKCPYLNFF QLLVLAGLSH FCSGEQKLIS EEDLVIHVTK EVKEVATLSC    60
GHNVSVEELA QTRIYWQKEK KMVLTMMSGD MNIWPEYKNR TIFDITNNLS IVILALRPSD   120
EGTYECVVLK YEKDAFKREH LAEVTLSVKA DFPTPSISDF EIPTSNIRRI ICSTSGGFPE   180
PHLSWLENGE ELNAINTTVS QDPETELYAV SSKLDFNMTT NHSFMCLIKY GHLRVNQTFN   240
WNTTKQEHFP DNLLPSWAIT LISVNGIFVI CCLGCGCSSH PEDDWMENID VCENCHYPIV   300
PLDGKGTLLI RNGSEVRDPL VTYEGSNPPA SPLQDNLVIA LHSYEPSHDG DLGFEKGEQL   360
RILEQSGEWW KAQSLTTGQE GFIPFNFVAK ANSLEPEPWF FKNLSRKDAE RQLLAPGNTH   420
GSFLIRESES TAGSFSLSVR DFDQNQGEVV KHYKIRNLDN GGFYISPRIT FPGLHELVRH   480
YTNASDGLCT RLSRPCQTQK PQKPWWEDEW EVPRETLKLV ERLGAGQFGE VWMGYYNGHT   540
KVAVKSLKQG SMSPDAFLAE ANLMKQLQHQ RLVRLYAVVT QEPIYIITEY MENGSLVDFL   600
KTPSGIKLTI NKLLDMAAQI AEGMAFIEER NYIHRDLRAA NILVSDTLSC KIADFGLARL   660
IEDNEYTARE GAKFPIKWTA PEAINYGTFT IKSDVWSFGI LLTEIVTHGR IPYPGMTNPE   720
VIQNLERGYR MVRPDNCPEE LYQLMRLCWK ERPEDRPTFD YLRSVLEDFF TATEGQFQPQ   780
PRSKRSLLH SDYMNMTPRR PGPTRKHYQP YAPPRDFAAY RSKKVAKKPT NKAPHPKQEP    840
QEINFPDDLP GSNTAAPVQE TLHGCQPVTQ EDGKESRISV QERQ                   884

SEQ ID NO: 91           moltype = AA  length = 293
FEATURE                 Location/Qualifiers
REGION                  1..293
                        note = synthetic construct
source                  1..293
                        mol_type = protein
                        organism = synthetic construct
SEQUENCE: 91
MALPVTALLL PLALLLHAAR PEQKLISEED LMEEAILVPC VLGLLLLPIL AMLMALCVHC    60
HRLPGSYDST SSDSLYPRGI QFKRPHTVAP WPPAYPPVTS YPPLSQPDLL PIPRSPQPLG   120
GSHRTPSSRR DSDGANSVAS YENEGASGIR GAQAGWGVWG PSWTRLTPVS LPPEPACEDA   180
DEDEDDYHNP GYLVVLPDST PATSTAAPSA PALSTPGIRD SAFSMESIDD YVNVPESGES   240
AEASLDGSRE YVNVSQELHP GAAKTEPAAL SSQEAEEVEE EGAPDYENLQ ELN          293

SEQ ID NO: 92           moltype = AA  length = 396
FEATURE                 Location/Qualifiers
REGION                  1..221
                        note = synthetic construct
source                  1..396
                        mol_type = protein
                        organism = synthetic construct
SEQUENCE: 92
MALPVTALLL PLALLLHAAR PEQKLISEED LMEEAILVPC VLGLLLLPIL AMLMALCVHC    60
HRLPGSYDST SSDSLYPRGI QFKRPHTVAP WPPAYPPVTS YPPLSQPDLL PIPRSPQPLG   120
GSHRTPSSRR DSDGANSVAS YENEGASGIR GAQAGWGVWG PSWTRLTPVS LPPEPACEDA   180
DEDEDDYHNP GYLVVLPDST PATSTAAPSA PALSTPGIRD SAFSMESIDD YVNVPESGES   240
AEASLDGSRE YVNVSQELHP GAAKTEPAAL SSQEAEEVEE EGAPDYENLQ ELNRSKRSRL   300
LHSDYMNMTP RRPGPTRKHY QPYAPPRDFA AYRSKKVAKK PTNKAPHPKQ EPQEINFPDD   360
LPGSNTAAPV QETLHGCQPV TQEDGKESRI SVQERQ                             396

SEQ ID NO: 93           moltype = AA  length = 468
FEATURE                 Location/Qualifiers
REGION                  1..202
```

```
                        note = synthetic construct
source                  1..468
                        mol_type = protein
                        organism = synthetic construct
SEQUENCE: 93
MNRGVPFRHL LLVLQLALLP AATQGEQKLI SEEDLKKVVL GKKGDTVELT CTASQKKSIQ    60
FHWKNSNQIK ILGNQGSFLT KGPSKLNDRA DSRRSLWDQG NFPLIIKNLK IEDSDTYICE   120
VEDQKEEVQL LVFGLTANSD THLLQGQSLT LTLESPPGSS PSVQCRSPRG KNIQGGKTLS   180
VSQLELQDSG TWTCTVLQNQ KKVEFKIDIV VLAFQKASSI VYKKEGEQVE FSFPLAFTVE   240
KLTGSGELWW QAERASSSKS WITFDLKNKE VSVKRVTQDP KLQMGKKLPL HLTLPQALPQ   300
YAGSGNLTLA LEAKTGKLHQ EVNLVVMRAT QLQKNLTCEV WGPTSPKLML SLKLENKEAK   360
VSKREKAVWV LNPEAGMWQC LLSDSGQVLL ESNIKVLPTW STPVQPMALI VLGGVAGLLL   420
FIGLGIFFCV RCRHRRRQAE RMSQIKRLLS EKKTCQCPHR FQKTCSPI                468

SEQ ID NO: 94           moltype = AA  length = 571
FEATURE                 Location/Qualifiers
REGION                  1..209
                        note = synthetic construct
source                  1..571
                        mol_type = protein
                        organism = synthetic construct
SEQUENCE: 94
MNRGVPFRHL LLVLQLALLP AATQGEQKLI SEEDLKKVVL GKKGDTVELT CTASQKKSIQ    60
FHWKNSNQIK ILGNQGSFLT KGPSKLNDRA DSRRSLWDQG NFPLIIKNLK IEDSDTYICE   120
VEDQKEEVQL LVFGLTANSD THLLQGQSLT LTLESPPGSS PSVQCRSPRG KNIQGGKTLS   180
VSQLELQDSG TWTCTVLQNQ KKVEFKIDIV VLAFQKASSI VYKKEGEQVE FSFPLAFTVE   240
KLTGSGELWW QAERASSSKS WITFDLKNKE VSVKRVTQDP KLQMGKKLPL HLTLPQALPQ   300
YAGSGNLTLA LEAKTGKLHQ EVNLVVMRAT QLQKNLTCEV WGPTSPKLML SLKLENKEAK   360
VSKREKAVWV LNPEAGMWQC LLSDSGQVLL ESNIKVLPTW STPVQPMALI VLGGVAGLLL   420
FIGLGIFFCV RCRHRRRQAE RMSQIKRLLS EKKTCQCPHR FQKTCSPIRS KRSRLLHSDY   480
MNMTPRRPGP TRKHYQPYAP PRDFAAYRSK KVAKKPTNKA PHPKQEPQEI NFPDDLPGSN   540
TAAPVQETLH GCQPVTQEDG KESRISVQER Q                                 571

SEQ ID NO: 95           moltype = AA  length = 488
FEATURE                 Location/Qualifiers
REGION                  1..190
                        note = synthetic construct
source                  1..488
                        mol_type = protein
                        organism = synthetic construct
SEQUENCE: 95
MALPVTALLL PLALLLHAAR PEQKLISEED LSQFRVSPLD RTWNLGETVE LKCQVLLSNP    60
TSGCSWLFQP RGAAASPTFL LYLSQNKPKA AEGLDTQRFS GKRLGDTFVL TLSDFRRENE   120
GYYFCSALSN SIMYFSHFVP VFLPAKPTTT PAPRPPTPAP TIASQPLSLR PEACRPAAGG   180
AVHTRGLDFA CDIYIWAPLA GTCGVLLLSL VITLYCNHRN RRRVCKCPRP VVKSGDKPSL   240
SARYVRAKRG SGEGRGSLLT CGDVEENPGP MRPRLWLLLA AQLTVLHGNS VDYKDDDDKL   300
QQTPAYIKVQ TNKMVMLSCE AKISLSNMRI YWLRQRQAPS SDSHHEFLAL WDSAKGTIHG   360
EEVEQEKIAV FRDASRFILN LTSVKPEDSG IYFCMIVGSP ELTFGKGTQL SVVDFLPTTA   420
QPTKKSTLKK RVCRLPRPET QKGPLCSPIT LGLLVAGVLV LLVSLGVAIH LCCRRRRARL   480
RFMKQFYK                                                            488

SEQ ID NO: 96           moltype = AA  length = 694
FEATURE                 Location/Qualifiers
REGION                  1..209
                        note = synthetic construct
source                  1..694
                        mol_type = protein
                        organism = synthetic construct
SEQUENCE: 96
MALPVTALLL PLALLLHAAR PEQKLISEED LSQFRVSPLD RTWNLGETVE LKCQVLLSNP    60
TSGCSWLFQP RGAAASPTFL LYLSQNKPKA AEGLDTQRFS GKRLGDTFVL TLSDFRRENE   120
GYYFCSALSN SIMYFSHFVP VFLPAKPTTT PAPRPPTPAP TIASQPLSLR PEACRPAAGG   180
AVHTRGLDFA CDIYIWAPLA GTCGVLLLSL VITLYCNHRN RRRVCKCPRP VVKSGDKPSL   240
SARYVRSKRS RLLHSDYMNM TPRRPGPTRK HYQPYAPPRD FAAYRSKKVA KKPTNKAPHP   300
KQEPQEINFP DDLPGSNTAA PVQETLHGCQ PVTQEDGKES RISVQERQRA KRGSGEGRGS   360
LLTCGDVEEN PGPMRPRLWL LLAAQLTVLH GNSVDYKDDD DKLQQTPAYI KVQTNKMVML   420
SCEAKISLSN MRIYWLRQRQ APSSDSHHEF LALWDSAKGT IHGEEVEQEK IAVFRDASRF   480
ILNLTSVKPE DSGIYFCMIV GSPELTFGKG TQLSVVDFLP TTAQPTKKST LKKRVCRLPR   540
PETQKGPLCS PITLGLLVAG VLVLLVSLGV AIHLCCRRRR ARLRFMKQFY KRSKRSRLLH   600
SDYMNMTPRR PGPTRKHYQP YAPPRDFAAY RSKKVAKKPT NKAPHPKQEP QEINFPDDLP   660
GSNTAAPVQE TLHGCQPVTQ EDGKESRISV QERQ                              694

SEQ ID NO: 97           moltype = AA  length = 221
FEATURE                 Location/Qualifiers
REGION                  1..190
                        note = synthetic construct
source                  1..221
                        mol_type = protein
                        organism = synthetic construct
```

```
SEQUENCE: 97
MALPVTALLL PLALLLHAAR PEQKLISEED LELTDTLQAE TDQLEDEKSA LQTEIANLLK    60
EKEKLEFILA AHNCTYGCTG PGLEGCPTNG PKIPSIATGM VGALLLLLVV ALGIGLFMRS   120
KRSRLLHSDY MNMTPRRPGP TRKHYQPYAP PRDFAAYRSK KVAKKPTNKA PHPKQEPQEI   180
NFPDDLPGSN TAAPVQETLH GCQPVTQEDG KESRISVQER Q                      221

SEQ ID NO: 98           moltype = AA  length = 202
FEATURE                 Location/Qualifiers
REGION                  1..202
                        note = synthetic construct
source                  1..202
                        mol_type = protein
                        organism = synthetic construct
SEQUENCE: 98
MALPVTALLL PLALLLHAAR PEQKLISEED LELTDTLQAE TDQLEDEKSA LQTEIANLLK    60
EKEKLEFILA AHFWVLVVVG GVLACYSLLV TVAFIIFWVR SKRSRLLHSD YMNMTPRRPG   120
PTRKHYQPYA PPRDFAAYRS KKVAKKPTNK APHPKQEPQE INFPDDLPGS NTAAPVQETL   180
HGCQPVTQED GKESRISVQE RQ                                           202

SEQ ID NO: 99           moltype = AA  length = 209
FEATURE                 Location/Qualifiers
REGION                  1..209
                        note = synthetic construct
source                  1..209
                        mol_type = protein
                        organism = synthetic construct
SEQUENCE: 99
MALPVTALLL PLALLLHAAR PEQKLISEED LLEEKVKTLK AQNSELASTA NMLREQVAQL    60
NCTYGCTGPG LEGCPTNGPK IPSIATGMVG ALLLLLVVAL GIGLFMRSKR SRLLHSDYMN   120
MTPRRPGPTR KHYQPYAPPR DFAAYRSKKV AKKPTNKAPH PKQEPQEINF PDDLPGSNTA   180
APVQETLHGC QPVTQEDGKE SRISVQERQ                                    209

SEQ ID NO: 100          moltype = AA  length = 190
FEATURE                 Location/Qualifiers
REGION                  1..183
                        note = synthetic construct
source                  1..190
                        mol_type = protein
                        organism = synthetic construct
SEQUENCE: 100
MALPVTALLL PLALLLHAAR PEQKLISEED LLEEKVKTLK AQNSELASTA NMLREQVAQL    60
FWVLVVGGV LACYSLLVTV AFIIFWVRSK RSRLLHSDYM NMTPRRPGPT RKHYQPYAPP   120
RDFAAYRSKK VAKKPTNKAP HPKQEPQEIN FPDDLPGSNT AAPVQETLHG CQPVTQEDGK   180
ESRISVQERQ                                                         190

SEQ ID NO: 101          moltype = AA  length = 209
FEATURE                 Location/Qualifiers
REGION                  1..209
                        note = synthetic construct
source                  1..209
                        mol_type = protein
                        organism = synthetic construct
SEQUENCE: 101
MALPVTALLL PLALLLHAAR PEQKLISEED LETQHKVLEL TAENERLQKK VEQLSRELST    60
NCTYGCTGPG LEGCPTNGPK IPSIATGMVG ALLLLLVVAL GIGLFMRSKR SRLLHSDYMN   120
MTPRRPGPTR KHYQPYAPPR DFAAYRSKKV AKKPTNKAPH PKQEPQEINF PDDLPGSNTA   180
APVQETLHGC QPVTQEDGKE SRISVQERQ                                    209

SEQ ID NO: 102          moltype = AA  length = 190
FEATURE                 Location/Qualifiers
REGION                  1..190
                        note = synthetic construct
source                  1..190
                        mol_type = protein
                        organism = synthetic construct
SEQUENCE: 102
MALPVTALLL PLALLLHAAR PEQKLISEED LETQHKVLEL TAENERLQKK VEQLSRELST    60
FWVLVVGGV LACYSLLVTV AFIIFWVRSK RSRLLHSDYM NMTPRRPGPT RKHYQPYAPP   120
RDFAAYRSKK VAKKPTNKAP HPKQEPQEIN FPDDLPGSNT AAPVQETLHG CQPVTQEDGK   180
ESRISVQERQ                                                         190

SEQ ID NO: 103          moltype = AA  length = 781
FEATURE                 Location/Qualifiers
REGION                  1..781
                        note = synthetic construct
source                  1..781
                        mol_type = protein
                        organism = synthetic construct
SEQUENCE: 103
```

```
MRPSGTAGAA LLALLAALCP ASRAEQKLIS EEDLLEEKKV CQGTSNKLTQ LGTFEDHFLS   60
LQRMFNNCEV VLGNLEITYV QRNYDLSFLK TIQEVAGYVL IALNTVERIP LENLQIIRGN  120
MYYENSYALA VLSNYDANKT GLKELPMRNL QEILHGAVRF SNNPALCNVE SIQWRDIVSS  180
DFLSNMSMDF QNHLGSCQKC DPSCPNGSCW GAGEENCQKL TKIICAQQCS GRCRGKSPSD  240
CCHNQCAAGC TGPRESDCLV CRKFRDEATC KDTCPPLMLY NPTTYQMDVN PEGKYSFGAT  300
CVKKCPRNYV VTDHGSCVRA CGADSYEMEE DGVRKCKKCE GPCRKVCNGI GIGEFKDSLS  360
INATNIKHFK NCTSISGDLH ILPVAFRGDS FTHTPPLDPQ ELDILKTVKE ITGFLLIQAW  420
PENRTDLHAF ENLEIIRGRT KQHGQFSLAV VSLNITSLGL RSLKEISDGD VIISGNKNLC  480
YANTINWKKL FGTSGQKTKI ISNRGENSCK ATGQVCHALC SPEGCWGPEP RDCVSCRNVS  540
RGRECVDKCN LLEGEPREFV ENSECIQCHP ECLPQAMNIT CTGRGPDNCI QCAHYIDGPH  600
CVKTCPAGVM GENNTLVWKY ADAGHVCHLC HPNCTYGCTG PGLEGCPTNG PKIPSIATGM  660
VGALLLLLVV ALGIGLFMRS KRSRLLHSDY MNMTPRRPGP TRKHYQPYAP PRDFAAYRSK  720
KVAKKPTNKA PHPKQEPQEI NFPDDLPGSN TAAPVQETLH GCQPVTQEDG KESRISVQER  780
Q                                                                781

SEQ ID NO: 104           moltype = AA  length = 324
FEATURE                  Location/Qualifiers
REGION                   1..324
                         note = synthetic construct
source                   1..324
                         mol_type = protein
                         organism = synthetic construct
SEQUENCE: 104
MRPSGTAGAA LLALLAALCP ASRAEQKLIS EEDLGTSGQK TKIISNRGEN SCKATGQVCH   60
ALCSPEGCWG PEPRDCVSCR NVSRGRECVD KCNLLEGEPR EFVENSECIQ CHPECLPQAM  120
NITCTGRGPD NCIQCAHYID GPHCVKTCPA GVMGENNTLV WKYADAGHVC HLCHPNCTYG  180
CTGPGLEGCP TNGPKIPSIA TGMVGALLLL LVVALGIGLF MRSKRSRLLH SDYMNMTPRR  240
PGPTRKHYQP YAPPRDFAAY RSKKVAKKPT NKAPHPKQEP QEINFPDDLP GSNTAAPVQE  300
TLHGCQPVTQ EDGKESRISV QERQ                                        324

SEQ ID NO: 105           moltype = AA  length = 183
FEATURE                  Location/Qualifiers
REGION                   1..183
                         note = synthetic construct
source                   1..183
                         mol_type = protein
                         organism = synthetic construct
SEQUENCE: 105
MRPSGTAGAA LLALLAALCP ASRAEQKLIS EEDLNCTYGC TGPGLEGCPT NGPKIPSIAT   60
GMVGALLLLL VVALGIGLFM RSKRSRLLHS DYMNMTPRRP GPTRKHYQPY APPRDFAAYR  120
SKKVAKKPTN KAPHPKQEPQ EINFPDDLPG SNTAAPVQET LHGCQPVTQE DGKESRISVQ  180
ERQ                                                               183

SEQ ID NO: 106           moltype = AA  length = 788
FEATURE                  Location/Qualifiers
REGION                   1..298
                         note = synthetic construct
source                   1..788
                         mol_type = protein
                         organism = synthetic construct
SEQUENCE: 106
MELAALCRWG LLLALLPPGA ASEQKLISEE DLTQVCTGTD MKLRLPASPE THLDMLRHLY   60
QGCQVVQGNL ELTYLPTNAS LSFLQDIQEV QGYVLIAHNQ VRQVPLQRLR IVRGTQLFED  120
NYALAVLDNG DPLNNTTPVT GASPGGLREL QLRSLTEILK GGVLIQRNPQ LCYQDTILWK  180
DIFHKNNQLA LTLIDTNRSR ACHPCSPMCK GSRCWGESSE DCQSLTRTVC AGGCARCKGP  240
LPTDCCHEQC AAGCTGPKHS DCLACLHFNH SGICELHCPA LVTYNTDTFE SMPNEGRYT  300
FGASCVTACP YNYLSTDVGS CTLVCPLHNQ EVTAEDGTQR CEKCSKPCAR VCYGLGMEHL  360
REVRAVTSAN IQEFAGCKKI FGSLAFLPES FDGDPASNTA PLQPEQLQVF ETLEEITGYL  420
YISAWPDSLP DLSVFQNLQV IRGRILHNGA YSLTLQGLGI SWLGLRSLRE LGSGLALIHH  480
NTHLCFVHTV PWDQLFRNPH QALLHTANRP EDECVGEGLA CHQLCARGHC WGPGPTQCVN  540
CSQFLRGQEC VEECRVLQGL PREYVNARHC LPCHPECPQP NGSVTCFGPE ADQCVACAHY  600
KDPPFCVARC PSGVKPDLSY MPIWKFPDEE GACQPCPINC THSCVDLDDK GCPAEQRASP  660
LTSIISAVVG ILLVVVLGVV FGILIRSKRS RLLHSDYMNM TPRRPGPTRK HYQPYAPPRD  720
FAAYRSKKVA KKPTNKAHPH KQEPQEINFP DDLPGSNTAA PVQETLHGCQ PVTQEDGKES  780
RISVQERQ                                                          788

SEQ ID NO: 107           moltype = AA  length = 788
FEATURE                  Location/Qualifiers
REGION                   1..298
                         note = synthetic construct
source                   1..788
                         mol_type = protein
                         organism = synthetic construct
SEQUENCE: 107
MELAALCRWG LLLALLPPGA ASEQKLISEE DLTQVCTGTD MKLRLPASPE THLDMLRHLY   60
QGCQVVQGNL ELTYLPTNAS LSFLQDIQEV QGYVLIAHNQ VRQVPLQRLR IVRGTQLFED  120
NYALAVLDNG DPLNNTTPVT GASPGGLREL QLRSLTEILK GGVLIQRNPQ LCYQDTILWK  180
DIFHKNNQLA LTLIDTNRSR ACHPCSPMCK GSRCWGESSE DCQSLTRTVC AGGCARCKGP  240
LPTDCCHEQC AAGCTGPKHS DCLACLHFNH SGICELHCPA LVTYNTDTFE SMPNEGRYT  300
```

```
FGASCVTACP YNYLSTDVGS CTLVCPLHNQ EVTAEDGTQR CEKCSKPCAR VCYGLGMEHL    360
REVRAVTSAN IQEFAGCKKI FGSLAFLPES FDGDPASNTA PLQPEQLQVF ETLEEITGYL    420
YISAWPDSLP DLSVFQNLQV IRGRILHNGA YSLTLQGLGI SWLGLRSLRE LGSGLALIHH    480
NTHLCFVHTV PWDQLFRNPH QALLHTANRP EDECVGEGLA CHQLCARGHC WGPGPTQCVN    540
CSQFLRGQEC VEECRVLQGL PREYVNARHC LPCHPECQPQ NGSVTCFGPE ADQCVACAHY    600
KDPPFCVARC PSGVKPDLSY MPIWKFPDEE GACQPCPINC THSCVDLDDK GCPAEQRASP    660
LTSIISAVEG ILLVVVLGVV FGILIRSKRS RLLHSDYMNM TPRRPGPTRK HYQPYAPPRD    720
FAAYRSKKVA KKPTNKAPHP KQEPQEINFP DDLPGSNTAA PVQETLHGCQ PVTQEDGKES    780
RISVQERQ                                                            788

SEQ ID NO: 108         moltype = AA  length = 788
FEATURE                Location/Qualifiers
REGION                 1..298
                       note = synthetic construct
source                 1..788
                       mol_type = protein
                       organism = synthetic construct
SEQUENCE: 108
MELAALCRWG LLLALLPPGA ASEQKLISEE DLTQVCTGTD MKLRLPASPE THLDMLRHLY     60
QGCQVVQGNL ELTYLPTNAS LSFLQDIQEV QGYVLIAHNQ VRQVPLQRLR IVRGTQLFED    120
NYALAVLDNG DPLNNTTPVT GASPGGLREL QLRSLTEILK GGVLIQRNPQ LCYQDTILWK    180
DIFHKNNQLA LTLIDTNRSR ACHPCSPMCK GSRCWGESSE DCQSLTRTVC AGGCARCKGP    240
LPTDCCHEQC AAGCTGPKHS DCLACLHFNH SGICELHCPA LVTYNTDTFE SMPNPEGRYT    300
FGASCVTACP YNYLSTDVGS CTLVCPLHNQ EVTAEDGTQR CEKCSKPCAR VCYGLGMEHL    360
REVRAVTSAN IQEFAGCKKI FGSLAFLPES FDGDPASNTA PLQPEQLQVF ETLEEITGYL    420
YISAWPDSLP DLSVFQNLQV IRGRILHNGA YSLTLQGLGI SWLGLRSLRE LGSGLALIHH    480
NTHLCFVHTV PWDQLFRNPH QALLHTANRP EDECVGEGLA CHQLCARGHC WGPGPTQCVN    540
CSQFLRGQEC VEECRVLQGL PREYVNARHC LPCHPECQPQ NGSVTCFGPE ADQCVACAHY    600
KDPPFCVARC PSGVKPDLSY MPIWKFPDEE GACQPCPINC THSCVDLDDK GCPAEQRASP    660
LTSIISAVVD ILLVVVLGVV FGILIRSKRS RLLHSDYMNM TPRRPGPTRK HYQPYAPPRD    720
FAAYRSKKVA KKPTNKAPHP KQEPQEINFP DDLPGSNTAA PVQETLHGCQ PVTQEDGKES    780
RISVQERQ                                                            788

SEQ ID NO: 109         moltype = AA  length = 788
FEATURE                Location/Qualifiers
REGION                 1..158
                       note = synthetic construct
source                 1..788
                       mol_type = protein
                       organism = synthetic construct
SEQUENCE: 109
MELAALCRWG LLLALLPPGA ASEQKLISEE DLTQVCTGTD MKLRLPASPE THLDMLRHLY     60
QGCQVVQGNL ELTYLPTNAS LSFLQDIQEV QGYVLIAHNQ VRQVPLQRLR IVRGTQLFED    120
NYALAVLDNG DPLNNTTPVT GASPGGLREL QLRSLTEILK GGVLIQRNPQ LCYQDTILWK    180
DIFHKNNQLA LTLIDTNRSR ACHPCSPMCK GSRCWGESSE DCQSLTRTVC AGGCARCKGP    240
LPTDCCHEQC AAGCTGPKHS DCLACLHFNH SGICELHCPA LVTYNTDTFE SMPNPEGRYT    300
FGASCVTACP YNYLSTDVGS CTLVCPLHNQ EVTAEDGTQR CEKCSKPCAR VCYGLGMEHL    360
REVRAVTSAN IQEFAGCKKI FGSLAFLPES FDGDPASNTA PLQPEQLQVF ETLEEITGYL    420
YISAWPDSLP DLSVFQNLQV IRGRILHNGA YSLTLQGLGI SWLGLRSLRE LGSGLALIHH    480
NTHLCFVHTV PWDQLFRNPH QALLHTANRP EDECVGEGLA CHQLCARGHC WGPGPTQCVN    540
CSQFLRGQEC VEECRVLQGL PREYVNARHC LPCHPECQPQ NGSVTCFGPE ADQCVACAHY    600
KDPPFCVARC PSGVKPDLSY MPIWKFPDEE GACQPCPINC THSCVDLDDK GCPAEQRASP    660
LTSIISAVVR ILLVVVLGVV FGILIRSKRS RLLHSDYMNM TPRRPGPTRK HYQPYAPPRD    720
FAAYRSKKVA KKPTNKAPHP KQEPQEINFP DDLPGSNTAA PVQETLHGCQ PVTQEDGKES    780
RISVQERQ                                                            788

SEQ ID NO: 110         moltype = AA  length = 298
FEATURE                Location/Qualifiers
REGION                 1..158
                       note = synthetic construct
source                 1..298
                       mol_type = protein
                       organism = synthetic construct
SEQUENCE: 110
MELAALCRWG LLLALLPPGA ASEQKLISEE DLQLCARGHC WGPGPTQCVN CSQFLRGQEC     60
VEECRVLQGL PREYVNARHC LPCHPECQPQ NGSVTCFGPE ADQCVACAHY KDPPFCVARC    120
PSGVKPDLSY MPIWKFPDEE GACQPCPINC THSCVDLDDK GCPAEQRASP LTSIISAVVG    180
ILLVVVLGVV FGILIRSKRS RLLHSDYMNM TPRRPGPTRK HYQPYAPPRD FAAYRSKKVA    240
KKPTNKAPHP KQEPQEINFP DDLPGSNTAA PVQETLHGCQ PVTQEDGKES RISVQERQ      298

SEQ ID NO: 111         moltype = AA  length = 298
FEATURE                Location/Qualifiers
REGION                 1..158
                       note = synthetic construct
source                 1..298
                       mol_type = protein
                       organism = synthetic construct
SEQUENCE: 111
MELAALCRWG LLLALLPPGA ASEQKLISEE DLQLCARGHC WGPGPTQCVN CSQFLRGQEC     60
```

```
VEECRVLQGL PREYVNARHC LPCHPECQPQ NGSVTCFGPE ADQCVACAHY KDPPFCVARC    120
PSGVKPDLSY MPIWKFPDEE GACQPCPINC THSCVDLDDK GCPAEQRASP LTSIISAVEG    180
ILLVVVLGVV FGILIRSKRS RLLHSDYMNM TPRRPGPTRK HYQPYAPPRD FAAYRSKKVA    240
KKPTNKAPHP KQEPQEINFP DDLPGSNTAA PVQETLHGCQ PVTQEDGKES RISVQERQ      298

SEQ ID NO: 112          moltype = AA  length = 298
FEATURE                 Location/Qualifiers
REGION                  1..158
                        note = synthetic construct
source                  1..298
                        mol_type = protein
                        organism = synthetic construct
SEQUENCE: 112
MELAALCRWG LLLALLPPGA ASEQKLISEE DLQLCARGHC WGPGPTQCVN CSQFLRGQEC    60
VEECRVLQGL PREYVNARHC LPCHPECQPQ NGSVTCFGPE ADQCVACAHY KDPPFCVARC    120
PSGVKPDLSY MPIWKFPDEE GACQPCPINC THSCVDLDDK GCPAEQRASP LTSIISAVVD    180
ILLVVVLGVV FGILIRSKRS RLLHSDYMNM TPRRPGPTRK HYQPYAPPRD FAAYRSKKVA    240
KKPTNKAPHP KQEPQEINFP DDLPGSNTAA PVQETLHGCQ PVTQEDGKES RISVQERQ      298

SEQ ID NO: 113          moltype = AA  length = 298
FEATURE                 Location/Qualifiers
REGION                  1..298
                        note = synthetic construct
source                  1..298
                        mol_type = protein
                        organism = synthetic construct
SEQUENCE: 113
MELAALCRWG LLLALLPPGA ASEQKLISEE DLQLCARGHC WGPGPTQCVN CSQFLRGQEC    60
VEECRVLQGL PREYVNARHC LPCHPECQPQ NGSVTCFGPE ADQCVACAHY KDPPFCVARC    120
PSGVKPDLSY MPIWKFPDEE GACQPCPINC THSCVDLDDK GCPAEQRASP LTSIISAVVR    180
ILLVVVLGVV FGILIRSKRS RLLHSDYMNM TPRRPGPTRK HYQPYAPPRD FAAYRSKKVA    240
KKPTNKAPHP KQEPQEINFP DDLPGSNTAA PVQETLHGCQ PVTQEDGKES RISVQERQ      298

SEQ ID NO: 114          moltype = AA  length = 158
FEATURE                 Location/Qualifiers
REGION                  1..158
                        note = synthetic construct
source                  1..158
                        mol_type = protein
                        organism = synthetic construct
SEQUENCE: 114
MELAALCRWG LLLALLPPGA ASEQKLISEE DLSIISAVVG ILLVVVLGVV FGILIRSKRS    60
RLLHSDYMNM TPRRPGPTRK HYQPYAPPRD FAAYRSKKVA KKPTNKAPHP KQEPQEINFP    120
DDLPGSNTAA PVQETLHGCQ PVTQEDGKES RISVQERQ                            158

SEQ ID NO: 115          moltype = AA  length = 158
FEATURE                 Location/Qualifiers
REGION                  1..158
                        note = synthetic construct
source                  1..158
                        mol_type = protein
                        organism = synthetic construct
SEQUENCE: 115
MELAALCRWG LLLALLPPGA ASEQKLISEE DLSIISAVEG ILLVVVLGVV FGILIRSKRS    60
RLLHSDYMNM TPRRPGPTRK HYQPYAPPRD FAAYRSKKVA KKPTNKAPHP KQEPQEINFP    120
DDLPGSNTAA PVQETLHGCQ PVTQEDGKES RISVQERQ                            158

SEQ ID NO: 116          moltype = AA  length = 158
FEATURE                 Location/Qualifiers
REGION                  1..158
                        note = synthetic construct
source                  1..158
                        mol_type = protein
                        organism = synthetic construct
SEQUENCE: 116
MELAALCRWG LLLALLPPGA ASEQKLISEE DLSIISAVVD ILLVVVLGVV FGILIRSKRS    60
RLLHSDYMNM TPRRPGPTRK HYQPYAPPRD FAAYRSKKVA KKPTNKAPHP KQEPQEINFP    120
DDLPGSNTAA PVQETLHGCQ PVTQEDGKES RISVQERQ                            158

SEQ ID NO: 117          moltype = AA  length = 158
FEATURE                 Location/Qualifiers
REGION                  1..158
                        note = synthetic construct
source                  1..158
                        mol_type = protein
                        organism = synthetic construct
SEQUENCE: 117
MELAALCRWG LLLALLPPGA ASEQKLISEE DLSIISAVVR ILLVVVLGVV FGILIRSKRS    60
RLLHSDYMNM TPRRPGPTRK HYQPYAPPRD FAAYRSKKVA KKPTNKAPHP KQEPQEINFP    120
```

```
DDLPGSNTAA PVQETLHGCQ PVTQEDGKES RISVQERQ                              158

SEQ ID NO: 118          moltype = AA   length = 546
FEATURE                 Location/Qualifiers
REGION                  1..543
                        note = synthetic construct
source                  1..546
                        mol_type = protein
                        organism = synthetic construct
SEQUENCE: 118
MALPVTALLL PLALLLHAAR PEQKLISEED LQEQLVESGG RLVTPGTPLT LTCTASGFSL    60
GSDFMSWVRQ APGKGLEWIG YIDPRSDIPY YASWAKGRFT ISKTSTTVDL KITSPTTEDT   120
ATYFCARDLN AGYFNGIFYI WGPGTLVTVS SGGGGSGGGG SGGGGSELVM TQTPSSVSAA   180
VGDTVTINCQ ASETVATLLA WYQQKPGQPP KLLIYGASNL ESGVPSRFRG SGSGTEFTLT   240
ISGMKAEDAA TYYCQYGYIS TGSNTFGAGT NVEIKAAAGS GGSGILVKQS PMLVAYDNAV   300
NLSCKYSYNL FSREFRASLH KGLDSAVEVC VVYGNYSQQL QVYSKTGFNC DGKLGNESVT   360
FYLQNLYVNQ TDIYFCKIEV MYPPPYLDNE KSNGTIIHVK GKHLCPSLF PGPSKPFWVL   420
VVVGGVLACY SLLVTAFII FWVRSKRSRL LHSDYMNMTP RRPGPTRKHY QPYAPPRDFA   480
AYRSKKVAKK PTNKAPHPKQ EPQEINFPDD LPGSNTAAPV QETLHGCQPV TQEDGKESRI   540
SVQERQ                                                              546

SEQ ID NO: 119          moltype = AA   length = 546
FEATURE                 Location/Qualifiers
REGION                  1..226
                        note = synthetic construct
source                  1..546
                        mol_type = protein
                        organism = synthetic construct
SEQUENCE: 119
MALPVTALLL PLALLLHAAR PEQKLISEED LELVMTQTPS SVSAAVGDTV TINCQASETV    60
ATLLAWYQQK PGQPPKLLIY GASNLESGVP SRFRGSGSGT EFTLTISGMK AEDAATYYCQ   120
YGYISTGSNT FGAGTNVEIK GGGGSGGGGS GGGGSQEQLV ESGGRLVTPG TPLTLTCTAS   180
GFSLGSDFMS WVRQAPGKGL EWIGYIDPRS DIPYYASWAK GRFTISKTST TVDLKITSPT   240
TEDTATYFCA RDLNAGYFNG IFYIWGPGTL VTVSSAAAGS GGSGILVKQS PMLVAYDNAV   300
NLSCKYSYNL FSREFRASLH KGLDSAVEVC VVYGNYSQQL QVYSKTGFNC DGKLGNESVT   360
FYLQNLYVNQ TDIYFCKIEV MYPPPYLDNE KSNGTIIHVK GKHLCPSLF PGPSKPFWVL   420
VVVGGVLACY SLLVTAFII FWVRSKRSRL LHSDYMNMTP RRPGPTRKHY QPYAPPRDFA   480
AYRSKKVAKK PTNKAPHPKQ EPQEINFPDD LPGSNTAAPV QETLHGCQPV TQEDGKESRI   540
SVQERQ                                                              546

SEQ ID NO: 120          moltype = AA   length = 548
FEATURE                 Location/Qualifiers
REGION                  1..154
                        note = synthetic construct
source                  1..548
                        mol_type = protein
                        organism = synthetic construct
SEQUENCE: 120
MALPVTALLL PLALLLHAAR PEQKLISEED LQEQLVESGG RLVTPGTPLT LTCTASGFSL    60
GSDFMSWVRQ APGKGLEWIG YIDPRSDIPY YASWAKGRFT ISKTSTTVDL KITSPTTEDT   120
ATYFCARDLN AGYFNGIFYI WGPGTLVTVS SGGGGSELDM TQTPSSTSEP             180
VGGTVTINCQ ASQTISSYLS WYQQKPGHPP KLLIYDASDL ASGVPSRFSG SRSGTQFTLT   240
ISGVQCDDAA TYYCLGVYDY RSDDGAAFGG GTELEILAAA GSGGSGILVK QSPMLVAYDN   300
AVNLSCKYSY NLFSREFRAS LHKGLDSAVE VCVVYGNYSQ QLQVYSKTGF NCDGKLGNES   360
VTFYLQNLYV NQTDIYFCKI EVMYPPPYLD NEKSNGTIIH VKGKHLCPSP LFPGPSKPFW   420
VLVVVGGVLA CYSLLVTAF IIFWVRSKRS RLLHSDYMNM TPRRPGPTRK HYQPYAPPRD   480
FAAYRSKKVA KKPTNKAPHP KQEPQEINFP DDLPGSNTAA PVQETLHGCQ PVTQEDGKES   540
RISVQERQ                                                            548

SEQ ID NO: 121          moltype = AA   length = 548
FEATURE                 Location/Qualifiers
REGION                  1..386
                        note = synthetic construct
source                  1..548
                        mol_type = protein
                        organism = synthetic construct
SEQUENCE: 121
MALPVTALLL PLALLLHAAR PEQKLISEED LQEQLVESGG RLVTPGTPLT LTCTASGFSL    60
GSDFMSWVRQ APGKGLEWIG YIDPRSDIPY YASWAKGRFT ISKTSTTVDL KITSPTTEDT   120
ATYFCARDLN AGYFNGIFYI WGPGTLVTVS SGGGGSGGGG SGGGGSELDM TQTPSSTSEP   180
VGGTVTINCQ ASQTISSYLS WYQQKPGHPP KLLIYDASDL ASGVPSRFSG SRSGTQFTLT   240
ISGVQCDDAA TYYCLGVYDY RSDDGAAFGG GTELEILAAA GSGGSGILVK QSPMLVAYDN   300
AVNLSCKYSY NLFSREFRAS LHKGLDSAVE VCVVYGNYSQ QLQVYSKTGF NCDGKLGNES   360
VTFYLQNLYV NQTDIYFCKI EVMYPPPYLD NEKSNGTIIH VKGKHLCPSP LFPGPSKPFW   420
VLVVVGGVLA CYSLLVTAF IIFWVRSKRS RLLHSDYMNM TPRRPGPTRK HYQPYAPPRD   480
FAAYRSKKVA KKPTNKAPHP KQEPQEINFP DDLPGSNTAA PVQETLHGCQ PVTQEDGKES   540
RISVQERQ                                                            548

SEQ ID NO: 122          moltype = AA   length = 543
```

```
FEATURE                 Location/Qualifiers
REGION                  1..160
                        note = synthetic construct
source                  1..543
                        mol_type = protein
                        organism = synthetic construct
SEQUENCE: 122
MALPVTALLL PLALLLHAAR PEQKLISEED LQSLEESGGR LVTPGTPLTL TCTVSGFSLS    60
TNDMNWVRQA PGKGLEWIGV IYSDDTPDYA TWAKGRFTIS RTSTTVDLKI TSPTTEDTAT   120
YFCARGHYDS AVYAYALNIW GPGTLVTVSS GGGGSGGGGS GGGGSELVMT QTPSSVSAAV   180
GGTVTITCQA SQSLSNLLAW YQQKPGQPPK LLIYGASNLE SGVPSRFRGS GSGTDFTLTI   240
SGMKAEDAAT YYCQGGHYSG LTFGNGTNVE IKAAAGSGGS GILVKQSPML VAYDNAVNLS   300
CKYSYNLFSR EFRASLHKGL DSAVEVCVVY GNYSQQLQVY SKTGFNCDGK LGNESVTFYL   360
QNLYVNQTDI YFCKIEVMYP PPYLDNEKSN GTIIHVKGKH LCPSPLFPGP SKPFWVLVVV   420
GGVLACYSLL VTVAFIIFWV RSKRSRLLHS DYMNMTPRRP GPTRKHYQPY APPRDFAAYR   480
SKKVAKKPTN KAPHPKQEPQ EINFPDDLPG SNTAAPVQET LHGCQPVTQE DGKESRISVQ   540
ERQ                                                                 543

SEQ ID NO: 123          moltype = AA  length = 543
FEATURE                 Location/Qualifiers
REGION                  1..543
                        note = synthetic construct
source                  1..543
                        mol_type = protein
                        organism = synthetic construct
SEQUENCE: 123
MALPVTALLL PLALLLHAAR PEQKLISEED LELVMTQTPS SVSAAVGGTV TITCQASQSL    60
SNLLAWYQQK PGQPPKLLIY GASNLESGVP SRFRGSGSGT DFTLTISGMK AEDAATYYCQ   120
GGHYSGLTFG NGTNVEIKGG GGSGGGGSGG GGSQSLEESG GRLVTPGTPL TLTCTVSGFS   180
LSTNDMNWVR QAPGKGLEWI GVIYSDDTPD YATWAKGRFT ISRTSTTVDL KITSPTTEDT   240
ATYFCARGHY DSAVYAYALN IWGPGTLVTV SSAAAGSGGS GILVKQSPML VAYDNAVNLS   300
CKYSYNLFSR EFRASLHKGL DSAVEVCVVY GNYSQQLQVY SKTGFNCDGK LGNESVTFYL   360
QNLYVNQTDI YFCKIEVMYP PPYLDNEKSN GTIIHVKGKH LCPSPLFPGP SKPFWVLVVV   420
GGVLACYSLL VTVAFIIFWV RSKRSRLLHS DYMNMTPRRP GPTRKHYQPY APPRDFAAYR   480
SKKVAKKPTN KAPHPKQEPQ EINFPDDLPG SNTAAPVQET LHGCQPVTQE DGKESRISVQ   540
ERQ                                                                 543

SEQ ID NO: 124          moltype = AA  length = 226
FEATURE                 Location/Qualifiers
REGION                  1..162
                        note = synthetic construct
source                  1..226
                        mol_type = protein
                        organism = synthetic construct
SEQUENCE: 124
MYGKIIFVLL LSEIVSISAE QKLISEEDLS STTGVAMHTS TSSSVTKSYI SSQTNDTHKR    60
DTYAATPRAH EVSEISVRTV YPPEEETGER VQLAHHFSEP EITLIIFGVM AGVIGTILLI   120
SYGRSKRSRL LHSDYMNMTP RRPGPTRKHY QPYAPPRDFA AYRSKKVAKK PTNKAPHPKQ   180
EPQEINFPDD LPGSNTAAPV QETLHGCQPV TQEDGKESRI SVQERQ                  226

SEQ ID NO: 125          moltype = AA  length = 154
FEATURE                 Location/Qualifiers
REGION                  1..154
                        note = synthetic construct
source                  1..154
                        mol_type = protein
                        organism = synthetic construct
SEQUENCE: 125
MYGKIIFVLL LSEIVSISAE QKLISEEDLI TLIIFGVMAG VIGTILLISY GRSKRSLLH     60
SDYMNMTPRR PGPTRKHYQP YAPPRDFAAY RSKKVAKKPT NKAPHPKQEP QEINFPDDLP   120
GSNTAAPVQE TLHGCQPVTQ EDGKESRISV QERQ                               154

SEQ ID NO: 126          moltype = AA  length = 386
FEATURE                 Location/Qualifiers
REGION                  1..162
                        note = synthetic construct
source                  1..386
                        mol_type = protein
                        organism = synthetic construct
SEQUENCE: 126
MDHLGASLWP QVGSLCLLLA GAAWEQKLIS EEDLAPPPNL PDPKFESKAA LLAARGPEEL    60
LCFTERLEDL VCFWEEAASA GVGPGNYSFS YQLEDEPWKL CRLHQAPTAR GAVRFWCSLP   120
TADTSSFVPL ELRVTAASGA PRYHRVIHIN EVVLLDAPVG LVARLADESG HVVLRWLPPP   180
ETPMTSHIRY EVDVSAGNGA GSVQRVEILE GRTECVLSNL RGRTRYTFAV RARMAEPSFG   240
GFWSAWSEPV SLLTPSDLDP LILTLSLILV VILVLLTVLA LLSRSKRSRL LHSDYMNMTP   300
RRPGPTRKHY QPYAPPRDFA AYRSKKVAKK PTNKAPHPKQ EPQEINFPDD LPGSNTAAPV   360
QETLHGCQPV TQEDGKESRI SVQERQ                                        386

SEQ ID NO: 127          moltype = AA  length = 160
```

```
FEATURE                 Location/Qualifiers
REGION                  1..160
                        note = synthetic construct
source                  1..160
                        mol_type = protein
                        organism = synthetic construct
SEQUENCE: 127
MDHLGASLWP QVGSLCLLLA GAAWEQKLIS EEDLLILTLS LILVVILVLL TVLALLSRSK    60
RSRLLHSDYM NMTPRRPGPT RKHYQPYAPP RDFAAYRSKK VAKKPTNKAP HPKQEPQEIN   120
FPDDLPGSNT AAPVQETLHG CQPVTQEDGK ESRISVQERQ                         160

SEQ ID NO: 128          moltype = AA  length = 628
FEATURE                 Location/Qualifiers
REGION                  1..162
                        note = synthetic construct
source                  1..628
                        mol_type = protein
                        organism = synthetic construct
SEQUENCE: 128
MPSWALFMVT SCLLLAPQNL AQVSSEQKLI SEEDLQDVSL LASDSEPLKC FSRTFEDLTC    60
FWDEEEAAPS GTYQLLYAYP REKPRACPLS SQSMPHFGTR YVCQFPDQEE VRLFFPLHLW   120
VKNVFLNQTR VLFVDSV GLPAPPSIIK AMGGSQPGEL QISWEEPAPE ISDFLRYELR      180
YGPRDPKNST GPTVIQLIAT ETCCPALQRP HSASALDQSP CAQPTMPWQD GPKQTSPSRE   240
ASALTAEGGS CLISGLQPGN SYWLQLRSEP DGISLGGSWG SWSLPVTVDL PGDAVALGLQ   300
CFTLDLKNVT CQWQQQDHAS SQGFFYHSRA RCCPRDRYPI WENCEEEEKT NPGLQTPQFS   360
RCHFKSRNDS IIHILVEVTT APGTVHSYLG SPFWIHQAVR LPTPNLHWRE ISSGHLELEW   420
QHPSSWAAQE TCYQLRYTGE GHQDWKVLEP PLGARGGTLE LRPRSRYRLQ LRARLNGPTY   480
QGPWSSWSDP TRVETATETA WISLVTALHL VLGLSAVLGL LLLRWRSKRS RLLHSDYMNM   540
TPRRPGPTRK HYQPYAPPRD FAAYRSKKVA KKPTNKAPHP KQEPQEINFP DDLPGSNTAA   600
PVQETLHGCQ PVTQEDGKES RISVQERQ                                     628

SEQ ID NO: 129          moltype = AA  length = 162
FEATURE                 Location/Qualifiers
REGION                  1..162
                        note = synthetic construct
source                  1..162
                        mol_type = protein
                        organism = synthetic construct
SEQUENCE: 129
MPSWALFMVT SCLLLAPQNL AQVSSEQKLI SEEDLISLVT ALHLVLGLSA VLGLLLLRWR    60
SKRSRLLHSD YMNMTPRRPG PTRKHYQPYA PPRDFAAYRS KKVAKKPTNK APHPKQEPQE   120
INFPDDLPGS NTAAPVQETL HGCQPVTQED GKESRISVQE RQ                      162

SEQ ID NO: 130          moltype = AA  length = 628
FEATURE                 Location/Qualifiers
REGION                  1..162
                        note = synthetic construct
source                  1..628
                        mol_type = protein
                        organism = synthetic construct
SEQUENCE: 130
MPSWALFMVT SCLLLAPQNL AQVSSEQKLI SEEDLQDVSL LASDSEPLKC FSRTFEDLTC    60
FWDEEEAAPS GTYQLLYAYP REKPRACPLS SQSMPHFGTR YVCQFPDQEE VRLFFPLHLW   120
VKNVFLNQTR VLFVDSV GLPAPPSIIK AMGGSQPGEL QISWEEPAPE ISDFLRYELR      180
YGPRDPKNST GPTVIQLIAT ETCCPALQRP HSASALDQSP CAQPTMPWQD GPKQTSPSRE   240
ASALTAEGGS CLISGLQPGN SYWLQLRSEP DGISLGGSWG SWSLPVTVDL PGDAVALGLQ   300
CFTLDLKNVT CQWQQQDHAS SQGFFYHSRA RCCPRDRYPI WENCEEEEKT NPGLQTPQFS   360
RCHFKSRNDS IIHILVEVTT APGTVHSYLG SPFWIHQAVR LPTPNLHWRE ISSGHLELEW   420
QHPSSWAAQE TCYQLRYTGE GHQDWKVLEP PLGARGGTLE LRPRSRYRLQ LRARLNGPTY   480
QGPWSSWSDP TRVETATETA WISLVTALHL VLGLNAVGL LLLRWRSKRS RLLHSDYMNM    540
TPRRPGPTRK HYQPYAPPRD FAAYRSKKVA KKPTNKAPHP KQEPQEINFP DDLPGSNTAA   600
PVQETLHGCQ PVTQEDGKES RISVQERQ                                     628

SEQ ID NO: 131          moltype = AA  length = 162
FEATURE                 Location/Qualifiers
REGION                  1..162
                        note = synthetic construct
source                  1..162
                        mol_type = protein
                        organism = synthetic construct
SEQUENCE: 131
MPSWALFMVT SCLLLAPQNL AQVSSEQKLI SEEDLISLVT ALHLVLGLNA VLGLLLLRWR    60
SKRSRLLHSD YMNMTPRRPG PTRKHYQPYA PPRDFAAYRS KKVAKKPTNK APHPKQEPQE   120
INFPDDLPGS NTAAPVQETL HGCQPVTQED GKESRISVQE RQ                      162

SEQ ID NO: 132          moltype = AA  length = 628
FEATURE                 Location/Qualifiers
REGION                  1..162
                        note = synthetic construct
```

```
source                  1..628
                        mol_type = protein
                        organism = synthetic construct
SEQUENCE: 132
MPSWALFMVT SCLLLAPQNL AQVSSEQKLI SEEDLQDVSL LASDSEPLKC FSRTFEDLTC   60
FWDEEEAAPS GTYQLLYAYP REKPRACPLS SQSMPHFGTR YVCQFPDQEE VRLFFPLHLW  120
VKNVFLNQTR TQRVLFVDSV GLPAPPSIIK AMGGSQPGEL QISWEEPAPE ISDFLRYELR  180
YGPRDPKNST GPTVIQLIAT ETCCPALQRP HSASALDQSP CAQPTMPWQD GPKQTSPSRE  240
ASALTAEGGS CLISGLQPGN SYWLQLRSEP DGISLGGSWG SWSLPVTVDL PGDAVALGLQ  300
CFTLDLKNVT CQWQQQDHAS SQGFFYHSRA RCCPRDRYPI WENCEEEEKT NPGLQTPQFS  360
RCHFKSRNDS IIHILVEVTT APGTVHSYLG SPFWIHQAVR LPTPNLHWRE ISSGHLELEW  420
QHPSSWAAQE TCYQLRYTGE GHQDWKVLEP PLGARGGTLE LRPRSRYRLQ LRARLNGPTY  480
QGPWSSWSDP TRVETATETA WISLVTALHL VLGLSAVLGL LLLRKRSKRS RLLHSDYMNM  540
TPRRPGPTRK HYQPYAPPRD FAAYRSKKVA KKPTNKAPHP KQEPQEINFP DDLPGSNTAA  600
PVQETLHGCQ PVTQEDGKES RISVQERQ                                    628

SEQ ID NO: 133          moltype = AA  length = 162
FEATURE                 Location/Qualifiers
REGION                  1..162
                        note = synthetic construct
source                  1..162
                        mol_type = protein
                        organism = synthetic construct
SEQUENCE: 133
MPSWALFMVT SCLLLAPQNL AQVSSEQKLI SEEDLISLVT ALHLVLGLSA VLGLLLLRKR   60
SKRSRLLHSD YMNMTPRRPG PTRKHYQPYA PPRDFAAYRS KKVAKKPTNK APHPKQEPQE  120
INFPDDLPGS NTAAPVQETL HGCQPVTQED GKESRISVQE RQ                    162

SEQ ID NO: 134          moltype = AA  length = 628
FEATURE                 Location/Qualifiers
REGION                  1..162
                        note = synthetic construct
source                  1..628
                        mol_type = protein
                        organism = synthetic construct
SEQUENCE: 134
MPSWALFMVT SCLLLAPQNL AQVSSEQKLI SEEDLQDVSL LASDSEPLKC FSRTFEDLTC   60
FWDEEEAAPS GTYQLLYAYP REKPRACPLS SQSMPHFGTR YVCQFPDQEE VRLFFPLHLW  120
VKNVFLNQTR TQRVLFVDSV GLPAPPSIIK AMGGSQPGEL QISWEEPAPE ISDFLRYELR  180
YGPRDPKNST GPTVIQLIAT ETCCPALQRP HSASALDQSP CAQPTMPWQD GPKQTSPSRE  240
ASALTAEGGS CLISGLQPGN SYWLQLRSEP DGISLGGSWG SWSLPVTVDL PGDAVALGLQ  300
CFTLDLKNVT CQWQQQDHAS SQGFFYHSRA RCCPRDRYPI WENCEEEEKT NPGLQTPQFS  360
RCHFKSRNDS IIHILVEVTT APGTVHSYLG SPFWIHQAVR LPTPNLHWRE ISSGHLELEW  420
QHPSSWAAQE TCYQLRYTGE GHQDWKVLEP PLGARGGTLE LRPRSRYRLQ LRARLNGPTY  480
QGPWSSWSDP TRVETATETA WISLVTALLL VLGLSAVLGL LLLRWRSKRS RLLHSDYMNM  540
TPRRPGPTRK HYQPYAPPRD FAAYRSKKVA KKPTNKAPHP KQEPQEINFP DDLPGSNTAA  600
PVQETLHGCQ PVTQEDGKES RISVQERQ                                    628

SEQ ID NO: 135          moltype = AA  length = 162
FEATURE                 Location/Qualifiers
REGION                  1..162
                        note = synthetic construct
source                  1..162
                        mol_type = protein
                        organism = synthetic construct
SEQUENCE: 135
MPSWALFMVT SCLLLAPQNL AQVSSEQKLI SEEDLISLVT ALLLVLGLSA VLGLLLLRWR   60
SKRSRLLHSD YMNMTPRRPG PTRKHYQPYA PPRDFAAYRS KKVAKKPTNK APHPKQEPQE  120
INFPDDLPGS NTAAPVQETL HGCQPVTQED GKESRISVQE RQ                    162

SEQ ID NO: 136          moltype = AA  length = 628
FEATURE                 Location/Qualifiers
REGION                  1..162
                        note = synthetic construct
source                  1..628
                        mol_type = protein
                        organism = synthetic construct
SEQUENCE: 136
MPSWALFMVT SCLLLAPQNL AQVSSEQKLI SEEDLQDVSL LASDSEPLKC FSRTFEDLTC   60
FWDEEEAAPS GTYQLLYAYP REKPRACPLS SQSMPHFGTR YVCQFPDQEE VRLFFPLHLW  120
VKNVFLNQTR TQRVLFVDSV GLPAPPSIIK AMGGSQPGEL QISWEEPAPE ISDFLRYELR  180
YGPRDPKNST GPTVIQLIAT ETCCPALQRP HSASALDQSP CAQPTMPWQD GPKQTSPSRE  240
ASALTAEGGS CLISGLQPGN SYWLQLRSEP DGISLGGSWG SWSLPVTVDL PGDAVALGLQ  300
CFTLDLKNVT CQWQQQDHAS SQGFFYHSRA RCCPRDRYPI WENCEEEEKT NPGLQTPQFS  360
RCHFKSRNDS IIHILVEVTT APGTVHSYLG SPFWIHQAVR LPTPNLHWRE ISSGHLELEW  420
QHPSSWAAQE TCYQLRYTGE GHQDWKVLEP PLGARGGTLE LRPRSRYRLQ LRARLNGPTY  480
QGPWSSWSDP TRVETATETA WISLVTALHL VLGLNAVLGL LLLRKRSKRS RLLHSDYMNM  540
TPRRPGPTRK HYQPYAPPRD FAAYRSKKVA KKPTNKAPHP KQEPQEINFP DDLPGSNTAA  600
PVQETLHGCQ PVTQEDGKES RISVQERQ                                    628
```

```
SEQ ID NO: 137            moltype = AA  length = 162
FEATURE                   Location/Qualifiers
REGION                    1..162
                          note = synthetic construct
source                    1..162
                          mol_type = protein
                          organism = synthetic construct
SEQUENCE: 137
MPSWALFMVT SCLLLAPQNL AQVSSEQKLI SEEDLISLVT ALHLVLGLNA VLGLLLLRKR    60
SKRSRLLHSD YMNMTPRRPG PTRKHYQPYA PPRDFAAYRS KKVAKKPTNK APHPKQEPQE   120
INFPDDLPGS NTAAPVQETL HGCQPVTQED GKESRISVQE RQ                      162

SEQ ID NO: 138            moltype = AA  length = 628
FEATURE                   Location/Qualifiers
REGION                    1..387
                          note = synthetic construct
source                    1..628
                          mol_type = protein
                          organism = synthetic construct
SEQUENCE: 138
MPSWALFMVT SCLLLAPQNL AQVSSEQKLI SEEDLQDVSL LASDSEPLKC FSRTFEDLTC    60
FWDEEEAAPS GTYQLLYAYP REKPRACPLS SQSMPHFGTR YVCQFPDQEE VRLFFPLHLW   120
VKNVFLNQTR TQRVLFVDSV GLPAPPSIIK AMGGSQPGEL QISWEEPAPE ISDFLRYELR   180
YGPRDPKNST GPTVIQLIAT ETCCPALQRP HSASALDQSP CAQPTMPWQD GPKQTSPSRE   240
ASALTAEGGS CLISGLQPGN SYWLQLRSEP DGISLGGSWG SWSLPVTVDL PGDAVALGLQ   300
CFTLDLKNVT CQWQQQDHAS SQGFFYHSRA RCCPRDRYPI WENCEEEEKT NPGLQTPQFS   360
RCHFKSRNDS IIHILVEVTT APGTVHSYLG SPFWIHQAVR LPTPNLHWRE ISSGHLELEW   420
QHPSSWAAQE TCYQLRYTGE GHQDWKVLEP PLGARGGTLE LRPRSYRYLQ LRARLNGPTY   480
QGPWSSWSDP TRVETATETA WISLVTALYL VLGLNAVLGL LLLRWRSKRS RLLHSDYMNM   540
TPRRPGPTRK HYQPYAPPRD FAAYRSKKVA KKPTNKAPHP KQEPQEINFP DDLPGSNTAA   600
PVQETLHGCQ PVTQEDGKES RISVQERQ                                      628

SEQ ID NO: 139            moltype = AA  length = 162
FEATURE                   Location/Qualifiers
REGION                    1..162
                          note = synthetic construct
source                    1..162
                          mol_type = protein
                          organism = synthetic construct
SEQUENCE: 139
MPSWALFMVT SCLLLAPQNL AQVSSEQKLI SEEDLISLVT ALYLVLGLNA VLGLLLLRWR    60
SKRSRLLHSD YMNMTPRRPG PTRKHYQPYA PPRDFAAYRS KKVAKKPTNK APHPKQEPQE   120
INFPDDLPGS NTAAPVQETL HGCQPVTQED GKESRISVQE RQ                      162

SEQ ID NO: 140            moltype = AA  length = 628
FEATURE                   Location/Qualifiers
REGION                    1..430
                          note = synthetic construct
source                    1..628
                          mol_type = protein
                          organism = synthetic construct
SEQUENCE: 140
MPSWALFMVT SCLLLAPQNL AQVSSEQKLI SEEDLQDVSL LASDSEPLKC FSRTFEDLTC    60
FWDEEEAAPS GTYQLLYAYP REKPRACPLS SQSMPHFGTR YVCQFPDQEE VRLFFPLHLW   120
VKNVFLNQTR TQRVLFVDSV GLPAPPSIIK AMGGSQPGEL QISWEEPAPE ISDFLRYELR   180
YGPRDPKNST GPTVIQLIAT ETCCPALQRP HSASALDQSP CAQPTMPWQD GPKQTSPSRE   240
ASALTAEGGS CLISGLQPGN SYWLQLRSEP DGISLGGSWG SWSLPVTVDL PGDAVALGLQ   300
CFTLDLKNVT CQWQQQDHAS SQGFFYHSRA RCCPRDRYPI WENCEEEEKT NPGLQTPQFS   360
RCHFKSRNDS IIHILVEVTT APGTVHSYLG SPFWIHQAVR LPTPNLHWRE ISSGHLELEW   420
QHPSSWAAQE TCYQLRYTGE GHQDWKVLEP PLGARGGTLE LRPRSYRYLQ LRARLNGPTY   480
QGPWSSWSDP TRVETATETA WISLVTAWCL VGLSAVLGL LLLRWRSKRS RLLHSDYMNM    540
TPRRPGPTRK HYQPYAPPRD FAAYRSKKVA KKPTNKAPHP KQEPQEINFP DDLPGSNTAA   600
PVQETLHGCQ PVTQEDGKES RISVQERQ                                      628

SEQ ID NO: 141            moltype = AA  length = 162
FEATURE                   Location/Qualifiers
REGION                    1..162
                          note = synthetic construct
source                    1..162
                          mol_type = protein
                          organism = synthetic construct
SEQUENCE: 141
MPSWALFMVT SCLLLAPQNL AQVSSEQKLI SEEDLISLVT AWCLVLGLSA VLGLLLLRWR    60
SKRSRLLHSD YMNMTPRRPG PTRKHYQPYA PPRDFAAYRS KKVAKKPTNK APHPKQEPQE   120
INFPDDLPGS NTAAPVQETL HGCQPVTQED GKESRISVQE RQ                      162

SEQ ID NO: 142            moltype = AA  length = 386
FEATURE                   Location/Qualifiers
```

```
REGION                      1..380
                            note = synthetic construct
source                      1..386
                            mol_type = protein
                            organism = synthetic construct
SEQUENCE: 142
MALPVTALLL PLALLLHAAR PEPKSCDKTH TCPPCPAPEL LGGPSVFLFP PKPKDTLMIS    60
RTPEVTCVVV DVSHEDPEVK FNWYVDGVEV HNAKTKPREE QYNSTYRVVS VLTVLHQDWL   120
NGKEYKCKVS NKALPAPIEK TISKAKGQPR EPQVYTLPPS RDELTKNQVS LTCLVKGFYP   180
SDIAVEWESN GQPENNYKTT PPVLDSDGSF FLYSKLTVDK SRWQQGNVFS CSVMHEALHN   240
HYTQKSLSLS PGKAAAFWVL VVVGGVLACY SLLVTVAFII FWVRSKRSRL LHSDYMNMTP   300
RRPGPTRKHY QPYAPPRDFA AYRSKKVAKK PTNKAPHPKQ EPQEINFPDD LPGSNTAAPV   360
QETLHGCQPV TQEDGKESRI SVQERQ                                       386

SEQ ID NO: 143              moltype = AA  length = 387
FEATURE                     Location/Qualifiers
REGION                      1..387
                            note = synthetic construct
source                      1..387
                            mol_type = protein
                            organism = synthetic construct
SEQUENCE: 143
MALPVTALLL PLALLLHAAR PAEPKSPDKT HTCPPCPAPP VAGPSVFLFP PKPKDTLMIA    60
RTPEVTCVVV DVSHEDPEVK FNWYVDGVEV HNAKTKPREE QYNSTYRVVS VLTVLHQDWL   120
NGKEYKCKVS NKALPAPIEK TISKAKGQPR EPQVYTLPPS RDELTKNQVS LTCLVKGFYP   180
SDIAVEWESN GQPENNYKTT PPVLDSDGSF FLYSKLTVDK SRWQQGNVFS CSVMHEALHN   240
HYTQKSLSLS PGKKDPKFWV LVVVGGVLAC YSLLVTVAFI IFWVRSKRSR LLHSDYMNMT   300
PRRPGPTRKH YQPYAPPRDF AAYRSKKVAK KPTNKAPHPK QEPQEINFPD DLPGSNTAAP   360
VQETLHGCQP VTQEDGKESR ISVQERQ                                      387

SEQ ID NO: 144              moltype = AA  length = 379
FEATURE                     Location/Qualifiers
REGION                      1..379
                            note = synthetic construct
source                      1..379
                            mol_type = protein
                            organism = synthetic construct
SEQUENCE: 144
MALPVTALLL PLALLLHAAR PERKCCVECP PCPAPPVAGP SVFLFPPKPK DTLMISRTPE    60
VTCVVVDVSH EDPEVQFNWY VDGVEVHNAK TKPREEQFNS TFRVVSVLTV VHQDWLNGKE   120
YKCKVSNKGL PAPIEKTISK TKGQPREPQV YTLPPSREEM TKNQVSLTCL VKGFYPSDIS   180
VEWESNGQPE NNYKTTPPML DSDGSFFLYS KLTVDKSRWQ QGNVFSCSVM HEALHNHYTQ   240
KSLSLSPGKF WVLVVVGGVL ACYSLLVTVA FIIFWVRSKR SRLLHSDYMN MTPRRPGPTR   300
KHYQPYAPPR DFAAYRSKKV AKKPTNKAPH PKQEPQEINF PDDLPGSNTA APVQETLHGC   360
QPVTQEDGKE SRISVQERQ                                               379

SEQ ID NO: 145              moltype = AA  length = 430
FEATURE                     Location/Qualifiers
REGION                      1..418
                            note = synthetic construct
source                      1..430
                            mol_type = protein
                            organism = synthetic construct
SEQUENCE: 145
MALPVTALLL PLALLLHAAR PELKTPLGDT THTCPRCPEP KSCDTPPPCP RCPEPKSCDT    60
PPPCPRCPEP KSCDTPPPCP RCPAPELLGG PSVFLFPPKP KDTLMISRTP EVTCVVVDVS   120
HEDPEVQFKW YVDGVEVHNA KTKPREEQYN STFRVVSVLT VLHQDWLNGK EYKCKVSNKA   180
LPAPIEKTIS KTKGQPREPQ VYTLPPSREE MTKNQVSLTC LVKGFYPSDI AVEWESSGQP   240
ENNYNTTPPM LDSDGSFFLY SKLTVDKSRW QQGNIFSCSV MHEALHNRFT QKSLSLSPGK   300
FWVLVVVGGV LACYSLLVTV AFIIFWVRSK RSRLLHSDYM NMTPRRPGPT RKHYQPYAPP   360
RDFAAYRSKK VAKKPTNKAP HPKQEPQEIN FPDDLPGSNT AAPVQETLHG CQPVTQEDGK   420
ESRISVQERQ                                                         430

SEQ ID NO: 146              moltype = AA  length = 380
FEATURE                     Location/Qualifiers
REGION                      1..380
                            note = synthetic construct
source                      1..380
                            mol_type = protein
                            organism = synthetic construct
SEQUENCE: 146
MALPVTALLL PLALLLHAAR PESKYGPPCP SCPAPEFLGG PSVFLFPPKP KDTLMISRTP    60
EVTCVVVDVS QEDPEVQFNW YVDGVEVHNA KTKPREEQFN STYRVVSVLT VLHQDWLNGK   120
EYKCKVSNKG LPSSIEKTIS KAKGQPREPQ VYTLPPSQEE MTKNQVSLTC LVKGFYPSDI   180
AVEWESNGQP ENNYKTTPPV LDSDGSFFLY SRLTVDKSRW QEGNVFSCSV MHEALHNHYT   240
QKSLSLSLGK FWVLVVVGGV LACYSLLVTV AFIIFWVRSK RSRLLHSDYM NMTPRRPGPT   300
RKHYQPYAPP RDFAAYRSKK VAKKPTNKAP HPKQEPQEIN FPDDLPGSNT AAPVQETLHG   360
CQPVTQEDGK ESRISVQERQ                                              380
```

```
SEQ ID NO: 147            moltype = AA  length = 380
FEATURE                   Location/Qualifiers
REGION                    1..380
                          note = synthetic construct
source                    1..380
                          mol_type = protein
                          organism = synthetic construct
SEQUENCE: 147
MALPVTALLL PLALLLHAAR PESKYGPPCP PCPAPEFEGG PSVFLFPPKP KDTLMISRTP   60
EVTCVVVDVS QEDPEVQFNW YVDGVEVHNA KTKPREEQFQ STYRVVSVLT VLHQDWLNGK  120
EYKCKVSNKG LPSSIEKTIS KAKGQPREPQ VYTLPPSQEE MTKNQVSLTC LVKGFYPSDI  180
AVEWESNGQP ENNYKTTPPV LDSDGSFFLY SRLTVDKSRW QEGNVFSCSV MHEALHNHYT  240
QKSLSLSLGK FWVLVVVGGV LACYSLLVTV AFIIFWVRSK RSRLLHSDYM NMTPRRPGPT  300
RKHYQPYAPP RDFAAYRSKK VAKKPTNKAP HPKQEPQEIN FPDDLPGSNT AAPVQETLHG  360
CQPVTQEDGK ESRISVQERQ                                             380

SEQ ID NO: 148            moltype = AA  length = 425
FEATURE                   Location/Qualifiers
REGION                    1..419
                          note = synthetic construct
source                    1..425
                          mol_type = protein
                          organism = synthetic construct
SEQUENCE: 148
MALPVTALLL PLALLLHAAR PEPKSCDKTH TCPPCPAPEL LGGPSVFLFP PKPKDTLMIS   60
RTPEVTCVVV DVSHEDPEVK FNWYVDGVEV HNAKTKPREE QYNSTYRVVS VLTVLHQDWL  120
NGKEYKCKVS NKALPAPIEK TISKAKGQPR EPQVYTLPPS RDELTKNQVS LTCLVKGFYP  180
SDIAVEWESN GQPENNYKTT PPVLDSDGSF FLYSKLTVDK SRWQQGNVFS CSVMHEALHN  240
HYTQKSLSLS PGKAAAIEVM YPPPYLDNEK SNGTIIHVKG KHLCPSPLFP GPSKPFWVLV  300
VVGGVLACYS LLVTVAFIIF WVRSKRSRLL HSDYMNMTPR RPGPTRKHYQ PYAPPRDFAA  360
YRSKKVAKKP TNKAPHPKQE PQEINFPDDL PGSNTAAPVQ ETLHGCQPVT QEDGKESRIS  420
VQERQ                                                              425

SEQ ID NO: 149            moltype = AA  length = 426
FEATURE                   Location/Qualifiers
REGION                    1..62
                          note = synthetic construct
source                    1..426
                          mol_type = protein
                          organism = synthetic construct
SEQUENCE: 149
MALPVTALLL PLALLLHAAR PAEPKSPDKT HTCPPCPAPP VAGPSVFLFP PKPKDTLMIA   60
RTPEVTCVVV DVSHEDPEVK FNWYVDGVEV HNAKTKPREE QYNSTYRVVS VLTVLHQDWL  120
NGKEYKCKVS NKALPAPIEK TISKAKGQPR EPQVYTLPPS RDELTKNQVS LTCLVKGFYP  180
SDIAVEWESN GQPENNYKTT PPVLDSDGSF FLYSKLTVDK SRWQQGNVFS CSVMHEALHN  240
HYTQKSLSLS PGKKDPKIEV MYPPPYLDNE KSNGTIIHVK GKHLCPSPLF PGPSKPFWVL  300
VVVGGVLACY SLLVTVAFII FWVRSKRSRL LHSDYMNMTP RRPGPTRKHY QPYAPPRDFA  360
AYRSKKVAKK PTNKAPHPKQ EPQEINFPDD LPGSNTAAPV QETLHGCQPV TQEDGKESRI  420
SVQERQ                                                             426

SEQ ID NO: 150            moltype = AA  length = 418
FEATURE                   Location/Qualifiers
REGION                    1..124
                          note = synthetic construct
source                    1..418
                          mol_type = protein
                          organism = synthetic construct
SEQUENCE: 150
MALPVTALLL PLALLLHAAR PERKCCVECP PCPAPPVAGP SVFLFPPKPK DTLMISRTPE   60
VTCVVVDVSH EDPEVQFNWY VDGVEVHNAK TKPREEQFNS TFRVVSVLTV VHQDWLNGKE  120
YKCKVSNKGL PAPIEKTISK TKGQPREPQV YTLPPSREEM TKNQVSLTCL VKGFYPSDIS  180
VEWESNGQPE NNYKTTPPML DSDGSFFLYS KLTVDKSRWQ QGNVFSCSVM HEALHNHYTQ  240
KSLSLSPGKI EVMYPPPYLD NEKSNGTIIH VKGKHLCPSP LFPGPSKPFW VLVVVGGVLA  300
CYSLLVTVAF IIFWVRSKRS RLLHSDYMNM TPRRPGPTRK HYQPYAPPRD FAAYRSKKVA  360
KKPTNKAPHP KQEPQEINFP DDLPGSNTAA PVQETLHGCQ PVTQEDGKES RISVQERQ    418

SEQ ID NO: 151            moltype = AA  length = 469
FEATURE                   Location/Qualifiers
REGION                    1..62
                          note = synthetic construct
source                    1..469
                          mol_type = protein
                          organism = synthetic construct
SEQUENCE: 151
MALPVTALLL PLALLLHAAR PELKTPLGDT THTCPRCPEP KSCDTPPPCP RCPEPKSCDT   60
PPPCPRCPEP KSCDTPPPCP RCPAPELLGG PSVFLFPPKP KDTLMISRTP EVTCVVVDVS  120
HEDPEVQFKW YVDGVEVHNA KTKPREEQYN STFRVVSVLT VLHQDWLNGK EYKCKVSNKA  180
LPAPIEKTIS KTKGQPREPQ VYTLPPSREE MTKNQVSLTC LVKGFYPSDI AVEWESSGQP  240
ENNYNTTPPM LDSDGSFFLY SKLTVDKSRW QQGNIFSCSV MHEALHNRFT QKSLSLSPGK  300
```

```
IEVMYPPPYL DNEKSNGTII HVKGKHLCPS PLFPGPSKPF WVLVVVGGVL ACYSLLVTVA    360
FIIFWVRSKR SRLLHSDYMN MTPRRPGPTR KHYQPYAPPR DFAAYRSKKV AKKPTNKAPH    420
PKQEPQEINF PDDLPGSNTA APVQETLHGC QPVTQEDGKE SRISVQERQ                469

SEQ ID NO: 152              moltype = AA   length = 419
FEATURE                     Location/Qualifiers
source                      1..419
                            mol_type = protein
                            organism = synthetic construct
SEQUENCE: 152
MALPVTALLL PLALLLHAAR PESKYGPPCP SCPAPEFLGG PSVFLFPPKP KDTLMISRTP    60
EVTCVVVDVS QEDPEVQFNW YVDGVEVHNA KTKPREEQFN STYRVVSVLT VLHQDWLNGK   120
EYKCKVSNKG LPSSIEKTIS KAKGQPREPQ VYTLPPSQEE MTKNQVSLTC LVKGFYPSDI   180
AVEWESNGQP ENNYKTTPPV LDSDGSFFLY SRLTVDKSRW QEGNVFSCSV MHEALHNHYT   240
QKSLSLSLGK IEVMYPPPYL DNEKSNGTII HVKGKHLCPS PLFPGPSKPF WVLVVVGGVL   300
ACYSLLVTVA FIIFWVRSKR SRLLHSDYMN MTPRRPGPTR KHYQPYAPPR DFAAYRSKKV   360
AKKPTNKAPH PKQEPQEINF PDDLPGSNTA APVQETLHGC QPVTQEDGKE SRISVQERQ    419

SEQ ID NO: 153              moltype = AA   length = 419
FEATURE                     Location/Qualifiers
source                      1..419
                            mol_type = protein
                            organism = synthetic construct
SEQUENCE: 153
MALPVTALLL PLALLLHAAR PESKYGPPCP PCPAPEFEGG PSVFLFPPKP KDTLMISRTP    60
EVTCVVVDVS QEDPEVQFNW YVDGVEVHNA KTKPREEQFN STYRVVSVLT VLHQDWLNGK   120
EYKCKVSNKG LPSSIEKTIS KAKGQPREPQ VYTLPPSQEE MTKNQVSLTC LVKGFYPSDI   180
AVEWESNGQP ENNYKTTPPV LDSDGSFFLY SRLTVDKSRW QEGNVFSCSV MHEALHNHYT   240
QKSLSLSLGK IEVMYPPPYL DNEKSNGTII HVKGKHLCPS PLFPGPSKPF WVLVVVGGVL   300
ACYSLLVTVA FIIFWVRSKR SRLLHSDYMN MTPRRPGPTR KHYQPYAPPR DFAAYRSKKV   360
AKKPTNKAPH PKQEPQEINF PDDLPGSNTA APVQETLHGC QPVTQEDGKE SRISVQERQ    419

SEQ ID NO: 154              moltype = AA   length = 62
FEATURE                     Location/Qualifiers
source                      1..62
                            mol_type = protein
                            organism = synthetic construct
SEQUENCE: 154
KKVAKKPTNK APHPKQEPQE INFPDDLPGS NTAAPVQETL HGCQPVTQED GKESRISVQE    60
RQ                                                                   62

SEQ ID NO: 155              moltype = AA   length = 124
FEATURE                     Location/Qualifiers
source                      1..124
                            mol_type = protein
                            organism = synthetic construct
SEQUENCE: 155
KKVAKKPTNK APHPKQEPQE INFPDDLPGS NTAAPVQETL HGCQPVTQED GKESRISVQE    60
RQKKVAKKPT NKAPHPKQEP QEINFPDDLP GSNTAAPVQE TLHGCQPVTQ EDGKESRISV   120
QERQ                                                                 124

SEQ ID NO: 156              moltype = AA   length = 62
FEATURE                     Location/Qualifiers
source                      1..62
                            mol_type = protein
                            organism = unidentified
SEQUENCE: 156
KKVAKKPTNK AAHPKQEPQE INFPDDLPGS NTAAPVQETL HGCQPVTQED GKESRISVQE    60
RQ                                                                   62

SEQ ID NO: 157              moltype = AA   length = 21
FEATURE                     Location/Qualifiers
source                      1..21
                            mol_type = protein
                            organism = synthetic construct
SEQUENCE: 157
MALPVTALLL PLALLLHAAR P                                               21

SEQ ID NO: 158              moltype = AA   length = 107
FEATURE                     Location/Qualifiers
source                      1..107
                            mol_type = protein
                            organism = synthetic construct
SEQUENCE: 158
ELVMTQTPSS VSAAVGGTVT ITCQASQSLS NLLAWYQQKP GQPPKLLIYG ASNLESGVPS    60
RFRGSGSGTD FTLTISGMKA EDAATYYCQG GHYSGLTFGN GTNVEIK                 107

SEQ ID NO: 159              moltype = AA   length = 15
FEATURE                     Location/Qualifiers
```

| | | |
|---|---|---|
| source | 1..15<br>mol_type = protein<br>organism = synthetic construct | |

SEQUENCE: 159
GGGGSGGGGS GGGGS                                               15

| | | |
|---|---|---|
| SEQ ID NO: 160<br>FEATURE<br>source | moltype = AA  length = 119<br>Location/Qualifiers<br>1..119<br>mol_type = protein<br>organism = synthetic construct | |

SEQUENCE: 160
QSLEESGGRL VTPGTPLTLT CTVSGFSLST NDMNWVRQAP GKGLEWIGVI YSDDTPDYAT   60
WAKGRFTISR TSTTVDLKIT SPTTEDTATY FCARGHYDSA VYAYALNIWG PGTLVTVSS   119

| | | |
|---|---|---|
| SEQ ID NO: 161<br>FEATURE<br>source | moltype = AA  length = 9<br>Location/Qualifiers<br>1..9<br>mol_type = protein<br>organism = synthetic construct | |

SEQUENCE: 161
AAAGSGGSG                                                      9

| | | |
|---|---|---|
| SEQ ID NO: 162<br>FEATURE<br>source | moltype = AA  length = 39<br>Location/Qualifiers<br>1..39<br>mol_type = protein<br>organism = synthetic construct | |

SEQUENCE: 162
IEVMYPPPYL DNEKSNGTII HVKGKHLCPS PLFPGPSKP                      39

| | | |
|---|---|---|
| SEQ ID NO: 163<br>FEATURE<br>source | moltype = AA  length = 27<br>Location/Qualifiers<br>1..27<br>mol_type = protein<br>organism = synthetic construct | |

SEQUENCE: 163
FWVLVVVGGV LACYSLLVTV AFIIFWV                                   27

| | | |
|---|---|---|
| SEQ ID NO: 164<br>FEATURE<br>source | moltype = AA  length = 41<br>Location/Qualifiers<br>1..41<br>mol_type = protein<br>organism = synthetic construct | |

SEQUENCE: 164
RSKRSRLLHS DYMNMTPRRP GPTRKHYQPY APPRDFAAYR S                   41

| | | |
|---|---|---|
| SEQ ID NO: 165<br>FEATURE<br>source | moltype = AA  length = 62<br>Location/Qualifiers<br>1..62<br>mol_type = protein<br>organism = synthetic construct | |

SEQUENCE: 165
KKVAKKPTNK APHPKQEPQE INFPDDLPGS NTAAPVQETL HGCQPVTQED GKESRISVQE   60
RQ                                                             62

| | | |
|---|---|---|
| SEQ ID NO: 166<br>FEATURE<br>source | moltype = AA  length = 440<br>Location/Qualifiers<br>1..440<br>mol_type = protein<br>organism = synthetic construct | |

SEQUENCE: 166
MALPVTALLL PLALLLHAAR PELVMTQTPS SVSAAVGGTV TITCQASQSL SNLLAWYQQK   60
PGQPPKLLIY GASNLESGVP SRFRGSGSGT DFTLTISGMK AEDAATYYCQ GGHYSGLTFG  120
NGTNVEIKGG GGSGGGGSGG GGSQSLEESG GRLVTPGTPL TLTCTVSGFS LSTNDMNWVR  180
QAPGKGLEWI GVIYSDDTPD YATWAKGRFT ISRTSTTVDL KITSPTTEDT ATYFCARGHY  240
DSAVYAYALN IWGPGTLVTV SSAAGSGGS GIEVMYPPPY LDNEKSNGTI IHVKGKHLCP  300
SPLFPGPSKP FWVLVVVGGV LACYSLLVTV AFIIFWVRSK RSRLLHSDYM NMTPRRPGPT  360
RKHYQPYAPP RDFAAYRSKK VAKKPTNKAP HPKQEPQEIN FPDDLPGSNT AAPVQETLHG  420
CQPVTQEDGK ESRISVQERQ                                          440

| | | |
|---|---|---|
| SEQ ID NO: 167<br>FEATURE<br>source | moltype = AA  length = 419<br>Location/Qualifiers<br>1..419<br>mol_type = protein<br>organism = synthetic construct | |

```
SEQUENCE: 167
ELVMTQTPSS VSAAVGGTVT ITCQASQSLS NLLAWYQQKP GQPPKLLIYG ASNLESGVPS  60
RFRGSGSGTD FTLTISGMKA EDAATYYCQG GHYSGLTFGN GTNVEIKGGG GSGGGGSGGG 120
GSQSLEESGG RLVTPGTPLT LTCTVSGFSL STNDMNWVRQ APGKGLEWIG VIYSDDTPDY 180
ATWAKGRFTI SRTSTTVDLK ITSPTTEDTA TYFCARGHYD SAVYAYALNI WGPGTLVTVS 240
SAAAGSGGSG IEVMYPPPYL DNEKSNGTII HVKGKHLCPS PLFPGPSKPF WVLVVVGGVL 300
ACYSLLVTVA FIIFWVRSKR SRLLHSDYMN MTPRRPGPTR KHYQPYAPPR DFAAYRSKKV 360
AKKPTNKAPH PKQEPQEINF PDDLPGSNTA APVQETLHGC QPVTQEDGKE SRISVQERQ  419

SEQ ID NO: 168         moltype = AA    length = 11
FEATURE                Location/Qualifiers
source                 1..11
                       mol_type = protein
                       organism = synthetic construct
SEQUENCE: 168
QASQSLSNLL A                                                      11

SEQ ID NO: 169         moltype = AA    length = 7
FEATURE                Location/Qualifiers
source                 1..7
                       mol_type = protein
                       organism = synthetic construct
SEQUENCE: 169
GASNLES                                                            7

SEQ ID NO: 170         moltype = AA    length = 8
FEATURE                Location/Qualifiers
source                 1..8
                       mol_type = protein
                       organism = synthetic construct
SEQUENCE: 170
QGGHYSGL                                                           8

SEQ ID NO: 171         moltype = AA    length = 5
FEATURE                Location/Qualifiers
source                 1..5
                       mol_type = protein
                       organism = synthetic construct
SEQUENCE: 171
TNDMN                                                              5

SEQ ID NO: 172         moltype = AA    length = 16
FEATURE                Location/Qualifiers
source                 1..16
                       mol_type = protein
                       organism = synthetic construct
SEQUENCE: 172
VIYSDDTPDY ATWAKG                                                 16

SEQ ID NO: 173         moltype = AA    length = 14
FEATURE                Location/Qualifiers
source                 1..14
                       mol_type = protein
                       organism = synthetic construct
SEQUENCE: 173
GHYDSAVYAY ALNI                                                   14

SEQ ID NO: 174         moltype = AA    length = 10
FEATURE                Location/Qualifiers
source                 1..10
                       mol_type = protein
                       organism = synthetic construct
SEQUENCE: 174
QKLISEEDLE                                                        10

SEQ ID NO: 175         moltype = AA    length = 93
FEATURE                Location/Qualifiers
source                 1..93
                       mol_type = protein
                       organism = synthetic construct
SEQUENCE: 175
LVKQSPMLVA YDNAVNLSCK YSYNLFSREF RASLHKGLDS AVEVCVVYGN YSQQLQVYSK  60
TGFNCDGKLG NESVTFYLQN LYVNQTDIYF CKI                               93
```